(12) United States Patent
Chen

(10) Patent No.: US 6,844,351 B1
(45) Date of Patent: Jan. 18, 2005

(54) CORTICOTROPIN RELEASING FACTOR ANTAGONISTS

(75) Inventor: Yuhpyng L. Chen, Waterford, CT (US)

(73) Assignee: Pfizer Inc., New York, NY (US)

(*) Notice: Subject to any disclaimer, the term of this patent is extended or adjusted under 35 U.S.C. 154(b) by 0 days.

(21) Appl. No.: 09/583,372

(22) Filed: May 31, 2000

Related U.S. Application Data

(63) Continuation of application No. 08/741,066, filed on Oct. 30, 1996, now Pat. No. 6,403,599, and a continuation-in-part of application No. 09/254,387, filed as application No. PCT/IB95/00439 on Jun. 6, 1995, now Pat. No. 6,316,631.
(60) Provisional application No. 60/006,333, filed on Nov. 8, 1995.

(51) Int. Cl.[7] ................. A61K 31/505; C07D 239/02
(52) U.S. Cl. ................. 514/269; 514/256; 514/332; 514/336; 514/344; 514/345; 514/352; 514/357; 544/298; 544/332; 544/334
(58) Field of Search ................. 514/269, 256, 514/332–345, 349–352, 357, 255, 274, 275, 312, 314, 354, 355, 356; 544/334, 298, 295, 296, 300, 310, 316, 317, 319, 320, 326, 328, 329, 331, 333, 405, 297, 309, 311, 313, 314, 315, 318, 321, 322, 323, 324, 325, 327, 330, 332, 335; 546/153, 155, 156, 157, 159, 167, 255, 256, 261–267, 296, 192, 207, 208, 212, 214, 215, 216, 217, 218, 219, 220, 221, 222, 223, 224, 225, 229, 230, 231, 232, 233, 234, 235, 236, 237, 238, 239, 240, 241, 242, 244, 245, 246, 247, 248

(56) References Cited

U.S. PATENT DOCUMENTS

| | | | |
|---|---|---|---|
| 4,605,642 A | 8/1986 | Rivier et al. | 514/12 |
| 4,839,353 A | 6/1989 | Hosoi et al. | 514/212 |
| 5,063,245 A | 11/1991 | Abreu et al. | 514/404 |
| 5,691,364 A | 11/1997 | Buckman et al. | 514/341 |

FOREIGN PATENT DOCUMENTS

| | | | | |
|---|---|---|---|---|
| DE | 3145287 | 5/1983 | | 487/4 |
| EP | 0475411 | 3/1992 | | |
| EP | 0482804 | 1/1997 | | |
| EP | 0773023 | 5/1997 | | |
| EP | 0951906 | 10/1999 | | |
| EP | 1040831 | 4/2000 | | |
| EP | 1059100 | 12/2000 | | |
| WO | WO 94135676 | 6/1994 | | 487/4 |
| WO | WO 95/33750 A1 | * 12/1995 | | |
| WO | 9533750 | 12/1995 | | |

OTHER PUBLICATIONS

Chhabria etal, Heterocycles, vol. 51, No. 11, 1999.
Kamel et al, Pharmazie 1990, 45 (2), 139–140.
Demina et al., Khim. Farm. Zh., 1993, 27(7), pp. 34–35 (with English summary).

Demina et al., Geterotsikl Soedin, 192 (11), pp. 1506–1508 (with English summary).

Chalmers, D. T., et al., Corticotrophin–releasing factors molecular biology to drug design. Trends in Pharmacological Sciences, (1996), vol. 17, pp. 166–172.

Cossey, A. L., et al. "Pyridines & Pyridinium Salts from Cyanocetamides" Australian Journal of Chem. (1976), 29, p. 1039–50.

Owens, et al., "Physiology and Pharmacology of Corticotropin–releasing factor", Pharm. Rev., (1991), vol. 43, pp. 425–473.

Fujikakwa, K., et al. "Herbicidal activities of phenoxypyridines", Chemical Abstract (1970), Abstract No. 11080v.

Fujikawa, K., et al., "Studies on Herbicidal Activities of Phenoxypyridines", Agr. Biol. Chemical, (1970), vol. 34, No. 1 p. 68–79.

(List continued on next page.)

*Primary Examiner*—Dwayne Jones
(74) *Attorney, Agent, or Firm*—Ladas & Parry LLP

(57) ABSTRACT

Corticotropin-releasing factor (CRF) antagonists having the formulae

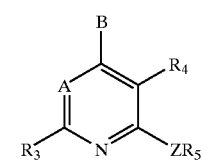

I

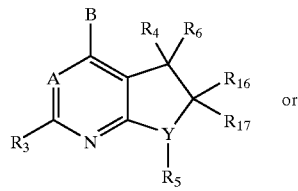

II
or

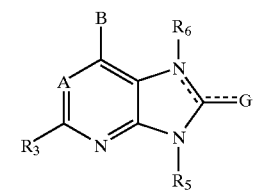

III wherein the dashed lines, A, B, Y, Z, G, $R_3$, $R_4$, $R_5$, $R_6$, $R_{16}$ and $R_{17}$ are as defined in the application, and processes for preparing them. These compounds and their pharmaceutically acceptable salts are useful in the treatment disorders including CNS and stress-related disorders.

13 Claims, No Drawings

OTHER PUBLICATIONS

DeSouza, E.B., "Corticotropin–releasing Factor Receptors Physiology, Pharmacology, Biochemistry & Role in Central Nervous System & Immune Disorders.", (1995), vol. 20, No. 8, pp. 789–819.

Fackelmann, K.A. & Raloff, J. "Physological Street Linked to Cancer", Science News, (Sep. 25, 1993), vol. 144, p. 196.

Lyons, M.K., et al., "Corticotropin releasing factor antagonist reduces ischemic hippocampal neuronal injury", Brain Research, (1991), vol. 545, Issue 1–2, pp. 339–342.

Stratakis, C.A. & Chrousos, G. P., "Hypothalamic Hormones, GnRH, TRH, CHRH, SRIF, CRH, & Dopamine, Endocrinology" Basic & Clinical Principles, (1997), pp. 185–209 (Humana Press, Tofowa, NJ, 1997).

Strijbos, P. J. L. M., et al. Brain Research, vol. 656, (1991), pp. 405–408.

Robbins, M.J., et al., Can. J. Chem. (1997), vol. 55, pp. 1252–1259.

* cited by examiner

CORTICOTROPIN RELEASING FACTOR ANTAGONISTS

This application is a continuation in part of Ser. No. 08/741,066 filed on Oct. 30, 1997, (now issued as U.S. Pat. No. 6,403,599) which claims benefit of 60/006,333 filed Nov. 8, 1995, and is also a continuation in part of application Ser. No. 09/254,387 filed Mar. 4, 1999 (now issued as U.S. Pat. No. 6,316,631) which is the United States part of International Patent Application PCT/IB95/00437 which was filed on Jun. 6, 1995.

BACKGROUND OF THE INVENTION

This invention relates to pyridines, pyrimidines, purinones, pyrrolopyrimidinones and, pyrrolopyridinones, processes for preparing them, pharmaceutical compositions containing them, and methods of using them to treat certain central nervous system (CNS) and other disorders.

CRF antagonists are mentioned in U.S. Pat. No. 4,605,642, issued Aug. 12, 1986, and 5,063,245, issued Nov. 5, 1991, referring to peptides and pyrazolinones, respectively. CRF antagonists are also described in U.S. Pat. No. 5,962,479, issued Oct. 5, 1999. The importance of CRF antagonists is set out in the literature, eg., as discussed in U.S. Pat. No. 5,063,245, which is incorporated herein by reference. A recent outline of the different activities, possessed by CRF antagonists is found in M. J. Owens et al., *Pharm. Rev., Vol.* 43, pages 425 to 473 (1991), also incorporated herein by reference. Based on the research described in these two and other references, CRF antagonists are effective in the treatment of a wide range of stress-related illnesses, such as depression, anxiety, headache, irritable bowel syndrome, inflammatory diseases, immune suppression, Alzheimer's disease, gastrointestinal diseases, anorexia nervosa, hemorrhagic stress, drug and alcohol withdrawal symptoms, drug addiction, infertility, head trauma, stroke, and stress-induced infections in humans and animals. The use of CRF antagonists for treatment of Syndrome X has also been described in U.S. Provisional Patent Application No. 60/162,340, filed Oct. 29, 1999, which is also incorporated in its entirety herein by reference. Methods for using CRF antagonists to treat congestive heart failure are described in U.S. Ser. No. 09/248,073, filed Feb. 10, 1999, which is also incorporated herein in its entirety by reference.

SUMMARY OF THE INVENTION

The present invention provides compounds of the formula

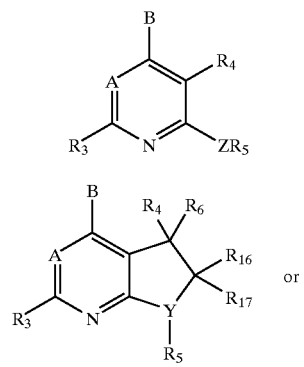

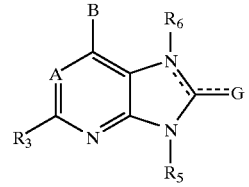

and pharmaceutically acceptable salts thereof, wherein
the dashed lines represent optional double bonds, with the proviso that when the dashed line in C=G represent a double bond, then the dashed line In $N(R_6)$=C does not represent a double bond; and with the proviso that when the dashed line in $N(R_6)$=C represents a double bond, $R_6$ is absent in formula III and the dashed line in C=G does not represent a double bond;

A is —$CR_7$ or N;

B is $NR_1R_2$, —$CR_1R_2R_{11}$, —$C(=CR_2R_{12})R_1$, —$NHCHR_1R_2$, —$OCHR_1R_2$, —$SCHR_1R_2$, —$CHR_2OR_1$, —$CHR_1OR_2$, —$CHR_2SR_1$, —$C(S)R_2$, —$C(O)R_2$, $CHR_2NR_1R_2$, —$CHR_1NHR_2$, $CHR_1N(CH_3)R_2$, or —$NR_{12}NR_1R_2$;

when the dashed line in C=G represents a double bond, then G is hydrogen, oxygen, sulfur, NH, or $N(C_1$–$C_4$ alkyl);

when the dashed line in C=G does not represent a double bond, then C=G is —C(H)(NH$_2$), CH$_2$, —C(H)(methoxy), —C(H)(ethoxy), —C(H)(O($C_3$–$C_4$ alkyl)), —C(H)(halo), —C(H)(trifluoromethoxy), —C(H)(methyl), —C(H)(ethyl), —C(H)($C_3$–$C_4$ alkyl), —C(H)(S($C_1$–$C_4$ alkyl)), —C($C_1$–$C_4$ alkyl)($C_1$–$C_4$ alkyl), cyclopropyl, —C(H)(cyclopropyl), thiomethoxy, —C(H)(NH$_2$), —C(H)(NHCH$_3$), —C(H)(N(CH$_3$)$_2$), or —C(H)(trifluoromethyl);

wherein said cyclopropyl, methoxy, ethoxy, $C_3$–$C_4$ alkyl, and $C_1$–$C_4$ alkyl groups of C=G may optionally be substituted by one OH, methoxy, or trifluoromethoxy, or may optionally be substituted by from one to six fluoro atoms;

Y is CH or N;

Z is NH, O, S, —N($C_1$–$C_2$ alkyl), —NC(O)CF$_3$, or —C($R_{13}R_{14}$), wherein $R_{13}$ and $R_{14}$ are each, independently, hydrogen, trifluoromethyl or methyl, or one of $R_{13}$ and $R_{14}$ is cyano and the other is hydrogen or methyl, or —C($R_{13}R_{14}$) is a cyclopropyl group, or Z is nitrogen or CH and forms a five or six membered heterocyclic ring fused with $R_5$, which ring optionally comprises two or three further hetero members selected independently from oxygen, nitrogen, $NR_{12}$, and $S(O)_m$, and optionally comprises from one to three double bonds, and is optionally substituted with halo, $C_1$–$C_4$ alkyl, —O($C_1$–$C_4$ alkyl), NH$_2$, NHCH$_3$, N(CH$_3$)$_2$, CF$_3$, or OCF$_3$, with the proviso that said ring does not contain any —S—S—, —S—O—, —N—S—, or —O— bonds, and does not comprise more than two oxygen or $S(O)_m$ heterologous members;

$R_1$ is C(O)H, C(O)($C_1$–$C_6$ alkyl), C(O)$C_1$–$C_8$ alkylene) ($C_3$–$C_8$ cycloalkyl), C(O)($C_3$–$C_8$ cycloalkylene) ($C_3$–$C_8$ cycloalkyl), C(O)($C_1$–$C_6$ alkylene)($C_4$–$C_8$ heterocycloalkyl), —C(O)($C_3$–$C_8$ cycloalkylene) ($C_4$–$C_8$ heterocycloalkyl), $C_1$–$C_6$ alkyl, $C_3$–$C_8$ cycloalkyl, $C_4$–$C_8$ heterocycloalkyl, —($C_1$–$C_8$ alkylene)($C_3$–$C_8$ cycloalkyl), —($C_3$–$C_8$ cycloalkylene)

($C_3$-$C_8$ cycloalkyl), —($C_1$-$C_8$ alkylene)($C_4$-$C_8$ heterocycloalkyl), —($C_3$-$C_8$ cycloalkylene)($C_4$-$C_8$ heterocycloalkyl), or —O-aryl, or —O—($C_1$-$C_6$ alkylene)-aryl; wherein said aryl, $C_4$-$C_8$ heterocycloalkyl, $C_1$-$C_6$ alkyl, $C_3$-$C_8$ cycloalkyl, $C_3$-$C_8$ cycloalkylene, and $C_1$-$C_6$ alkylene groups may each independently be optionally substituted with from one to six fluoro and may each independently be optionally substituted with one or two substituents $R_8$ independently selected from the group consisting of $C_1$-$C_4$ alkyl, —$C_3$-$C_8$ cycloalkyl, hydroxy, fluoro, chloro, bromo, iodo, $CF_3$, —O—($C_1$-$C_8$ alkyl), —O—($C_3$-$C_5$ cycloalkyl), —O—CO($C_1$-$C_4$ alkyl), —O—CO—NH($C_1$-$C_4$ alkyl), —O—CO—N($R_{24}$)($R_{25}$), —N($R_{24}$)($R_{25}$), —S($C_1$-$C_4$ alkyl), —S($C_3$-$C_5$ cycloalkyl), —N($C_1$-$C_4$alkyl)CO($C_1$-$C_4$ alkyl), —NHCO($C_1$-$C_4$ alkyl), —COO($C_1$-$C_4$ alkyl), —CONH($C_1$-$C_4$ alkyl), —CON($C_1$-$C_4$ alkyl)($C_1$-$C_4$ alkyl), CN, $NO_2$, —$OSO_2$($C_1$-$C_4$ alkyl), $S^+$($C_1$-$C_6$ alkyl)($C_1$-$C_2$ alkyl)$1^-$, —SO($C_1$-$C_4$ alkyl) and —$SO_2$ ($C_1$-$C_4$ alkyl); and wherein the C—$C_5$ alkyl, $C_1$-$C_6$ alkylene, $C_5$-$C_8$ cycloalkyl. $C_5$-$C_8$ cycloalkylene, and $C_5$-$C_8$ heterocycloalkyl moieties of $R_1$ may optionally independently contain from one to three double or triple bonds; and wherein the $C_1$-$C_4$ alkyl moieties and the $C_1$-$C_6$ alkyl moieties of $R_8$ can optionally independently be substituted with hydroxy. $C_1$-$C_4$ alkyl, amino, aryl, —$CH_2$-aryl, —$C_3$-$C_5$ cycloalkyl, or —O—($C_1$-$C_4$ alkyl), and can optionally independently be substituted with from one to five fluoro, and can optionally contain one or two double or triple bonds; and wherein each heterocycloalkyl group of $R_1$ contains from one to three heteromoieties selected from oxygen, $S(O)_m$, nitrogen, and $NR_{12}$;

$R_2$ is hydrogen, $C_1$-$C_{12}$ alkyl, $C_3$-$C_8$ cycloalkyl, $C_4$-$C_8$ heterocycloalkyl, —($C_1$-$C_6$ alkylene)($C_3$-$C_8$ cycloalkyl), —($C_3$-$C_8$ cycloalkylene)($C_3$-$C_8$ cycloalkyl), $C_1$-$C_6$ alkylene)($C_4$-$C_8$ heterocycloalkyl), —($C_3$-$C_8$ cycloalkylene)($C_4$-$C_8$ heterocycloalkyl), aryl, —($C_1$-$C_6$ alkylene)aryl, or —($C_3$-$C_8$ cycloalkylene)(aryl); wherein each of the foregoing $R_2$ groups may optionally be substituted with from one three substituents independently selected from chloro, fluoro, and —($C_1$-$C_6$ alkyl, wherein one of said one to three substituents can further be selected from bromo, iodo, $C_1$-$C_6$ alkoxy, —OH, —O—CO—($C_1$-$C_6$ alkyl), —O—CO—N($C_1$-$C_4$ alkyl)($C_1$-$C_2$ alkyl), —S($C_1$-$C_8$ alkyl), —S(O)($C_1$-$C_8$ alkyl), —$S(O)_2$($C_1$-$C_6$ alkyl), $S^+$($C_1$-$C_6$ alkyl)($C_1$-$C_2$ alkyl)$1^-$, CN, and $NO_2$; and wherein the $C_1$-$C_{12}$ alkyl, —($C_1$-$C_6$ alkylene), $C_5$-$C_8$ cycloalkyl), —($C_5$-$C_8$ cycloalkylene), and —($C_5$-$C_8$ heterocycloalkyl) moieties of $R_2$ may optionally independently contain from one to three double or triple bonds; and wherein each heterocycloalkyl group of $R_2$ contains from one to three heteromoieties selected from oxygen, $S(O)_m$, nitrogen, and $NR_{12}$;

or where $R_1$ and $R_2$ are as in —$NHCHR_1R_2$, —$OCHR_1R_2$, —$SCHR_1R_2$, —$CHR_1R_2$ or —$NR_1R_2$, $R_1$ and $R_2$ of B may form a saturated 5- to 8-membered ring which may optionally contain one or two double bonds and in which one or two of the ring carbons may optionally be replaced by an oxygen, $S(O)_m$, nitrogen or $NR_{12}$; and which carbocyclic ring can optionally be substituted with from 1 to 3 substituents selected from the group consisting of hydroxy, $C_1$-$C_4$ alkyl, fluoro, chloro, bromo, iodo, $CF_3$, —O($C_1$-$C_4$ alkyl), —O—CO—(C—$C_4$ alkyl), —O—CO—NH($C_1$-$C_4$ alkyl), O—CO—N($C_1$-$C_4$ alkyl)($C_1$-$C_2$ alkyl), —NH ($C_1$-$C_4$ alkyl), —N($C_1$-$C_2$ alkyl)($C_1$-$C_4$ alkyl), S($C_1$-$C_4$ alkyl), —N($C_1$-$C_4$ alkyl)CO($C_1$-$C_4$ alkyl), —NHCO($C_1$-$C_4$ alkyl), —COO($C_1$-$C_4$ alkyl), —CONH($C_1$-$C_4$ alkyl), —CON($C_1$-$C_4$ alkyl)($C_1$-$C_2$ alkyl), CN, $NO_2$, —$SO_2$($C_1$-$C_4$ alkyl), —SO($C_1$-$C_4$ alkyl), and —$SO_2$($C_1$-$C_4$ alkyl), wherein one of said one to three substituents can further be selected from phenyl;

$R_3$ is methyl, ethyl, fluoro, chloro, bromo, iodo, cyano, methoxy, $OCF_3$, $NH_2$, $NH(C_1$-$C_2$ alkyl), $N(CH_3)_2$, —$NHCOCF_3$, —$NHCH_2CF_3$, $S(O)_m$($C_1$-$C_4$ alkyl), $CONH_2$, —$CONHCH_3$, $CON(CH_3)$, —$CF_3$, or $CH_2OCH_3$;

$R_4$ is hydrogen, $C_1$-$C_4$ alkyl, $C_3$-$C_5$ cycloalkyl, —($C_1$-$C_4$ alkylene)($C_3$-$C_5$ cycloalkyl), —($C_3$-$C_5$ cycloalkylene) ($C_3$-$C_5$ cycloalkyl), cyano, fluoro, chloro, bromo, iodo, —$OR_{24}$, $C_1$-$C_6$ alkoxy, —O—($C_3$-$C_5$ cycloalkyl), —O—($C_1$-$C_4$ alkylene)($C_3$-$C_5$ cycloalkyl), —O— ($C_3$-$C_5$ cycloalkylene)($C_3$-$C_5$ cycloalkyl), —$CH_2SC$ $(S)O(C_1$-$C_4$ alkyl), —$CH_2OCF_3$, $CF_3$, amino, nitro, —$NR_{24}R_{25}$, $C_1$-$C_4$ alkylene)—$OR_{24}$, —($C_1$-$C_4$ alkylene)Cl, —($C_1$-$C_4$ alkylene)$NR_{24}R_{25}$ —$NHCOR_{24}$, —$NHCONR_{24}R_{25}$, —C=$NOR_{24}$, —$NHNR_{24}R_{25}$, —$S(O)_mR_{24}$, —$C(O)R_{24}$, —OC(O) $R_{24}$, —C(O)CN, —$C(O)NR_{24}R_{25}$, $C(O)NHNR_{24}R_{25}$, and —$COOR_{24}$, wherein the alkyl and alkylene groups of $R_4$ may optionally independently contain one or two double or triple bonds and may optionally independently be substituted with one or two substituents $R_{10}$ independently selected from hydroxy, amino, —$NHCOCH_3$, —$NHCOCH_2Cl$, —NH(C—$C_2$ alkyl), —N($C_1$-$C_2$ alkyl)($C_1$-$C_2$ alkyl), —COO($C_1$-$C_4$ alkyl), —COOH, —CO($C_1$-$C_4$ alkyl), $C_1$-$C_6$ alkoxy, $C_1$-$C_3$ thioalkyl, cyano and nitro, and with one to four substituents independently selected from fluoro and chloro;

$R_5$ is aryl or heteroaryl and is substituted with from one to four substituents $R_{27}$ independently selected from halo, $C_1$-$C_{10}$ alkyl, —($C_1$-$C_4$ alkylene)($C_3$-$C_8$ cycloalkyl), —($C_1$-$C_4$ alkylene)($C_{4-C8}$ heterocycloalkyl), —($C_3$-$C_8$ cycloalkyl), —($C_4$-$C_8$ heterocycloalkyl), —($C_3$-$C_8$ cycloalkylene)($C_3$-$C_8$ cycloalkyl), —($C_3$-$C_8$ cycloalkylene)($C_4$-$C_8$ heterocycloalkyl), $C_1$-$C_4$ haloalkyl, $C_1$-$C_4$ haloalkoxy, nitro, cyano, —$NR_{24}R_{25}$, —$NR_{24}COR_{25}$, —$NR_{24}CO_2R_{26}$, —$COR_{24}$, —OR25, —$CONR_{24}R_{25}$, —$CO(NOR_{22})R_2$, —$CO_2R_{26}$, —C=$N(OR_{22})R_{23}$, and —S(O), $R_{23}$; wherein said $C_1$-$C_{10}$ alkyl, $C_3$-$C_8$ cycloalkyl, ($C_1$-$C_4$ alkylene), ($C_3$-$C_8$ cycloalkyl), ($C_3$-$C_8$ cycloalkylene), and ($C_4$-$C_8$ heterocycloalkyl) groups can be optionally substituted with from one to three substituents independently selected form $C_1$-$C_4$ alkyl, $C_3$-$C_8$ cloalkyl, ($C_1$-$C_4$ alkylene)($C_3$-$C_8$ cycloalkyl), —($C_3$-$C_8$ cycloalkylene)($C_3$-$C_8$ cycloalkyl), $C_1$-$C_4$ haloalkyl, hydroxy, $C_1$-$C_6$ alkoxy, nitro halo, cyano, —$NR_{24}R_{25}$, —$NR_{24}COR_{25}$, $NR_{24}CO_{24}R_{25}$, —$COR_{24}$, —$OR_{25}$, —$CONR_{24}R_{25}$, $CO_2R_{26}$, —$CO(NOR_{22})R_{25}$, and —$S(O)_mR_{23}$; and wherein two adjacent substituents of the $R_5$ group can optionally form a 5–7 membered ring, saturated or unsaturated, fused to $R^5$, which ring optionally can contain one, two, or three heterologous members independently selected from O, $S(O)_m$, and N, but not any —S—S—, —O—O—, or —N—S— bonds, and which ring is optionally substituted with $C_1$-$C_4$ alkyl, $C_3$-$C_8$ cycloalkyl, —($C_1$-$C_4$ alkylene)($C_3$-$C_8$ cycloalkyl), —($C_3$–$C_8$ cycloalkylene)($C_3$–$C_8$ cycloalkyl), $C_1$–$C_4$ haloalkyl, nitro, halo, cyano —$NR_{24}R_{25}$, $NR_{24}COR_{24}$ $NR_{26}CO_2R_{26}$, —$COR_{24}$, $R_{25}$, —$CONR_{24}R_{25}$, $CO_2R_{26}$, —$CO(NOR_{26})R_{25}$, or —$S(O)_m R_{23}$; wherein one of said one to four optional substituents $R_{27}$ can further be selected from —$SO_2NH(C_1$–$C_4$ alkyl), —$SO_2NH(C$—$C_4$ alkylene)($C_3$–$C_8$ cycloalkyl), —$SO_2NH(C_3$–$C_8$ cycloalkyl), —$SO_2NH(C_1$–$C_4$ cycloalkylene)($C_3$–$C_8$ cycloalkyl), —$SO_2N(C_1$–$C_4$ alkyl)($C_1$–$C_2$ alkyl), —$SO_2NH_2$, —$NHSO_2(C_1$–$C_4$ alkyl), —$NHSO_2$ ($C_{11}$–$C_4$ cycloalkyl), —$NHSO_2(C_1$–$C_4$ alkylene) ($C_3$–$C_8$ cycloalkyl), and —$NHSO_2(C_3$–$C_8$ cycloalkylene)($C_3$–$C_8$ cycloalkyl); and wherein the alkyl, and alkylene groups of $R_5$ may independently optionally contain one double or triple bond;

$R_6$ is hydrogen, $C_1$–$C_6$ alkyl, $C_3$–$C_8$ cycloalkyl, $C_1$–$C_6$ alkylene)($C_3$–$C_8$ cycloalkyl), or —($C_3$–$C_8$ cycloalkylene)($C_3$–$C_8$ cycloalkyl), wherein said alkyl and cycloalkyl may optionally be substituted with one hydroxy, methoxy, ethoxy or fluoro group;

or, wherein the compound is a compound of formula II, $R_6$ and $R_4$ can together form an oxo (=O) group or can be connected to form a 3–8 membered carbocyclic ring, optionally containing one to three double bonds, and optionally containing one, two, or three heterologous ring members selected from O, $SO_m$, N, and $NR_{12}$, but not containing any —O—, O, —S—S—, or N—S— bonds, and further optionally substituted with $C_1$–$C_4$ alkyl or $C_3$–$C_8$ cycloalkyl, wherein said $C_1$–$C_4$ alkyl substituent may optionally contain one double or triple bond;

$R_7$ is hydrogen, methyl, fluoro, chloro, bromo, iodo, cyano, hydroxy, —$O(C_1$–$C_2$ alkyl), —O(cyclopropyl), —$COO(C_1$–$C_2$ alkyl), —$COO(C_3$–$C_8$ cycloalkyl), $OCF_3$, $CF_3$, —$CH_2OH$, or $CH_2OCH_3$;

$R_{11}$ is hydrogen, hydroxy, fluoro, ethoxy, or methoxy;

$R_{12}$ is hydrogen or $C_1$–$C_4$ alkyl;

$R_{16}$ and $R_{17}$ are each, independently, hydrogen, hydroxy, methyl, ethyl, methoxy, or ethoxy, except that $R_{16}$ and $R_{17}$ are not both methoxy or ethoxy;

or $R_{16}$ and $R_{17}$ together form an oxo (=O) group;

or $R_{16}$ and $R_{17}$, are connected to form a 3–8 membered carbocyclic ring, optionally containing one to three double bonds, and optionally containing from one to three heterologous ring members selected from O, $SO_m$, N, and $NR_{12}$, but not containing any —O—O—, —S—O—, —S—, or N—S— bonds, and further optionally substituted with $C_1$–$C_4$ alkyl or $C_3$–$C_8$ cycloalkyl, wherein said $C_1$–$C_4$ alkyl substituent may optionally contain one double or triple bond;

$R_{22}$ is independently at each occurrence selected from hydrogen, $C_1$–$C_4$ alkyl, $C_1$–$C_4$ haloalkyl, $C_3$–$C_6$ alkenyl, $C_3$–$C_6$ alkynyl, $C_3$–$C_8$ cycloalkyl, ($C_3$–$C_8$ cycloalkylene)($C_3$–$C_8$ cycloalkyl); and ($C_1$–$C_4$ alkylene)($C_3$–$C_8$ cycloalkyl);

$R_{23}$ is independently at each occurrence selected from $C_1$–$C_4$ alkyl, $C_1$–$C_4$ haloalkyl, $C_2$–$C_8$ alkoxyalkyl, $C_3$–$C_8$ cycloalkyl, $C_1$–$C_4$ alkylene)($C_3$–$C_5$ cycloalkyl), —($C_3$–$C_8$ cycloalkylene)($C_3$–$C_8$ Cycloalkyl), aryl, —($C_1$–$C_4$ alkylene)aryl, piperidine, pyrrolidine, piperazine, N-methylpiperazine, morpholine, and thiomorpholine;

$R_{24}$ and $R_{25}$ are independently at each occurrence selected from hydrogen, —$C_1$–$C_4$ alkyl, $C_1$–$C_4$ haloalkyl, especially $CF_3$, —$CHF_2$, $CF_2CF_3$, or $CH_2CF_3$, —($C_1$–$C_4$ alkylene)OH, —($C_1$–$C_4$ alkylene)—C—($C_1$–$C_4$ alkyl), —($C_1$–$C_4$ alkylene)—O—($C_3$–$C_5$ cycloalkyl), $C_3$–$C_8$ cycloalkyl, —($C_1$–$C_4$ alkylene)($C_4$–$C_8$ heterocycloalkyl), —($C_3$–$C_8$ cycloalkylene)($C_3$–$C_8$ cycloalkyl), —($C_4$–$C_8$ heterocycloalkyl), —($C_1$–$C_4$ alkylene)($C_4$–$C_8$ heterocycloalkyl), —($C_{3-8}$ cycloalkylene)($C_4$–$C_8$ heterocycloalkyl), aryl, and —($C_1$–$C_4$ alkylene)(aryl), wherein the —$C_4$–$C_8$ heterocycloalkyl groups can each independently optionally be substituted with aryl, $CH_2$-aryl, or $C_1$–$C_4$ alkyl, and can optionally contain one or two double or triple bonds; or, when $R_{24}$ and $R_{25}$ are as $NR_{24}R_{25}$, —C(O)$NR_{24}R_{25}$, —($C_1$–$C_4$ alkylene)$NR_{24}R_{25}$, or —$NHCONR_{24}R_{25}$, then $NR_{24}R_{25}$ may further optionally form a 4 to 8 membered heterocyclic ring optionally containing one or two further hetero members independently selected from $S(O)_m$, oxygen, nitrogen, and $NR_{12}$, and optionally containing from one to three double bonds;

$R_{26}$ is independently at each occurrence selected from $C_1$–$C_4$ alkyl, $C_1$–$C_4$ haloalkyl, $C_3$–$C_8$ cycloalkyl, —($C_1$–$C_4$ alkylene)($C_3$–$C_8$ cycloalkyl), —($C_3$–$C_8$ cycloalkylene)($C_3$–$C_8$ cycloalkyl), aryl, and —($C_1$–$C_4$ alkylene)(aryl); and wherein each m is independently zero, one, or two, with the proviso that heterocycloalkyl groups of the compound of formula I, II, or III do not comprise any —S—S—, —S—O, —N—S—, or —O— bonds, and do not comprise more than two oxygen or $S(O)_m$ heterologous members.

In one embodiment of the invention, the compound of the invention is of formula

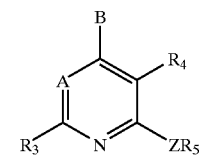

I

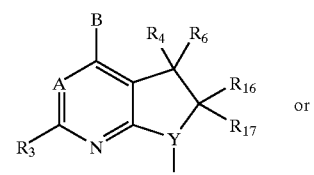

II or

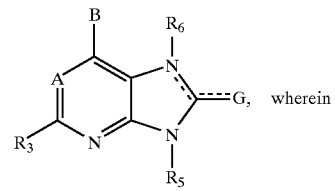

III wherein the dashed lines represent optional double bonds;

A is —$CR_7$ or N;

B is —$NR_1R_2$, —$CR_1R_2R_{11}$, —C(=$CR_2R_{12}$)$R_1$ $NHCHR_1R_2$, $OCHR_1R_2$, —$SCHR_1R_2$, —$CHR_2OR_{12}$, —$CHR_2SR_{12}$, —$C(S)R_2$ or $C(O)R_2$;

G is oxygen, sulfur, NH, $NH_3$, hydrogen, methoxy, ethoxy, trifluoromethoxy, methyl, ethyl, thiomethoxy, $NH_2$, $NHCH_3$, $N(CH_3)_2$ or trifluoromethyl;

Y is —CH or N;

Z is NH, O, S, —N($C_1$–$C_2$ alkyl) or —C($R_{13}R_{14}$), wherein $R_{13}$ and $R_{14}$ are each, independently, hydrogen, trifluoromethyl or methyl, or one of $R_{13}$ and $R_{14}$ is cyano and the other is hydrogen or methyl;

$R_1$ is $C_1$–$C_6$ alkyl which may optionally be substituted with one or two substituents $R_6$ independently selected from the group consisting of hydroxy, fluoro, chloro, bromo, iodo, $CF_3$, $C_1$–$C_4$ alkoxy, —O—CO—($C_1$–$C_4$ alkyl), —O—CO—NH($C_1$–$C_4$ alkyl), —O—CO—N($C_1$–$C_4$ alkyl)($C_1$–$C_2$ alkyl), —NH($C_1$–$C_4$ alkyl), —N($C_1$–$C_2$ alkyl)($C_1$–$C_4$ alkyl), —S($C_1$–$C_4$ alkyl), —N($C_1$–$C_4$alkyl)CO($C_1$–$C_4$ alkyl), —NHCO($C_1$–$C_4$ alkyl), —COO($C_1$–$C_4$ alkyl), —CONH($C_1$–$C_4$ alkyl), —CON($C_1$–$C_4$ alkyl)($C_1$–$C_2$ alkyl), CN, $NO_2$, —SO($C_1$–$C_4$ alkyl) and —$SO_2$($C_1$–$C_4$ alkyl), and wherein said $C_1$–$C_6$ alkyl and the (C—$C_4$)alkyl moieties in the foregoing $R_1$ groups may optionally contain one carbon-carbon double or triple bond;

$R_2$ is $C_1$–$C_{12}$ alkyl, aryl or —($C_1$–$C_4$ alkylene)aryl wherein said aryl is phenyl, naphthyl, thienyl, benzothienyl, pyridyl, quinolyl, pyrazinyl, pyrimidyl, imidazolyl, furanyl, benzofuranyl, benzothiazolyl, isothiazolyl, benzisothiazolyl, benzisoxazolyl, benzimidazolyl, indolyl, or benzoxazolyl; 3- to 8-membered cycloalkyl or $C_1$–$C_6$ alkylene)cycloalkyl, wherein one or two of the ring carbons of said cycloalkyl having at least 4 ring members and the cycloalkyl moiety of said —($C_1$–$C_6$ alkylene) cycloalkyl having at least 4 ring members may optionally be replaced by an oxygen or sulfur atom or by N—$R_9$ wherein $R_9$ is hydrogen or $C_1$–$C_4$ alkyl; and wherein each of the foregoing $R_2$ groups may optionally be substituted with from one to three substituents independently selected from chloro, fluoro and $C_1$–$C_4$ alkyl, or with one substituent selected from bromo, iodo, $C_1$–$C_6$ alkoxy, —O—($C_1$–$C_6$ alkyl), —O—CO—N($C_1$–$C_4$ alkyl)($C_1$–$C_2$ alkyl), —S($C_1$–$C_8$ alkyl), CN, $NO_2$, —SO($C_1$–$C_4$ alkyl), and —$SO_2$($C_1$–$C_4$ alkyl), and wherein said $C_1$–$C_{12}$ alkyl and the $C_1$–$C_4$ alkylene moiety of said —($C_1$–$C_4$ alkylene)aryl may optionally contain one carbon—carbon double or triple bond;

or —$NR_1R_2$ or —$CR_1R_2R_{11}$ may form a saturated 5- to 8-membered carbocyclic ring which may optionally contain one or two carbon—carbon double bonds and in which one or two of the ring carbons may optionally be replaced by an oxygen or sulfur atom;

$R_3$ is methyl, ethyl, fluoro, chloro, bromo, iodo, cyano, methoxy, $OCF_3$, methylthio, methylsulfonyl, $CH_2OH$, or $CH_2OCH_3$;

$R_4$ is hydrogen, $C_1$–$C_4$ alkyl, fluoro, chloro, bromo, iodo, $C_1$–$C_4$ alkoxy, trifluoromethoxy, —$CH_2OCH_3$, —$CH_2OCH_2CH_3$, —$CH_2CH_2OCH_3$, —$CH_2OF_3$, $CF_3$, amino, nitro, —NH($C_1$–$C_4$ alkyl), —N($CH_3$)$_2$, —$NHCOCH_3$, —$NHCONHCH_3$, —$SO_1$($C_1$–$C_4$ alkyl) wherein n is 0, 1 or 2, cyano, hydroxy, —CO($C_1$–$C_4$ alkyl), —CHO, cyano or —COO($C_1$–$C_4$ alkyl) wherein said $C_1$–$C_4$ alkyl may optionally contain one double or triple bond and may optionally be substituted with one substituent selected from hydroxy, amino, —$NHCOCH_3$, —NH($C_1$–$C_2$ alkyl), —N($C_1$–$C_2$ alkyl)$_2$, —COO($C_1$–$C_4$ alkyl), —CO($C_1$–$C_4$ alkyl), $C_1$–$C_3$ alkoxy, $C_1$–$C_3$ thioalkyl, fluoro, chloro, cyano and nitro;

$R_5$ is phenyl, naphthyl, thienyl, benzothienyl, pyridyl, quinolyl, pyrazinyl, pyrimidyl, furanyl, benzofuranyl, benzothiazolyl, or indolyl, wherein each of the above groups $R_5$ is substituted with from one to three substituents independently selected from fluoro, chloro, $C_1$–$C_8$ alkyl, and $C_1$–$C_8$ alkoxy, or with one substituent selected from hydroxy, iodo, bromo, formyl, cyano, nitro, trifluoromethyl, amino, —($C_1$–$C_6$ alkyl)O($C_1$–$C_6$)alkyl, —$NHCH_3$, —N($CH_3$)$_2$, —COOH, —COO($C_1$–$C_4$ alkyl), —CO($C_1$–$C_4$ alkyl), —$SO_2NH$($C_1$–$C_4$ alkyl), —$SO_2N$(C—$C_4$ alkyl)($C_1$–$C_2$ alkyl), —$SO_2NH_2$, —$NHSO_2$($C_1$–$C_4$ alkyl), —S($C_1$–$C_6$ alkyl) and —$SO_2$($C_1$–$C_6$ alkyl), and wherein the $C_1$–$C_4$ alkyl and $C_1$–$C_6$ alkyl moieties of the foregoing $R_5$ groups may optionally be substituted with one or two fluoro groups or with one substituent selected from hydroxy, amino, methylamino, dimethylamino and acetyl;

$R_6$ is hydrogen or $C_1$–$C_6$ alkyl, wherein said $C_1$–$C_8$ alkyl may optionally be substituted with one hydroxy, methoxy, ethoxy or fluoro group;

$R_7$ is hydrogen, methyl, fluoro, chloro, bromo, iodo, cyano, hydroxy, —O($C_1$–$C_4$ alkyl), —C(O)($C_1$–$C_4$ alkyl), —C(O)O($C_1$–$C_4$ alkyl), —$OCF_3$, $CF_3$, —$CH_2OH$, —$CH_2OCH_3$ or —$CH_2OCH_2CH_3$;

$R_{11}$ is hydrogen, hydroxy, fluoro, or methoxy;

$R_{12}$ is hydrogen or $C_1$–$C_4$ alkyl; and $R_{16}$ and $R_{17}$ are each, independently, hydrogen, hydroxy, methyl, ethyl, methoxy, or ethoxy, except that $R_{16}$ and $R_{17}$ are not both methoxy or ethoxy;

or $R_{16}$ and $R_{17}$ together form an oxo (=O) group;

with the proviso that when G is oxygen, sulfur, NH or $NCH_3$, it is double bonded to the five membered ring of structure III, and with the further proviso that $R_6$ is absent when the nitrogen to which it is attached is double bonded to an adjacent ring carbon atom;

or a pharmaceutically acceptable salt of such compound.

More specific embodiments of this invention include compounds of the formula I, II or III wherein: (a) B is —$NR_1R_2$, —$NHCHR_1R_2$, —$SCHR_1R_2$ or —$OCHR_1R_2$; $R_1$ is $C_1$–$C_6$ alkyl, which may optionally be substituted with one hydroxy, fluoro, $CF_3$, or $C_1$–$C_2$ alkoxy group and may optionally contain one double or triple bond; and $R_2$ is benzyl or $C_1$–$C_6$ alkyl which may optionally contain one carbon-carbon double or triple bond, wherein said $C_1$–$C_6$ alkyl or the phenyl moiety of said benzyl may optionally be substituted with fluoro, $CF_3$, $C_1$–$C_2$ alkyl, or $C_1$–$C_2$ alkoxy; or (b) B is —$CR_1R_2R_{11}$ wherein $R_1$ is $C_1$–$C_6$ alkyl which may optionally be substituted with one $C_1$–$C_2$ alkoxy, $CF_3$, fluoro or hydroxy group; $R_2$ is benzyl or $C_1$–$C_6$ alkyl wherein said $C_1$–$C_6$ alkyl or the phenyl moiety of said benzyl may optionally be substituted with one $C_1$–$C_2$ alkyl, $CF_3$, $C_1$–$C_2$ alkoxy, fluoro, chloro or bromo group; and $R_{11}$ is hydrogen or fluoro.

Other more specific embodiments of this invention include compounds of the formula I, II or III wherein $R_1$ is $C_1$–$C_6$ alkyl which may optionally be substituted by fluoro, $CF_3$, hydroxy, $C_1$–$C_2$ alkyl or $C_1$–$C_2$ alkoxy and may optionally contain one carbon-carbon double or triple bond, and $R_2$ is $C_1$–$C_4$ alkyl which may optionally be substituted with fluoro, chloro, $CF_3$, $C_1$–$C_4$ alkyl or $C_1$–$C_4$ alkoxy.

Other more specific embodiments of this invention include compounds of the formula I, II or III wherein $R_3$ is methyl, chloro, or methoxy, $R_4$ is methyl, —$CH_2OH$, cyano, trifluoromethoxy, methoxy, trifluoromethyl, chloro, —$COOCH_3$, —$CH_2OCH_3$, —$CH_2C_1$, —$CH_2F$, amino or nitro; $R_6$ is hydrogen, methyl or ethyl and $R_5$ is phenyl or pyridyl wherein said phenyl or pyridyl is substituted by two or three substituents independently selected from fluoro, chloro, bromo, iodo, $C_1$–$C_4$ alkoxy, trifluoromethyl, $C_1$–$C_6$ alkyl which may optionally be substituted with one hydroxy, $C_1$–$C_2$ alkoxy or fluoro group and may optionally contain one carbon-carbon double or triple bond, —($C_1$–$C_4$ alkylene)O($C_1$–$C_2$ alkyl), $C_1$–$C_3$ hydroxyalkyl, hydroxy, formyl, —COO($C_1$–$C_2$ alkyl), $C_1$–$C_2$ alkylene)amino, and —C(O)($C_1$–$C_4$ alkyl).

Examples of preferred compounds of this invention are:

4-(1-ethyl-propoxy 2,5-dimethyl-6-(2,4,6-t methyl-benzyl)-pyrimidine;

2-(4bromo-2,6-dimethyl-phenoxy)$_4$-(1-ethyl-propoxy)-3,6-dimethyl-pyridine;

2-(4-ethyl-2,6-dimethyl-phenoxy-4-(1-ethyl-propoxy)-3,6-dimethyl-pyridine;

3-ethyl-4-(1-ethyl-propoxy)-6-methyl-2-(2,4,6trimethyl-phenoxy)-pyridine;

2-(2,6-dimethyl-4-propyl-phenoxy)-4(1-ethyl-propoxy)-3,6-dimethyl-pyridine;

4-(1-ethyl-propoxy-2-(4methoxy-2,6-dimethyl-phenoxy) 3,6-dimethyl-pyridine;

2-(4-ethoxy-2,6-dimethyl-phenoxy)41-ethyl-propoxy)3,6-dimethyl-pyridine;

2-(4-chloro-2,6-dimethyl-phenoxy)-4-(1-ethyl-propoxy)-3,6-dimethyl-pyridine;

4-(methoxymethyl-propoxy)-3,6-dimethyl-2-(2,4,6-trimethyl-phenoxy)-pyridine;

[3,6-dimethyl-2-(2,4,6trimethyl-phenoxy)-pyridin-4-yl]-diethyl-amine;

[3,6-dimethyl-2-(2,4,6-trimethyl-phenoxy)pyridin-4yl]-ethyl-propyl-amine;

[2,5-dimethyl-6-(2,4,6-trimethyl-phenoxy-pyrimidin-4-yl](1-ethyl-propyl)-amine;

butyl-[3,6-dimethyl-2-(2,4,6-trimethyl-phenoxy)pyridin-4-yl]-ethyl-amine;

4-(1-ethyl-propoxy) 3,6-dimethyl-2-(2,4,6-trimethyl-phenylsulfanyl)pyridine;

butyl-[2-(4chloro-2,6-trimethyl-phenoxy)-3,6dimethyl-pyridin-4-yl]-ethyl-amine;

4-(1-ethyl-propylamino)-6methyl-2-(2,4,6trimethyl-phenoxy)-nicotinic acid methyl ester,

[3,6-dimethyl-[2-(2,4,6-trimethyl-phenylsulfanyl) pyridin-4-yl]-ethyl-propylamine;

4 -(1-ethyl-propylamino)-6ethyl-[2-(2,4,6-trimethyl-phenoxy)-pyridin-3-y]-methanol;

[2-(4chloro-2,6-dimethyl-phenoxy)3,6-dimethyl-pyridin-4-yl]ethyl-propyl-amine;

1-(ethyl-propyl)-[6-methyl-3-nitro-2-(2,4,6-trimethyl-phenoxy)pyridin-4yl]-amine;

N4-(1-ethyl-propyl)methyl-3-nitro-N2-(2,4,6-trimethyl-phenyl)-pyridine-2,4-diamine;

N4-(1-ethyl-propyl)-6-methyl-2-(2,4,6-trimethyl-phenoxy)-pyridine-3,4-diamine;

3,6-dimethyl-2-(2,4, 6-trimethyl-phenoxy)pyridin-4-yl]-ethyl-(2, 2,2-trifluoro-ethyl)-amine;

N4-(1-ethyl-propyl 6methyl-2-(2,4,6-trimethyl-phenyl) pyridine-2,3,4-triamine;

[3-chloromethyl-6-methyl-2-(2,4,6-trimethyl-phenoxy) pyridin-4-yl](1-ethyl-propyl)-amine;

[3,6-dimethyl-2-(2,4,6-trimethyl-phenoxy)-pyridin 4yl]-(1-ethyl-propyl)-amine;

(1-ethyl-propyl)-[2-methyl-5-nitro-642,4,6-trimethyl-pyrimidin-3-yloxy)pyrimidin-4-yl]amine;

(1-ethyl-propyl)-[3-methoxymethyl-6-methyl-2-(2,4,6-trimethyl-phenoxy)pyridin-4-yl]-amine;

(N-(1-ethyl-propyl)-2-methyl-5-nitro-N'-(2,4,6-trimethyl-pyridin-3-yl)pyrimidine-4,6-diamine;

[2-(4-chloro-2,6-dimethyl-phenoxy)-3.6-dimethyl-pyridin-4-y]-diethyl-amine;

4(1-ethyl-propoxy)-3,6-dimethyl-2-(2,4,6-trimethyl-phenoxy)-pyridine;

butyl-[2,5-dimethyl-7-(2,4,6-trimethyl-phenyl)6,7-dihydro-5H-pyrrolo[2,3 d]pyrimidin-4-yl]-ethyl-amine;

4-(butyl-ethylamino)-2,5-dimethyl-7-(2,4,6-trimethyl-phenyl)-5,7-dihydro-pyrrolo[2,3-d]pyrimidin-6-one;

4-(1-ethyl-propoxy)-2,5-dimethyl-S(2,4,6-trimethyl-phenoxy)pyrimidine;

N-butyl-N-ethyl-2,5-dimethyl N'-(2,4,6-trimethyl-phenyl)pyrimidine-4,6-diamine;

(1-ethyl-propyl)-[5-methyl-3-(2,4,6-trimethyl-phenyl)-3H-imidazo[4,5-b]pyridin-7-yl]-amine;

[2,5-dimethyl-3-(2,4,6-trimethyl-phenyl)-3H-imidazo[4,5-b]pyridin-7-yl]-(1-ethyl-propyl)-amine;

N4-(1-ethyl-propyl)6, N3-dimethyl-2-(2,4,6-trimethyl-phenoxy)-pyridine-3,4-diamine;

N4-(1-ethyl-propyl)6,N3,N3-trimethyl-2-(2,4,6-trimethyl-phenoxy)pyridine-3.4-diamine;

6-(1-ethyl-propoxy)2-methyl-N-4-(2,4,6-trimethyl-phenyl)pyrimidine-4,5-diamine;

[4-(1-ethyl-propoxy)3,6-dimethyl-pyridin-2-yl]2,4,6-trimethyl-phenyl)-amine; and 6-(ethyl-propyl-amino)2,7-dimethyl-9-(2,4,6-trimethyl-phenyl)7,9-dihydro-purin-8-one.

Other preferred compounds of this invention are:

4-(1-ethyl-propoxy)-2,5-dimethyl-6-(2,4,6-trimethyl-benzyl)pyrimidine;

2-(4-bromo-2,6-dimethyl-phenoxy)-4-(1-ethyl-propoxy) 3,6-dimethyl-pyridine;

2-(4-ethyl-2,6-dimethyl-phenoxy)4-(1-ethyl-propoxy)-3,6-dimethyl-pyridine;

3-ethyl-4-(1-ethyl-propoxy)-6-methyl-2-(2,4,6-trimethyl-phenoxy)pyridine;

2-(2,6-dimethyl-4-propyl-phenoxy)-(1-ethyl-propoxy-3,6-dimethyl-pyridine;

4-(1-ethyl-propoxy)2-(4-methoxy-2,6-dimethyl-phenoxy-3,y)-3,6-dimethyl-pyridine;

2-(4-ethoxy-2,6-dimethyl-phenoxy)-4-(1-ethyl-propoxy) 3,6-dimethyl-pyridine;

2-(4-chloro-2,6-dimethyl-phenoxy) 4-(1-ethyl-propoxy)-3,6-dimethyl-pyridine;

4-(1-methoxymethyl-propoxy)-3,6-dimethyl-2-(2,4,6-trimethyl-phenoxy)pyridine;

[3,6-dimethyl-2-(2,4,6-trimethyl-phenoxy)pyridin-4-yl] diethyl-amine;

[3,6-dimethyl-2-(2,4,6-trimethyl-phenoxy)pyridin-4-y] ethyl-propyl-amine;

[2,5-dimethyl-6-(2,4,6-dimethyl-phenoxy)pyrimidin-4-yl](1-ethyl-propyl-amine;

butyl-[3,6-dimethyl-2-(2,4,6-trimethyl-phenoxy)-pyridin-4-yl]ethyl-amine;

4-(1-ethyl-propoxy)3,6-dimethyl-2-(2,4,6-trimethyl-phenylsulfanyl)-pyridine;

butyl-[2-(4-chloro-2,6-dimethyl-phenoxy)-3,6-dimethyl-pyridin 4-yl]-ethyl-amine;

4-(1-ethyl-propylamino)-6-methyl-2,4,6-trimethyl-phenoxy)nicotinic acid methyl ester;

[3,6-dimethyl-[2-(2,4,6-trimethyl-phenylsulfanyl)-pyridin-4-yl]-ethyl-propyl-amine;

4-(1-ethyl-propyl-amino)-6-methyl-2-(2,4,6-trimethyl-phenoxy)pyridin-3-yl]methanol;

[2-(4-chloro-2,6-dimethyl-phenoxy)-3,6-dimethyl-pyridin-4-yl]ethyl-propyl-amine;

1-(ethyl-propyl)-[6-methyl-3-nitro-2-(2,4,6-trimethyl-phenoxy)-pyridin-4-yl]-amine;

N4-(ethyl-prop)Omethyl-3-nitro-N22,4,6-trimethyl-phenyl)-pyridine-2,4-diamine;

N4-(1 ethyl-propyl) 6-methyl-2,4,6-trimethyl-phenoxy) pyridine-3,4-diamine;

3,6-dimethyl-2-(2,4,6-trimethyl-phenoxy)pyridin-4-ylethyl-(2,2,2-trifluoro-ethyl-amine;

N4-(1-ethyl-propyl(methyl-N2-(2,4,6-trimethyl-phenyl) pyridine-2,3,4-triamine;

[3-chloromethyl-6-methyl-2-(2,4,6-trimethyl-phenoxy) pyridin-4-yl]-(1-ethyl-propyl)-amine;

[3,6-dimethyl-2-(2,4,6-trimethyl-phenoxy)pyridin-4-yl]-(1-ethyl-propyl)amine;

(1-ethyl-propyl)-2-methyl-5-nitro-[6-(2,4,6-trimethyl-pyridin-3-yloxy-pyrimidin-4-yl]-amine;

(1-ethyl-propyl)[3-methoxymethyl-6-methyl-2-(2,4,6-trimethyl-phenoxy)-pyridin-4-yl]-amine;

(N-(1-ethyl-propyl)-2-methyl-5-nitro-N'-(2,4,6-trimethyl-pyridin-3-yl)-pyrimidine-4,6-diamine;

[2-(4-chloro-2,6-dimethyl-phenoxy)-3,6-dimethyl-pyridin-4-yl]-diethyl-amine;

4-(1-ethyl-propoxy)-3,6-dimethyl-2-(2,4,6-trimethyl-phenoxy)-pyridine;

butyl-[2,5-dimethyl-7-(2,4,6-trimethyl-phenyl)6,7-dihydro-5H-pyrrolo[2,3-d]pyrimidin-4-yl]-ethyl-amine;

4-butyl-ethyl-amino-2,5-dimethyl-7-(2,4,6-trimethyl-phenyl)5,7-dihydro-pyrrolo[2,3-d]pyrimidin-6-one;

4-(1-ethyl-propoxy) 2,5-dimethyl-2,4,6-trimethyl-phenoxy)pyrimidine;

N-butyl-N-ethyl-2,5-dimethyl-N'-(2,4,6-trimethyl-phenyl)pyrimidine-4,6-diamine;

(1-ethyl-propyl)-[5-methyl-3-(2,4,6-trimethyl-phenyl)-3-imidazo[4,5-b]pyridin-7-yl]-amine;

[2,5-dimethyl-3-(2,4,6-trimethyl-phenyl)-3H-imidazo[4,5-b]pyridin-7-yl](1-ethyl-propyl)-amine;

N4-(1-ethyl-propyl)-6,N3N3-dimethyl-2-(2,4,6-trimethyl-phenoxy)pyridine-3,4-diamine;

N4-(1-ethyl-propyl-6,N3,N3-trimethyl-2-(2,4,6-trimethyl-phenoxy)-pyridine-3.4-diamine;

6-(1-ethyl-propoxy)2-methyl-N4-(2,4,6-trimethyl-phenyl-5-pyrimidine-4,5-diamine;

[4(1-ethyl propoxy)3,6-dimethyl-pyridin-9-yl(2,4,6-trimethyl-phenyl)-amine; and 6-(ethyl-propyl-amino)2,7-dimethyl-g-(2,4,6-trimethyl-phenyl)7,9-dihydro-purin-8-one.

Examples of preferred compounds of this invention are:

2-[2-(4-chloro-2,6-dimethyl-phenoxy)6-methyl-3-nitro-pyridin-4—(S)—ylamino]-butan-1-ol;

(1-methoxymethyl-propyl)6-methyl-3-nitro-2-(4-trifluoromethoxy-phenoxy)-pyridin-4-yl]-amine;

2-[2-amino-4,6-dichloro-phenoxy)-methyl-3-nitro-pyridin-4-yl]-(1-methoxymethyl-propyl)amine;

3-methoxy-2-[4-(1-methoxymethyl-propylamino-6-methyl-3-nitro-pyridin-2-yloxy]-benzaldehyde;

[2-(2,6-dibromo-4-trifluoromethoxy-phenoxy)-6-methyl-3-nitro-pyridin-4-yl]-(1-methoxymethyl-propyl)amine;

[2-(2-bromo-4-chloro-6-methoxy-phenoxy)-6-methyl-3-nitro-pyridin-4-yl]-(1-methoxymethyl-propyl)-amine;

[2-(2,4-dichloro-phenoxy)-6-methyl-3-nitro-pyridin-4-yl]-(1-methoxymethyl-propyl)-amine;

[2-(2-bromo-6-chloro-4-methoxy-phenoxy)-6-methyl-3-nitro-pyridin-4-yl]-(1-methoxymethyl-propyl)-amine;

(1-methoxymethyl-propyl)-[6-methyl-3-nitro-2-(2,4,6-trimethoxy-phenoxy)-pyridin-4-yl]-amine;

2-chloro-N-[4-(1-ethyl-propylamino)-6-methyl-2-(2,4,6-trimethyl-phenoxy)-pyridin-3-y]-acetamide;

3-chloro-N-[4-(1-ethyl-propylamino)-6-ethyl-2-(2,4,6-trimethyl-phenoxy)-pyridin-3-yl]-propionamide;

2-chloro-N-[41-ethyl-propylamino)-6-methyl-2-(2,4,6-trimethyl-phenoxy)-pyridin-3-yl]-propionamide;

N3-allyl-N-4-(1-ethyl-propyl)6-methyl-2-(2,4,6-trimethyl-phenoxy)-pyridine-3,4-diamine;

N3-(3-chloro-propyl)N4-(1-ethyl-propyl)6-methyl-2-(2,4,6-trimethyl-phenoxy)pyridine-3,4-diamine;

N4-ethyl-propyl)-6-ethyl-N-3-propa-1,2-dienyl-2-(2,4,6-trimethyl-phenoxy)pyridine-3,4-diamine;

2-[3-amino-2-(4-chloro-2,6-dimethyl-phenoxy)6-methyl-pyridin-4-(S)ylamino]-butan-1-ol;

2-[4-chloro-2,6-dimethyl-phenoxy)4-(1-ethyl-propylamino)6-methyl-nicotinic acid methyl ester;

2-[4-bromo-2,6-dimethyl-phenoxy)4(1-ethyl-propylamino)-6-methyl-nicotinic acid methyl ester;

4-(1-ethyl-prop-2-ynylamino)-6-methyl-22,4,6-trimethyl-phenoxy)-nicotinic acid methyl ester;

4-(S)-(1-hydroxymethyl-propylamino)-6-methyl-2-(2,4,6-trimethyl-phenoxy)-nicotinic acid methyl ester, 4(1 ethyl-2-hydroxy-propylamino)6-methyl-2-(2,4,6-trimethyl-phenoxy)-nicotinic acid methyl ester;

2-(4-bromo-2,6-dimethyl-phenoxy)4—(S)(1-hydroxymethyl-propylamino)₆-methyl-nicotinic acid methyl ester;

2-(4-bromo-2,6-dimethyl-phenoxy)-4—(S)-(1-methoxymethyl-propylamino)-6-methyl-nicotinic acid methyl ester;

2-(4-chloro-2,6-dimethyl-phenoxy)4-(1-hydroxymethyl-propylamino)-6 methyl-nicotinic acid methyl ester;

2-(4-chloro-2-methoxy-phenoxy)4—(S)-(1-hydroxymethyl-propylamino-6-methyl-nicotinic acid methyl ester, 2-(4-chloro-2,6-dimethyl-phenoxy-4-(1-ethyl-2-hydroxy-propylamino)-6-methyl-nicotinic acid methyl ester;

2-(4-chloro-2.6-dimethyl-phenoxy)-4-(1-ethyl-2-methoxy-propylamino)6-methyl-nicotinic acid methyl ester, 2-(4-chloro-2,6-dimethyl-phenoxy)4-(1-ethyl-2-oxo-propylamino)-6-methyl-nicotinic acid methyl ester;

2-(4-chloro-2,6-dimethyl-phenoxy)4-(1-ethyl-2-oxo-propylamino)6-methyl-nicotinic acid methyl ester, 2-(4-chloro-2,6-dimethyl-phenoxy)4—(S)-(4-ethyl-2-oxo-oxazolidin-3-yl)-6-methyl-nicotinic acid methyl ester, 2-(4-chloro-2,6-dimethyl-phenoxy)-4-(S)-[(2-hydroxy-ethylamino)-methyl]-propylamino)-6-methyl-nicotinic acid methyl ester;

4-[ethyl-(2-hydroxy-ethyl)-amino-6-methyl-2-(2,4,6-trimethyl-phenoxy)nicotinic acid 1 methyl ester, 4-[ethyl-(2-methanesulfonyloxy-ethyl)-amino]-6-methyl-2-(2,4,6-trimethyl-phenoxy)-nicotinic acid methyl ester, 4[(2-hydroxy-ethyl)thiophen-2-ylmethyl-amino]-6-methyl-2-(2,4,6-trimethyl-phenoxy) nicotinic acid methyl ester, 4-(2,2-dimethyl-4-phenyl-[1,3]dioxan-5-ylamino)6-methyl-2-(2,4,6-trimethyl-phenoxy)-nicotinic acid methyl ester;

2-(4-chloro-2,6-dimethyl-phenoxy)-4-(S)(1-hydroxymethyl-propylamino-6-methyl-nicotinic acid ethyl ester;

4-[ethyl-(2-methoxy-ethyl)amino]-6-methyl-2-(2,4,6-trimethyl-phenoxy)nicotinic acid methyl ester;

2-(4-chloro-2,6-dimethyl-phenoxy)-4-(S,R)-&(S,S)(1-ethyl-2-hydroxy-propylamino)-6-methyl-nicotinic acid methyl ester, 2-(4-chloro-2,6-dimethyl-phenoxy)4—(R)1-hydroxymethyl-propylamino)-6-methyl-nicotinic acid methyl ester 4-(2-hydroxy-1-hydroxymethyl-ethylamino)6-methyl-2-(2,4,6-trimethyl-phenoxy) nicotinic acid methyl ester;

4-(2-methoxy-1-methoxymethyl-ethylamino)-6-methyl-2-(2,4,6-trimethyl-phenoxy)-nicotinic acid methyl ester;

4-(1-hydroxymethyl-2-methoxy-ethylamino)-6-methyl-2-(2,4,6-trimethyl-phenoxy)-nicotinic acid methyl ester;

2-(4-chloro-2,6-dimethyl-phenoxy)4 1-ethyl-2-hydroxy-butylamino)-6-methyl-nicotinic acid methyl ester;

[2-(4-chloro-2,6-dimethyl-phenoxy)4-(1-ethyl-propylamino)$_6$-methyl-pyridin-3-yl]-methanol;

[2-(4-bromo-2,6-dimethyl-phenoxy)41-ethyl-propylamino-6-methyl-pyridin-3-yl]-methanol;

2-[3-hydroxymethyl-6-methyl-2-(2,4,6-trimethyl-phenoxy)-pyridin-4-(S)-ylamino]-butan-1-ol;

3-[24-chloro-2,6-dimethyl-phenoxy)-3-hydroxymethyl-6-methyl-pyridin-4-ylamino]-pentan-2-ol;

2-[2-(2,6-dimethyl-phenoxy)-3-hydroxymethyl-6-methyl-pyridin-4-ylamino]-buten-1-ol;

3-13-hydroxymethyl-6-methyl-2-(2,4,6-trimethyl-phenoxy)-pyridin-4-ylamino]-pentan-2-ol;

2-[2-(4-chloro-2-methoxy-phenoxy)3-hydroxymethyl-6-methyl-pyridin-4-ylamino]-4 butan-1-ol;

2-[2-(4-chloro-2,6-dimethyl-phenoxy)-3-hydroxymethyl-6-methyl-pyridin-4-ylamino]-butan-1-ol;

2-(ethyl-[-hydroxymethyl-6-methyl-2,4,6-trimethyl-phenoxy)-pyridin-4-ylamino]-ethanol;

4-(2-(4-chloro-2,6-dimethyl-phenoxy)3-hydroxymethyl-6-methyl-pyridin-4-ylamino]-hexan-3-ol;

2-[2-(4-chloro-2-methoxy-phenoxy)3-hydroxymethyl-6-methyl-pyridin-4-(S)-ylamino)-butan-1-ol;

4-[2-(4-chloro-2,6-dimethyl-phenoxy)3-hydroxymethyl-6-methyl-pyridin-4-ylamino]-hexan-3-ol;

[2-(2,4-dimethoxy-phenylamino)-4-(1-methoxymethyl-propoxy)-6-methyl-pyridin-3-yl]-methanol;

2-(4-chloro-2,6-dimethyl-phenoxy)4—(S)(1-hydroxymethyl-propylamino)6-methyl-nicotinic acid;

4-(1-ethyl-prop-2-ynylamino)-6-methyl-2-(2,4,6-trimethyl-phenoxy)-nicotinic acid;

2-(4-bromo-2,6-dimethyl-phenoxy)4—(S)(1-methoxymethyl-propylamino)-6-methyl-nicotinic acid;

4-(2-methoxy-1-methoxymethyl-ethylamino)-6-methyl-2-(2,4,6-trimethyl-phenoxy)-nicotinic acid;

[2-(4-chloro-2,6-dimethyl-phenoxy)-3-isobutoxymethyl-6-methyl-pyridin-4-yl]-(1-ethyl-propyl)amine;

[3-ethoxymethyl-6-methyl-2-(2,4,6-trimethyl-phenoxy)-pyridin-4-yl]-(1-ethyl-propyl)-amine;

2-[3-butoxymethyl-6-methyl-2-(2,4,6-trimethyl-phenoxy)-pyridin-4-ylamino]-butan-ol;

1-[4-(1-ethyl-propylamino)-6-methyl-2-(2,4,6-trimethyl-phenoxy)pyridin-3-yl]-ethanol;

acetic acid 4-(1-ethyl-propylamino-6-methyl-2-(2,4,6-trimethyl-phenoxy)pyridin-3-ylmethyl ester;

2-[2-(4-chloro-2,6-dimethyl-phenoxy)31-hydroxy-1-methyl-ethyl)methyl-pyridin-4-(S)-ylamino]-butan-1-ol;

[2-(4-chloro-2,6-dimethyl-phenoxy)-3,6-dimethyl-pyridin-4-yl]-(1-ethyl-propylamine;

[2-(2,6-dimethyl-phenoxy)3,6-dimethyl-pyridin-4-yl](1-ethyl-propyl)amine:

[2-(4-bromo-2,6-dimethyl-phenoxy)3,6-dimethyl-pyridin-4-yl]-(1-ethyl-propyl)amine;

4-[4-(1-ethyl-propylamino-3,6-dimethyl-pyridin-2-yloxy]-3,5-dimethyl-benzaldehyde;

[4-[4-(1-ethyl-propylamino)-3,6-dimethyl-pyridin-2-yloxy]-3,5-dimethyl-phenyl]-methanol;

(1-ethyl-propyl)-[2-(4-methoxymethyl-2,6-dimethyl-phenoxy)3,6-dimethyl-pyridin-4-yl]-amine;

[2-(4-ethyl-2,6-dimethyl-phenoxy)-3,6-dimethyl-pyridin-4-yl]-(1-ethyl-propyl)-amine;

4-(4-(1-ethyl-propylamino)-3,6-dimethyl-pyridin-2-yloxy]-3,5-dimethyl-phenyl) propan-2-ol;

4-(1-ethyl-propylamino)-3,6-dimethyl-pyridin-[2-yloxy]-3,5-dimethyl-phenyl)-ethanol;

(1-ethyl-propyl)-[2-(4-isopropenyl-2,6-dimethyl-phenoxy)3,6-dimethyl-pyridin-4-yl]-amine;

(1-ethyl-propyl)[2-(4-isopropenyl-2,6-dimethyl-phenoxy)-o-3,6-dimethyl-pyridin-4-yl]-amine;

[3,6-dimethyl-2-(2,4,6-trimethyl-phenoxy)pyridin-4-yl]-(1-ethyl-allyl)-amine;

(1-ethyl-propyl) [2-(4-fluoro-2-dimethyl-phenoxy)3,6-dimethyl-pyridin-4-yl]-amine;

2-[2-(2,6-dimethyl-phenoxy)3,6-dimethyl-pyridin-4-ylamino]-butan-1-ol;

2-[3,6-dimethyl-22,4,6-trimethyl-phenoxy)pyridin-4-(S) ylamino]-butan-1-01;

3-[3,6-dimethyl-22,4,6-trimethyl-phenoxy)-pyridin-4-ylamino]-pentan-2;

3-[2-(4-chloro-2,6-dimethyl-phenoxy)-3,6-dimethyl-pyridin-4-yl]amino]pentan-2-ol;

benzyl-[3,6-dimethyl-22,4,6-trimethyl-phenoxy)pyridin-4-yl]-ethyl-amine;

[2-(4 chloro-2,6-dimethyl-phenoxy)-3,6-dimethyl-pyridin-4-yl]-(1-methoxymethyl-propyl)-amine;

2-[3,6-dimethyl-22,4,6-trimethyl-phenoxy)-pyridin-4-yl]-amino-3-phenyl-propan-1 ol;

[2-(4-chloro-2.6-dimethyl-phenoxy)-3,6-dimethyl-pyridin-4-yl]-(1-methoxymethyl-propyl)-amine;

[2-(4-chloro-2,6-dimethyl-phenoxy-13,6-dimethyl-pyridin-4-yl]-(1-ethoxymethyl-propyl)-amine;

[3,6-dimethyl-2-(2,4,6-trimethoxy-phenoxy)pyridin-4-yl]-(1-methoxymethyl-propyl)-amine;

[2-(4-bromo-2,6-dimethyl-phenoxy)-3-methoxy-6-methyl-pyridin 4-yl]-(1-ethyl-propyl)-amine;

(1-ethyl-propyl)-[3-methoxy-6-methyl-2,4,6-trimethyl-phenoxy)-pyridin-4-yl-amine;

[2-(4-chloro-2,6-dimethyl-phenoxy)-6-methyl-3-propyl-pyridin-4-yl]-(1-ethyl-propyl) amine;

[2-(4-bromo-2,6-dimethyl-phenoxy)-6-methyl-3-propyl-pyridin-4-yl]-(1-ethyl-propyl) amine;

(1-ethyl-propyl)-[6-methyl-3-propyl-2-(2,4,6-trimethyl-phenoxy)-pyridin-4-yl]-amine;

[2-(2,4-chloro-2,6-dimethyl-phenoxy)3-methoxy-6-methyl-propyl)-amine;

[2-(4-chloro-2,6-dimethyl-phenoxy)-3-methoxymethyl-pyridin-4-yl]-(1-ethyl-propyl)-amine;

[2-(4-chloro-2,6-dimethyl-phenoxy)3-methoxymethyl-pyridin-4-yl]-(1-methoxymethyl-propyl)amine;

[2-(2,4-dichloro-6-methyl-phenoxy-3-methoxy-6-methyl-pyridin-4-yl]-(1-methoxymethyl-propyl)-amine;

[2-(4-chloro-2-methoxy-phenoxy)3-methoxy-6-methyl-pyridin-4-yl]-(1-methoxymethyl-propyl)amine;

[2-(3-chloro-2,6-dimethoxy-phenoxy)₃-methoxymethyl-pyridin-4-yl]-(1-methoxymethyl-propyl)amine;

(1-methoxymethyl-propyl)-(3-methoxy-6-methyl-2-(2.4.6-trimethoxy-phenoxy)pyridin-4-yl]-amine;

[3-methoxy-2-(4-methoxy-2-dimethyl-phenoxy)-6-methyl-pyridin-4-yl]-(1-ethoxymethyl-propyl]amine;

[2-(4-chloro-2,6-dimethyl-phenoxy)3-ethoxy-6-methyl-pyridin-4-yl]-(1-methoxymethyl-propyl)-amine;

2-[2-(4-chloro-2,6-dimethyl-phenoxy-3,6-dimethyl-pyridin-4-(S)-ylamino]-butan-1-ol;

2-[3-methoxy-6-methyl-2-(2,4,6-trimethyl-phenoxy)-pyridin-4-(S)-ylamino]-butan-1-ol;

2-[2-(4-chloro-2,6-dimethyl-phenoxy)-3-methoxy-6-methyl-pyridin-4-ylamino]-butan-1—ol 4-14-(1-hydroxymethyl-propylamino)-3-methoxy-6-methyl-pyridin-2-yloxy-3,5-dimethyl-benzonitrile;

3-[2-(4-chloro-2,6-dimethyl-phenoxy)3,6-dimethyl-pyridin-4-ylamino]-pentan-2-ol;

2-[2-methyl-6-(2,4,6-trimethyl-phenoxy)-pyridin-4-ylamino]-butan-1-ol;

(1-ethyl-prop-2-ynyl)-[2-methyl-6-(2,4,6-trimethyl-phenoxy)-pyridin-4-yl]-amine)

2-(4-bromo-2,6-dimethyl-phenoxy)4-(1-ethyl-propylamino)-6-methyl-pyridin-3-ol;

4-(1-ethyl-propylamino)6-methyl-2-(2,4,6-trimethyl-phenoxy)-pyridin-3-ol;

4-(S)(1-hydroxymethyl-propylamino)6-methyl-2-(2,4,6-trimethyl-phenoxy)pyridin-3-ol:

2-(4-chloro-2,6-dimethyl-p hen oxy)4-(1-hydroxymethyl-propylamino)-6-met hyl-pyridin-3-ol;

2-(4-chloro-2,6-dimethyl-phenoxy)4-(1-ethyl-propylamino)-6-methyl-pyridin-3-ol;

chloro-acetic acid 4-(1-ethyl-propylamino)6-methyl-2-(2,4,6-trimethyl-phenoxy)pyridin-3-yl ester, 2-(4-chloro-2,6-dimethyl-phenoxy)-4-[(1-ethyl-propyl)-methyl-amino]-6-methyl-pyridin-3-ol;

[4-(1-ethyl-propylamino)6-methyl-2-(2,4,6-trimethyl-phenoxy)-pyridin-3-yl-acetonitrile;

4-(1-ethyl-propylamino)-6-methyl-2-(2,4,6-trimethyl-phenoxy)-pyridine-3-carbaldehyde;

4-(1-ethyl-propyl)-[3-[(1-ethyl-propyl]-amino)-methyl]-6-methyl-2-(2,4,6-trimethyl-phenoxy) pyridin-4-yl]-amine;

2-[4-(1-ethyl-propylamino)6-methyl-2-(2,4,6-trimethyl-phenoxy)-pyridin-3-ylmethyl]-malonic acid dimethyl ester;

2-[4-(1-ethyl-propylamino)6-methyl-2-(2,4,6-trimethyl-phenoxy)pyridin-3-ylmethyl]-malonic acid diisopropyl ester;

4-(1-ethyl-propoxy)-6-methyl-3-nitro-2-(2,4,6-trimethyl-phenoxy)-pyridine;

4-(1-ethyl-propoxy)-6-methyl-2-(2,4,6-trimethyl-phenoxy)pyridin-3-yl-amine;

(4-(1-ethyl-propoxy)-6-methyl-2-(2,4,6-trimethyl-phenoxy)-pyridin-3-yl]-dimethyl-amine;

N-[4-(1-ethyl-propoxy)-6-methyl-2-(2,4,6-trimethyl-phenoxy)-pyridin-3-yl]-succinamic acid;

4-(1-ethyl-propoxy)-3,6-dimethyl-2[3-(2,4,6-trimethyl-pyridinoxy)]-pyridine;

6-ethyl-4-(1-ethyl-propoxy)-3-methyl-2-(2,4,6-trimethyl-phenoxy)pyridine;

4-(1-ethyl-propoxy)-2-(4-fluoro-2,6-dimethyl-phenoxy) 3,6-dimethyl-pyridine;

[4-(1-ethyl-propoxy)3,6-dimethyl-pyridin-2-yl]-(2,4,6-trimethyl-phenyl)amine;

[4-(1-ethyl-propoxy)-6-methyl-2-(2,4,6-trimethyl-phenylamino)-pyridin-3-yl]-methanol;

[4-(1-ethyl-propoxy)-6-methyl-2-(2,4,6-trimethyl-phenylamino)-pyridin-3-yl]-oxo-acetonitrile;

2-[4-(1-ethyl-propoxy)-6-methyl-2-(2,4,6-trimethyl-phenylamino)-pyridin-3-yl]-propan-2-ol;

2-[4-(1-ethyl-propoxy)6-methyl-2-(2,4,6-trimethyl-phenylamino)-pyridin-3-ylmethyl]-malonic acid dimethyl ester;

3-[4-(1-ethyl-propoxy-6-methyl-2-(2,4,6-trimethyl-phenylamino)-pyridin-3-yl]-propionic acid;

[3-aminomethyl-4-(1-ethyl-propoxy)-6-methyl-pyridin-2-yl]-(2,4,6-trimethyl-phenyl) amine;

2-chloro-N-[4-(1-ethyl-propoxy)-6-methyl-2-(2,4,6-trimethyl-phenylamino)-pyridin-3-ylmethyl]-acetamide;

[3-dimethylaminomethyl-4-(1-ethyl-propoxy)-6-methyl-pyridin-2-yl]-(2,4,6-trimethyl-phenyl)-amine hydrochloride salt;

dithiocarbonic acid O-ethyl ester S-[4-(1-ethyl-propoxy) 6-methyl-2-(2,4,6-trimethyl-phenylamino)pyridin-3-ylmethyl] ester;

4-(1-ethyl-propoxy)-6-methyl-2-(2,4,6-trimethyl-phenylamino)-nicotinamide;

4-(1-ethyl-propoxy)-6-methyl-2-(2,4,6-trimethyl-phenylamino)nicotinonitrile;

4-(1-ethyl-propoxy)-6,N,N-trimethyl-2-(2,4,6-trimethyl-phenylamino)-nicotinamide;

[4-(1-ethyl-propoxy)-6-methyl-2-(2,4,6-trimethyl-phenylamino)-pyridin-3-yl]-acetonitrile;

[2-(4-bromo-2,6-dimethyl-phenylamino)4-(1-ethyl-propoxy)-6-methyl-pyridin-3-yl]-methanol;

[24-chloro-2,6-dimethyl-phenylamino)-4-(1-ethyl-propoxy)-6-methyl-pyridin-3-yl]-methanol;

[2-(2,4-dichloro-phenylamino)-4-(1-ethyl-propoxy)-6-methyl-pyridin-3-yl]-methanol;

[2-(2,4-dimethoxy-phenylamino)4-(1-methoxymethyl-propoxy)6-methyl-pyridin-3-yl]-methanol;

[4-(1-ethyl-propylamino)-6-methyl-2-(2,4,6-trimethyl-phenoxy)-pyridin-3-yl]-imidazol-1-yl-methanone;

1-[4-(1-ethyl-propylamino)-6-methyl-2-(2,4,6-trimethyl-phenoxy)pyridin-3-yl]ethanone;

[1-ethyl-propyl)-6-methyl-3-propyl-2-(2,4,6-trimethyl-phenoxy)pyridin-4-yl]-amine;

2-[41-ethyl-propylamino)6-methyl-2-(2,4,6-trimethyl-phenoxy)-pyridin-3-ylmethyl]-2-methyl-malonic acid dimethyl ester;

4-(1-ethyl-propoxy)6-methyl-pyridin-2-yl)-(2,4,6-trimethyl-phenyl)-amine;

2-ethyl)-[3-methoxy-6-methyl-2-(2,4,6-trimethyl-phenoxy)pyridin-4-yl]-butan-1-ol;

1-[3-methoxy-6-methyl-2-(2,4,6-trimethyl-phenoxy)-pyridin-4-yl]-2-methyl-butan-1-ol; 1-[3,6-dimethyl-2-(2,4,6-trimethyl-phenoxy)-pyridin-4-yl]-propan-1-ol;

4-(1-methoxy-propyl)3,6-dimethyl-2-(2,4,6-trimethyl-phenoxy)-pyridine;

4-(1-ethoxy-propyl)3,6-dimethyl-2-(2,4,6-trimethyl-phenoxy)-pyridine;

4-(1-allyloxy-propyl)3.6-dimethyl-2-(2,4,6-trimethyl-phenoxy)pyridine;

4-(1-butoxy-propyl)-3,6-dimethyl-2-(2,4,6-trimethyl-phenoxy)-pyridine;

1-[2-(2,4-dichloro-6-methyl-phenoxy)-3-methoxy-6-methyl-pyridin yl]-2-ethyl-butan-1-ol;

1-[3,6-dimethyl-2-(2,4,6-trimethyl-phenoxy)-pyridin-4-yl]-2,2,2-trifluoro-ethanol;

1-[2-(4-chloro-2.6-dimethyl-phenoxy)-3,6-dimethyl-pyridin-4-yl]-2,2,2-trifluoro-ethanol;

[2-(4-chloro-2,6-dimethyl-phenoxy)3,6-dimethyl-pyridin-4-yl]pyridin-2-yl-methanol;

1-[2-(4-chloro-2,6-dimethyl-phenoxy)-3-methoxy-6-methyl-pyridin-4-yl]-2-ethyl-butan 1-ol;

1-[3,6-dimethyl-22,4,6-trimethyl-phenoxy)pyridin-4-yl]-propan-1-one;

1-[2-(4-chloro-2,6-dimethyl-phenoxy)-3,6-dimethyl-pyridin-4-yl]-2,2,2-trifluoro-ethanol;

[2-(4-chloro-2,6-dimethyl-phenoxy)-3,6-dimethyl-pyridin-4-yl]-pyridin-2-yl-methanone;

1-[2-(4-chloro-2,6-dimethyl-phenoxy)-3-methoxy-6-methyl-pyridin-4-yl]-2-ethyl-butan-1-one;

4-(1-ethoxy-2,2,2-trifluoro-ethyl)-3,6-dimethyl-2-(2,4,6-methyl-phenoxy)pyridine;

2-[3,6-dimethyl-2-(2,4,6-trimethyl-phenoxy)-pyridin-4-yl]-butan-2-ol;

[3-(3,6-dimethyl-2-(2,4,6-trimethyl-phenoxy)pyridin-4-yl]-pentan-3-ol;

[2-(4-chloro-2,6-dimethyl-phenoxy)₃-hydroxy-6-methyl-pyridin-4-yl]-2-ethyl-butan-1-one;

4-(1-ethyl-propylamino-6-methyl-2-(2,4,6-trimethyl-phenoxy)-nicotinamide;

4-(1-ethyl-propylamino)-6-N-dimethyl-2-(2,4,6-trimethyl-phenoxy)nicotinamide;

2-(4-chloro-2,6-dimethyl-phenoxy)4—(S)-(1-hydroxymethyl-propylamino)6-methyl-nicotinamide;

2-(4-chloro-2,6-dimethyl-1 phenoxy)4-S)-(1-hydroxymethyl-propylamino)6-methyl-nicotinic acid hydrazide;

2-(4-chloro-2,6-dimethyl-phenoxy)-N-ethyl-4-(S)1-hydroxymethyl-propyl amino)6-methyl-nicotinamide;

2-(4-chloro-2,6-dimethyl-phenoxy)-4—(S)-(1-hydroxymethyl-propylamino)-6-N-dimethyl-nicotinamide;

2-(4-chloro-2,6-dimethyl-phenoxy)-N-cyclopentyl-4-(S)-(1-hydroxymethyl-propylamino)-6-methyl-nicotinamide;

2-(4-chloro-2,6-dimethyl-phenoxy)-N-cyclopropyl-methyl-4-(S)(1-hydroxymethyl-propylamino)-6-methyl-nicotinamide;

4-(1-ethyl-propylamino-6-methyl-2-(2,4,6-trimethyl-phenylamino)-nicotinamide;

4-(1-ethyl-propoxy) 2-methyl-6-(2,4,6-trimethyl-phenylamino)pyrimidine-5-carboxylic acid amide;

4-(1-ethyl-propylamino)-6-methyl-2-(2,4,6-trimethyl-phenoxy)nicotinonitrile;

[4-(1-ethyl-propoxy)1-ethyl-3-nitro-pyridin-2-yl]-(2,4,6-trimethyl-phenylamine;

4-(1-ethyl-propoxy)-6-methyl-N-2-(2,4,6-trimethyl-phenyl)pyridine-2,3-diamine;

2-chloro-N-[4-(1-ethyl-propoxy)6-methyl-2-(24,6-trimethyl-phenylamino)-pyridin-3-yl]-acetamide;

N-butyl-N-ethyl-6-methyl-3-nitro-N-(2,4,6-trimethyl-phenyl)-pyridine-2,4-diamine;

4-(1-ethyl-propylamino)6-methyl-2-(2,4,6-trimethyl-phenylamino)-nicotinic acid;

4-(1-ethyl-propylamino)-6-methyl-2-(2,4,6-trimethyl-phenylamino)nicotinic acid methyl ester;

N4-(1-ethyl-propyl)-3,6-dimethyl-N-2-(2,4,6-trimethyl-phenyl)-pyridine-2,4-diamine;

2-[4-(1-ethyl-propylamino)-6-methyl-2-(2,4,6-trimethyl-phenylamino)pyridin-3-ylmethyl]-malonic acid dimethyl ester;

[2-(4-bromo-2,6-dimethyl-phenylamino)4-(1-ethyl-propylamino)-6-methyl-pyridin-3-yl]-methanol;

N2-(2,4-dichloro-phenyl)-N4-(1-ethyl-propyl)-3,6-dimethyl-pyridine-2,4-diamine;

[2-(2,4-dichloro-phenylamino)4-(1-ethyl-propylamino)-6-methyl-pyridin-3-yl]-methanol;

2-[6-methyl-3-nitro-2-(2,4,6-trimethyl-phenylamino)-pyridin-4-ylamino]-butan-1-ol;

2-[4-(1-ethyl-propylamino)-2-methyl-6-(2,4,6-trimethyl-phenoxy)-pyrimidin-5-yl]-propionic acid ethyl ester;

[3-aminomethyl-6-methyl-2-(2,4,6-trimethyl-phenoxy)-pyridin-4-yl]-(1-ethyl-propyl)-amine;

[2-(4-bromo-2,6-dimethyl-phenoxy)4-(1-ethyl-propyl-amino)-6-methyl-pyridin-3-yl]-acetonitrile;

[2-(4-chloro-2,6-dimethyl-phenoxy)4-(1-ethyl-propylamino)methyl-pyridin-3-yl]-acetonitrile hydrogen chloride;

[6-(1-ethyl-propoxy)-2-methyl-pyrimidin-4-yl]-(2,4,6-trimethyl-phenyl)amine;

2[2-(4-chloro-2,6-methyl-phenoxy)-6-methyl-pyridin-4-(S)ylamino]-butan-1-ol;

[3-aminomethyl-2-(4-chloro-2,6-dimethyl-phenoxy)-6-methyl-pyridin-4-(S)-yl-(1-chloromethyl-propyl)-amine;

2-2-(4-chloro-2,6-dimethyl-phenoxy)6-methyl-3-methylaminomethyl-pyridin-4-(S)-ylamino]-butan-1-ol;

2-[3-aminomethyl-2-(4-chloro-2,6-dimethyl-phenoxy)-6-methyl-pyridin-4-(S)ylamino]-butan-1-ol;

[3-bromo-6-methyl-2-(2,4,6-trimethyl-phenoxy)pyridin-4-yl]-(1-ethyl-propyl)-amine;

2-[3,5-dibromo-2-(4-chloro-2,6-dimethyl-phenoxy)-6-methyl-pyridin-4-ylamino]-butan-1-ol;

2-[3-bromo-6-(4-chloro-2,6-dimethyl-phenoxy)2-methyl-pyridin-4-(S)-ylamino]-butan-1-ol;

2-[3-chloro-2-(4-chloro-2,6-dimethyl-phenoxy)-6-methyl-pyridin-4-(S)ylamino]-butan-1-ol;

2-[3,5-dichloro-2-(4-chloro-2,6-dimethyl-phenoxy)-6-methyl-pyridin-4-ylamino]butan-1-ol;

2-[3-chloro-6-(4-chloro-2,6-dimethyl-phenoxy)-2-methyl-pyridin-4-(S)ylamino]-buten-1-01; 2-(4-chloro-2,6-dimethyl-phenoxy)4—(S)-(4-ethyl-2-oxo-oxazolidin-3-yl)$_6$-methyl nicotinonitrile;

2-(2,4-dimethoxy-phenylamino)4-(1-methoxymethyl-propoxy) 6-methyl-nicotinic acid;

4-(1-ethyl-propoxy)-2-methyl-6-(2,4,6-trimethyl-phenylamino)-pyrimidine-5-carbonitrile;

N-(1-ethyl-propyl)2,5-dimethyl-N'-(2,4,6-trimethyl-phenyl)pyrimidine-4,6-diamine;

5-chloro-N-4-(1-ethyl-propyl)-2-methyl-N(2,4,6-trimethyl-phenyl)-pyrimidine-4,6-diamine;

5-bromo-N-(1-ethyl-propyl)-2-methyl-N'-(2,4,6-trimethyl-phenyl)pyrimidine-4,6-diamine;

4-(1-ethyl-propylamino)-2-methyl-6-(2,4,6-trimethyl-phenylamino-1-pyrimidine-5-carboxylic acid;

[4-(cyclopropylmethyl-propyl-amino)2-methyl-6-(2,4,6-trichloro-phenylamino)-pyrimidin-5-yl]-methanol;

6-(1-ethyl-propoxy)-2,N5,N5-trimethyl-N-4-(2,4,6-trimethyl-phenyl)pyrimidine-4,5-diamine;

[5-bromo-6-(1-ethyl-propoxy-2-methyl-pyrimidin-4-yl] 2,4,6-trimethyl-phenyl)amine;

4-(1-ethyl-propoxy)-2-methyl-6-(2,4,6-trimethyl-phenylamino)-pyrimidine-5-carboxylic acid;

[4 (1-ethyl-propoxy)-2-methyl-6-(2,4,6-trimethyl-phenylamino)-pyrimidin-5-yl]-methanol;

[6-(1-ethyl-propoxy) 5 methoxymethyl-2-methyl-pyrimidin-4-yl]-(2,4,6-trimethyl-phenyl)-amine;

[5-aminomethyl (1-ethyl-propoxy)-2-methyl-pyrimidin-4-yl]-(2,4,6-trimethyl phenyl)-amine;

4-(1-ethyl-propoxy)-2-methyl(2,4,6-trimethyl-phenylamino)-pyrimidine-5-carbonitrile;

7-(ethyl-propoxy)-5-methyl-3-(2,4,6-trimethyl-phenyl)-3H-imidazo[4,5-b]pyridin-2-ylamine;

7-(1-ethyl-propoxy)-y-5-methyl-3-(2,4,6-trimethyl-phenyl)-3H-imidazo[4,5-b]pyridine;

7-(1-ethyl-propoxy-5-methyl-3-(2,4,6-trimethyl-phenyl)-1,3-dihydro-imidazo[4,5-b]pyridin-2-one;

7-(1-ethyl-propoxy)1,5-dimethyl-3-(2,4,6-trimethyl-phenyl)-1,3-dihydro-imidazo[4,5-b]pyridin-2-one;

(1-ethyl-propyl)-[5-methyl-3-(2,4,6-trimethyl-phenyl)-3H-imidazo[4,5-b]pyridin-7-yl]-amine;

[2,dimethyl-3-(2,4,6-trimethyl-phenyl)3H-imidazo[4,5-b]pyridin-7-yl]-(1-ethyl-propyl)-amine;

N7-(1-ethyl-propyl)-5-methyl-3-(2,4,6-trimethyl-phenyl)-3H-imidazo[4,5-b]pyridine-2,7-diamine;

6-(1-ethyl-propylamino)-2,7-dimethyl-9-(2,4,6-trimethyl-phenyl)-7,9-dihydro-purin-8-one;

6-(1-ethyl-propoxy)-2,7-dimethyl-9-(2,4,6-trimethyl-phenyl)-7,9-dihydro-purin-8-one;

[2-(4-methoxy-2,6-dimethyl-phenoxy)-6-methyl-3-nitro-pyridin-4-yl]-(1-methoxymethyl-propyl)-amine;

(1-ethyl-propyl)-[2-(4-methoxy-2,6-dimethyl-phenoxy)-3,6-dimethyl-pyridin-4-y]amine;

2-[2-(4-methoxy-2,6-dimethyl-phenoxy)3,6-dimethyl-pyridin-4-ylamino]butan-1-ol;

sec-butyl-[3-methoxy-2-(4-methoxy-2,6-dimethyl-phenoxy)-6-methyl-pyridin-4-yl]-amine;

2-(4-chloro-2,6-dimethyl-phenoxy)-4-(4-ethyl-oxazolidin-3-yl)3,6-dimethyl-pyridine;

4-(4-ethyl-oxazolidin-3-yl)-2-(4-methoxy-2,6-dimethyl-phenoxy)-3,6-dimethyl-pyridine;

2-(4-methoxy-2,6-dimethyl-phenoxy)-N%4&-(1-methoxymethyl-propyl)-6-methyl-pyridine-3,4-diamine;

3-[2-(4-chloro-2,6-dimethyl-phenoxy)-3-hydroxymethyl-6-methyl-pyridin-4-ylamino-]-pentan-2-ol;

3-[2-(4-chloro-2,6-dimethyl-phenoxy)-4-(1-ethyl-2-oxo-propylamino)-6-methyl-nicotinic acid methyl ester;

2-(4-chloro-2,6-dimethyl-phenoxy)-3-methoxymethyl-6-methyl-pyridin-4-ylamino]-pentan-2-ol;

3-[2-(4-methoxy-2,6-dimethyl-phenoxy)3,6-dimethyl-pyridin-4-ylamino]-pentan-2-ol;

4-sec-butylamino-2-(4-methoxy-2,6-dimethyl-phenoxy)-6-methyl-nicotinic acid methyl ester;

2-(4-chloro-2,6-dimethyl-phenoxy-4-(1-ethyl-2-hydroxy-2-methyl-propylamino)-6-methyl-nicotinic acid methyl ester;

4-(1-hydroxymethyl-propylamino)-2-(4-methoxy-2,6-dimethyl-phenoxy methyl-nicotinic acid methyl ester;

2-(4-chloro-2,6-dimethyl-phenoxy)-4-(1-hydroxymethyl-3-methylsulfanyl-propylamino)-6-methyl-nicotinic acid methyl ester;

2-(4-chloro-2,6-dimethyl-phenoxy)-6-methyl-4-(tetrahydro-furan-3-ylamino)nicotinic acid methyl ester;

{3-[2-(4-chloro-2,6-dimethyl-phenoxy)-3-methoxycarbonyl-6-methyl-pyridin-4-ylamino]-4-hydroxy-butyl}-dimethyl-sulfonium iodide;

4-(1-hydroxymethyl-3-methylsulfanyl-propylamino)-2-(4-methoxy-2,6-dimethyl-phenoxy)-6-methyl-nicotinic acid methyl ester;

4-(1-hydroxymethyl-propylamino)-2-(4-methoxy-2,6 dimethyl-phenoxy)-6,N-dimethyl-nicotinamide;

4-sec-butylamino-2-(4-methoxy-2,6-dimethyl-phenoxy)-6,N-dimethyl-nicotinamide;

2-(4-methoxy-2,6-dimethyl-phenoxy)-6-methyl-4-(tetrahydro-furan-3-ylamino)-nicotinic acid methyl ester;

4-sec-butylamino-2-(4-methoxy-2,6-dimethyl-phenoxy)-methyl-nicotinamide; and and pharmaceutically acceptable salts thereof.

The invention also relates to a pharmaceutical composition for the treatment of (a) a disorder or condition the treatment of which can be effected or facilitated by antagonizing CRF, including but not limited to disorders induced or facilitated by CRF, or (b) a disorder or condition selected from inflammatory disorders such as rheumatoid arthritis and osteoarthritis, pain, asthma, psoriasis and allergies; generalized anxiety disorder; panic; phobias, including social phobia, agoraphobia, and specific phobias; obsessive-compulsive disorder; post-traumatic stress disorder; sleep disorders induced by stress; pain perception such as fibromyalgia; mood disorders such as depression, including major depression, single episode depression, recurrent depression, child abuse induced depression, mood disorders associated with premenstrual syndrome, and postpartum depression; dysthemia; bipolar disorders; cyclothymia; chronic fatigue syndrome; stress-induced headache; cancer; irritable bowel syndrome, Crohn's disease; spastic colon;

post operative ileus; ulcer; diarrhea; stress-induced fever; human immunodeficiency virus infections; neurodegenerative diseases such as Alzheimer's disease, Parkinson's disease and Huntington's disease; gastrointestinal diseases; eating disorders such as anorexia and bulimia nervosa; hemorrhagic stress; chemical dependencies or addictions, including dependencies or addictions to alcohol, cocaine, heroin, benzodiazapines, or other drugs; drug or alcohol withdrawal symptoms; stress-induced psychotic episodes; euthyroid sick syndrome; syndrome of inappropriate antidiuretic hormone; obesity; infertility; head trauma; spinal cord trauma; ischemic neuronal damage, including cerebral ischemia, for example cerebral hippocampal ischemia; excitotoxic neuronal damage; epilepsy; stroke; immune dysfunctions including stress induced immune dysfunctions, including porcine stress syndrome, bovine shipping fever, equine paroxysmal fibrillation, confinement dysfunction in chicken, sheering stress in sheep, and human-animal interaction stress in dogs; muscular spasms; urinary incontinence; senile dementia of the Alzheimer's type; multiinfarct dementia; amyotrophic lateral sclerosis; hypertension; tachycardia; congestive heart failure; osteoporosis; premature birth; hypoglycemia, and Syndrome X in a mammal, including a human, or bird comprising an amount of a compound of the formula I, II or III, or a pharmaceutically acceptable salt thereof, that is effective in the treatment of such disorder or condition, and a pharmaceutically acceptable carrier.

The invention further includes a method for the treatment of (a) a disorder or condition the treatment of which can be effected or facilitated by antagonizing CRF, including but not limited to disorders induced or facilitated by CRF, or (b) a disorder or condition selected from inflammatory disorders such as rheumatoid arthritis and osteoarthritis, pain, asthma, psoriasis and allergies; generalized anxiety disorder; panic; phobias, including social phobia, agoraphobia, and specific phobias; obsessive-compulsive disorder; post-traumatic stress disorder; sleep disorders induced by stress; pain perception such as fibromyalgia; mood disorders such as depression, including major depression, single episode depression, recurrent depression, child abuse induced depression, mood disorders associated with premenstrual syndrome, and postpartum depression; dysthemia; bipolar disorders; cyclothymia; chronic fatigue syndrome; stress-induced headache; cancer; irritable bowel syndrome, Crohn's disease; spastic colon; post operative ileus; ulcer; diarrhea; stress-induced fever; human immunodeficiency virus infections; neurodegenerative diseases such as Alzheimer's disease, Parkinson's disease and Huntington's disease; gastrointestinal diseases; eating disorders such as anorexia and bulimia nervosa; hemorrhagic stress; chemical dependencies or addictions, including dependencies or addictions to alcohol, cocaine, heroin, benzodiazapines, or other drugs; drug or alcohol withdrawal symptoms; stress-induced psychotic episodes; euthyroid sick syndrome; syndrome of inappropriate antidiuretic hormone; obesity; infertility; head trauma; spinal cord trauma; ischemic neuronal damage, including cerebral ischemia, for example cerebral hippocampal ischemia; excitotoxic neuronal damage; epilepsy; stroke; immune dysfunctions including stress induced immune dysfunctions, including porcine stress syndrome, bovine shipping fever, equine paroxysmal fibrillation, confinement dysfunction in chicken, sheering stress in sheep, and human-animal interaction stress in dogs; muscular spasms; urinary incontinence; senile dementia of the Alzheimer's type; multiinfarct dementia; amyotrophic lateral sclerosis; hypertension; tachycardia; congestive heart failure; osteoporosis; premature birth; hypoglycemia, and Syndrome X in a mammal, including a human, or bird comprising administering to a subject in need of said treatment an amount of a compound of the formula I, II or III or a pharmaceutically acceptable salt thereof, that is effective in treating such disorder or condition.

Specific embodiments of the invention provide a pharmaceutical composition and a method for treatment of (a) a disorder the treatment of which can be effected or facilitated by antagonizing CRF, including but not limited to disorders induced or facilitated by CR, or (b) a disorder selected from inflammatory disorders such as rheumatoid arthritis and osteoarthrits, pain, asthma, psoriasis and allergies; generalized anxiety disorder; panic; phobias; obsessive-compulsive disorder; post-traumatic stress disorder; sleep disorders induced by stress; pain perception such as fibromyalgia; mood disorders such as depression, including major depression, single episode depression, recurrent depression, child abuse induced depression, and postpartum depression; dysthemia; bipolar disorders; cyclothymia; fatigue syndrome; stress-induced headache; cancer, irritable bowel syndrome, Crohn's disease; spastic colon; human immunodeficiency virus (HIV) infections; neurodegenerative diseases such as Alzheimer's disease, Parkinson's disease and Huntington's diseases; gastrointestinal diseases; eating disorders such as anorexia and bulimia nervosa; hemorrhagic stress; chemical dependencies and addictions (e.g., dependencies on alcohol, cocaine, heroin, benzodiazepines, or other drugs); drug and alcohol withdrawal symptoms; stress-induced psychotic episodes; euthyroid sick syndrome; syndrome of inappropriate antidiuretic hormone (ADH); obesity; infertility; head traumas; spinal cord trauma; ischemic neuronal damage (e.g., cerebral ischemia such as cerebral hippocampal ischemia); excitotoxic neuronal damage; epilepsy; stroke; immune dysfunctions including stress induced immune dysfunctions (e.g., porcine stress syndrome, bovine shipping fever, equine paroxysmal fibrillation, and dysfunctions induced by confinement in chickens, sheering stress in sheep or human-animal interaction related stress in dogs); muscular spasms; urinary incontinence; senile dementia of the Alzheimer's type; multiinfarct dementia; amyotrophic lateral sclerosis; and hypoglycemia in a mammal, including a human.

The present invention also provides a pharmaceutical composition for and a method of treating a condition comprising administering a compound of I, II, or III, in an amount effective to treat said condition, wherein said condition is selected from the group consisting of: a) abnormal circadian rhythm; b) depression, further wherein a second compound for treating depression is administered, said second compound for treating depression having an onset of action that is delayed with respect to that of said CRF antagonist; and c) emesis. The aforementioned method can practiced according to the information provided in U.S. Provisional Patent Application No. 60/151,183, filed Aug. 27, 1999, which describes treatment of the aforementioned conditions using CRF antagonists in general and which is incorporated herein by reference in its entirety.

The compounds of formula I, II, and III, described herein can also be used to treat forms of heart failure described in U.S. Ser. No. 09/248,073, supra, and can be made into pharmaceutical compositions therefore.

Examples of more specific forms or manifestations of abnormal circadian rhythm that can be treated according to the present invention include, but are not limited to, time zone change syndrome resulting, seasonal affective disorder, shift-work sleep disorder, irregular sleep-wake pattern, delayed sleep phase syndrome resulting from said abnormal circadian rhythm, advanced sleep phase syndrome, or non-24 hour sleep wake disorder resulting from said abnormal circadian rhythm. Moreover, the compound of formula I, II, or III can be combined in the method or pharmaceutical composition for treatment of abnormal circadian rhythm with a second compound that is useful for treating a sleep disorder, for example tachykinin antagonists, agonists for GABA brain receptors, metalonergic compounds, GABA brain receptor agonists, 5-HT$_2$ receptor antagonists, and D4 receptor binding compounds. However, other compounds or substances useful for treating a sleep disorder can be combined with a compound of formula I, II, or III. Such methods and compositions are described in greater detail in U.S. Provisional Patent Application No. 60/151,183, supra.

In another embodiment, said condition is depression, and the second compound having delayed action for treating depression is selected from the group consisting of selective serotonin reuptake inhibitors, tricyclic antidepressants, norepinephrine uptake inhibitors, lithium, bupropion, sertraline, fluoxetine, trazodone, and a tricyclic antidepressant selected from the group consisting of imipramine, amitriptyline, trimipramine, doxepin, desipramine, nortriptyline, protriptyline, amoxapine, clomripramine, maprotiline, and carbamazepine, and pharmaceutically acceptable salts and esters of the above-recited compounds.

In another embodiment, the condition being treated is emesis, and the method further comprises administering a second compound for treating emesis. The second compound for treating emesis can be selected from, but is not limited to, tachykinin antagonists, 5-HT3 antagonists, GABA agonists, and substance P inhibitors. More specific categories of emesis encompassed in the present invention include emesis induced by a condition or agent selected from the group consisting of pregnancy, vestibular disorder, post-operative sickness, gastrointestinal obstruction, reduced gastrointestinal motility, visceral pain, migraine, change in intercranial pressure, chemotherapy, radiation, toxins, and opioid analgesics.

The invention further includes intermediate compounds of formula

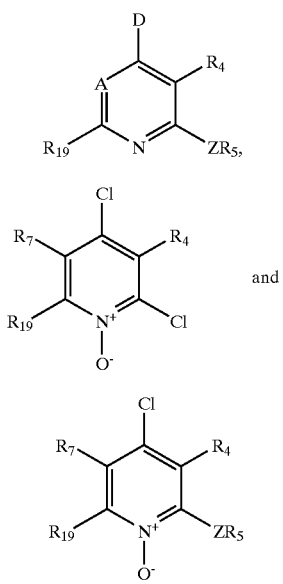

IV and

XI

X wherein R$_4$ and R$_7$, are defined as they are for formula I above; D is chloro, hydroxy or cyano; R$_{19}$ is methyl or ethyl; R$_5$ is phenyl or pyridyl and R$_5$ is substituted by two or three substituents independently selected from C$_1$–C$_4$ alkyl, chloro and bromo, except that no more than one such substituent can be bromo; A is N, CH or CCH$_3$; and Z is O, NH, N(CH$_3$), S or CH$_2$, with the proviso that when A is CH or CCH$_3$, then Z must be O or S.

More specific embodiments of this invention relate to compounds of the formula X or XI wherein R$_7$ is hydrogen or methyl.

This invention further include intermediate compounds of formula

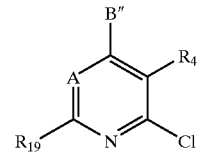

XII wherein R$_{19}$ is methyl or ethyl; A is N, CH or CCH$_3$; and wherein when A is N, then B" and R$_4$, are defined, respectively, as B and R$_4$ are defined for formula I, and when A is CH or CH$_3$, then B" is —NR$_1$R$_2$, —NHR$_1$R$_2$, —OCHR$_1$R$_2$ or cyano and R$_4$ is an electron deficient group such as NO$_2$, —COO(c$_1$–C$_4$ alkyl), —C(=O)CH$_3$, —COOH or CN.

A more specific embodiment of this invention relates to compounds of the formula XII wherein B" is —NR$_1$R$_2$ or —NHCHR$_1$R$_2$ and A is CH or CH$_3$.

This invention also relates to a process for preparing a compound of the formula I,

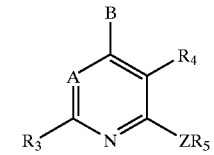

I or a pharmaceutically acceptable salt thereof, wherein
A is —CR$_7$ or N;
B is —NR$_1$R$_2$, —NHCHR$_1$R$_2$, —OCHR$_1$R$_2$ or —SCHR$_1$R$_2$;
Z is NH, O, S, —N(C$_1$–C$_2$ alkyl) or —C(R$_{13}$R$_{14}$), wherein R$_{13}$ and R$_{14}$ are each, independently, hydrogen, trifluoromethyl or methyl, or one of R$_{13}$ and R$_{14}$ is cyano and the other is hydrogen or methyl;
R$_1$ is C$_1$–C$_6$ alkyl which may optionally be substituted with one or two substituents R$_8$ independently selected from the group consisting of hydroxy, fluoro, chloro, bromo, iodo, CF$_3$ and C$_1$–C$_4$ alkoxy, and wherein said C$_1$–C$_6$ alkyl and the (C$_1$–C$_4$)alkyl moiety of said C$_1$–C$_4$ alkoxy may optionally contain one carbon-carbon double or triple bond;
R$_2$ is C$_1$–C$_{12}$ alkyl, aryl or —(C$_1$–C$_4$ alkylene)aryl wherein said aryl is phenyl, naphthyl, thienyl, benzothienyl, pyridyl, quinolyl, pyrazinyl, pyrimidyl, imidazolyl, furanyl, benzofuranyl, benzothiazolyl, isothiazolyl, benzisothiazolyl, benzisoxazolyl, benzimidazolyl, indolyl, or benzoxazolyl; 3- to 8-membered cycloalkyl or —(C$_1$–C$_6$ alkylene)cycloalkyl, wherein one or two of the ring carbons of said cycloalkyl having at least 4 ring members and the cycloalkyl moiety of said —(C$_1$–C$_6$ alkylene)cycloalkyl having at least 4 ring members may optionally be replaced by an oxygen or sulfur atom or by N—$R_9$ wherein $R_9$ is hydrogen or $C_1$–$C_4$ alkyl; and wherein each of the foregoing $R_2$ groups may optionally be substituted with from one to three substituents independently selected from chloro, fluoro and $C_1$–$C_4$ alkyl, or with one substituent selected from bromo, iodo, $C_1$–$C_6$ alkoxy, —O—CO—($C_1$–$C_6$ alkyl), OCO—N($C_1C_4$ alkyl)($C_1$–$C_2$ alkyl), —S($C_1$–$C_6$ alkyl), CN, $NO_2$, —SO($C_1$–$C_4$ alkyl), and —$SO_2$ ($C_1$–$C_4$ alkyl), and wherein said $C_1$–$C_{12}$ alkyl and the $C_1$–$C_4$ alkylene moiety of said —($C_1$–$C_4$ alkylene)aryl may optionally contain one carbon-carbon double or triple bond;

or —$NR_1R_2$ may form a saturated 5- to 8-membered carbocyclic ring which may optionally contain one or two carbon-carbon double bonds and in which one or two of the ring carbons may optionally be replaced by an oxygen or sulfur atom;

$R_3$ is methyl or ethyl;

$R_4$ is hydrogen, $C_1$–$C_4$ alkyl, fluoro, chloro, bromo, iodo, $C_1$–$C_4$ alkoxy, trifluoromethoxy, —$CH_2OCH_3$, —$CH_2OCH_2CH_3$, $CH_2CH_2OCH_3$, $CH_2OF_3$, $CF_3$, amino, nitro, —NH($C_1$ $C_4$ alkyl), —N($CH_3$)$_2$, —$NHCOCH_3$, —$NHCONHCH_3$, —$SO_n$($C_1$–$C_4$ alkyl) wherein n is 0, 1 or 2, cyano, hydroxy, —CO($C_1$–$C_4$ alkyl), —CHO, cyano or —COO($C_1$–$C_4$ alkyl) wherein said $C_1$–$C_4$ alkyl may optionally contain one double or triple bond and may optionally be substituted with one substituent selected from hydroxy, amino, —$NHCOCH_3$, —NH($C_1$–$C_2$ alkyl), —N($C_1$–$C_2$ alkyl)$_2$, —COO($C_1$–$C_4$ alkyl), —CO($C_1$–$C_4$ alkyl), $C_1$–$C_3$ alkoxy, $C_1$–$C_3$ thioalkyl, fluoro, chloro, cyano and nitro;

$R_5$ is phenyl or pyridyl, and % is substituted with from one to three substituents independently selected from fluoro, chloro, $C_1$–$C_6$ alkyl, and $C_1$–$C_6$ alkoxy, or with one substituent selected from hydroxy, iodo, bromo, formyl, cyano, nitro, trifluoromethyl, amino, —$C_1$–$C_6$ alkyl)O($C_1$–$C_6$)alkyl, —$NHCH_3$, —N($CH_3$)$_2$, —COOH, —COO($C_1$–$C_4$ alkyl), —CO($C_1$–$C_4$ alkyl), —$SO_2NH(C_1$–$C_4$ alkyl), —$SO_2N(C_1$–$C_4$ alkyl)($C_1$–$C_2$ alkyl), —$SO_2NH_2$, —$NHSO_2(C_1$–$C_4$ alkyl), —S($C_1$ $C_6$ alkyl) and —$SO_2(C_1$–$C_6$ alkyl), and wherein the $C_1$–$C_4$ alkyl and $C_1$–$C_8$ alkyl moieties of the foregoing $R_5$ groups may optionally be substituted with one or two fluoro groups or with one substituent selected from hydroxy, amino, methylamino, dimethylamino and acetyl; and $R_7$ is hydrogen or methyl;

or a pharmaceutically acceptable salt of such compound; comprising reacting a compound of the formula

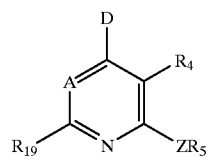

IV wherein $R_{19}$ is methyl or ethyl, D is chloro and A, Z, $R_4$ and $R_5$ are defined as above, with a compound of the formula BH, wherein B is defined as above, in the presence of a base; and then optionally converting the compound of formula I formed in such reaction into a pharmaceutically acceptable salt.

This invention also relates to a process for preparing a compound of the formula

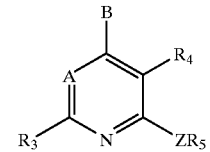

I or a pharmaceutically acceptable salt thereof, wherein

A is —$CR_7$ or N;

B is —$NR_1R_2$, —$CR_1R_2R_{11}$, —C(=$CR_2R_{12}$)$R_1$, —$NHCHR_1R_2$, —$OCHR_1R_2$, —$SCHR_1R_2$, —$CHR_2OR_{12}$, —$CHR_2SR_{12}$, —C(S)$R_2$ or —C(O)$R_2$;

Z is NH, O, S, —N($C_1$–$C_2$ alkyl) or —C($R_{13}R_{14}$), wherein $R_{13}$ and $R_{14}$ are each, independently, hydrogen, trifluoromethyl or methyl, or one of $R_{13}$ and $R_{14}$ is cyano and the other is hydrogen or methyl;

$R_1$ is $C_1$–$C_6$ alkyl which may optionally be substituted with one or two substituents $R_8$ independently selected from the group consisting of hydroxy, fluoro, chloro, bromo, iodo, $CF_3$ and $C_1$–$C_4$ alkoxy, and wherein said $C_1$–$C_4$ alkyl and the ($C_1$–$C_4$)alkyl moiety of said $C_1$–$C_4$ alkoxy may optionally contain one carbon-carbon double or triple bond;

$R_2$ is $C_1$–$C_{12}$ alkyl, aryl or —($C_1$–$C_4$ alkylene)aryl wherein said aryl is phenyl, naphthyl, thienyl, benzothienyl, pyridyl, quinolyl, pyrazinyl, pyrimidyl, imidazolyl, furanyl, benzofuranyl, benzothiazolyl, isothiazolyl, benzisothiazolyl, benzisoxazolyl, benzimidazolyl, indolyl, or benzoxazolyl; 3- to 8-membered cycloalkyl or —($C_1$–$C_6$ alkylene) cycloalkyl, wherein one or two of the ring carbons of said cycloalkyl having at least 4 6 ng members and the cycloalkyl moiety of said —($C_1$–$C_6$ alkylene) cycloalkyl having at least 4 ring members may optionally be replaced by an oxygen or sulfur atom or by N-$R_9$ wherein $R_9$ is hydrogen or $C_1$–$C_4$ alkyl; and wherein each of the foregoing $R_2$ groups may optionally be substituted with from one to three substituents independently selected from chloro, fluoro and $C_1$–$C_4$ alkyl, or with one substituent selected from bromo, iodo, $C_1$–$C_6$ alkoxy, —O—CO-($C_1$–$C_6$ alkyl), —O—CO—N($C_1$–$C_4$ alkyl)($C_1$–$C_2$ alkyl), —S($C_1$–$C_6$ alkyl), CN, $NO_2$, —SO($C_1$–$C_4$ alkyl), and —$SO_2$ ($C_1$–$C_4$ alkyl), and wherein said $C_1$–$C_{12}$ alkyl and the $C_1$–$C_4$ alkylene moiety of said —($C_1$–$C_4$ alkylene)aryl may optionally contain one carbon-carbon double or triple bond;

or —$NR_1R_2$ may form a saturated 5- to 8-membered carbocyclic ring which may optionally contain one or two carbon-carbon double bonds and in which one or two of the ring carbons may optionally be replaced by an oxygen or sulfur atom;

$R_3$ is methyl, ethyl, fluoro, chloro, bromo, iodo, cyano, methoxy, $OCF_3$, methylthio, methylsulfonyl, $CH_2OH$, or $CH_2OCH_3$;

$R_4$ is hydrogen, $C_1$–$C_4$ alkyl, fluoro, chloro, bromo, iodo, $C_1$–$C_4$ alkoxy, trifluoromethoxy, —$CH_2OCH_3$, —$CH_2OCH_2CH_3$, —$CH_2CH_2OCH_3$, —$CH_2OF_3$, $CF_3$, amino, nitro, —NH($C_1$–$C_4$ alkyl), —N($CH_3$)$_2$, —$NHCOCH_3$, —$NHCONHCH_3$, —$SO_n$($C_1$–$C_4$ alkyl) wherein n is 0, 1 or 2, cyano, hydroxy, —CO($C_1$–$C_4$ alkyl), —CHO, cyano or —COO($C_1$–$C_4$ alkyl) wherein said $C_1$–$C_4$ alkyl may optionally contain one double or triple bond and may optionally be substituted with one substituent selected from hydroxy, amino, —NHCOCH$_3$, —NH($C_1$–$C_2$ alkyl), —N($C_1$–$C_2$ alkyl)$_2$, —COO($C_1$–$C_4$ alkyl), —CO($C_1$–$C_4$ alkyl), $C_1$–$C_3$ alkoxy, $C_1$–$C_3$ thioalkyl, fluoro, chloro, cyano and nitro;

$R_5$ is phenyl or pyridyl and $R_5$ is substituted with from one to three substituents independently selected from fluoro, chloro, $C_1$–$C_6$ alkyl, and $C_1$–$C_6$ alkoxy, or with one substituent selected from hydroxy, iodo, bromo, formyl, cyano, nitro, trifluoromethyl, amino, —($C_1$–$C_6$ alkyl)O($C_1$–$C_6$)alkyl, —NHCH$_3$, —N(CH$_3$)$_2$, —COOH, —COO($C_1$–$C_4$ alkyl), —CO($C_1$–$C_4$ alkyl), —SO$_2$NH($C_1$–$C_4$ alkyl), —SO$_2$N($C_1$–$C_4$ alkyl)($C_1$–$C_2$ alkyl), O$_2$NH$_2$, —NHSO$_2$($C_1$–$C_4$ alkyl), —S($C_1$–$C_6$ alkyl) and —SO$_2$-($C_1$–$C_6$ alkyl), and wherein the $C_1$–$C_4$ alkyl and $C_1$–$C_6$ alkyl moieties of the foregoing $R_5$ groups may optionally be substituted with one or two fluoro groups or with one substituent selected from hydroxy, amino, methylamino, dimethylamino and acetyl; and $R_7$ is hydrogen or methyl;

with the proviso that when A is CH or CCH$_3$, then $R_4$ is an electron deficient group such as NO$_2$, —COO($C_1$–$C_4$)alkyl, —C(=O)CH$_3$, —COOH or CN;

or a pharmaceutically acceptable salt of such compound;

comprising reacting a compound of the formula

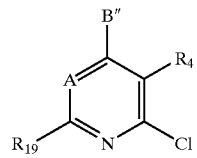

XII wherein $R_{19}$ is methyl or ethyl and A is N, CH or CCH$_3$; and wherein when A is N, then B" and $R_4$ are defined, respectively, as B and $R_4$ are defined in claim 1, and when A is CH or CH$_3$, then B" is —NR$_1$R$_2$, —NHR$_1$R$_2$, —OCHR$_1$R$_2$ or cyano and $R_4$ is an electron deficient group such as NO$_2$, —COO($C_1$–$C_4$ alkyl), —C(=O)CH$_3$, —COOH or CN;

with a compound of the formula R$_5$ZH, wherein R$_5$ and Z are defined as above, and then optionally converting the compound of formula I formed by such reaction into a pharmaceutically acceptable salt.

This invention also relates to a process for preparing a compound of the formula

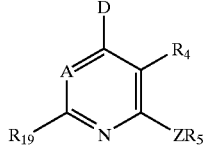

IV a wherein $R_{19}$ is methyl or ethyl;

D is chloro;

A is —CR$_7$ or N;

Z is NH, O, S, —N($C_1$–$C_2$ alkyl) or —C(R$_{13}$R$_{14}$), wherein R$_{13}$ and R$_{14}$ are each, independently, hydrogen, trifluoromethyl or methyl, or one of R$_{13}$ and R$_{14}$ is cyano and the other is hydrogen or methyl;

$R_4$ is hydrogen, $C_1$–$C_4$ alkyl, fluoro, chloro, bromo, iodo, $C_1$–$C_4$ alkoxy, trifluoromethoxy, —CH$_2$OCH$_3$, —CH$_2$OCH$_2$CH$_3$, —CH$_2$CH$_2$OCH$_3$, —CH$_2$OF$_3$, CF$_3$, amino, nitro, —NH($C_1$–$C_4$ alkyl), —N(CH$_3$)$_2$, —NHCOCH$_3$, —NHCONHCH$_3$, SO$_n$(C—$C_4$ alkyl) wherein n is 0, 1 or 2, cyano, hydroxy, —CO($C_1$–$C_4$ alkyl), —CHO, cyano or —COO($C_1$–$C_4$ alkyl) wherein said $C_1$–$C_4$ alkyl may optionally contain one double or triple bond and may optionally be substituted with one substituent selected from hydroxy, amino, —NHCOCH$_3$, —NH($C_1$–$C_2$ alkyl), N($C_1$—C alkyl)$_2$, —COO(C, —$C_4$ alkyl), —CO($C_1$–$C_4$ alkyl), $C_1$–$C_3$ alkoxy, $C_1$–$C_3$ thioalkyl, fluoro, chloro, cyano and nitro; and $R_5$ is phenyl or pyridyl, and $R_5$ is substituted with from one to three substituents independently selected from fluoro, chloro, $C_1$–$C_6$ alkyl, and $C_1$–$C_6$ alkoxy, or with one substituent selected from hydroxy, iodo, bromo, formyl, cyano, nitro, trifluoromethyl, amino, —($C_1$–$C_6$ alkyl)O($C_1$–$C_6$)alkyl, —NHCH$_3$, —N(CH$_3$)$_2$, —COOH, —COO($C_1$–$C_4$ alkyl), —CO($C_1$–$C_4$ alkyl), —SO$_2$NH($C_1$–$C_4$ alkyl), —SO$_2$N($C_1$–$C_4$ alkyl)($C_1$–$C_2$ alkyl), —SO$_2$NH$_2$, —NHSO$_2$($C_1$–$C_4$ alkyl), —S($C_1$–$C_6$ alkyl) and —SO$_2$($C_1$–$C_6$ alkyl), and wherein the $C_1$–$C_4$ alkyl and $C_1$–$C_6$ alkyl moieties of the foregoing R$_5$ groups may optionally be substituted with one or two fluoro groups or with one substituent selected from hydroxy, amino, methylamino, dimethylamino and acetyl;

comprising reacting a compound of the formula

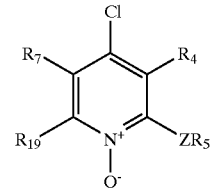

X wherein $R_{19}$, $R_4$ and $R_5$ are defined as above and $R_7$ is hydrogen, methyl, fluoro, chloro, bromo, iodo, cyano, hydroxy, —O($C_1$–$C_4$ alkyl), —C(O)($C_1$–$C_4$ alkyl), —C(O)O($C_1$–$C_4$ alkyl), —OCF$_3$, CF$_3$, —CH$_2$OH, —CH$_2$OCH$_3$ or —CH$_2$OCH$_2$CH$_3$, with phosphorus trichloride.

This invention also relates to a process for preparing a compound of the formula

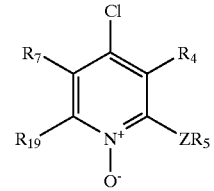

X wherein $R_{19}$ is methyl or ethyl;

A is —CR$_7$ or N;

Z is O, S, or —C(R$_{13}$R$_{14}$), wherein R$_{13}$ and R$_{14}$ are each, independently, hydrogen, trifluoromethyl or methyl, or one of R$_{13}$ and R$_{14}$ is cyano and the other is hydrogen or methyl;

$R_4$ is hydrogen, $C_1$–$C_4$ alkyl, fluoro, chloro, bromo, iodo, $C_1$–$C_4$ alkoxy, trifluoromethoxy, —CH$_2$OCH$_3$, —CH$_2$OCH$_2$CH$_3$, —CH$_2$CH$_2$OCH$_3$, —CH$_2$OF$_3$, CF$_3$, amino, nitro, —NH($C_1$–$C_4$ alkyl), —N($CH_3$)$_2$, —NHCOCH$_3$, —NHCONHCH$_3$, —SO$_n$($C_1$–$C_4$ alkyl) wherein n is 0, 1 or 2, cyano, hydroxy, —CO($C_1$–$C_4$ alkyl), —CHO, cyano or —COO($C_1$–$C_4$ alkyl) wherein said $C_1$–$C_4$ alkyl may optionally contain one double or triple bond and may optionally be substituted with one substituent selected from hydroxy, amino, —NHCOCH$_3$, —NH($C_1$–$C_2$ alkyl), —N($C_1$–$C_2$ alkyl)$_2$, —COO($C_1$–$C_4$ alkyl), —CO($C_1$–$C_4$ alkyl), $C_1$–$C_3$ alkoxy, $C_1$–$C_3$ thioalkyl, fluoro, chloro, cyano and nitro; and R$_5$ is phenyl or pyridyl, and R$_5$ is substituted with from one to three substituents independently selected from fluoro, chloro, $C_1$–$C_6$ alkyl, and $C_1$–$C_6$ alkoxy, or with one substituent selected from hydroxy, iodo, bromo, formyl, cyano, nitro, trifluoromethyl, amino, —($C_1$–$C_6$ alkyl)O($C_1$–$C_6$) alkyl, —NHCH$_3$, —N(CH$_3$)$_2$, —COOH, —COO($C_1$–$C_4$ alkyl), —CO($C_1$–$C_4$ alkyl), —SO$_2$NH($C_1$–$C_4$ alkyl), —SO$_2$N($C_1$–$C_4$ alkyl)($C_1$–$C_2$ alkyl), —SO$_2$NH$_2$, —NHSO$_2$ ($C_1$–$C_4$ alkyl), —S($C_1$, alkyl) and —SO$_2$($C_1$–$C_6$ alkyl), and wherein the $C_1$–$C_4$ alkyl and $C_1$–$C_6$ alkyl moieties of the foregoing R$_5$ groups may optionally be substituted with one or two fluoro groups or with one substituent selected from hydroxy, amino, methylamino, dimethylamino and acetyl; comprising reacting a compound of the formula

XI

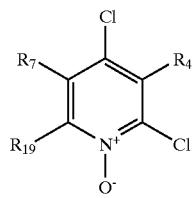

wherein R$_4$, R$_7$ and R$_{19}$ are defined as above, with a compound of the formula R$_5$OH or R$_5$SH, wherein R$_5$ is defined as above, in the presence of a base.

DETAILED DESCRIPTION OF THE INVENTION

Methods of preparing the compounds and compositions of this invention are described below. In the discussion and reaction schemes that follow, R$_1$ through R$_9$, R$_{11}$, R$_{12}$, R$_{16}$, R$_{17}$, R$_{19}$, A, B. G, the dashed lines and structural formulae I, II, III, X, XI, XII and IV, unless otherwise indicated, are defined as above.

Whenever reference is made herein to alkyl, both straight and branched chain alkyl groups are encompassed. For example, "$C_1$–$C_5$ alkyl" encompasses both straight and branched chain alkyl groups of one to six carbon atoms, including (but not limited to) methyl, ethyl, isopropyl, t-butyl and hexyl.

Whenever R$_2$ or R$_5$ is a heterocyclic group, attachment of the group is through a carbon atom.

Whenever reference is made herein to $C_1$–$C_4$ alkyl or $C_1$–$C_6$ alkyl which "may contain one double or triple bond" in the above definitions, it is understood that at least two carbons are present in the alkyl for one double or triple bond.

Whenever reference is made herein to halo or halogen; fluoro, chloro, bromo or iodo is meant unless indicated otherwise.

The terms "treatment", "treating", and the like, are meant to include both slowing or reversing the progression of a disorder, as well as curing the disorder. These terms also include alleviating or reducing the symptoms of a disorder or condition, even if the disorder or condition is not actually eliminated and even if progression of the disorder or condition is not itself slowed or reversed. The term "treatment" and like terms also include prophylactic treatment of disorders and conditions.

The term "haloalkyl" refers to an alkyl group substituted by one or more halogen atoms, i.e. one or more fluoro, bromo, iodo, or chloro atoms. Moreover, it is understood that when an alkyl group can be, according to this specification and claims, substituted with, e.g., one to nine, e.g., nine atoms, that the optional one to nine fluorine atoms are only an option when a sufficient number of carbon atoms is present in the alkyl group.

The term "aryl" in the definitions above means, unless otherwise indicated, an organic radical derived from an aromatic hydrocarbon by removal of one hydrogen atom, which aromatic hydrocarbon. Examples of aryl groups are phenyl and naphthyl.

The term "heterocycloalkyl", unless otherwise specified means a 4 to 8 membered mono-carbocyclic ring or bicyclic ring, wherein at least one carbon atom is replaced with a hetero member selected from oxygen, nitrogen, N-(alkyl), or S(O)$_m$, wherein m is zero, 1, 2, or 3. Generally, heterocycloalkyl groups comprise up to four hetero members, preferably 1, 2, or 3 hetero members. Heterocycloalkyl groups of the compounds of the invention can contain optionally from one to three double bonds. The term "heterocycloalkyl" also includes heteroaryl groups. Examples of heteroaryl groups include thienyl, benzothienyl, pyridyl, thiazolyl, quinolyl, pyrazinyl, pyrimidyl, imidazolyl, furanyl, benzofuranyl, benzothiazolyl, isothiazolyl, benzisothiazolyl, benzisoxazolyl, benzimidazolyl, indolyl, and benzoxazolyl. Other examples of aryl groups are pyrazolyl, triazolyl, tetrazolyl, isoxazolyl, oxazolyl, pyrrolyl, isoquinolinyl, cinnolinyl, indazolyl, indolizinyl, phthalazinyl, pyridazinyl, triazinyl, isoindolyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Preferred heteroaryl groups are thiazolyl, thienyl, benzothienyl, pyridyl, quinolyl, quinazolinyl, quinoxalinyl, pyrazinyl, pyrimidinyl, indazolyl, imidazolyl, furanyl, benzimidazolyl, benzofuranyl, benzothiazolyl, benzisoxazolyl, isothiazolyl, pyrazolyl, pyrrolyl, indolyl, pyrrolopyridyl, oxazolyl, benzoxazolyl, and benzothiadiazolyl. Other preferred heterocycloalkyl groups are tetrahydrofurano, tetrahydropyrano, morpholino, pyrrolidino, piperidino, piperazino, [2,2,1]-azabicyclic rings, [2,2,2]-azabicyclic rings, [3,3,1]azabicyclic rings, quinuclidino, azetidino, azetidinono, oxindolo, dihydroimidazolo, and pyrrolidinono. Heterocyclolalkyl groups in the compounds of the invention may be C-attached or N-attached where such is possible.

Compounds of the formula I wherein B is —NR$_1$R$_2$, —NHCHR$_1$R$_2$, —OCHR$_1$R$_2$ or —SCHR$_1$R$_2$, and R$_3$ is methyl, ethyl or chloro (hereinafter R$_{19}$) may be prepared by reaction of a compound of the formula IV wherein D is Cl, and A, R$_4$, R$_5$, and Z are as defined above with reference to formula I, with a compound of the formula BH wherein B is as defined immediately above. The reaction is carried out in a solvent in the presence of a base at a temperature of between about 0° to about 230° C. Suitable solvents are organic solvents such as tetrahydrofuran (THF), acetonitrile, dimethylsulfoxide (DMSO), acetone, $C_2$–$C_{15}$ alkyl alcohol, chloroform (CHCl$_3$), benzene, xylene, toluene, sulfolane, pyridine, quinoline, 2,4,6-trimethylpyridine, acetamide, di-($C_1$–$C_2$)alkylacetamide or 1-methyl-2-pyrrolidinone.

A preferred method of preparing compounds of the formula I wherein A is —CR$_7$ and B is —NR$_1$R$_2$ or —NHCHR$_1$R$_2$ is the two step procedure described below. First, a compound of the formula IV is reacted with an excess of R$_1$NH$_2$ or NH$_3$ or an equivalent NH$_3$ precursor (e.g., NaN$_3$, nBu$_4$N$^+$N$_3$— or NH$_2$OH) at temperature from about 75° C. to about 250° C. and at a pressure from about 0 to about 300 psi, in an appropriate solvent, as described above, to form a compound of the formula I wherein B is —NHR$_1$, —NH$_2$, —NH$_2$OH or —N$_3$. Compounds of the formula I wherein B Is —N$_3$ or —NH$_2$OH can be converted into the corresponding compounds of formula I wherein B is —NH$_2$ by methods well known in the art such as hydrogenation or reduction. Alkylation of a compound of the formula I wherein B is NHR$_1$ or —NH$_2$ with an appropriate alkyl halide in the presence of an appropriate base such as lithium or sodium bistrimethylsilylamide, lithium or sodium diisopropylamide, n-butyllithium or potassium t-butoxide, in an appropriate solvent such as THF, dioxane or methylene chloride, will yield the corresponding compound of formula I wherein B Is —NR$_1$R$_2$. Alternatively, reductive amination of a compound of the formula I wherein B is —NHR$_1$ or —NH$_2$, for example, acylation, followed by reduction with a borohydride (e.g., sodium borohydride) will form the corresponding compound of formula I wherein B is —NR$_1$R$_2$ or NHCHR$_1$R$_2$.

When B is —NR$_1$R$_2$ or —NHCHR$_1$R$_2$, an excess of BH may be used both as a reagent and as a base. Bases other than BH such as potassium carbonate, tri-(C$_1$–C$_6$)alkylamine or sodium hydride may also be used. The reaction is carried out at a temperature of about 75° to 230° C. When the reaction is carried out in the presence of a base, such as sodium hydride, potassium C$_1$–C$_4$ alkoxide, or an organolithium compound such as n-butyllithium, a molar equivalent of the amine is used.

When B is —OCHR$_1$R$_2$ or —SCHR$_1$R$_2$, a base which is capable of deprotonating BH may be used, such as an alkali metal hydride such as sodium or potassium hydride, or an organometallic base such as sodium diisopropylamide, sodium bis(trimethylsilyl)amide, lithium diisopropylamide, lithium bis(trimethylsilyl)amide, sodium or potassium C$_1$–C$_4$ alkoxide, or n-butyllithium. The solvent used can be, for example, tetrahydrofuran, acetonitrile, dimethylsulfoxide, acetone, methylene chloride, toluene, a C$_2$–C$_5$ alcohol, chloroform, benzene, xylene, or 1-methyl-2-pyrrolidinone, and the reaction temperature can range from about 0° C. to about 180° C., and is preferably from about 50° C. to about 80° C.

Compounds of the formulae I, II and III wherein B is as defined with reference to formulae I, IIand III and R$_3$ is defined with reference to the same except that R$_3$ is not methyl or ethyl (hereinafter R$_{20}$, which is defined as R$_3$ with the exception that it can not be methyl or ethyl) may be prepared by reacting a compound of the formulae I, II or III wherein R$_3$ is chloro with a nucleophile of the formula R$_{20}$H with or without an organic or inorganic base. Suitable bases include sodium and sodium hydride, when R$_2$OH is an alkanol or an alkane thiol; and weaker bases such as potassium carbonate or triethylamine when R H is an amine. The compounds of formula I wherein R$_{20}$ is fluoro may be prepared from the corresponding compounds wherein R$_2$D is chloro on reaction with tetrabutylammonium fluoride. Suitable solvents are dimethylsulfoxide, tetrahydrofuran, or methylene chloride, preferably tetrahydrofuran.

Compounds of the formula I wherein B is —CR$_1$R$_2$R$_{11}$, —C(C=CR$_2$R$_{12}$)R$_1$, —CHR$_2$OR$_{12}$, —CHR$_2$SR$_{12}$, or —C(O)R$_2$, and R$_3$ is R$_{19}$, as defined above, may be prepared as depicted in Scheme I.

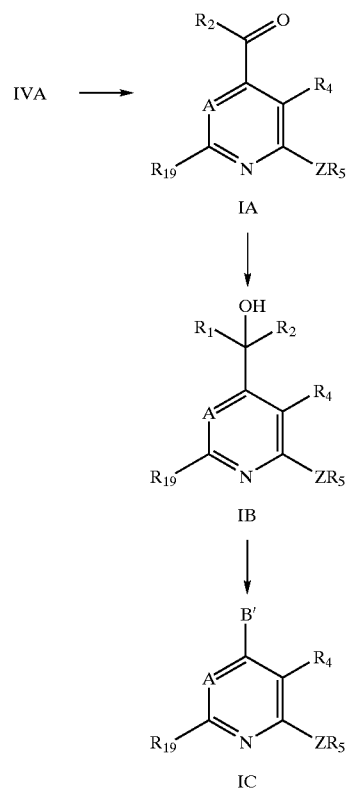

SCHEME 1

Compounds of the formula IV wherein D is cyano and A, R$_4$, R$_5$, and R$_{19}$ are as defined above having formula IVA (not shown), prepared by reacting the corresponding compound wherein D is chloro with potassium cyanide or copper cyanide in dimethylsulfoxide, 1-methyl-2-pyrrolidinone, N,N-dimethylformamide (DMF) or acetamide, are reacted with a Grignard reagent containing group R$_2$, as defined above, to form the compounds of formula IA Further reaction of the compound of formula IA with a Grignard reagent containing R$_1$ as defined above provides the compound of formula IB. Corresponding compounds of formula IC wherein B" is —CR$_1$R$_2$R$_{11}$, or —C(C=CR$_2$R$_{12}$)R$_1$ may be prepared by conventional methods. Thus, reaction of IB with an acid, such as concentrated sulfuric acid in acetic acid, or Burgess inner salt, such as (carboxysulfamoyl) triethylammonium hydroxide methyl ester, gives a compound of formula IC wherein B' is —C(=CR$_2$R$_{12}$)R$_1$. Hydrogenation of a compound wherein B' is —C(=CR$_2$R$_{12}$)R$_1$ using a palladium/carbon (Pd/C) or platinum dioxide catalyst gives a compound IC wherein B' is CHR$_1$R$_2$. Reaction of compound IB with diethylaminosulfur trifluoride or triphenylphosphine/carbontetrachloride affords a compound IC wherein B' is —CR$_1$R$_2$F or —CR$_1$R$_2$Cl, respectively. Reduction of a compound of formula IA with sodium borohydride gives a compound I wherein B Is —CHR$_2$OH. Alkylation of this —CHR$_2$OH group with alkyl halide such as alkyl iodide in the presence of a base such as sodium hydride at room temperature affords a compound of formula I wherein B is —CHR$_2$OR$_{12}$.

Compounds of the formula II wherein R$_3$ is R$_{19}$ as defined above may be prepared from compounds of the formula IV wherein R$_1$, R$_4$, R$_5$ and A are as defined before, D is chloro, and YR$_{21}$ is NH or —CHR$_{21}$ wherein R$_{21}$ is cyano or —COO($C_1$–$C_4$ alkyl), hereafter formula IVB, as shown In Scheme 2.

SCHEME 2

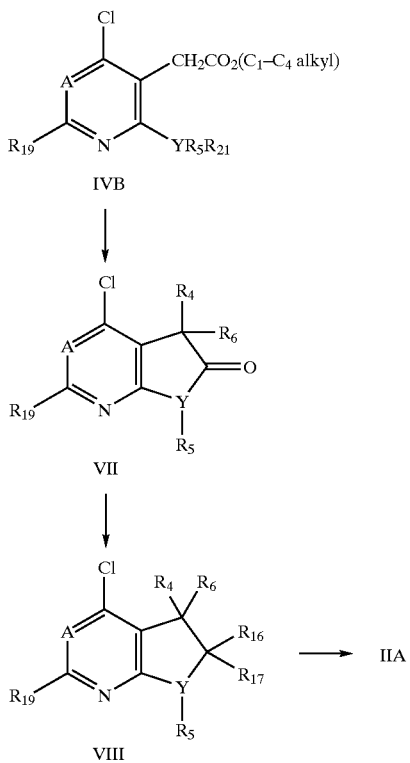

IVB

VII

VIII

→ IIA

Compounds of the formula VII wherein $R_4$ and $R_6$ are each hydrogen and Y is N may be prepared by heating compounds of formula IVB with an acid catalyst in a suitable solvent such as toluene, benzene, t-butanol, acetonitrile and acetone, preferably toluene. The acid catalyst may be sulfuric acid, hydrochloric acid, p-toluene sulfonic acid, or methylsulfonic acid, preferably p-toluene sulfonic acid.

When Y in formula IVB is CH or N, a base may be used to deprotonate the proton of the compound of formula IVB. Suitable solvents are tetrahydrofuran, toluene, and methylene chloride, suitable reaction temperatures are between about −78° C. and 100° C., preferably −78° to 50° C., and suitable bases are sodium hydride, potassium hydride, potassium t-butoxide, lithium bis(trimethylsilyl) amide, and lithium or sodium diisopropylamide.

Compounds of the formula VII wherein $R_4$ and $R_6$ are each hydrogen may be deprotonated with a base such as sodium hydride, or an organometallic compound such as lithium bis(trimethylsilyl)amide followed by quenching with an electrophile compound containing the group $R_4$, such as $R_4L$ wherein L is a leaving group such as iodo, bromo, mesylate, tosylate or with p-tolyl-N-fluoro-N-$C_1$–$C_6$ alkyl sulfonamide, iodine, p-nitrobenzene, dimethylformamide, di($C_1$–$C_4$ alkyl)ketone, formaldehyde, ($C_1$–$C_4$ alkyl) aldehyde or bromine, to provide a compound of formula VII wherein $R_4$ is fluoro, chloro, bromo, iodo, hydroxy, $C_1$–$C_4$ alkyl, S($C_1$–$C_4$ alkyl), CHO, CH(OH)($C_1$–$C_4$ alkyl), C(OH)(di-$C_1$–$C_4$ alkyl) or $CH_2OH$. Further conventional alkylation of the hydroxy group or oxidation of the thioalkyl group leads to compounds of formula VII wherein $R_4$ is $C_1$–$C_4$ alkoxy and $SO_n$($C_1$–$C_4$ alkyl) wherein n is 1 or 2, respectively. Oxidation of compounds of formula VII wherein $R_4$ is hydroxy and $R_6$ is hydrogen affords corresponding compounds wherein $CR_4R_6$ is C=O, which on reductive amination with an appropriate amine convert into corresponding compounds wherein $R_4$ is amino. The compounds of formula VII wherein $R_4$ is nitro or amino may be formed by reacting compounds of formula VII wherein $R_4$ and $R_6$ are both hydrogen with alkyl nitrite to form compounds wherein $CR_4R_6$ is C=NOH and oxidizing or reducing to give the compounds of formula VII wherein $R_4$ is nitro or amine, respectively.

Compounds of the formula VII, when one of $R_4$ and $R_6$ is hydrogen, may be converted into corresponding compounds wherein $R_{16}$ and $R_{17}$ are both hydrogen by reduction with a reducing agent such as lithium aluminum hydride in tetrahydrofuran. The same reduction leads to compounds wherein $R_{16}$ is hydrogen and $R_{17}$ is hydroxy, when both of $R_4$ and $R_6$ are not hydrogen. Alkylation of $R_{17}$ is hydroxy with $C_1$–$C_4$ alkyl iodide in the presence of sodium hydride gives the corresponding compound wherein $R_{17}$ is O($C_1$–$C_4$ alkyl). Reaction of compounds of formula VII with an organometallic compound such as di($C_1$–$C_6$ alkyl)zinc, $C_1$–$C_6$ alkyl lithium, or $C_1$–$C_6$ alkyl magnesiumbromide affords compounds of formula VIII wherein one of $R_{16}$ or $R_{17}$ is $C_1$–$C_6$ alkyl and the other is hydroxy.

The conversion of compounds of formula VIII to corresponding compounds of formula IIA is by the methods described above for preparation of compounds of formula I.

The compounds of formula III wherein G is oxygen or sulfur and Re is hydrogen may be prepared by reacting compounds of formula I wherein $R_4$ is amino and Z is NH with phosgene, diphosgene, triphosgene or thiophosgene. The reaction is in the presence of a base such as tri($C_1$–$C_4$ alkyl)amine in a suitable solvent, preferable tetrahydrofurane at about −78° to about 50° C., preferably at 0° C. to room temperature. Standard alkylation of these compounds wherein $R_6$ is hydrogen with a suitable base such as sodium hydride in a suitable solvent such as dry tetrahydrofuran provides compounds of the formula III wherein $R_6$ is $C_1$–$C_4$ alkyl.

Compounds of the formula III wherein G is alkyl may be prepared by reacting a compound of the formula I wherein $R_4$ is amino and Z is NH with a compound of the formula GC(O$C_1$–$C_2$ alkyl)$_3$ in the presence of an acid such as p-toluenesulfonic acid (p-TsOH), methanesulfonic acid (MsOH), hydrogen chloride gas (HCl$_g$) or concentrated sulfuric acid ($H_2SO_4$) in an appropriate sovlent such as toluene, xylene, benzene, dioxane or THF at a temperature from about room temperature to about 140° C., preferably from about 50° C. to about the reflux temperature. Alternatively, a compound of the formula I wherein $R_4$ is amino and Z is NH can be reacted with [G(C=O)]$_2$O, G(C=O)Cl or G(C=O)F in the presence of a base such as pyridine, a derivative of pyridine or a tri-($C_1$–$C_4$) alkylamine, in an appropriate solvent such as $CH_2C_{12}$, $CHCl_3$, THF, dioxane, toluene or benzene, at a temperature from about 0° C. to about the reflux temperature of the reaction mixture, preferably from about 0° C. to about room temperature, followed by ring cyclization under acidic conditions (e.g., with pTSOH, MSOH, HCl$_g$, hydrogen bromide gas (HBr$_g$) or concentrated $H_2SO_4$). The ring cyclization can be carried out in an appropriate solvent such as a $C_1$–$C_5$ alcohol, toluene, xylene, benzene, dioxane or THF. Suitable temperatures for this reaction can range from about room temperature to about 140° C. Preferably, the reaction temperature is between about 50° C. and about the reflux temperature.

Compounds of the formula III wherein G Is —O—($C_1$–$C_2$ alkyl) or $OCF_3$ may be prepared by reacting a compound of the formula III wherein G is oxygen and $R_6$ is hydrogen with a compound of the formula $GOSO_2CF_3$ in the presence of a base such as tri($C_1$–$C_4$ alkyl)amine, or with lithium bistrimethylsilylamide in HMPA or DMF, and then quenching the reaction with a compound of the formula $GOSO_2OG$ or G-X wherein X is bromo, chloro or $SO_3CF_3$.

The compounds of formula IV wherein D Is chloro and $ZR_5$ is $NHR_5$ may be prepared from compounds of formula V:

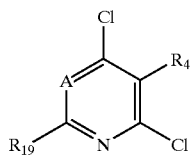

V wherein A and $R_4$ are as defined with reference to formula I and $R_{19}$ is as defined above, by reaction with $R_5NH_2$. The reaction is in tetrahydrofuran or dimethylsulfoxide at about 0° C. to about 150° C., preferably 50° to 130° C. The compounds of formula IV wherein D is chloro and Z is O, S, $CHR_{21}$ wherein $R_2$, is an electron deficient group such as cyano, C(=O)R, COOR, wherein R is $C_1$–$C_4$ alkyl, benzoyl or allyl, or $SO_n$-phenyl wherein n=0, 1 or 2 may be prepared by reacting compounds of formula V with $R_5OH$, FISH, $R_5NH_2$ or $R_5CHR_{21}$. The reaction proceeds in the presence of a base which is capable of deprotonating $R_5ZH$, such as sodium hydride, potassium hydride, potassium carbonate, lithium or sodium bis(trimethylsilyl)amide, lithium or sodium dialkylamide, sodium or potassium ($C_1$–$C_4$ alkoxide) or n-butyllithium, with or without other organometal halides such as copper (I) bromide, iodide or chloride, copper (II) oxide, copper (I) oxide, copper metal and trialkyltinchloride. Examples of solvents that may be used are tetrahydrofuran, dimethylsulfoxide, acetonitrile, methylene chloride, 1-methyl-2-pyrrolidinone, pyridine, quinoline, N,N-dialkylacetamides, 2,4,6-trimethylpyridine, N,N-dialkylformamides, e.g., N,N-dimethylformamide (DMF), hexamethyl phosphoramide and toluene. The reaction or temperature may range from about 0° C. to about 180° C., and is preferably from about 0° to about 150° C.

Compounds of the formula IV wherein A is $CR_7$, D is chloro and Z is O, S, $CHR_{21}$ may be prepared by reduction of compounds of formula X, depicted below, wherein $R_7$ and Z are as defined immediately above, with a reducing agent such as phosphorous trichloride in an appropriate solvent such as methylene chloride or chloroform at temperature from about 0° C. to about 100° C., preferably from about room temperature to about the reflux temperature of the solvent.

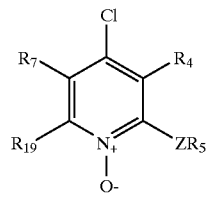

X

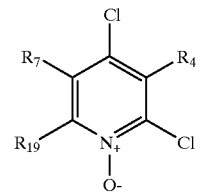

XI

Compounds of the formula X may be prepared from compounds of the formula XI, depicted above, wherein $R_4$ is as defined as it is for formula I and $R_{19}$ is as defined above (i.e., methyl or ethyl), by reaction with a compound of the formula $R_5OH$, $R_5SH$ or $R_5CHR_{21}$. This reaction proceeds in the presence of a base which is capable of deprotonating $R_5ZH$, such as sodium hydride, potassium hydride, lithium, sodium or potassium bis(trimethylsilyl)amide, lithium, sodium or potassium dialkylamide, sodium or potassium $C_1$–$C_4$alkoxide, or n-butyllithium. Suitable solvents include tetrahydrofuran, dioxane, dimethylsulfoxide, 1-methyl-2-pyrrolidinone, pyridine, N,N-di-($C_1$–$C_4$ alkyl)acetamides, acetamide, N,N-di($C_1$–$C_4$ alkyl)formamides, acetonitrile, methylene chloride, touluene and xylene. Suitable reaction temperatures may range from about −78° C. to about 150° C., and are preferably between about 40° C. to about 150° C.

Compounds of the formula XI may be prepared by reacting the corresponding compounds of formula V wherein A is —$CR_7$ and $R_4$ and $R_{19}$ are defined as above, with an oxidizing agent such as m-chloroperbenzoic acid, peracetic acid or pertrifluoroacetic acid, in a solvent such as methylene chloride, chloroform, acetic acid, DMF, methanol or a mixture of one or more of the foregoing solvents, at temperature from about 0° C. to about 100° C., preferably from about room temperature to about 60° C.

When $R_4$ is an electron withdrawing group such as a $NO_2$, —COO($C_1$–$C_4$ alkyl), —COOH, CN or —CO($C_1$–$C_4$)alkyl, the reaction order for the coupling reactions that introduce the B and $ZR_5$ groups in the synthesis of compounds of formula I may be reversed. The B group may be introduced before the $ZR_5$ coupling step using the methods analogous to those described above. For example, compounds of the formula I wherein $R_4$ is an election deficient group may be prepared by reacting a compound of the formula XII with a compound of the formula $HZR_5$. Compounds of the formula XII may be prepared by reacting a compound of the formula V wherein A is $CR_7$ and $R_{19}$ and $R_4$ are defined as above with a compound of the formula B"H in the presence of a base.

Compounds of the formula IV wherein D is chloro and Z is —N($C_1$–$C_4$ alkyl) may be prepared by reacting the corresponding compounds wherein Z is NH with a base, at a temperature from about −78° C. to about 1 00C, preferably from about 0° C. to about room temperature, followed by quenching with $C_1$–$C_4$ alkyl iodide or bromide. Suitable bases include, for example, sodium hydride, lithium or sodium bis(trimethylsilyl)amide, lithium or sodium dialkylamide, and n-butyllithium. Suitable solvents Include, for example, tetrahydrofuran, dimethylsulfoxide, toluene, benzene or methylene chloride.

Compounds of the formula IV wherein D is chloro, hydroxy or OP wherein P is a standard protecting group for hydroxy and Z is —$CR_{13}R_{14}$ may be prepared by alkylation, using an $R_{13}$ containing alkylating agent such as $R_{13}I$, compounds of the formula IV wherein Z is —$CHR_{21}$ in the presence of a base that is capable of deprotonating the proton in the Z group, as mentioned above, followed by quenching with an $R_{14}$ containing alkylating agent such as $R_{14}I$. Heating compounds of the formula IV wherein D Is chloro or hydrogen and Z is —CH(CN) in about 85% phosphoric acid at about the reflux temperature yields the corresponding compounds of formula IV wherein D is hydroxy and Z is $CH_2$. Deprotonation of the compounds of formula IV wherein Z is $CH_2$ with a base, such as described above for deprotonation of $R_5ZH$, followed by quenching with a suitable electrophile such as a ($C_1$–$C_6$ alkyl)iodide, iodine, bromine, acetylchloride, formaldehyde, acetone, p-tolyl-N-fluoro-N-($C_1$–$C_6$ alkyl)sulfonamide, nitrobenzene, $C_1$–$C_8$ alkylnitrite, ethylene oxide or dihaloethane yields the corresponding compounds of formula IV wherein Z is —$CHR_{13}$, —CH(OH), cyclopropyl or —C(NOH). Further alkylation of compounds wherein Z is —$CHR_{13}$, e.g., as described immediately above, with an alkylating agent of the formula $R_{14}I$, produces the corresponding compounds wherein Z is —$C(R_{13}R_{14})$.

Conversion of —$C(R_5)$NOH or —CH(OH)$R_5$ to $C(O)R_5$ may be accomplished by known methods. Hydrogenation or reduction of compounds wherein Z is —C=NOH provides compounds wherein Z is —$CHNH_2$. Some of the intermediates may require a protecting or deprotecting procedure to control the reaction selectivity using standard organic chemistry.

Compounds of the formula V wherein A is N (hereinafter referred to as compounds of the formula VB) or A Is $CR_7$ (i.e., compounds of the formula VA), and $R_4$ and $R_{19}$ are defined as they are for formula I, may be prepared by reacting the corresponding compounds of formulae VIB and VIA, respectively, with 1 equivalent or an excess of $POCl_3$ at a temperature from about room temperature to about 180° C., preferably at the reflux temperature, with or without a solvent. Compounds of formula VIA may be prepared by the methods analogous to those described in the literature and well known to those skilled in the art. (See *Helv. Chimica Acta.,* 25, p. 1306–1313 (1942)).

Compounds of formula VIB may be prepared by reacting 1 equivalent of the HCl salt of $R_{19}C(=NH)(NH_2)$, 1 equivalent of $R_4CH(COO—(C_1-C_2$ alkyl))$_2$, and 2 equivalents of a base such as a sodium alkoxide, e.g., sodium methoxide in a mixture of an alcohol (e.g., methanol), and acetone at a temperature from about 50° C. to about 200° C., preferably at the reflux temperature.

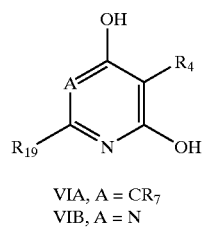

VIA, A = $CR_7$
VIB, A = N

When compounds of this invention contain one or more chiral centers, it is understood that the invention includes the racemic mixtures as well as all individual enantiomers and diastereomers of such compounds, and mixtures thereof.

The acid addition salts of compounds of the formulae I, II, and III (the active compounds of this invention) can be prepared in a conventional manner by treating a solution or suspension of the corresponding free base with one chemical equivalent of a pharmaceutically acceptable acid. Conventional concentration or crystallization techniques can be employed to isolate the salts. Illustrative of suitable acids are acetic, lactic, succinic, maleic, tartaric, citric, gluconic, ascorbic, benzoic, cinnamic, fumaric, sulfuric, phosphoric, hydrochloric, hydrobromic, hydroiodic, sulfamic, sulfonic acids such as methanesulfonic, benzene sulfonic, p-toluenesulfonic, and related acids.

The active compounds of this invention may be administered alone or in combination with pharmaceutically acceptable carriers, in either single or multiple doses. Suitable pharmaceutical carriers include inert solid diluents or fillers, sterile aqueous solutions and various organic solvents. The pharmaceutical compositions formed by combining the novel compounds of formulae I, II and III and their pharmaceutically acceptable carriers can then be readily administered in a variety of dosage forms such as tablets, powders, lozenges, syrups, injectable solutions and the like. These pharmaceutical compositions can, if desired, contain additional ingredients such as flavorings, binders, excipients and the like. Thus, for purposes of oral administration, tablets containing various excipients such as sodium citrate, calcium carbonate and calcium phosphate may be employed along with various disintegrants such as starch, methylcellulose, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in soft and hard filled gelatin capsules. Preferred materials for this include lactose or milk sugar and high molecular weight polyethylene glycols. When aqueous suspensions or elixirs are desired for oral administration, the essential active ingredient therein may be combined with various sweetening or flavoring agents, coloring matter or dyes and, if desired, emulsifying or suspending agents, together with diluents such as water, ethanol, propylene glycol, glycerin and combinations thereof.

For parenteral administration, solutions containing an active compound of this invention or a pharmaceutically acceptable salt thereof in sesame or peanut oil, aqueous propylene glycol, or in sterile aqueous solution may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. The sterile aqueous media employed are all readily available by standard techniques known to those skilled in the art.

The effective dosages for compounds of the formulae I, II or III and their salts will depend on the intended route of administration and factors such as the age and weight of the patient, as generally known to a physician. The dosages will also depend on the particular illness to be treated. For instance, the daily dosage for stress-induced illnesses, inflammatory disorders, Alzheimer's disease, gastrointestinal diseases, anorexia nervosa, hemorrhagic stress and drug and alcohol withdrawal symptoms will generally range from about 0.1 to about 50 mg/kg body weight of the patient to be treated. The effective dose can be determined by those of ordinary skill in the art by reference to texts pertaining to treatment of the particular disorder or condition to be treated.

Methods that may be used to determine the CRF antagonist activity of the active compounds of this invention and their pharmaceutically acceptable salts are described in *Endocrinology*, 116, 1653–1659 (1985) and *Peptides,* 10, 179–188 (1985). The binding activities for compounds of formulae I, II and III, expressed as $IC_{50}$ values, generally range from about 0.5 nanomolar to about 10 micromolar.

The present invention is illustrated by the following examples. It will be understood, however, that the invention is not limited to the specific details of these examples. Melting points are uncorrected. Proton nuclear magnetic resonance spectra ($^1$H NMR) and $C^{13}$ nuclear magnetic resonance spectra ($C^{13}$ NMR) were measured for solutions in deuterochloroform ($CDCl_3$) and peak positions are expressed in parts per million (ppm) downfield from tetramethylsilane (TMS). The peak shapes are denoted as follows: s, singlet; d, doublet; t, triplet; q, quartet; m, multiplet; b, broad.

The following abbreviations are used in the Examples: Ph=phenyl; iPr=isopropyl; HRMS=high resolution mass spectrum.

EXAMPLE 1

A. Butyl-(6-chloro-2,5-dimethyl-pyrimidinyl)ethyl-amine

A mixture of 2,5-methyl-4,6-dichloro-pyrimidine (0.999 g, 5.64 mmol) in 5 ml of acetonitrile was treated with triethylamine (0.571 g, 5.65 mmol) and N-butyl-ethyl-amine (0.570 g. 5.65 mmol) and heated at reflux overnight. The mixture was cooled, diluted with water and dilute hydrogen chloride, and extracted with ethyl acetate. The organic layer was neutralized with saturated potassium carbonate, washed with brine, dried and concentrated to give 0.877 g (64%) of title compound as a yellow oil. $^1$H NMR ($CDCl_3$) δ 0.90 (t, 3H), 1.15 (t, 3H), 1.22–1.36(m, 2H), 1.5–1.6(m, 2H), 2.20 (s, 3H), 2.45 (s, 3H), 3.25–3.48 (m, 4H) ppm.

B. N-Butyl-N-ethyl-2,5-dimethyl-N(2,4,6-trimethylphenyl)-pyrimidine-4.6-diamine A mixture of butyl-(6chloro-2,5-dimethyl-pyrimidin-4-yl)-ethylamine (398 mg, 1.65 mmol), 2,4,6-trimethylaniline (4.04 g, 30 mmol) and diisopropyl-ethyl-amine (200 mg, 1.55 mmol) was heated at 210 to 230° C. overnight. The mixture was quenched with water and dilute hydrogen chloride, and extracted with ethyl acetate. The organic layer was neutralized with saturated potassium carbonate, washed with brine, dried and concentrated to give a dark oil. The oil was distilled to give 579 mg of dark oil which was then purified through silica gel column chromatography using 1:1 hexane to chloroform as eluent to give 327 mg of title compound as a yellow solid. $^1$H NMR ($CDCl_3$) δ 0.92 (t, 3H), 1.14 (t, 3H), 1.2–1.4 (m, 2h), 1.45–1.60 (m, 2H), 1.85 (s, 3H), 2.16 (s, 6H), 2.30 (s, 3H), 2.33 (s, 3H), 3.2–3.4 (m, 4H), 5.8 (brs, 1H), 6.90 (s, 2H) ppm.

EXAMPLE 2

Butyl-(6-chloro-2-methyl-pyrimidin-4-yl)ethyl-amine

A mixture of 2-methyl-4,6-dichloro-pyrimidine (1.63 g, 10 mmol) in 5 ml of acetonitrile was treated with N-butyl-ethyl-amine (2.000 g, 20 mmol) and heated at reflux for 0.5 hours. The mixture was cooled, diluted with water and extracted with ethyl acetate. The organic layer was washed with brine, dried and concentrated to give 2.271 g (100%) of title compound as a light-brown oil. $^1$H NMR ($CDCl_3$) δ 0.93 (t, 3H), 1.13 (t, 3H), 1.22–1.36 (m, 2H), 1.45–1.6 (m, 2H), 2.43 (s, 3H), 3.25–3.60 (m, 4H), 6.15 (s, 1H) ppm.

B. N-Butyl-N-thyl-2-methyl-N 2,4,6-trimethylphenyl)-pyrimidine-4,6-diamine

A mixture of butyl-(6-chloro-2-methyl-pyrimidin-4-yl)-ethylamine (1.006 g, 4.42 mmol), and 2,4,6-trimethylaniline (3 ml) was heated at reflux overnight. The mixture was quenched with water and extracted with ethyl acetate. The organic layer was dried and concentrated to give 2.862 g of a brown oil. The oil was purified through silica gel column chromatography to give 981 mg (68%) of title compound as a yellow oil. $^1$H NMR ($CDCl_3$) δ 0.80 (t, 3H), 1.1–1.3 (m, 2H), 1.3–1.5 (m, 2H), 2.17 (s, 6H), 2.27 (s, 3H), 2.41 (s, 3H), 3.2 (m, 2H), 3.36 (m, 2H), 4.66 (s, 1H), 6.90 (s, 2H) ppm.

EXAMPLE 3

A. Butyl-(6-chloro-2-methyl-5-ethyl-pyrimidin-4-yl) ethyl-amine

A mixture of 2-methyl-5-ethyl-4,6-dichloro-pyrimidine (1.009 g, 5.28 mmol) in 5 ml of acetonitrile was treated with triethylamine (0.571 g, 5.65 mmol) and N-butyl-ethyl-amine (0.540 g, 5.31 mmol) and heated at reflux overnight. The mixture was diluted with water and dilute hydrogen chloride, and extracted with ethyl acetate. The organic layer was neutralized with saturated potassium carbonate and washed with brine, dried and concentrated to give 1.193 g of yellow oil which was purified through silica gel column chromatography to give 1.157 g (86%) of title compound as a yellow oil. $^1$H NMR ($CDCl_3$) δ 0.90 (t, 3H), 1.13 (t, 3H), 1.18 (t, 3H), 1.1–1.33 (m, 2H), 1.4–1.6 (m, 2h), 2.41 (s, 3H), 2.62 (q, 2H), 3.25–3.48 (m, 4H) ppm.

B. N-Butyl-N-ethyl-2-methyl-5-ethyl-N'-(2,4,6trimethylphenyl)-pyrimidine-4,6-diamine A mixture of butyl-6-chloro-2-methyl-5ethyl-pyrimidin-4-yl)-ethylamine (200 mg, 0.78 mmol) and 2,4,6-trimethylaniline (0.963 g, 7.1 mmol) was heated at reflux for 4 hours. The mixture was quenched with water and extracted with ethyl acetate. The organic layer was washed with saturated potassium carbonate and brine, dried and concentrated to give a dark oil. The oil was distilled to give 579 mg of the dark oil which was then purified through silica gel column chromatography using chloroform as eluent to give the title compound as a brown oil. 1H NMR ($CDCl_3$) δ 0.93 (t, 3H), 1.14 (t, 3H), 1.1–1.4 (m, 4H), 1.45–1.60 (m, 2H), 2.17 (s, 6H), 2.30 (s, 3H), 2.33 (s, 3H), 3.2–3.4 (m, 4H), 6.90 (s, 2H) ppm.

EXAMPLE 4

2-Methyl-5nitro-N,N'-bis(2,4,6-trimethylphenyl) pyrimidine-4,6-diamine

A mixture of 2-methyl-5-nitro-4,6-dichloropyrimidine (0.513 g, 2.47 mmol) in 6 ml of acetonitrile was treated with 2,4,6-trimethylaniline (0.333 g, 2.46 mmol) and triethylamine (1 ml) and stirred at room temperature for 4 hours. The mixture was quenched with water and extracted with ethyl acetate. The organic layer was washed with brine, dried and concentrated to give 0.622 g of bright yellow solid. The solid was purified through silica gel column chromatography to give (6-chloro-2methyl-5-nitro-pyrimidin-4-yl)-(2,4,6-trimethylphenyl) amine and the title compound. $^1$H NMR ($CDCl_3$) for 6(chloro 2-methyl-5-nitro-pyrimidin-4- yl)-2,4,6-trimethylphenyl)amine δ2.16 (s, 6H), 2.33 (s, 3H), 2.43 (s, 3H), 6.95 (s, 2H), 8.79 (s, 1H) ppm. $^1$H NMR (CDCl$_3$) for 2-methyl-5-nitro-N,N'-bis-2,4,6-trimethylphenyl)pyrimidine-4,6-diamine: δ 2.11 (s, 3H), 2.22 (s, 12H), 2.33 (s, 3H), 6.96 (s, 4H), 10.44 (s, 2H) ppm.

EXAMPLE 5

N-Butyl-N-ethyl-2-methyl-5-nitro-N'-(2,4,6-trimethylphenyl)-pyrimidine-4,6-diamine A mixture of 6-chloro-2-methyl-5-nitropyrimidin-4-yl)-(2,4,6-trimethyl-phenyl)amine (838 mg, 2.10 mmol) and N-ethyl-butyl-amine (555 mg, 5.48 mmol) in 15 ml acetonitrile was heated at reflux for 2 hours. The mixture was quenched with water and extracted with ethyl acetate. The organic layer was washed with brine, dried and concentrated to give 0.837 g of yellow oil. The solid was purified through silica gel column chromatography using 1:1 hexane to chloroform as eluent to give 753 mg of the title compound as a yellow oil. $^1$H NMR (CDCl$_3$) δ 0.95 (t, 3H), 1.26 (t, 3H), 1.2–1.4 (m, 2H), 1.55–1.75 (m, 2H), 2.17 (s, 6H), 2.23 (s, 3H), 2.31 (s, 3H), 3.4–3.6 (m, 4H), 6.93 (s, 2H), 9.43 (s, 1H) ppm.

EXAMPLE 6

The following compounds were prepared by a method analogous to that of Examples 3 or 5 starting with an appropriate amine and appropriate (6-chloro-2-methyl-5-substituted-pyrimidin-4-yl)-2,4,6-trimethylphenyl)amine.

N-Propyl-N-ethyl-2-methyl-5-nitro-N'-(2,4,6-trimethylphenyl)-pyrimidine-4,6-diamine: $^1$H NMR (CDCl$_3$) δ 0.93 (t, 3H), 1.26 (t, 3H). 1.6-1.8 (m, 2H), 2.17 (s, 6H), 2.23 (s, 3H). 2.31 (s, 3H), 3.4–3.55 (m, 4H), 6.93 (s, 2H), 9.41 (s, 1H) ppm.

N-Butyl-5-ethyl-2-methyl-N'-(2,4,6-trimethylphenyl)-pyrimidine-4,6-diamine: $^1$H NMR (CDCl$_3$) δ 0.98 (t, 3H), 1.12 (t, 3H), 1.3–1.5 (m, 2H), 1.5–1.7 (m, 2H), 2.17 (s, 3H), 2.30 (s, 3H), 3.4–3.5 (m. 2H), 4.30 (brs, 1H), 5.65 (brs, 1H), 6.91 (s, 2H) ppm.

5,N-Diethyl-2-methyl-N'-(2,4,6-trimethylphenyl)pyrimidine-4,6-diamine: $^1$H NMR (CDCl$_3$) δ 1.09 (t, 3H), 1.25 (t, 3H), 2.17 (s, 3H), 2.30 (s, 3H), 2.31 (s, 3H), 3.4–3.6 (m, 2H), 4.35 (brs, 1H), 6.90 (s, 2H) ppm.

EXAMPLE 7

N-Butyl-N-ethyl-2-methyl-N'-(2,4,6-trimethylphenyl)-pyrimidine-4,5,6-triamine

A mixture of N-butyl-N-ethyl-2-methyl-5-nitro-N'-2,4,6-trimethylphenyl)-pyrimidine-4,6-diamine (242 mg, 0.65 mmol) and platinum oxide (35 mg) in 50 ml ethanol was hydrogenated at 40 psi for 24 hours. The mixture was filtered through celite and concentrated to dryness to give 217 mg of yellow oil. The oil was purified through silica gel column chromatography to give 135 mg (61%) of title compound. $^1$H NMR (CDCl$_3$) δ 0.91 (t, 3H), 1.09 (t, 3H), 1.2–1.4 (m, 2H), 1.4–1.6 (m, 2H), 2.18 (s, 6H), 2.30 (s, 3H), 2.34 (s, 3H), 3.0 (brs, 2H), 3.1–3.3 (m, 4H), 5.89 (s, 1H), 6.92 (s, 2H) ppm.

EXAMPLE 8

The following compounds were prepared by the method of Example 7 by hydrogenation of the corresponding 5-nitro derivatives.

N-Propyl-N-ethyl-2-methyl-N'-(2,4,6-trimethylphenyl)pyrimidine-4,5,6-triamine:

$^1$H NMR (CDCl$_3$) δ 0.89 (t, 3H), 1.09 (t, 3H), 1.45–1.60 (m, 2H), 2.18 (s, 6H), 2.30 (s, 3H), 2.34 (s, 3H), 3.80 (brs, 2H), 3.1–3.30 (m, 4H), 5.95 (brs,1H), 6.92 (s, 2H) ppm.

2-Methyl-N,N'-bis-(2,4,6-trimethylphenyl)-pyrimidine-4,5,6-triamine:

$^1$H NMR (CDCl$_3$) δ 2.04 (brs, 2H), 2.21 (s, 12H), 2.22 (s, 3H), 2.30 (s, 6H), 6.30 (s, 2H), 6.92 (s, 4H) ppm.

6-(Ethyl-propyl-amino-2-methyl-9-(2,4,6-trimethylphenyl)-7,9-dihydropurin-8-one

A mixture of N-propyl-N-ethyl-2-methyl-N-(2,4,6-trimethylphenyl)-pyrimidine-4,5,6-triamine (120 mg, 0.35 mmol) and triethylamine (87 mg, 0.86 mmol) in 5 ml of dry tetrahydrofuran was treated with triphosgene (41 mg, 0.14 mmol) at 0° C. Precipitate formed immediately and the reaction mixture was warmed to room temperature. After stirring for 30 minutes the mixture was filtered. The filtrate was concentrated to dryness to give 125 mg (100%) of title compound of a greenish color. $^1$H NMR (CDCl$_3$) δ 0.90 (t, 3H), 1.21 (t, 3H), 1.65 (m, 2H), 2.10 (s, 6H), 2.34 (s, 3H), 2.39 (s, 3H), 3.48 (dd, 2H), 3.58 (q, 2H), 6.99 (s, 2H), 9.63 (s, 1H) ppm.

EXAMPLE 10

6-(Ethyl-propyl-amino-2,7-dimethyl-9-(2,4,6-trimethylphenyl)-7,9-dihydropurin-8-one A mixture of the title compound of Example 9 (54 mg, 0.15 mmol) in 3 ml of dry tetrahydrofuran was treated with sodium hydride (9 mg, 0.23 mmol, 60% in oil) at room temperature. The mixture was then treated with 0.02 ml of methyl iodide and stirred at room temperature overnight. The mixture was quenched with water and extracted with ethyl acetate. The organic layer was dried and concentrated to give 60 mg of brown oil. The oil was purified through silica gel column chromatography using chloroform as eluent to give 56 mg of the title compound as a yellow oil which crystallized on standing. $^1$H NMR (CDCl$_3$) δ 0.92 (t, 3H), 1.17 (t, 3H), 1.63 (m, 2H), 2.06 (s, 6H), 2.33 (s, 3H), 2.46 (s, 3H), 3.32 (dd, 2H), 3.40 (q, 2H), 3.63 (s, 3H), 7.00 (s, 2H) ppm.

EXAMPLE 11

The following compounds were prepared by the method of Example 10 by reacting the title compound of Example 9 with an appropriate alkyl iodide.

7-Ethyl-6-ethyl-propyl-amino)-2-methyl-9-(2,4,6-trimethylphenyl)-7,9-dihydropurin-8-one:

$^1$H NMR (CDCl$_3$) δ 0.92 (t, 3H), 1.14 (t, 3H), 1.23 (m, 3H), 1.58 (m, 2H), 2.04 (s, 6H), 2.31 (s, 3H), 2.45 (s, 3H). 3.32 (dd, 2H), 3.36 (q, 2H), 4.08 (q, 2H), 7.00 (s, 2H) ppm.

6-(Ethyl-propyl-amino)-2-methyl-7-propyl-9-(2,4,6-trimethylphenyl)7,9-dihydropurin-8-one:

$^1$H NMR (CDCl$_3$) δ 0.87 (t, 3H), 0.90 (t, 3H), 1.15 (t, 3H), 1.5–12.8 (m, 4H), 2.05 (s, 6H), 2.33 (s, 3H), 2.47 (s, 3H), 3.32 (dd, 2H), 3.38 (q, 2H), 4.01 (q, 2H), 7.00 (s, 2H) ppm.

EXAMPLE 12

[4-Chloro-2-methyl-6-(2,4,6-trimethylphenylamino)pyrimidin-5-yl]-acetic acid ethyl ester A mixture of (2-methyl-4,6-dichloro-pyrimidine-5-yl)-acetic acid ethyl ester (1.470 g, 5.9 mmol) and 2,4,6-trimethylaniline (2.56 ml, 17.7 mmol), in 15 ml of dimethylsulfoxide was heated at 120° C. overnight and 138° C. for 5 hours. The mixture was quenched with water and extracted with ethyl acetate. The organic layer was washed with brine, dried and concentrated to give a brown oil. The oil was purified through silica gel column chromatography to give 1.070 g (52%) of the title compound as a tan solid. $^1$H NMR (CDCl$_3$) δ 1.30 (t, 3H), 2.14 (s, 6H), 2.32 (s, 3H), 2.37 (s, 3H), 3.79 (s, 2H), 4.23 (q, 2H), 7.00 (s, 2H), 7.02 (s, 1H) ppm.

EXAMPLE 13

A. 4-Chloro-2-methyl-7-(2,4,6-trimethylphenylamino)-5,7-dihydro-pyrrolo[2,3-d]pyrimidin-6-one A mixture of the title compound of Example 12 (960 mg, 2.76 mmol) and p-toluene sulfonic acid (105 mg, 0.55 mmol) in 10 ml of toluene was heated at reflux under Dean-Stark trap for 8 hours. The mixture was quenched with water and extracted with ethyl acetate. The organic layer was washed with brine, dried and concentrated to give 800 mg of a brown mass which was purified through silica gel column chromatography to give 348 mg (42%) of the title compound as a yellow powder. $^1$H NMR (CDCl$_3$) δ 2.06 (s, 6H), 2.34 (s, 3H), 2.56 (s, 3H), 3.75 (s, 2H), 7.02 (s, 2H) ppm.

cl 4-(1-Hydroxymethyl-propylamino)-2-methyl-7-(2,4,6-trimethylphenyl)-5,7-dihydro-pyrrolo[2,3-d]pyrimidine-6-one A mixture of the compound prepared under A (168 mg, 0.557 mmol) and (S)$_2$-amino-butanol (0.27 ml, 2.78 mmol) in 5 ml of dimethyl sulfoxide was heated at 145° C. for 5 hours. The mixture was quenched with water and extracted with ethyl acetate. The organic layer was washed with brine, dried and concentrated to give an oil. The oil was purified through silica gel column chromatography, followed by recrystallization with diethyl ether to give 166 mg of the title compound as a grey solid.

$^1$H NMR (CDCl$_3$) δ 1.25 (t, 6H), 1.5–1.8 (m, 2H), 2.07 (s, 6H), 2.31 (s, 3H), 2.37 (s, 3H), 3.50 (s, 2H). 3.4-3.9 (m. 2H), 4.*(m, 1H), 4.*(d, 1H), 7.00 (s, 2H) ppm.

EXAMPLE 14

4-Diethylamino-2-methyl-7-(2,4,6-trimethylphenyl)-5,7-dihydro-pyrrolo[2,3-d]pyrrolo-pyrimidin-6-one The title compound was prepared by the method of Example 13-B with diethyl-amine instead of (S)-2-amino-butanol. $^1$H NMR (CDCl$_3$) δ 1.02 (t, 3H), 2.08 (s, 6H), 2.31 (s, 3H), 2.37 (s, 3H), 3.55 (q, 4H), 3.85 (s, 2H), 6.95 (s, 2H) ppm.

EXAMPLE 15

A. 4-Chloro-2,5,5-trimethyl-7-(2,4,6-trimethylphenylamino)-5,7-dihydro-pyrrolo[2,3-d]pyrimidin-6-one and 4-Chloro-2,5-dimethyl-7-(2,4,6-trimethylphenyl)-5,7-dihydro-pyrrolo[2,3-d]pyrimidin-6-one A mixture of 4-chloro-2-methyl-7-(2,4,6-trimethylphenylamino)-5,7-dihydro-pyrrolo[2,3-d]pyrimidin-6-one (93 mg, 0.31 mmol) and sodium hydride (14 mg, 0.34 mmol, 60% in oil) in tetrahydrofuran (THF) was stirred for 5 minutes, then treated with an excess of methyl iodide and stirred for 1 hour. The mixture was quenched with water and extracted with ethyl acetate. The organic layer was washed with brine, dried and concentrated to give an oil. The oil was purified through silica gel column chromatography to give 32 mg of 4-chloro-2,5,5-trimethyl-7-(2,4,6-trimethylphenyl-amino)-5,7-dihydro-pyrrolo[2,3-d]pyrimidin-6-one and 64 mg of 4-chloro-2,5-dimethyl-7-(2,4,6-trimethyl)-phenylamino)-5,7-dihydro-pyrrolo[2,3-d]pyrimidin-6-one.

$^1$H NMR (CDCl$_3$) (4-chloro-2,5,5-trimethyl-7-(2,4,6-trimethylphenylamino)-5,7-dihydro-pyrrolo[2,3-d]pyrimidin-6-one) δ 1.61 (s, 6H), 2.03 (s, 6H), 2.32 (s, 3H), 2.53 (s, 3H), 7.00 (s, 2H) ppm.

$^1$H NMR (CDCl$_3$) (4-chloro-2,5-dimethyl-7-(2,4,6-trimethylphenylamino)-5,7-dihydro-pyrrolo[2,3-d]pyrimidin-6-one) δ 1.65 (d, 2H), 2.03 (s, 3H), 2.06 (s, 3H), 2.34 (s, 3H), 2.56 (s, 3H), 3.72 (q, 1H), 7.00 (s, 2H) ppm.

B. 4-(1-hydroxymethyl-propylamino)2,5,5-trimethyl-7-(2,4,6-trimethylphenyl)5,7-dihydro-pyrrolo[2,3-d]pyrimidin-6-one The title compound was prepared by the method of Example 13-B from 4-chloro-2,5,5-trimethyl-7-(2,4,6-trimethylphenylamino)-5,7-dihydro-pyrrolo[2,3-d]pyrimidin-6-one) and (S)-2-amino-butanol in dimethylsulfoxide at 140-C. $^1$H NMR (CDCl$_3$) δ 1.02 (t, 3H), 1.53 (s, 6H), 1.5–1.8 (m, 2H), 2.04 (s, 6H), 2.32 (s, 3H), 2.38 (s, 3H), 3.6–3.9 (m, 2H), 4.0 (m, 1H), 4.5 (d, 1H), 5.25 (brs, 1H), 7.00 (s, 2H) ppm.

EXAMPLE 16

5-Hydroxy-4-(1-hydroxymethylpropylamino)2,5-dimethyl-72,4,6-trimethyl-phenyl)5,7-dihydro-pyrrolo[2,3 d]pyrimidin-6-one The title compound was prepared by the method of Example 13-B from 4-chloro-2,5-dimethyl-7-(2,4,6-trimethylphenylamino)5,7-dihydropyrrolo[2,3-d]pyrimidin-6-one) and (S)-2-amino-butanol in dimethylsulfoxide (DMSO) at 140° C. Two diastereomers were obtained. The spectra for both diastereomers are shown below:

One isomer: $^1$H NMR (CDCl$_3$) δ 1.03 (t, 3H), 1.55–1.75 (m, 2H), 1.77 (s, 3H), 2.05 (s, 3H), 2.07 (s, 3H), 2.32 (s, 3H), 2.37 (s, 3H), 3.55–3.85 (m, 2H), 4.0 (m, 1H). 5.1 (d, 1H), 5.3 (brs, 1H), 7.00 (s, 2H) ppm.

The other isomer: $^1$H NMR (CDCl$_3$) δ 103 (t, 3H), 1.55–1.75 (m, 2H), 1.73 (s, 3H), 2.02 (s, 3H), 2.05 (s, 3H), 2.32 (s, 3H), 2.36 (s, 3H), 3.58 (dd, 1H), 3.77 (dd, 1H), 4.1 (m, 1H), 5.03 (d, 1H), 7.00 (s, 2H) ppm.

EXAMPLE 17

5-Methoxy-4-butyl-ethyl-amino)-2,5-methyl-7-(2,4,6-trimethylphenyl)-5,7-hydro-pyrrolo[2,3-d]pyrimidin-6-one 5-Hydroxy 4(butyl-ethyl-amino)2,5-dimethyl-7-(2,4,6-trimethylphenyl)-5,7-dihydro-pyrrolo[2,3-d]pyrimidin-6-one was prepared by the method analogous to that of Example 16 starting with 4-chloro-2,5-dimethyl-7-(2,4,6-trimethylphenylamino)5,7-dihydro-pyrrolo[2,3-d]pyrimidin-6-one) and N-butyl-ethyl-amine in DMSO at 140° C. Methylation of 5-hydroxy-4-butyl-ethyl-amino)-2,5-dimethyl-7-(2,4,6-trimethylphenyl)-5,7-dihydro-pyrrolo[2,3-d]pyrimidin-6-one with sodium hydride and methyl iodide using the method of Example 10 provides the title compound. $^1$H NMR (CDCl$_3$) δ 6.97 (d, 2H), 3.54.0 (m, 4H), 3.23 (s, 3H), 2.34 (s, 3H), 2.32 (s, 3H), 2.12 (s, 3H), 2.03 (s, 3H), 1.69 (s, 3H), 1.61.8 (m, 2H), 1.3–1.5 (m, 2H), 1.24 (t, 3H), 0.99 (t, 3H) ppm.

EXAMPLE 18

4-(Butyl-ethyl-amino)-2-methyl-7-(2,4,6-trimethylphenyl)-5,7-dihydropyrrolo[2,3-d]pyrimidinone The title compound was prepared by the method analogous to that of Example 13 (B) starting with 4-chloro-2- methyl-742,4,6-trimethylphenylamino)-5,7-dihydro-pyrrolo [2,3-d]pyrimidin-6-one) and N-butyl-ethyl-amine in DMSO at 135° C. for 2.5 hours to give an oil. $^1$H NMR (CDCl$_3$) 7.00 (s, 2H), 3.85 (s, 2H), 3.62 (q, 2H), 3.53 (t. 2H), 2.35 (s, 3H), 2.32 (s, 3H), 2.10 (s, 3H), 1.55–1.70 (m, 2H), 1.35–1.50 (m, 2H), 1.25 (t, 3H), 1.00 (t. 3H) ppm.

EXAMPLE 19

4-(Butyl-ethyl-amino)-2,5-dimethyl-7-(2,4,6-trimethylphenyl)-5,7-dihydro-pyrrolo[2,3-d] pyrimidin-6-one A solution of 4-butyl-ethyl-amino)-2-methyl-7-(2,4,6-trimethylphenyl)5,7-dihydro-pyrrolo[2,3-d]pyrimidin-6-one (285 mg, 0.78 mmol) in 5 ml of dry THF was treated with lithium bis(trimethylsilyl)amide (1.05 mmol) at −78° C. and stirred for 5 minutes. The mixture was quenched with methyl iodide (0.054 ml, 0.858 mmol) at −78° C. After stirring for 10 minutes, the mixture was warmed to 0° C. and stirred at that temperature for 20 minutes. The mixture was quenched with saturated ammonium chloride and extracted with ethyl acetate. The organic layer was washed with brine, dried and concentrated to give a purple form. The form was purified through silica gel column chromatography to give 4(butyl-ethyl-amino)2,5-dimethyl-7-(2,4,6-trimethylphenyl)5,7-dihydro-pyrrolo[2,3,4 pyrimidinone (120 mg) as a purple glass, 4-(butyl-ethyl-amino)-2,5,5-trimethyl-7-(2,4,6-trimethylphenyl)-5,7-dihydro-pyrrolo[2,3-d]pyrimidin-6-one (35 mg) as a purple glass, and 98 mg of a mixture of the two components as a purple glass.

$^1$H NMR (CDCl$_3$) (4-(butyl-ethyl-amino)-2,5,5-dimethyl-7-(2,4,6-trimethylphenyl)5,7-dihydro-pyrrolo[2,3-d]pyrimidin-6-one) δ 6.96 (s, 2H), 3.7–3.9 (m, 2H), 3.51 (q, 1H), 3.15–3.4 (m, 2H), 2.34 (s, 3H), 2.30 (s, 3H), 2.08 (s, 3H), 2.05 (s, 3H), 1.53 (d, 3H), 1.5–1.65 (m, 2H), 1.3–1.4 (m, 2H), 1.17 (t, 3H), 0.95 (t, 3H) ppm.

$^1$H NMR (CDCl$_3$) (4-(butyl-ethyl-amino)-2,5,5-trimethy-7-(2,4,6-trimethylphenyl)-5,7-dihydro-pyrrolo[2,3-d] pyrimidinone) δ 6.98 (s, 2H), 3.45 (q, 2H), 3.34 (t, 2H), 2.34 (s, 3H), 2.33 (s, 3H), 2.06 (s, 6H), 1.55–1.7 (m, 2H), 1.3–1.45 (m, 2H), 1.23 (t, 3H), 0.99 (t, 3H) ppm.

EXAMPLE 20

Butyl-[2,5-dimethyl-7-(2,4,6-trimethylphenyl)-6,7-dihydro-5H-pyrrolo[2,3-d]pyrimidin-4-yl]-ethyl-amine A solution of (4-butyl-ethyl-amino)-2,5-dimethyl-7-(2,4,6-trimethylphenyl)-5,7-dihydro-pyrrolo[2,3-]pyrimidin-6-one) (111 mg, 0.292 mmol) in dry THF was treated with lithium aluminum hydride at room temperature. The resulting mixture was heated at reflux for 5 hours. After standard work-up, 97 mg of crude material as an oil was obtained. The oil was purified through a chromatotron using 10% ethyl acetate in hexane as eluent to give butyl-42;5-dimethyl-7-(2,4,6-trimethylphenyl)6,7-dihydro-5H-pyrrolo [2,3-d]pyrimidin-4-yl]-ethylamine as a clear pale yellow oil. $^1$H NMR (CDCl$_3$) δ 6.91 (d, 2H), 3.7–3.9 (rm., 2H), 3.2–3.4 (m, 4H), 2.5 (q, 1H), 2.28 (s, 6H), 2.22 (s, 3H), 2.05 (s, 3H), 1.5–1.7 (m, 2H), 1.3–1.5 (m, 5H), 1.17 (t, 3H), 0.97 (t, 3H) ppm. High MS (C23H34N4) calc. 366.2776, found 366.27622.

EXAMPLE 21

4-(Butyl-ethyl-amino)-2,5,5-trimethyl-7-(2,4,6-trimethylphenyl)-6,7-dihydro-5H-pyrrolo[2,3-d] pyrimidin-6-ol The title compound was prepared by the method of Example 20 starting from (4-(butyl-ethyl-amino)-2,5,5-trimethyl-7-(2,4,6-trimethylphenyl)-5,7-dihydro-pyrrolo[2,3-d]pyrimidin-6-one) to give a pale yellow solid, mp 142-1450-C; $^1$H NMR (CDCl$_3$) δ 6.95 (d, 2H), 4.90 (s, 1H), 3.1–3.4 (m, 4H), 2.4 (brs, 1H), 2.33 (s, 3H), 2.31 (s. 3H), 2.21 (s, 3H), 2.17 (s, 3H), 1.50 (s, 3H), 1.45 (s, 3H), 1.25–1.60 (m, 4H), 1.11 (t, 3H), 0.93 (t, 3H) ppm.

EXAMPLE 22

Butyl-ethyl-[6-methoxy-2,5,5-trimethyl-7-(2,4,6-trimethylphenyl)-6,7-dihydro-5H-pyrrolo[2,3-d]pyrimidin-4-yl]-amine To a solution of 4-(butyl ethyl-amino)-2,5,5-trimethyl-7-(2,4,6-trimethylphenyl)6,7-dihydro-5H-pyrrolo[2,3-d] pyrimidin-6-ol)(20 mg, 0.05 mmol) in 1 ml of dry THF was treated with sodium hydride (60% in oil, 4 mg, 0.1 mmol) and then methyl iodide (0.3 ml) was added at room temperature. After stirring at room temperature for 2.5 hours, the mixture was quenched with saturated ammonium chloride and extracted with ethyl acetate. The organic layer was washed with brine, dried and concentrated to give 26 mg of crude material. After silica gel column purification with 10% ethyl acetate in hexane, 19 mg of a colorless oil of the title compound was obtained. $^1$H NMR (CDCl$_3$) δ 6.92(s, 1H), 6.89 (s, 1H), 4.48 (s, 1H), 3.1–3.3 (m, 4H), 3.11 (s, 3H), 2.32 (s, 3H), 2.28 (s, 3H), 2.20 (s, 3H), 2.19 (s, 3H), 1.45 (s, 3H), 1.44 (s, 3H), 1.4–1.52 (m, 2H), 1.2–1.4 (m, 2H), 1.10 (t, 3H), 0.90 (t, 3H) ppm.

EXAMPLE 23

4-(Butyl-ethyl-amino)-2-methyl-7-(2,4,6-trimethylphenyl)-7H-pyrrolo[-2,3-d]pyrimidine-5,6-dione To a solution of 4(butyl-ethyl-amino)-2-methyl-7-(2,4,6-trimethylphenyl)-5,7-dihydro-pyrrolo[2,3-d]pyrimidin-6-one (76 mg, 0.207 mmol), POCl$_3$ (0.039 ml, 0.415 mmol), triethylamine (0.059 ml), and dimethylamine (1 ml) in 2 ml acetonitrile was heated at reflux for 1 hour. The mixture was quenched with water and extracted with ethyl acetate. The organic layer was dried and concentrated to give a brown form (105 mg). After silica gel column chromatography, the title compound was isolated as a yellow glass (10 mg). $^1$H NMR (CDCl$_3$) δ 7.00 (s, 2H), 3.95–4.15 (m, 2H), 3.653.85 (m, 2H), 2.38 (s, 3H), 2.32 (s, 3H), 2.10 (s, 6H), 1.55–1.75 (m, 2H), 1.35–1.55 (m, 2H), 1.25 (t, 3H), 1.00 (t, 3H) ppm.

EXAMPLE 24

N-Butyl-N-ethyl-2,5,N'-trimethyl-N'-(2,4,6-trimethylphenyl)-pyrimidine-4,6-diamine A mixture of (6-chloro-2,5-dimethyl-pyrimidin-4-yl)-methyl-2,4,6-trimethylphenyl)-amine (200 mg) and N-butyl-ethylamine (0.3 ml) in 1 ml of DMSO was heated in oil bath of 160° C. for 15 hours. The mixture was quenched with water and extracted with ethyl acetate. The organic layer was separated, dried and concentrated to give the crude material. After silica gel column purification using chloroform as eluent, the tide compound was obtained as an oil. $^1$H NMR (CDCl$_3$) δ 6.83 (s, 2H), 3.22 (s, 3H), 3.12 (m, 4H), 2.44 (s, 3H), 2.26 (s, 3H), 2.01 (s, 6H), 1.35–1.42 (m, 2H), 1.1–1.25(m, 2H), 1.00 (t, 3H), 0.90 (t, 3H) ppm.

EXAMPLE 25

[2,5-Dimethyl-6-(tetrahydrofuran-3-yloxy)-pyrimidin-4-yl-(2,4,6-trimethylphenyl)-amine A mixture of 3-hydroxy-tetrahydrofuran (0.5 ml) and sodium hydride (60% in oil, 53 mg, 1.33 mmol) in dry THF was stirred at room temperature for 5 minutes, (6-chloro-2, 5-dimethyl-pyrimidin-4-yl)-2,4,6-trimethylphenyl)amine (107 mg, 0.388 mmol) was added. The mixture was heated at reflux for 15 hours. The mixture was quenched with water and extracted with ethyl acetate. The organic layer was separated, dried and concentrated to give a yellow oil. The oil was purified through silica gel column chromatography using 20% ethyl acetate in hexane as eluent to give 48 mg of the tide compound as off-white crystals, mp 126-128-C. $^1$H NMR (CDCl$_3$) δ 6.89 (s, 2H), 5.60 (brs, 2H), 3.8–4.0 (m, 4H), 2.27 (s, 6H), 2.13 (s, 6H), 2.1–2.25 (m, 2H), 1.93 (s, 3H) ppm.

EXAMPLE 26

2-(S)-[2,5-Dimethyl-6-(2,4,6-trimethyl-phenoxy) pyrimidin-4-ylamino]-butan-ol

A mixture of 4-chloro-2,5-dimethyl 62,4,6-trimethyl-phenoxy)-pyrimidine (30 mg) and 2-(S)amino-1-butanol (0.5 ml) in 0.5 ml of DMSO was heated at 130° C. for 4 hours. The mixture was quenched with water and extracted with ethyl acetate. The organic layer was separated, dried and concentrated to give a crude material. The crude residue was purified through silica gel column chromatography to give 24 mg of the title compound as white crystals. High MS for (C$_{19}$H$_{27}$N$_3$O$_2$) calc. 329.2103, found 329.21249; IR(KBr) 3400, 2940, 1580 cm-1; $^1$H NMR (CDCl$_3$) δ 6.841 (s, 2H), 5.72 (brs, 1H), 4.45 (d, 1H), 3.82–3.96 (m, 1H), 3.72–3.9 (m, 1H), 3.5–3.6 (m, 1H), 227 (s, 3H), 2.21 (s, 3H), 2.08 (s, 3H), 2.02 (s, 6H), 1.4–1.7 (m, 2H), 1.03 (t, 3H) ppm.

EXAMPLE 27

4-(1-Ethyl-propoxy) 2,5-dimethyl-6(2,4,6-methyl-phenoxy)-pyrimidine

A mixture of 3-pentanol (0.3 ml) and sodium hydride (60% in oil, 32 mg, 0.81 mmol) in DMSO was stirred at room temperature for 5 minutes. 4-Chloro-2,5-dimethyl(2,4,6-trimethyl-phenoxy)-pyrimidine (150 mg, 0.54 mmol) was added and the resulting mixture was heated at 150° C. for 5 hours. The mixture was quenched with water and extracted with ethyl acetate. The organic layer was separated, dried and concentrated to give a beige solid. The solid was purified through silica gel column chromatography using 20% chloroform in hexane as eluent to give the title compound as white crystals, mp 93.595.5° C. $^1$H NMR (CDCl$_3$) δ 6.85 (s, 2H). 5.11 (t, 1H), 2.27 (s, 3H), 2.26 (s, 3H), 2.11 (s, 3H), 2.03 (s, 6H), 1.68 (p. 4H), 0.92 (t, 6H) ppm.

EXAMPLE 28

[[6-(Butyl-N-ethylamino)-2-methyl-pyrimidin-4-yl]-(2,4,6-trimethylphenyl)-amino]-acetic acid ethyl ester A mixture of [(6-chloro-2-methyl-pyrimidin-4-yl)(2,4,6-trimethylphenyl)-amino]-acetic acid ethyl ester (85 mg, 0.244 mmol) and N-butyl-ethylamine (0.17 ml, 1.1 mmol) in 4 ml DMSO was heated at 135° C. for 15 hours. An additional 1 ml of N-butylethylamine was added and the reaction was heated at that temperature for an additional 15 hours (tlc showed no starting material). The mixture was quenched with water and extracted with ethyl acetate. The organic layer was separated, dried and concentrated to give 123 mg of a light amber oil. The oil was purified through silica gel chromatotron using 5% ethyl acetate in hexane as eluent to give 92 mg (91%) of the title compound as a white glass. $^1$H NMR (CDCl$_3$) δ 6.94 (s, 2H), 4.69 (s, 1H), 4.23 5,<; (s, 2H), 4.22 (q, 2H), 3.35 (q, 2H), 3.15 (t, 2H), 2.36 (s, 3H), 2.31 (s, 3H), 2.21 (s, 6H). 1.3-1.5 (m, 2H), 1.34 (tL 3H), 1.1–1.3 (m, 2H), 1.01 (t. 3H), 0.80 (t, 3H) ppm.

EXAMPLE 29

4-(1-Ethyl-propoxy)3,6-dimethyl-2-(2,4,6-trimethyl-phenoxy)-pyridine

To a solution of 3-pentanol (0.2 ml, 0.5205 mol) in DMSO (1 ml) was added 60% sodium hydride in oil (30 mg) in a portionwise. After stirring at room temperature for 5 min. a solution of 4-chloro-2,5-dimethyl-6-(2,4,6-trimethyl-phenoxy)pyridine (98 mg) in 0.5 ml of dry THF was added and the resulting mixture was heated at 130° C. for 5 hours. The mixture was quenched with water and extracted with ethyl acetate. The organic layer was separated, dried and concentrated to give a yellow solid. The solid was purified through silica gel column chromatography using 20% chloroform in hexane to chloroform as eluent to give 7 mg of the title compound as white crystals, mp 72.5–74° C. $^1$H NMR (CDCl$_3$) δ 6.84 (s, 2H), 6.26 (s, 1H), 4.16 (m, 1H), 2.27 (s, 3H), 2.17 (s, 6H). 2.04 (s, 6H), 1.69 (m, 4H), 0.95 (t, 6H) ppm.

The mesylate salt of 4-(1-ethyl-propoxy)-3,6-dimethyl-2,4,6-trimethyl-phenoxy)-pyridine was prepared by addition of 1 equivalent of methanesulfonic acid in ethyl acetate. The white crystals formed from ethyl acetate. Mp 117–119° C.

EXAMPLE 30

[6-(Butyl-ethyl-amino)-2,5-dimethylpyrimidin-4-yl]-(2,4,6-trimethylphenyl)-acetonitrile A solution of mesitylacetonitrile (66 mg, 0.41 mmol) in 1 ml of DMSO was treated with NaH (60% in oil, 20 mg, 0.50 mmol) and stirred at room temperature for 20 minutes, butyl-6-chloro-2,5-dimethylpyrimidin-4-yl)-ethylamine (100 mg, 0.414 mmol) was added and the resulting mixture was heated at 130° C. for 15 hours. The mixture was quenched with water and extracted with ethyl acetate. The organic layer was separated, dried and concentrated to give 160 mg of brown oil. The oil was purified through silica gel column chromatography using 5% ethyl acetate in hexane as eluent to give the title compound as a brown oil. $^1$H NMR (CDCl$_3$) δ 6.83 (s, 2H), 5.49 (s, $^1$H), 3.2–3.4 (m, 2H), 3.0–3.2 (m, 2H), 2.51 (s, 3H), 2.24 (s, 3H), 2.21 (s, 6H), 1.66 (s, 3H), 1.35–1.50 (m, 2H), 1.1–1.3 (m, 2H), 1.05 (t, 3H), 0.84 (t. 3H) ppm.

EXAMPLE 31

2-[6-(1-Ethyl-propoxy)2.5-dimethylpyrimidin-4-yl]-2-(2,4,6-trimethylphenyl)-propionitrile To a solution of 3-pentanol (140 mg, 1.59 mmol) in 2 ml of dry THF was added sodium hydride (60% in oil, 38 mg) and the mixture was stirred at room temperature for 5 minutes. 2-(6-Chloro-2,5-dimethylpyrimidin-4-yl)22,4,6-trimethylphenyl)-propionitrile (100 mg, 0.319 mmol) was added to the reaction mixture, and the resulting mixture was heated at reflux for 4 hours. The mixture was quenched with water and extracted with ethyl acetate. The organic layer was separated, dried and concentrated to give a brown oil (170 mg). The residue was purified through chromatotron using 20% ethyl acetate in hexane as eluent to give a mixture of two isomers as a yellow glass form and both having a M+of 365 from GC/Ms. $^1$H NMR (CDCl$_3$) δ 6.8 and 6.76 (s, 2H), 4.08 and 3.96 (m, 1H), 3.25 and 3.22 (s, 3H), 2.36 and 2.30 (s, 3H), 2.21, 2.20 and 2.06 (s, total of 9H), 1.5–1.7 (m, 4H), 1.04 (s, 3H), 0.96 and 0.90 (t, 3H) ppm.

EXAMPLE 32

4-(1-Ethyl-propoxy)-2,5-dimethyl-6-(2,4,6-trimethylbenzyl)-pyrimidine

The title compound was prepared by the method analogous to that in Example 32 starting with 4-Chloro-2,5-dimethyl-6-(2,4,6-trimethyl-benzyl)pyrimidine and 3-pentanol. White crystals, mp. 82–84° C.

The title compounds of Example 33–39 were prepared by a method analogous to that of Example 27, starting with the appropriate 4-chloro-2-methyl-5-substituted 6-substituted-phenoxy)-pyrimidine and 3-pentanol.

EXAMPLE 33

4-(2,4-Dimethylphenoxy)(1-ethyl-propoxy),2,5-dimethyl-pyrimidine $^1$H NMR (CDCl$_3$) δ 6.8–7.0 (m, 3H), 5.13 (m, 1H), 2.30 (s, 6H), 2.10 (s, 3H), 2.09 (s, 3H), 1.68 (m, 4H), 0.92 (t, 6H) ppm.

EXAMPLE 34

4-(2,6-Dimethyl-phenoxy)-6-(1-ethyl-propoxy)2,5-dimethyl-pyrimidine $^1$H NMR (CDCl$_3$) δ 7.04 (m, 3H), 5.12 (m, 1H), 2.25 (s, 3H), 2.13 (s, 3H), 2.07 (s, 6H), 1.66 (m, 4H), 0.92 (t, 6H) ppm.

EXAMPLE 35

4-(1-Ethyl-propoxy)-2-methyl-B-(2,4,6-trimethyl-phenoxy)-pyrimidine-5-carbonitrile mp 128–130° C., $^1$H NMR (CDCl$_3$) δ 6.8 (s, 2H), 5.18 (m, 1H), 2.30 (s, 3H), 2.21 (s, 3H), 2.00 (s, 6H), 1.4–1.58 (m, 4H), 0.90 (t, 6H) ppm.

EXAMPLE 36

5-tert-Butyl-4-(1-ethyl-propoxy)-2-methyl(2,4,6-trimethyl-phenoxy)pyrimidine $^1$H NMR (CDCl$_3$) δ 6.85 (s, 2H), 5.25 (m, 1H), 2.29 (s. 3H), 2.20 (s, 3H), 2.03 (s, 6H), 1.65–1.80 (m, 4H), 1.52 (s, 9H), 0.90 (t, 6H) ppm.

EXAMPLE 37

4(1-Ethyl-propoxy)-5-isopropyl-2-methyl-6-(2,4,6-trimethyl-phenoxy)-pyrimidine $^1$H NMR (CDCl$_3$) δ 6.85 (s, 2H), 5.17 (m, 1H), 3.50 (m, 1H), 2.27 (s, 3H), 2.23 (s, 3H), 2.03 (s, 6H), 1.69 (m, 4H), 1.33 (s, 3H), 1.31 (s, 3H), 0.92 (t. 6H) ppm.

EXAMPLE 38

5-Bromo-4-(1-ethyl-propoxy)-2-methyl-6-(2,4,6-trimethyl-phenoxy)-pyrimidine $^1$H NMR (CDCl$_3$) δ 6.86 (s, 2H), 5.16 (m, 1H), 2.29 (s, 3H), 2.28 (s, 3H), 2.06 (s, 6H), 1.65–1.80 (m, 4H), 1.52 (s, 9H), 0.95 (t, 6H) ppm.

EXAMPLE 39

5-Chloro-4-(1-ethyl-propoxy)-2-methyl-6-(2,4,6-trimethyl-phenoxy)pyrimidine $^1$H NMR (CDCl$_3$) δ 6.86 (s, 2H), 5.16 (m, 1H), 2.28 (s, 3H), 2.27 (s, 3H), 2.06 (s, 6H), 1.65–1.80 (m, 4H), 1.52 (s, 9H), 0.94 (t, 6H) ppm.

The title compounds of Examples 40–41 were prepared by a method analogous to that described in Example 24, starting from 4-chloro-2,5-dimethyl-6-(2,4,6-trimethyl-phenoxy) pyrimidine and the appropriate amine.

EXAMPLE 40

[2,5-Dimethyl-6-(2,4,6-trimethyl-phenoxy)pyrimidin-4-yl](1-ethyl-propyl)-amine $^1$H NMR (CDCl$_3$) δ 6.84 (s, 2H), 4.10 (m, 2H, NH and CH), 2.27 (s, 3H), 2.21 (s, 3H), 2.04 (s, 9H), 1.3–1.6 (m, 4H), 0.91 (t, 6H) ppm.

EXAMPLE 41

Butyl-[2,dimethyl-6-(2,4,6-trimethyl-phenoxy)pyrimidin-4-yl]-ethyl-amine

1H NMR (CDCl$_3$) δ6.87 (s, 2H), 3.76 (m, 2H), 3.68 (t, 2H), 2.73 (s, 3H), 2.28 (s, 6H), 1.99 (s, 6H), 1.51.7 (m, 4H), 1.27 (t, 3H), 0.94 (t, 3H) ppm.

The title compounds of Examples 42–54 were prepared by a method analogous to that described in Example 29, starting with the appropriate 4-chloro-2-methyl-6-substituted phenoxy or thiophenoxy)-pyridine and the appropriate alcohol.

EXAMPLE 42

2-(4-Bromo-2,6-dimethyl-phenoxy)-4-(1-ethyl-propoxy)-3,6-dimethyl-pyridine $^1$H NMR (CDCl$_3$) δ 7.18 (s, 2H), 6.30 (s, 1H), 4.22 (m, 1H), 2.20 (s, 6H), 2.05 (s, 6H), 1.73 (m. 4H), 1.00 (t, 6H) ppm.

EXAMPLE 43

2-(4-Chloro-2,6-dimethyl-phenoxy)-4-(1-ethyl-propoxy)-3,6-dimethyl-pyridine $^1$H NMR (CDCl$_3$) δ 7.05 (s, 2H), 6.31 (s, 1H), 4.20 (m, 1H), 2.20 (s, 6H), 2.08 (s, 6H), 1.73 (m, 4H), 0.99 (t, 6H) ppm.

EXAMPLE 44

3-Ethyl-4-(1-ethyl-propoxy)-6-methyl-2-(2,4,6-trimethyl-phenoxy)-pyridine $^1$H NMR (CDCl$_3$) δ 6.85 (s, 2H), 6.26 (s, 1H), 4.18 (m, 1H), 2.73-(q,2H), 2.28 (s, 3H), 2.17 (s, 3H), 2.05 (s, 6H), (m, 4H), 1.18 (t, 3H), 0.96 (t, 6H) ppm.

EXAMPLE 45

4-(1-ethyl-propenyloxy)-3,6-dimethyl-2-(2,4,6-trimethyl-phenoxy)pyridine (A mixture of cis and trans isomers) 115 $^1$H NMR (CDCl$_3$) δ 6.85 (s, 2H), 6.30 (s, 0.3H), 6.21 (s, 0.7H), 5.10 (m, 0. H), 4.95 (m, 0.3H), 2.27 (s, 3H), 2.24 (s, 2.1H), 2.19 (s, 0.9H), 2.14 (s, 3H), 2.05 (s, 6H), 1.65 (d, 0.9H), 1.50 (d, 2.1H), 1.08 (t, 1.8H), 1.05 (t, 4.2H) ppm.

EXAMPLE 46

Methanesulfonic acid salt of 4-(1-ethyl-propoxy y2,3,5-trimethyl-6-(2,4,6-trimethyl-phenoxy)-pyridine Mp 58–60° C. $^1$H NMR (CDCl$_3$) δ 6.90 (s, 2H), 4.20 (m, 1H), 2.70 (s, 3H), 2.61 (s, 3H), 2.28 (s, 3H), 2.16 (s, 3H), 2.08 (s, 6H), 1.5–1.8 (m, 4H), 096 (t, 6H) ppm.

EXAMPLE 47

4-(1-Ethyl-propoxy)methyl-2-(2,4,6-trimethyl-phenoxy) nicotinic acid methyl ester $^1$H NMR (CDCl$_3$) δ 6.84 (s, 2H). 6.39 (s, 1H), 5.04 (m, 1H), 3.85 (s, 3H), 2.27 (s. 3H), 2.23 (s, 3H), 2.05 (s, 6H), 1.5–1.7 (m, 4H), 0.95 (s, 6H) ppm.

EXAMPLE 48

4-(1-Ethyl-propoxy)-2-methyl-642,4,6-trimethyl-phenoxy)-pyridine $^1$H NMR (CDCl$_3$) δ 6.90 (s, 2H), 6.34 (d, J=2 Hz, 1H), 5.70 (d, J=2 Hz, 1H), 4.05 (m, 1H), 2.40 (s, 3H), 2.30 (s, 3H), 2.11 (s, 6H), 1.62 (m. 4H), 0.89 (t, 6H) ppm.

EXAMPLE 49

3,6-Dimethyl-4-(tetrahydro-furan-3-yloxy)-2-(2,4,6-trimethyl-phenoxy)pyridine $^1$H NMR (CDCl$_3$) δ 6.88 (s, 2H), 6.25 (s, 1H), 4.99 (m, 1H), 3.94.1 (m, 4H), 2.31 (s, 3H), 2.23 (s, 3H), 2.20 (s, 3H), 2.1–2.3 (m, 2H), 2.07 (s, 6H) ppm.

EXAMPLE 50

4-(1-Methoxymethyl-propoxy)3,6-dimethyl-2-(2,4,6-trimethyl-phenoxy)-pyridine $^1$H NMR (CDCl$_3$) δ 6.88 (s, 2H), 6.38 (s, 1H), 4.42 (m, 1H), 3.5–3.7 (m, 2H), 3.42 (s, 3H), 2.31 (s, 3H), 2.21 (s. 6H), 2.07 (s, 6H), 1.7–1.85 (m, 2H), 1.02 (t, 3H) ppm.

EXAMPLE 51

3-[3,6-Dimethyl-2-(2,4,6-trimethyl-phenoxy)-pyridin-4-pentan-2-ol $^1$H NMR (CDCl$_3$) δ 6.88 (s, 2H), 6.34 (s, 1H), 4.25–4.45 (m, 1H0, 3.6–3.8 (m, $^1$H), 2.30 (s, 3H)2.21 (s, 3H), 2.20 (s, 3H), 2.06 (s, 6H), 1.2–1.4 (m, 5-HO, 1.07 (t, 3H) ppm.

EXAMPLE 52

4-sec-Butoxy-3,6-dimethyl-2-(2,4,6-trimethyl-phenoxy)-pyridine $^1$H NMR (CDCl$_3$) δ 6.88 (s, 2H), 6.31 (s, 1H), 4.35 (m, 1H), 2.30 (s, 3H), 2.21 (s, 3H), 2.19 (s, 3H), 2.07 (s, 6H0, 1.7-1.9 (m, 2H), 1.34 (d, 3H), 1.01 (t, 3H) ppm.

EXAMPLE 53

2-(2,4-Dimethyl-phenylsulfanyl)-4-(1-ethyl-propoxy)-3,6-dimethyl-pyridine

Golden oil. $^1$H NMR (CDCl$_3$) δ7.19 (d, j=8 Hz, 1 H0, 7.06 (s, 1H), 6.94 (d, J=8 Hz, 1H), 6.42 (s, 1H), 4.19 (m, 1H), 2.34 (s, 3H), 2.33 (s, 3H), 2.32 (s, 3H), 2.18 (s, 3H), 1.69 (m, 4H), 0.95 (t, 6H) ppm.

EXAMPLE 54

4-(1-Ethyl-propoxy)3,6-dimethyl-2-(2,4,6-trimethyl-phenylsulfanyl)pyridine $^1$H NMR (CDCl$_3$) δ 6.97 (s, 2H), 6.30 (s, 1H), 4.15 (m, 1H), 2.35 (s, 6H), 2.30 (s, 3H), 2.23 (s, 3H), 2.20 (s, 3H), 1.68 (m, 4H), 0.95 (t, 6H) ppm.

EXAMPLE 55

2-(4-Ethyl-2,6-dimethyl-phenoxy)-4-(1-ethyl-propoxy)-3,6-dimethyl-pyridine

To a solution of 2.5 N n-BuLi in hexane (0.47 ml, 1.18 mmol) in. 5 ml of dry THF was added a solution of 244-bromo-2,6-dimethyl-phenoxy-4 ]-ethyl-propoxy)3,6-dimethyl-pyridine (465 mg, 1.18 mmol) in 5 ml of dry THF at −78° C. After stirring at that temperature for 5 min, an excess of ethyl iodide (0.4 ml) was added and the resulting mixture was stirred at −78° C. for 30 min, then at 0° C. for 15 min. The mixture was quenched with saturated ammonium chloride and extracted with ethyl acetate. The organic layer was dried and concentrated to give a light brown oil. The oil was purified through silica gel column chromatography using chloroform as eluent to give 260 mg of the title compound as white solid. $^1$H NMR (CDCl$_3$) δ 6.90 (s, 2H), 6.38 (s, 1H), 4.20 (m, 1H), 2.61-(q, 2H), 2.24 (s, 3H), 2.21 (s, 3H), 2.10 (s, 6H), 1.70 (m, 4H), 1.30 (t, 3H), 0.98 (t, 6H) ppm.

The title compounds of Examples 56–62 were prepared by a method analogous to that described in Example 55, starting from n-BuLi and 2-(4-bromo-2,6-dimethyl-phenoxy)-4-ethyl-propoxy)-3,6-dimethyl-pyridine, followed by quenching with an appropriate electrophile.

EXAMPLE 56

4-[4-(1-Etyl-propoxy) 3,6-dimethyl-pyridin-2-yloxy]-3,5-dimethyl-benzaldehyde $^1$H NMR (CDCl$_3$) δ 9.94 (s, 1H), 7.61 (s, 2H), 6.32 (s, 1H), 4.20 (m, 1H), 2.21 (s, 3H), 2.16 (s, 9H)1.70 (m, 4H), 0.98 (t, 6H) ppm.

EXAMPLE 57

2-(2,6-Dimethyl-4-propyl-phenoxy)-4-(1 ethyl-propoxy)-3,6-dimethyl-pyridine $^1$H NMR (CDCl$_3$) δ 6.88 (s, 2H), 6.30 (s, 1H), 4.20 (m, 1H), 2.54-(dd, 2H), 2.22 (s, 3H), 2.20 (s, 3H), 2.09 (s, 6H), 1.6–1.8 (m, 6H), 0.9–1.1 (m, 9H) ppm.

EXAMPLE 58

2-(2,6-Dimethyl-phenoxy)-4-(1-ethyl-propoxy)3,6-dimethyl-pyridine $^1$H NMR (CDCl$_3$) δ 7.06 (m, 3H), 6.30 (s, 1H), 4.20 (m, 1H), 2.21 (s, 6H), 2.11 (s, 6H), 1.73 (m, 4H), 0.99 (t, 6H) ppm.

EXAMPLE 59

2{4-[41-(1-Ethyl-propoxy)-3,6-dimethyl-pyridin-2-yloxy]-3,5-dimethyl-phenyl}propan-2 ol $^1$H NMR (CDCl$_3$) δ 7.15 (s, 2H), 6.25 (s, 1H), 4.20 (m, 1H), 2.20 (s,3H), 2.19 (s, 0.3H), 2.10 (s, 6H), 1.85 (brs, 1H), 1.70 (m, 4H), 1.60 (s, 6H), 0.95 (t, 6H) ppm.

EXAMPLE 60

4-(1-Ethyl-propoxy)-2-(4-iodo-2,6-dimethyl-phenoxy)-3,6-dimethyl-pyridine $^1$H NMR (CDCl$_3$) δ 7.39 (s, 2H), 6.30 (s, 1H), 4.19 (m, 1H), 2.20 (s, 3H), 2.18 (s, 3H), 2.05 (s, 6H), 1.72 (m, 4H), 0.98 (t, 6H) ppm.

EXAMPLE 61

4-[4-(1-Ethyl-propoxy)3,6-dimethyl-pyridin-2-yloxy]-3,5-dimethyl-phenol $^1$H NMR (CDCl$_3$) δ 7.85 (brs, 1H), 6.36 (s, 1H), 6.24 (s, 2H), 4.24 (m, 1H), 2.39 (s, 3H), 220 (s, 3H), 2.02 (s, 6H), 1.74 (m, 4H), 1.00 (t, 6H) ppm.

EXAMPLE 62

1{-4-[4-(1-Ethyl-propoxy)-3,6-dimethyl-pyridin-2-yloxy]-3,5-dimethyl-phenyl}-pyrrolidin-2-one $^1$H NMR (CDCl$_3$) δ 7.30 (s, 2H), 6.30 (s, 1H), 4.20 (m, 1H), 3.88 (t, 2H), 2.61 (t, 2H) ppm.

EXAMPLE 63

{4-[4-(1-Ethyl-propoxy)-3,6-dimethyl-pyridin-2-yloxy]-3,5-dimethylphenyl}-methanol A mixture of 4-[4-(1-ethyl-propoxy)-3,6-dimethyl-pyridin-2-yloxy]-3,5-dimethyl-benzaldehyde (114 mg, 0.41 mmol) and sodium borohydride (63 mg, 1.6 mmol) in. 3 ml of methanol was stirred at room temperature for 2 hours. The reaction mixture was quenched with water and extracted with ethyl acetate. The organic layer was dried and concentrated to give yellow oil. The oil was purified through silica gel using chloroform as eluent to give 70 mg of the title compound as a colorless oil. $^1$H NMR (CDCl$_3$) δ 7.04 (s, 2H), 6.32 (s, 1H), 4.55 (s, 2H), 4.21 (m, 1H), 2.30 (brs, 1H), 2.22 (s, 3H), 2.21 (s, 3H), 2.12 (s, 6H), 1.73 (m, 4H), 0.91 (t, 6H) ppm.

EXAMPLE 64

4-(1-Ethyl-propoxy)-2-(4-methoxy-2,6-dimethyl-phenoxy)-3.6-dimethyl-pyridine

To a solution of 4-[4-(1-ethyl-propoxy)-3,6-dimethyl-pyridin-2-yloxy]-3,5-methyl-phenol (40 mg, 0.12 mmol) in 3 ml of dry THF was added 10 mg of 60% sodium hydride in oil at room temperature. After stirring for 5 min, 0.3 ml of methyl iodide was added and the resulting mixture was stirred at room temperature overnight. The mixture was quenched with water and extracted with ethyl acetate. The organic layer was dried and concentrated to give a yellow solid. The solid was purified through silica gel column chromatography using hexane to 1:1 chloroform:hexane as eluent to yield 20 mg of the title compound as yellow solid. $^1$H NMR (CDCl$_3$) δ 6.66 (s, 2H), 6.28 (s, 1H). 4.20 (m, 1H), 3.79 (s, 3H), 2.20 (s, 3H), 2.19 (s, 3H0, 2.08 (s, 6H), 1.71 (m, 4H), 0.97 (t, 6H) ppm.

EXAMPLE 65

4-(1-Ethyl-propoxy)-2-(4-isopropoxy-2.6-dimethyl-phenoxy)3,6-dimethyl-pyridine

To a solution of 4-[4-(1-ethyl-propoxy)-3,6-dimethyl-pyridin-2-yloxy]-3,5-dimethyl-phenol (58 mg, 0.176 mmol) in 3 ml of dry THF was added triphenylphosphine (70 mg, 0.264 mmol) and isopropanol (60 mg, 0.22 mmol). The resulting mixture was stirred at room temperature for 5 min. diethyl azodicarboxylate (46 mg, 0.264 mmol) was added. The mixture was stirred at room temperature overnight. An additional 20 mg of diethyl azodicarboxylate was added and the a mixture was stirred for an additional 4 hours. The mixture was quenched with water and extracted with methylene chloride. The organic layer was dried and concentrated to give an oil. The oil residue was purified through silica gel column chromatography using 1:1 hexane:chloroform to 1:2 hexane: chloroform as eluent to give 38 mg (58%) of the tithe compound as a colorless oil. $^1$H NMR (CDCl$_3$) δ6.60 (s, 2H), 6.28 (s, 1H), 4.50 (m, 1H), 4.18 (m, 1H), 2.20 (s, 3H), 2.19 (s, 3H), 2.079-s, 6H), 1.71 (m, 4H), 1.34 (d, 6H), 0.98 (t, 6H) ppm.

The title compounds of Examples 66–67 were prepared by a method analogous to that described in Example 64, starting with an appropriate pyridine-3,5-dimethylphenol or pyridine-3,5-dimethyl-phenyl methanol with a base, followed by quenching with an appropriate alkyl halide.

EXAMPLE 66

2-(4-Ethoxy-2,6-dimethyl-phenoxy)(1-ethyl-propoxy)-3,6-dimethyl-pyridine $^1$H NMR (CDCl$_3$) δ 6.60 (s, 2H), 6.28 (s, 1H), 4.19 (m, 1H), 3.99-(q, 2H), 2.19 (s, 3H), 2.18 (s, 3H). 2.07 (s, 6H), 1.74 (m, 4H), 1.40 (t, 3H), 0.97 (t. 6H) ppm.

EXAMPLE 67

4-(1-Ethyl-propoxy)-2-(4-methoxymethyl-2,6-dimethyl-phenoxy)-3,6-dimethyl-pyridine Mp 58–60° C. $^1$H NMR (CDCl$_3$) δ 7.05 (s, 2H), 6.30 (s, 1H), 4.41 (s, 2H), 4.19 (m, 1H), 3.42 (s. 3H), 2.21 (s, 3H), 2.18 (s, 3H), 2.11 (s, 6H), 1.72 (m, 4H), 0.98 (s, 6H) ppm.

EXAMPLE 68

[3,6-Dimethyl-2-(2,4,6-trimethyl-phenoxy)-pyridin-4-yl]-ethyl-amine

A mixture of 4-chloro-3,6-dimethyl-2-(2,4,6-trimethyl-phenoxy)-pyridine (1.330 g, 4.822 mmol) and 20 ml of ethyl amine in 13 ml of 1-methyl 2-pyrrolidinone was heated at 150° C. at 250 psi overnight in a pressure reactor. The reaction was heated an additional 24 hours at 175° C. and 300 psi. The reaction mixture cooled to room temperature and diluted with water and extracted with ethyl acetate. The organic layer was dried and concentrated to give a brown oil. The oil residue was purified through silica gel column chromatography using chloroform to 2% methanol in chloroform as eluent to give 0.820 g (60%) of the title compound as a white solid, mp 115–116° C.

$^1$H NMR (CDCl$_3$) δ 6.87 (s, 2H), 6.11 (s, 1H), 3.85 (t, 1H), 3.24 (m, 2H), 2.30 (s, 3H), 2.17 (s, 3H), 2.13 (s, 3H), 2.08 (s, 6H), 1.32 (t, 3H) ppm.

The title compounds of Examples 69–71 were prepared by the method analogous to that described in Example 68 starting with an appropriate 4-chloro-2-substituted phenoxypyridine and an appropriate amine.

EXAMPLE 69

[3,6-Dimethyl-2-(2,4,6-trimethyl-phenylsulfanyl)-pyridin-4-(1-ethyl-propyl)-amine Mp 108–110° C. $^1$H NMR (CDCl$_3$) δ 6.95 (s, 2H), 6.09 (s, 1H), 3.63 (d, 1H), 3.28 (m, 1H), 2.36 (s, 6H), 2.30 (s, 3H), 2.17 (s, 3H), 2.11 (s, 3H), 1.4–1.75 (m, 4H0, 0.93 (t, 6H) ppm. The hydrogen chloride salt, mp 148–150° C.; $^1$H NMR (CDCl$_3$) δ 6.95 (s, 2H), 6.30 (s, 1H), 5.75 (d, 1H), 3.38 (m. 1H), 2.69 (s, 3H), 2.33 (s, 6H), 2.28 (s, 3H0, 2.02 (s, 3H), 1.72 (m, 4H), 0.93 (t, 6H) ppm.

EXAMPLE 70

2-(4-Chloro-2,6-dimethyl-phenoxy)3,6-dimethyl-pyridin-4-yl]-ethyl-amine; white solid $^1$H NMR (CDCl$_3$) δ 7.04 (s, 2H), 6.13 (s, 1H), 3.88 (t, 1H), 3.24 (m, 2H), 2.17 (s, 3H), 2.17 (s, 3H), 2.08 (s, 6H), 1.32 (t, 3H) ppm.

EXAMPLE 71

[3,6-dimethyl-22,4,6-trimethyl-phenylsulfanyl)pyridin-4-yl]-ethyl-amine

Tan crystals, mp 114–116° C. $^1$H NMR (CDCl$_3$) δ6.94 (s, 2H), 6.12 (s, 1H), 3.76 (t, 1H), 3.21 (m, 2H), 2.35 (s, 6H), 2.30 (s, 3H), 2.19 (s, 3H), 2.10 (s, 3H), 1.29 (t, 3H) ppm.

EXAMPLE 72

[3,6-Dimethyl-2-(2,4,6-trimethyl-phenoxy)-pyridin-4-yl]-ethyl-propylamine

To a solution of [3,6-dimethyl-22,4,6-trimethyl-phenoxy)pyridin-4-yl]-ethyl-amine (7.00 g, 24.6 mmol) in 100 ml of dry THF was added 1.0 M lithium bis(trimethylsilyl)amide in hexane (32 ml, 32 mmol) at –78° C. After stirring at that temperature for 10 min, the reaction mixture was treated with iodopropane (13 ml, 125 mmol) at –70° C. After stirring at that temperature for 20 min, the dry ice bath was removed and the reaction mixture was stirred at room temperature for 3 hours. The reaction mixture was quenched with water and extracted with ethyl acetate. The organic layer was dried and concentrated to give an oil. The oil residue was purified through silica gel column chromatography using 1:1 chloroform:hexane to chloroform as eluent to give 5.04 g (62.5%) of [3,6-dimethyl-2-(2,4,6-trimethyl-phenoxy)-pyridin-4-yl]-ethyl-propyl-amine as yellow solid; $^1$H NMR (CDCl$_3$) δ 6.88 (s, 2H), 6.41 (s, 1H), 3.11 (q, 2H), 3.03-(dd, 2H), 2.30 (s, 3H), 2.25 (s, 3H), 2.19 (s, 3H), 2.07 (s, 6H), 1.55 (m, 2H), 1.08 (t, 3H), 0.90 (t, 3H) ppm. The corresponding HCl salt, white crystals; mp167–169° C.; $^1$H NMR (MeOH-d4) δ 7.00 (s, 2H), 6.75 (s, 1H), 3.54-(q, 2H), 3.43 (t, 2H), 2.35 (s, 3H), 2.31 (s, 3H), 2.27 (s, 3H), 2.08 (s, 6H), 1.69 (m, 2H), 1.25 (t, 3H0, 0.94 (t, 3H) ppm;

The title compounds of Examples 73–79 were prepared by the method analogous to that described in Example 72 starting with an appropriate 2-(substituted phenoxy or thiophenoxy)-pyridin-4-yl-ethyl amine and a base (lithium bis(trimethylsilyl)amide or lithium diisopropylamide), followed by quenching with an appropriate alkyl halide.

EXAMPLE 73

[3,6-dimethyl-2-(2,4,6-trimethyl-phenoxy)pyridin-4-yl]-diethyl-amine $^1$H NMR (CDCl$_3$) δ 6.87 (s, 2H), 6.40 (s, 1H), 3.10-(q, 4H), 2.30 (s, 3H), 2.24 (s, 3H), 2.19 (s, 3H), 2.06 (s, 6H), 1.08 (t, 6H) ppm. The HCl salt, white crystals, mp 180–181° C.; $^1$H NMR (CD$_3$OD) δ 7.01 (s, 2H), 6.78 (s, 1H), 3.58(q, 4H), 2.38 (s, 3H), 2.32 (s, 6H), 2.10 (s, 6H), 1.28 (t, 6H) ppm.

EXAMPLE 74

[3,6-Dimethyl-2-(2,4,6-trimethyl-phenoxy)pyridin-4-yl]-ethyl-methyl-amine $^1$H NMR (CDCl$_3$) δ 6.86 (s, 2H), 6.38 (s, 1H), 3.05-(q, 2H), 2.75 (s, 3H), 229 (s, 3H), 2.25 (s, 3H), 2.18 (s, 3H), 2.06 (s, 6H), 1.18 (t, 3H) ppm. The HCl salt, mp 173–174° C.

EXAMPLE 75

Butyl-[3,6-dimethyl-2-(2,4,6-trimethyl-phenoxy)-pyridin-4-yl]ethyl-amine $^1$H NMR (CDCl$_3$) δ 6.88 (s, 2H), 6.41 (s, 1H), 3.0–3.3 (m, 4H), 2.31 (s, 3H), 2.25 (s, 3H), 2.19 (s, 3H), 2.08 (s, 6H), 1.3–1.6 (m, 4H), 1.09 (t, 3H), 0.93 (t, 3H) ppm.

EXAMPLE 76

Butyl-[2-(4-chloro-2,6-dimethyl-phenoxy)-3,6-dimethyl-pyridin-4-yl]-ethyl-amine $^1$H NMR (CDCl$_3$) δ 7.03 (s, 2H), 6.39 (s, 1H), 3.09-(q, 2H), 3.01-(dd, 2H), 2.21 (s, 3H), 2.16 (s, 3H), 2.05 (s, 6H), 1.4–1.6 (m, 2H), 1.25–1.40 (m, 2H), 1.06 (t, 3H), 0.87 (t, 3H) ppm. The HCl salt, mp 177–178° C.; $^1$H NMR(DMSO-d6) δ 7.20 (s, 2H), 6.74 (s, 1H), 3.1–3.4 (m, 4H), 2.24 (s, 3H), 2.17 (s, 3H), 2.00 (si 6H), 1.4–1.6 (m, 2H), 1.251.40 (m, 2H), 1.05 (t, 3H), 0.86 (t, 3H) ppm.

EXAMPLE 77

[2-(4-chloro-2,6 dimethyl-phenoxy)-3,6-dimethyl-pyridin-4-yl]-ethyl-propylamine $^1$H NMR (CDCl$_3$) δ 7.04 (s, 2H), 6.41 (s, 1H), 3.11-(q, 2H), 3.00 (m, 2H), 2.24 (s, 3H), 2.17 (s, 3H), 2.07 (s, 6H), 1.54 (m, 2H), 1.08 (t, 3H), 0.90 (t, 3H) ppm. The HCl salt, white crystals, mp 74–76° C. $^1$H NMR(CD$_3$OD) δ 7.23 (s, 2H), 6.81 (s, 1H), 3.58-(q, 2H), 3.46 (m, 2H), 2.38 (s, 3H), 2.31 (s, 3H), 2.13 (s, 6H), 1.6–1.8 (m, 2H), 1.26 (t, 3H), 0.96 (t. 3H) ppm.

EXAMPLE 78

[24 chloro-2,6-dimethyl-phenoxy)-3,6 dimethyl-pyridin-4-yl]-diethyl-amine $^1$H NMR (CDCl$_3$) δ 7.05 (s, 2H), 6.41 (s, 1H), 3.11(q, 4H), 2.24 (s, 3H), 2.18 (s, 3H), 2.07 (s, 6H), 1.09 (t, 6H) ppm. The HCl salt, white crystals, mp 184–185° C. $^1$H NMR(CD$_3$OD) δ 7.23 (s, 2H), 6.81 (s, 1H), 3.56(q, 4H), 2.37 (s. 3H), 2.33 (s, 3H), 2.12 (s, 6H), 1.26 (t, 6H) ppm.

EXAMPLE 79

[3,6-Dimethyl-[2-(2,4,6-trimethyl-phenylsulfanyl)-pyridin-4-yl]-ethyl-propyl-amine $^1$H NMR (CDCl$_3$) δ 6.95 (s, 2H), 6.45 (s, 1H), 3.02 (q, 2H), 2.97 (dd, 2H), 2.35 (s, 6H), 2.31 (s, 3H), 2.21 (s, 3H), 2.20 (s, 3H), 1.49 (m, 2H), 1.02 (t, 3H), 0.86 (t, 3H) ppm. The HCl salt, white crystals, mp 110–112° C.; $^1$H NMR (CDCl$_3$) δ 6.92 (s, 2H), 6.51 (s, 1H), 3.27 (q, 2H), 3.19 (dd, 2H), 284 (s, 3H), 2.32 (s, 6H), 2.28 (s, 3H), 1.82 (s, 3H), 1.52 (m, 2H), 1.15 (t, 3H), 0.84 (t, 3H) ppm.

EXAMPLE 80

N-[3,6 Dimethyl-2-(2,4,6-trimethyl-phenoxy)-pyridin-4-yl]-N-ethyl-2,2,2-trifluoro-acetamide To a solution of [3,6-dimethyl-2-(2,4,6-trimethyl-phenoxy)pyridin-4-yl]-ethyl-amine (200 mg, 0.7 mmol) in dry methylene chloride was added triethylamine (0.1 ml, 0.73 mmol) and trifluoroacetic anhydride (0.11 ml, 0.74 mmol) and stirred at room temperature for 2 hours. The reaction mixture was quenched with water and extracted with ethyl acetate. The organic layer was dried and concentrated to give the crude material. The crude material was purified through silica gel column chromatography using 25% hexane in chloroform as eluent to give 225 mg (83%) of the tide compound as white crystals, mp 110–111° C., $^1$H NMR (CDCl$_3$) δ 6.91 (s, 2H), 6.57 (s, 1H), 4.16 (m, 1H), 3.39 (m, 1H), 2.32 (s, 3H), 2.27 (s, 3H), 2.24 (s, 3H), 2.07 (s, 3H), 2.05 (s, 3H), 1.26 (t, 3H) ppm.

EXAMPLE 81

3,6-Dimethyl-2-(2,4,6-trimethyl-phenoxy)pyridin-4-yl]-ethyl(2,2,2-trifluoro-ethyl)amine To a solution of N-[3,6 Dimethyl-2-(2,4,6-trimethyl enoxy)pyridin-4-yl]-N-ethyl-2,2,2-trifluoro-acetamide (292 mg, 0.77 mmol) in 15 ml of dry THF was added 2M $BH_3.DMS$ in THF (0.96 ml, 1.92 mmol) at room temperature. The resulting mixture was heated at reflux overnight. The mixture was quenched with water and extracted with ethyl acetate. The organic layer was dried and concentrated to give 300 mg of white solid. The solid was recrystallized from hexane and 2 drops of methanol to give white crystals (298 mg, 96%). $^1$H NMR (CDCl$_3$) δ 6.85 (s, 2H), 6.47 (s, 1H), 3.70 (q, 2H), 3.25 (q, 2H), 2.32 (s, 3H), 2.27 (s, 3H), 2.20 (s, 3H), 2.05 (s, 3H), 1.13 (t, 3H) ppm. The HCl salt, white crystals, mp 73-74 C. $^1$H NMR(CD$_3$OD) δ 6.97 (s, 1H), 6.96 (s, 2H), 4.09 (q, 2H), 3.46 (q, 2H), 2.34 (s, 3H), 2.30 (s, 3H), 2.28 (s, 3H), 2.05 (s, 6H), 1.17 (t, 3H) ppm.

EXAMPLE 82

4-(1-Ethyl-propylamino)-6-methyl-2-(2,4,6-trimethyl-phenoxy)nicotinic acid methyl ester A mixture of 4 chloro-6-methyl-2-(2,4,6-trimethyl-phenoxy)-nicotinic acid methyl ester (500 mg, 1.56 mmol) and 1-ethyl-propyl-amine (0.8 ml) in 1 ml of DMSO was heated at reflux for 15 hours. The mixture was quenched with sat. ammonium chloride and extracted with ethyl acetate. The organic layer was dried and concentrated to give 445.6 mg of yellow solid. The solid was purified through silica gel column chromatography using 1:1 ratio of chloroform:hexane as eluent to give (289 mg, 50%)of the title compound as white crystals, mp 98–102° C.; $^1$H NMR (CDCl$_3$) δ 8.04 (d, 1H), 6.85 (s, 2H), 6.06 (s, 1H), 3.85 (s, 3H), 3.32 (m, 1H), 2.28 (s, 3H), 2.10 (s, 3H), 2.07 (s, 3H), 1.62 (m, 4H), 0.95 (t, 6H) ppm.

EXAMPLE 83

4-(1-Ethyl-propylamino)methyl-2-(2,4,6-trimethyl-phenoxy-pyridin-3-yl-methanol

A mixture of 4(1-ethyl-propylamino)-6-methyl-2-(2,4,6-trimethyl-phenoxy)nicotinic acid methyl ester (220 mg, 0.594 mmol) and 1 M lithium aluminum hydride in THF (4 ml, 4 mmol) in dry THF (3 ml) was heated at reflux for 10 min, then stirred at rt overnight. The mixture was quenched with 0.3 ml of water, 0.3 ml of 2N NaOH, then 0.8 ml of water and stirred at room temperature for 10 min. White solid formed and was filtered through celite. The filtrate was concentrate to dryness to give 207 mg (100%) of the title compound as white solid. $^1$H NMR (CDCl$_3$) δ 6.83 (s, 2H), 6.06 (s, 1H), 4.96 (d, 1H, NH), 4.88 (d, 2H), 3.28 (m, 1H), 2.26 (s, 3H), 2.11 (s, 3H), 2.04 (s, 6H), 1.4–1.6 (m, 4H), 1.4 (t, 1H, OH), 0.93 (t. 6H) ppm.

EXAMPLE 84

4-(1-Ethyl-propylamino)-6-methyl-2-(2,4,6-trimethyl-phenoxy)nicotinic acid

A mixture of 4-(1-Ethyl-propylamino)-6-methyl-2-(2,4,6-trimethyl-phenoxy)nicotinic acid methyl ester (16 mg, 0.043 mmol) and lithium hydroxide (30 mg) in dioxane (1 ml) and water (1 ml) was stirred at rt over night. The mixture was quenched with water and adjusted to pH 7.0 and extracted with chloroform. The organic layer was dried and concentrated to give the crude material. The crude material was purified through silica gel column chromatography using 10% ethyl acetate in chloroform as eluent to give 7 mg of the title compound as white solid. $^1$H NMR (CDCl$_3$) δ 9.12 (d, 11H), 6.87 (s, 2H), 6.16 (s, 1H), 3.35 (m, 11H), 2.29 (s, 3H), 2.10 (s, 3H), 2.07 (s, 6H), 1.4-1.6 (m, 4H), 0.94 (t, 6H) ppm.

EXAMPLE 85

[3-Chloromethyl-6-methyl-2-(2,4,6-trimethyl-phenoxy)pyridin-4 yl]-1-ethyl-propyl)amine hydrogen chloride To a solution of 4-(1-ethyl propylamino)-6-methyl-2-(2, 4,6-trimethyl-phenoxy)-pyridin-3-yl]-methanol (40 mg, 0.117 mmol) in 0.3 ml of dry methylene chloride was added thionyl chloride (0.15 ml) and stirred at rt for 1 hr. The mixture was concentrated to dryness and pumped in vacuo to give white glass form. The glass form was triutated with ether to give the title compound (47 mg, 100%) as a white solid. $^1$H NMR (CDCl$_3$) δ6.92 (s, 2H), 6.24 (s, 1H), 5.50 (d, 1H), 4.72 (s, 2H), 3.50 (m, 11H), 2.73 (s, 3H), 2.27 (s, 3H), 2.15 (s, 6H), 1.5–1.8 (m, 4H), 0.97 (t, 6H) ppm.

EXAMPLE 86

[3,6 Dimethyl-2-(2,4,6-trimethyl-phenoxy)pyridin-4-yl-(1-ethyl-propyl)-amine

To a solution of [3-Chloromethyl-6-methyl-2-(2,4,6-trimethyl-phenoxy)-pyridin-4-yl]-(1-ethyl-propyl-amine (35 mg, 0.088 mmol) in dry THF (0.5 ml) was added 1M lithium aluminum hydride in THF (0.3 ml, 0.3 mmol) and the resulting mixture was stirred at rt for 1.5 hours. The mixture was quenched with 0.1 ml of water, 0.1 ml of 2N NaOH and 0.3 ml of water and stirred for min. The mixture was filtered and washed with THF. The filtrate was concentrated to dryness. The residue was dissolved in chloroform and dried over anhydrous sodium sulfate, filtered, and concentrated to dryness to give 28 mg (100%) of oil. The oil was purified through silica gel column chromatography using chloroform as eluent to give 26 mg of the title compound as an oil.

$^1$H NMR (CDCl$_3$) δ 6.85 (s, 2H), 6.08 (s, 1H), 3.72 (d, NH, 1H), 3.35 (m, 1H), 2.30 (s, 3H), 2.16 (s, 3H), 2.13 (s, 3H), 2.05 (s, 6H), 1.45–1.75 (m, 4H), 0.98 (t, 6H) ppm. The corresponding HCl salt was prepared and triutated with ether to give 20 mg of white solid. $^1$H NMR (CDCl$_3$) δ 6.88 (s, 2H), 6.19 (s, 1H), 4.98 (brs, 1H), 3.50 (m, 1H), 2.71 (s, 3H), 2.26 (s, 3H), 2.12 (s, 6H), 2.00 (s, 3H), 1.5–1.8 (m, 4H), 0.95 (t, 6H) ppm.

EXAMPLE 87

(1-Ethyl-propyl)-[3-methoxymethyl-6-methyl-2-(2,4,6-trimethyl-phenoxy)-pyridin-4-yl]-amine To a solution of 4-(1-ethyl propylamino)-6 methyl-2-(2, 4,6-trimethyl-phenoxy)pyridin-3-yl]methanol (46 mg, 0.134 mmol) in dry THF (0.5 ml) was added 60% sodium hydride in oil (6 mg, 0.134 mmol) and stirred for 2 min. Methyl iodide (0.1 ml) was added and the mixture was stirred at room temperature overnight. The reaction mixture was quenched with water and extracted with ethyl acetate. The organic layer was dried and concentrated to give the title compound as an oil (40 mg, 84%). $^1$H NMR (CDCl$_3$) δ 6.84 (s, 2H), 6.06 (s, 1H), 5.13 (d, 1H), 4.78 (s, 2H), 3.33 (s, 3H), 3.29 (m, 1H), 2.27 (s, 3H), 2.12 (s, 3H), 2.04 (s, 6H), 1.3–1.6 (m, 4H), 0.93 (t, 6H) ppm.

EXAMPLE 88

(1-Ethyl-propyl)[6-methyl-3-nitro-2-(2,4,6 -trimethyl-phenoxy)-pyridin-4-yl]amine To a mixture of (2-chloroethyl-3-nitro-pyridin-4-yl)-(1-ethyl-propyl)amine (80 mg, 0.31 mmol) and 2,4,6- trimethylphenol (43 mg, 0.31 mmol) in 2 ml of dry THF was added potassium tert-butoxide (35 mg, 0.31 mmol) and the resulting mixture was stirred at rt overnight. The mixture was quenched with water and extracted with ethyl acetate. The organic layer was dried and concentrated to give a yellow solid. The solid was purified through silica gel column chromatography using 6:4 ratio of chloroform:hexane as eluent to give 91 mg (83%) of the title compound as yellow solid, mp 160–162° C. $^1$H NMR (CDCl$_3$) δ 7.62 (d, 1H), 6.87 (s, 2H), 6.18 (s, 1H), 3.40 (m, 1H), 2.30 (s, 3H), 2.15 (s, 3H), 2.10 (s, 6H), 1.5–1.8 (m, 4H), 0.99 (t, 6H) ppm.

EXAMPLE 89

N4-(1-Ethyl-propyl)-6-methyl-3-nitro-N-2-(2,4,6-trimethyl-phenyl)pyridine-2,4-diamine A mixture of (2 chloro-6-methyl-3-nitro-pyridin-4-yl)(1-ethyl-propyl)amine (250 mg, 0.97 mmol) and 2,4,6-trimethylaniline (262 mg, 1.94 mmol) in 4 ml of dry DMSO was healed at 130° C. overnight. The mixture was quenched with water and extracted with ethyl acetate. The organic layer was dried and concentrated to give a yellow oil. The oil was purified through silica gel column chromatography to give 150 mg (43%) of the title compound as yellow solid, mp 104–107° C. $^1$H NMR (CDCl$_3$) δ 10.36 (s, 1H), 9.24 (d, 1H), 6.93 (s, 2H), 5.86 (s, 1H), 3.45 (m, 1H), 2.32 (s, 3H), 2.18 (s, 6H), 2.13 (s, 3H), 1.55–1.80 (m, 4H), 0.99 (t, 6H) ppm.

EXAMPLE 90

N4-(1-Ethyl-propyl)-6-methyl-2-(2,4,6-trimethyl-phenoxy)pyridine-3,4-diamine

A mixture of (1-ethyl-propyl)-[6-methyl-3-nitro-2-(2,4,6-trimethyl-phenoxy)-pyridin-4-yl]-amine (40 mg, 0.112 mmol) and 4 mg of 10% Pd/C in 10 ml of ethanol was hydrogenated at 50 psi overnight. The mixture was filtered through Celite™ and the filtrate was concentrated to dryness to give a light brown crystals which were purified through silica gel column chromatography using 1:1 chloroform:hexane as eluent to give the title compound as golden crystals (36 mg, 97%), mp 105107° C. $^1$H NMR (CDCl$_3$) δ 6.88 (s, 2H), 6.11 (s, 1H), 4.00 (brs, 1H), 3.28 (m, 1H), 3.10 (brs, 2H), 2.31 (s, 3H), 2.16 (s. 3H), 2.10 (s, 6H), 1.45–1.75 (m, 4H), 0.98 (t, 6H) ppm. The corresponding HCl salt was prepared as white solid, mp 174–178° C., 1H is NMR(D$_2$O) δ 7.09 (s, 2H), 6.63 (s, 1H), 3.65 (m, 1H), 2.31 (s, 3H), 2.25 (s, 3H), 2.11 (s, 6H), 1.45–1.80 (m, 4H), 0.91 (t, 6H) ppm.

EXAMPLE 91

[2-(4-Chloro-2,6-dimethyl-phenoxy)-6-methyl-3 nitro-pyridin-4-yl]1-ethyl-propyl)amine To a mixture of (2 chloro-[6-methyl-3-nitro-pyridin-4-yl]-(1-ethyl-propyl)-amine (850 mg, 3.30 mmol) and 4 chloro-2,6-dimethylphenol (516 mg, 3.30 mmol) in 25 ml of dry THF was added potassium tert-butoxide (370 mg, 3.30 mmol) and the resulting mixture was stirred at room temperature overnight. The mixture was quenched with water and extracted with ethyl acetate. The organic layer was dried and concentrated to give a yellow solid (1.31 g). The solid was purified through silica gel column chromatography using 6:4 ratio of chloroform:hexane as eluent to give 1.10 g (88%) of the title compound as yellow solid, mp 152–154° C. $^1$H NMR (CDCl$_3$) δ 7.65 (d, 1H), 7.05 (s, 2H), 6.21 (s, 1H), 3.41 (m, 1H), 2.15 (s, 3H), 2.11 (s, 6H), 1.5–1.8 (m, 4H), 0.99 (t, 6H) ppm.

EXAMPLE 92

2-(2,6-Dimethyl-phenoxy)-N4-(1-ethyl-propyl)methyl-pyridine-3,4-diamine

A mixture of (1-ethyl-propyl)-[6-methyl-3-nitro-2-(4 chloro-2,6-dimethyl-phenoxy)-pyridin-4-yl]-amine (800 mg, 2.12 mmol) and 160 mg of 10% Pd IC in 150 ml of ethanol was hydrogenated at 50 psi overnight. The mixture was filtered through Celite™ and the filtrate was concentrated to dryness to give a purple glass form (810 mg) which was purified through silica gel column chromatography using 1:1 chloroform:hexane as eluent to give the Ute compound as tan crystals (360 mg), mp 98–100° C. $^1$H NMR (CDCl$_3$) δ 7.05 (m, 3H), 6.11 (s, 1H), 4.00 (brs, 1H), 3.28 (m, 1H), 3.09 (brs, 2H), 2.14 (s, 9H), 1.451.75 (m, 4H), 0.98 (t, 6H) ppm. The corresponding HCl salt was prepared as white solid, mp 158–162° C., $^1$H NMR(D$_2$O) δ 7.27 (s, 3H), 6.67 (s, 1H), 3.65 (m, 1H), 2.27 (s, 3H), 2.16 (s, 6H), 1.45–1.80 (m, 4H), 0.93 (t, 6H) ppm.

EXAMPLE 93

N4-(1-Ethyl-propyl)methyl-N-2-(2,4,6-trimethyl-phenyl)-pyridine-2,3,4-triamine

A mixture of N4-(1-ethyl-propyl)-6-methyl-3-nitro-N2-(2,4,6-trimethyl-phenyl)-pyridine-2,4-diamine (40 mg, 0.112 mmol) and 8 mg of 10% palladium/carbon (Pd/C) in 20 ml of ethanol was hydrogenated at 50 psi overnight. The mixture was filtered through celite and the filtrate was concentrated to dryness to give a dark residue (40 mg). $^1$H NMR (CDCl$_3$) δ 6.88 (s, 2H), 5.97 (s, 1H), 4.32 (d, 1H), 3.28 (m, 1H), 2.27 (s, 3H), 2.26 (s, 3H), 2.18 (s, 6H), 1.45–1.75 (m, 4H), 0.93 (t, 6H) ppm. The corresponding di-HCl salt was prepared as a tan solid, mp 213–216° C., 1H NMR (DMSO-d6) δ 11.1 (s, 1H), 8.48 (s, 1H), 6.98 (s, 2H), 6.73 (brs, 1H), 6.38 (s, 1H), 3.36 (m, 1H), 2.28 (s, 3H), 2.19 (s, 3H), 2.08 (s, 6H), 1.54 (m, 4H), 0.88 (t, 6H) ppm.

EXAMPLE 94

2-(4-Chloro-2,6-dimethyl-phenoxy)N4-(1-ethyl-propyl)-6-methyl-pyridine-3,4-diamine A mixture of (1-ethyl-propyl)-[6-methyl-3-nitro-2-(4 chloro-2,6-dimethyl-phenoxy)-pyridin-4-yl]-amine (100 mg, 0.265 mmol) and iron (73 mg, 1.33 mmol) in 12 ml of AcOH/H$_2$O (1:1) was heated at 60° C. for 3 hours. The mixture was concentrated to dryness. The residue was diluted with water and extracted with ethyl acetate. The organic layer was dried and concentrated to give the title compound. $^1$H NMR (CDCl$_3$) δ 7.04 (s, 2H), 6.12 (s, 1H), 3.60 (brs, 2H), 3.28 (m, 1H), 2.14 (s, 3H), 2.10 (s, 6H), 1.45–1.80 (m, 4H), 0.97 (t, 6H) ppm.

EXAMPLE 95

N-(1-Ethyl-propyl)-2-methyl-5-nitro-N'-(2,4,6 trimethyl-pyridin-3-yl)-pyrimidine-4,6-diamine To a cooled solution of (6-chloro-2-methyl-5-nitro-pyrimidin-4-yl(2,4,6-trimethyl-pyridin-3-yl)-amine (88 mg, 0.29 mmol) in 1 ml of dry THF was added 1 ethyl-propyl-amine (80 mg, 0.92 mmol) at −78° C. The mixture was stirred at that temperature for 3 hrs, then warmed to −10° C. for 1 hour. The mixture was quenched with water and extracted with ethyl acetate. The organic layer was dried and concentrated to give the title compound (88 mg, 86%) as an orange solid, mp 151–152° C. $^1$H NMR (CDCl$_3$) δ 9.16 (d, 1H), 6.92 (s, 1H), 4.35 (m, 1H), 2.50 (s, 3H), 2.39 (s, 3H), 2.18 (s, 3H), 2.16 (s, 3H), 1.5–1.80 (m, 4H), 0.94 (t, 6H) ppm.

EXAMPLE 96

(1-Ethyl-propyl)-[2-methyl-nitro-6-(2,4,6-trimethyl-pyridin-3-yloxy)-pyrimidin-4-yl]-amine A solution of 3-hydroxy-2,4,6-trimethylpyridine (41 mg, 0.3 mmol) in 1 ml of dry THF was treated with 60% sodium hydride in oil (13 mg, 0.3 mmol) at rt. The reaction mixture was cooled to −78° C. and a solution of (6 chloro-2-methyl-5-nitro-pyrimidin-4-yl)-(1-ethyl-propyl)-amine (78 mg, 0.3 mmol) in 1 ml of dry THF was added. The reaction was stirred at −78° C. for 1 hour, quenched with water and extracted with ethyl acetate. The organic layer was dried and concentrated to give 91 mg (84%) of white solid of the title compound, mp 134–135° C. $^1$H NMR (CDCl$_3$) δ 8.30 (d, 1H), 6.89 (s, 2H), 4.30 (m, 1H), 2.31 (s, 3H), 2.26 (s, 3H), 2.10 (s, 6H), 1.5–1.8 (m, 4H), 0.97 (t, 6H) ppm.

EXAMPLE 97

2-(4-Chloro-2,6-dimethyl-phenoxy)-4-(1-ethyl-propyl)-6 methyl-pyridine-3,4-diamine A mixture of [2-(4-chloro-2,6-dimethyl-phenoxy)-6-methyl-3-nitro-pyridin-4-yl]1-ethyl-propyl)-amine (810 mg, 2.14 mmol) and iron (Fe) (594 mg, 10.72 mmol) in 96 ml of 1:1 of AcOH:H$_2$O was heated at reflux for 2 hours. Additional Fe (600 mg) was added. The mixture was heated for an additional 1.5 hours. The reaction mixture was concentrated to dryness. The residue was quenched with water, basified to pH 9.0 and filtered through celite. The filtrate was extracted with ethyl acetate. The organic layer was washed with brine, dried and concentrated to give the title compound as a yellow oil. The oil was purified through silica gel column chromatography using chloroform as eluent to give 570 mg of 2-(4-chloro-2,6-dimethyl-phenoxy)-N4-(1-ethyl-propyl)-methyl-pyridine-3,4-diamine as a tan solid, mp 72–74° C. $^1$H NMR(CDCl$_3$) δ 7.04(s, 2H), 6.11(s, 1H), 4.03(d, 1H), 3.30(m, 1H), 3.07(s, 1H), 2.14(s, 3H), 2.10(s, 6H), 1.4–1.75(m, 4H), 0.97(t, 6H)ppm. The corresponding di-HCl salt was prepared as a white solid, mp 208–210° C.

EXAMPLE 98

N-[4-(1-Ethyl-propylamino)-6-methyl-2-(2,4,6-trimethyl-phenoxy)pyridin-3-yl]-acetamide A mixture of 22,4,6-trimethyl-phenoxy)-N4-(1-ethyl-propyl methyl-pyridine-3,4-diamine (250 mg, 0.763 mmol), acetic anhydride (72 mg, 0.763 mmol) and triethylamine (77 mg, 0.763 mmol) in 5 ml of methylene chloride was stirred at room temperature for 3 hours. The mixture was quenched with water and extracted with ethyl acetate. The organic layer was dried and concentrated to dryness to give 310 mg of the crude material. The crude material was purified through silica gel column chromatography using 2% methanol in chloroform as eluent to give 250 mg (89% yield) of N-[4-(1-ethyl-propylamino)-6-methyl-2-(2,4,6-trimethyl-phenoxy)-pyridin-3-yl]-acetamide as tan solid, mp 154156° C. $^1$H NMR(CDCl$_3$) δ 6.97(0.64H), 6.86(s, 2H), 6.26 (0.36H), 6.14(0.64H), 6.12(s, 0.36H), 4.80(d, 0.64H), 4.40 (d, 0.36H), 3.2–3.4(m, 1H), 2.29(s, 3H), 2.26(s, 1.9H), 2.17(s, 1.1H), 2.16(s, 1.9H), 2.06(s, 6H), 1.99(s, 1.1H), 1.4–1.75(m, 4H), 0.97(t, 6H)ppm.

EXAMPLE 99

N-[24-Chloro-2,6-dimethyl-phenoxy-4-(1-ethyl-propylamino)methyl-pyridin-3-yl]acetamide The title compound (35 mg) was isolated as a side product from the reduction experiment described in the Example 97. Compound can be prepared by standard acylation method by reacting 2-(4-chloro-2,6-dimethyl-phenoxy)-4-(1-ethyl-propyl)-6-methyl-pyridine-3,4-diamine with acetic anhydride and triethylamine in methylene chloride. A tan solid was prepared, mp 161–164° C. $^1$H NMR(CDCl$_3$) δ 7.04(s, 2H), 6.88(s, 0.6H), 6.26(s, 0.4H), 6.15(s, 1H), 4.75(d, 0.6H), 4.40(d, 0.4H), 3.30(m, 1H), 2.27(s, 1.8H), 2.15(s, 3H), 2.06(s, 6H), 1.98(s, 1.2H), 1.4–1.8(m, 4H), 0.97(t, 6H) ppm.

EXAMPLE 100

1-Ethyl-3-[4-(1-ethyl-propylamino)-6-methyl-2-(2,4,6-trimethyl-phenoxy)-pyridin-3-yl]urea $^1$H NMR(CDCl$_3$) δ 6.85(s, 2H), 6.11(s, 1H), 5.38(s, 1H), 4.68(s, 1H), 4.65(m, 1H), 3.2–3.4(m, 3H), 2.28(s, 3H), 2.16(s, 3H), 2.08(s, 6H), 1.4–1.7(m, 4H), 1.10(t, 3H), 0.93(t, 6H) ppm.

EXAMPLE 101

N-[4-(1-Ethyl-propyl)-2-methyl-N"-(2,4,6-trimethyl-pyridin-3-yl)pyrimidine-4,5,6-triamine The title compound was prepared by hydrogenation of N1-ethyl-propyl-2-methyl-5 nitro-N"2,4,6-trimethyl-pyridin-3-yl)-pyrimidine-4,6-diamine by the method analogous to that described in Example 93. $^1$H NMR(CDCl$_3$) δ 6.9(s, 1H), 6.25(brs, 1H), 4.7(d, 1H), 4.08(m, 1H), 2.5(s, 3H), 2.45(s, 3H), 2.30(s, 3H), 2.20(s, 3H), 1.45–1.7(m, 4H), 0.98(t, 6H) ppm.

EXAMPLE 102

N4-(1-Ethyl-propyl)-2-methyl-6-(2,4,6-trimethyl-phenoxy)-pyrimidine-4,5-diamine

The title compound was prepared by hydrogenation of (1-ethyl-propyl)[2-methyl-5-nitro-6-(2,4,6-trimethyl-phenoxy)pyrimidin-4-yl]-amine by the method analogous to that described in Example 93. $^1$H NMR(CDCl$_3$) δ 6.88(s, 2H), 4.52(d, 1H), 4.10(m, 1H), 2.94(brs, 2H), 2.30(s, 3H), 2.23(s, 3H), 2.09(s, 6H), 1.4–1.8(m, 4H), 0.95(t, 6H) ppm. The corresponding HCl saHt, mp 248–250° C. $^1$H NMR (CD$_3$OD) δ 6.91(s, 2H), 4.00(m, 1H), 2.39(s, 3H), 2.28(s, 3H), 2.07(s, 6H), 1.6–1.8(m, 4H), 1.00(t, 6H) ppm.

EXAMPLE 103

[6-(1-Ethyl-propoxy)-2-methyl-5-nitro-pyrimidin-4-yl]-(2,4,6-trimethyl-phenyl)amine A mixture of 3 pentanol (0.5 ml) and 60% sodium hydride (NaH) in oil (89 mg, 2.22 mmol) in 2 ml of dry THF was stirred for 2 min, then treated with a solution of 6-(chloro-2-methyl-5-nitropyrimidin-4-yl)-(2,4,6-trimethylphenyl)-amine (350 mg, 1.14 mmol) in 3 ml of dry THF at −78° C. and stirred at that temperature for 1 hour, then stirred at room temperature overnight. The mixture was quenched with water and extracted with ethyl acetate. The organic layer was dried and concentrated to give the crude material which was purified through silica gel column chromatography using 2:1 of hexane/CHCl$_3$ as eluent to give 331 mg (85%) of the title compound as a yellow solid, mp 112–113° C. $^1$H NMR (CDCl$_3$) δ 9.48(brs, 1H), 6.49(s, 2H), 5.37(m, 1H), 2.33(s, 3H), 2.29(s, 3H), 2.18(s, 6H), 1.7–1.9(m, 4H), 0.99(t, 6H) ppm.

EXAMPLE 104

N-(1-Ethyl-propyl)-2-methyl-5-nitro-N'-(2,4,6-trimethyl-phenyl)-pyrimidine-4,6-diamine The title compound was prepared by the method analogous to that described in Example 5 using 1-ethylpropylamine. $^1$H NMR(CDCl$_3$) δ 10.48(s, 1H), 9.25 (d, 1H), 6.94(s,2H), 4.37(m,1H), 2.32(s, 3H), 2.21(s, 3H), 2.18(s,6H), 1.5–1.8(m,4H), 0.97(t,6H) ppm.

EXAMPLE 105

6-(1-Ethyl-propoxy)-2-methyl-N4-(2,4,6-trimethyl-phenyl)pyrimidine-4,5-diamine

The title compound was prepared by the method analogous to that described in Example 93 starting from [6(1-ethyl-propoxy-2-methyl-5-nitro-pyrimidin yl]-2,4,6-trimethyl-phenyl-amine. $^1$H NMR(CDCl$_3$) δ 6.92(s, 2H), 5.96(s, 1H), 5.12(m, 1H), 2.85(brs, 1H), 2.31(s, 3H), 2.30(s, 3H), 2.19(s, 6H), 1.70(m, 4H), 0.94(t, 6H) ppm.

EXAMPLE 106

6-(1-Ethyl-propoxy)-2-methyl-5-nitro-pyrimidin-4-yl-(2,4,6-trimethyl-pyridin-3-yl)-amine The title compound was prepared by the method analogous to that described in Example 103 starting from (6-chloro-2-methyl-5-nitro-pyrimidin-4-yl](2,4,6-trimethyl-pyridin-3-yl-amine and sodium 3-pentanoxide. $^1$H NMR (CDCl$_3$) δ 9.45(s, 1H), 6.95(s, 1H), 5.35(m, 1H), 2.53(s, 3H), 2.41(s, 3H), 2.29(s, 3H), 2.18(s, 3H),1.7–1.9(m,4H), 0.98(t,6H) ppm.

EXAMPLE 107

N-(1-Ethl-propyl)-2-methyl-N"-(2,4,6-trimethyl-phenyl)pyrimidine-4,5,6-triamine

The title compound was prepared by the method analogous to that described in Example 93 starting from N-4(1-ethyl-propyl)-2-methyl-5-nitro-N'-2,4,6-trimethyl-phenyl)-pyrimidine-4,6-diamine. $^1$H NMR(CDCl$_3$) δ 6.90(s,2H), 6.10(s,1H), 4.78(d,1H), 4.03(m, 1H), 2.31(s, 3H), 12.29(s, 3H), 2.20(s, 6H), 1.4–1.6(m, 4H), 0.91(t, 6H) ppm.

EXAMPLE 108

6-(1-Ethyl-propoxy)-2-methyl-9(2,4,6-trimethyl-phenyl) 7,9-dihydro-purin-8-one

A mixture of 6-(1-ethyl-propoxy)-2-methyl-N4-(2,4,6 trimethyl-phenyl)-pyrimidine-4,6-diamine (182 mg, 0.554 mmol), triethylamine (39 mg, 0.388 mmol) and triphosgene (58 mg, 0.196 mmol) in 6 ml of dry THF was stirred at room temperature for 30 min. The mixture was quenched with water and extracted with chloroform. The organic layer was dried and concentrated to give 177 mg (90%) of the title compound as a white solid, mp 159–160° C. 1H NMR (CDCl$_3$) δ 8.50(s, 1H), 6.99(s, 2H), 5.30(m, 1H), 2.47(s, 3H), 2.32(s, 3H), 2.08(s, 6H), 1.73(m, 4H), 0.94(t, 6H) ppm.

EXAMPLE 109

6-(1-Ethyl-propoxy)-2-methyl-N4-(2,4,6-trimethyl-pyridin-3-yl)-pyrimidine-4,5-diamine The title compound was prepared by the method analogous to that described in Example 93 starting from 6-(1-ethyl-propoxy)-2-methyl-5-nitro-pyrimidin-4-yl](2,4,6-trimethyl-pyridin-3-yl)-amine. 1H NMR(CDCl$_3$) δ 6.89(s, 1H), 5.97(s, 1H), 5.29(m, 1H), 2.90(brs, 1H), 2.48(s, 3H), 2.41 (s, 3H), 2.26(s, 3H), 2.17(s, 3H), 1.68(m, 4H), 0.93(t, 6H) ppm.

EXAMPLE 110

6-(1-Ethyl-propylamino)-2-methyl-9-(2,4,6-trimethyl-phenyl)7,9-dihydro-purin-8-one The title compound was prepared by the method analogous to that described in Example 108 starting from N-(1-ethyl-propyl)-2-methyl-N-(2,4,6-trimethyl-phenyl) pyrimidine-4,5,6-triamine.

$^1$H NMR(CDCl$_3$) δ 6.59(s, 2H), 5.28(d, 1H), 3.92(m, 1H), 2.40(s,3H), 2.32(s,3H), 2.08(s,6H), 1.25–1.45(m,4H), 0.80 (t,6H) ppm.

EXAMPLE 111

N4-(1-Ethyl-propyl)-6,N3,N3-trimethyl-2-(2,4,6-trimethyl-phenoxy)-pyridine-3,4-diamine and N4-(1-Ethyl-propyl-6,N3-dimethyl-2-(2,4,6-trimethyl-phenoxy) pyridine-3,4-diamine To a solution of N4-(1-ethyl-propyl)ethyl-2-(2,4,6-trimethyl-phenoxy) pyridine-3,4-diamine (0.250 g, 0.763 mmol) in dry THF (6 ml) was treated with 1 M LiN(SiMe$_3$)$_2$ in THF (1.0 ml, 1.0 mmol) at −78° C. and stirred for 10 min. an excess of methyl iodide was added and the resulting mixture was stirred at room temperature overnight. The mixture was quenched with water and extracted with ethyl acetate. The organic layer was dried and concentrated to give a crude material. The crude material was purified through silica gel column chromatography using 5% ethyl acetate in hexane as eluent to give N4-(1-ethyl-propyl-6,N3,N3-trimethyl-2-(2,4,6-trimethyl-phenoxy)pyridine-3.4-diamine and N4-(1-ethylpropyl)-6,N3-dimethyl-2(2,4,6-trimethyl-phenoxy)-pyridine-3,4-diamine.

N4(1-Ethyl-propyl)-6,N3,N3-trimethyl-2-(2,4,6-trimethyl-phenoxy)pyridine-3,4-diamine:

$^1$H NMR(CDCl) δ 6.88(s,2H), 6.02(s,1H), 5.55(d,1H), 3.21(m,1H), 2.79(s,6H), 2.30(s,3H), 2.10(s,3H), 2.09(s,6H), 1.4–1.75(m,4H), 0.95(t,6H) ppm.

N4-(1-Ethyl-propyl)-6,N3-dimethyl-2-(2,4,6-trimethyl-phenoxy)-pyridine-3,4-diamine: 1H NMR(CDCl$_3$) δ 6.89(s, 2H), 6.10(s,1H), 4.84(d,1H), 3.30(m,1H), 2.98(s,1H), 2.72 (s,3H), 2.32(s,3H), 2.16(s,3H), 2.12(s,6H), 1.45–1.70(m, 4H), 0.99(t, 6H) ppm.

EXAMPLE 112

N4-(1-Ethyl-propyl)-6-methyl-2-(2,4,6-trimethyl-phenoxy)-pyrimidine-3-chloro-4-amine The title compound was prepared by the method analogous to those of Examples 33–39 starting from 3,4-dichloro-6-methyl-242,4,6-trimethyl-phenoxy)-pyrimidine and 1-ethyl-propylamine. $^1$H NMR(CDCl$_3$) δ 6.87(s, 2H), 4.97 (d, 1H), 4.12(m, 1H), 2.30(s, 3H), 2.25(s, 3H), 2.10(s, 6H), 1.4–1.8(m, 4H), 0.96(t, 6H) ppm.

EXAMPLE 113

Butyl-(2,8-dimethyl-9-(2,4,6-trimethyl-phenyl)-9H-purin-6-yl)ethyl-amine

A mixture of N-butyl-N-ethyl-2-methyl-N'-(2,4,6-trimethylphenyl)pyrimidin-4, 5,6-triamine (105 mg, 0.63 mmol) and triethyl orthoacetate (0.204 g, 1.25 mmol) and 10 mg of p-TsOH in toluene was heated reflux overnight. The mixture was concentrated to dryness and the residue was quenched with water and extracted with ethyl acetate. The organic layer was dried and concentrated to give yellow oil. The oil was purified through silica gel column chromatography using 1:1 of hexane: chloroform as eluent to give the title compound. 1H NMR(CDCl$_3$) δ 7.01(s, 2H), 3.9–4.1(m, 4H), 2.45(s, 3H), 2.35(s, 3H), 2.20(s, 3H), 1.91(s, 6H), 1.6–1.8(m, 2H), 1.351.5(m, 2H), 1.29(t, 3H), 0.99(t, 3H) ppm.

EXAMPLE 114

The compounds below were prepared by reacting of (2-chloro-6-methyl-3-nitro-pyridin-4-yl)-(alkyl- or dialkyl)-amine with substituted phenol by a method analogous to the following: To a mixture of (2-chloro-6-methyl-3-nitro-pyridin-4-yl)-(alkyl- or dialkyl)amine (1 mmol) and 2,4,6-trimethylphenol (1 mmol) in dry THF was added potassium tert-butoxide (1 mmol) and the resulting mixture was stirred at room temperature until all starting material was consumed. The mixture was quenched with water and extracted with ethyl acetate. The organic layer was dried and concentrated to give the title compound after purification through silica gel column chromatography:

2-[2-(4-Chloro-2,6-dimethyl-phenoxy)-6-methyl-3-nitro-pyridin-4-(S)-ylamino]-butan-1-ol $^1$H NMR(CDCl$_3$) d 7.69(, 1H), 6.289-s, 1H), 3.65–3.80 (m, 2H), 3.60-m, 1H), 2.12(s, 3H), 2.08(s, 6H), 1.8(brs, 1H), 1.5–1.8(m, 2H), 1.01(t, 3H) ppm.

(1-Methoxymethyl-propyl)[6-methyl-3-nitro-2-(4-trifluoromethoxy-4-g phenoxy)pyridin-4-yl]-amine yellow solid, mp. 75–76° C., Anal. For C$_{18}$H$_{20}$N$_3$O$_5$F$_3$, calc. C$_{52.05}$; H, 4.85; N, 10.12; found, C, 52.14; H, 5.04; N, 10.13

2-(2-Amino-4,6-dichloro-phenoxy)-6-methyl-3-nitro-pyridin-4-yl-(1-methoxymethyl propyl)amine $^1$H NMR (CDCl$_3$) d 9.55(d, 1H), 7.23(d, 1H), 7.00(d, 1H), 6.05(s, 1H), 3.69(m, 1H), 3.49(m, 2H), 3.38(s, 3H), 2.35(s, 3H), 1.78(m, 1H), 1.65(m, 1H), 0.99(t, 3H) ppm.

3-Methoxy-2-[4-(1-methoxymethyl-propylamino)-6-methyl-3-nitro-pyridin-2-yloxy]-benzaldehyde yellow solid, mp. 126.5–130.5° C., Anal. For C$_{19}$H$_{23}$N$_3$O$_8$, calc. C58.60; H, 5.95; N, 10.79; found, C, 58.45; H, 6.11; N, 10.32

[2-(2,6-bromo-4-trifluoromethoxy-phenoxy)-6-methyl-3-nitro-pyridin-4-yl]-(1-methoxymethyl-propyl)amine yellow solid, $^1$H NMR(CDCl$_3$) d 8.00(d,1H), 7.49(,2H), 6.35(s,1H), 3.64(m,1H), 3.53(m,2H), 3.43(s,3H), 2.20 (s,3H), 1.6–1.9(m,4H), 1.04(t,3H) ppm.

[2-(2-Bromo-4-chloro-6-methoxy-phenoxy)-6-methyl-3-nitro-pyridin-4-yl]-(1-methoxymethyl-propyl)-amine yellow solid, mp. 111.8–113.6° C., Anal. For C$_{15}$H$_{21}$N$_3$O$_5$-Brcl, calc, C, 45.54; H, 4.46; N, 8.85; found, C, 45.94; H, 4.32; N. 8.68

[2-(2,4-Dichloro-phenoxy)-6-methyl-3-nitro-pyridin-4-yl]-(1-methoxymethyl-propyly)-amine $^1$H NMR (CDCl3) d 7.83(d,1H), 7.46(d,1H), 7.30(dd,1H), 7.15(dd,1H), 6.33(s,1H), 3.65(m,1H), 3.51(m,2H), 3.42(s,3H), 2.21(s,3H), 1.82(m,1H), 1.66(m.1H), 1.03 (t,3H) ppm.

[2-(2-Bromo-6-chloro-4-methoxy-phenoxy)-6-methyl-3-nitro-pyridin-4-yl]1-methoxy-methyl-propyl)-amine $^1$H NMR(CDCl$_3$) d 7.88(d,1H), 7.04(d,1H), 6.93(d.,H), 6.27(s,1H), 3.79(s,3H), 3.60(m,1H), 3.4–3.5(m,2H), 3.38(s,3H), 2.15(s,3H), 1.78(m,1H), 1.64(m,1H), 0.99 (t,3H)

(1-Methoxymethyl-propyl)-[6-methyl-3-nitro-2-(2,4,6-trimethoxy-phenoxy)-pyridin-4-yl]-amine mp. 126.8–129.5° C.; Anal. For C$_{20}$H$_{27}$N$_3$O$_7$ calc. C, 57.00; H, 6.46; N, 9.97; found C, 56.94; H, 6.85; N, 9.66.

EXAMPLE 115

2-Chloro-N-[4-(1-ethyl-propylamino)-6-methyl-2-(2,4,6-trimethyl-phenoxy)-pyridin-3-yl]-acetamide To a solution of N+(1-ethyl-propyl-6-methyl-2-(2,4,6-trimethyl-phenoxy)-pyridine-3,4-diamine (250 mg, 0.763 mmol) in dry THF was added chloroacetyl chloride (86 mg, 0.763 mmol) and triethylamine (77 mg, 0.763 mmol) at 0° C. The resulting mixture was warmed to room temperature and stirred for 1 hr. The mixture was quenched with water and extracted with ethyl acetate. The organic layer was dried over anhydrous sodium sulfate, filtered, and concentrated to dryness to give the title compound as a solid. The solid was purified through silica gel column chromatography to give 280 mg(91%) of tan crystals, mp. 152–154° C.

1H NMR(CDCl$_3$) d 8.07(brs,1H), 6.88(s,2H), 6.16(s,1H), 4.75(m,1H), 4.25(s,2H), 3.33(m,1H), 2.30(s,3H), 2.18(s, 3H), 2.08(s,6H), 1.4–1.75(m,4H), 0.97(t,6H) ppm.

The following compounds were prepared by an analogous method to that in the preceding paragraph:

3-Chloro-N-[4-(1-ethyl-propylamino-6-methyl-2-(2,4,6-trimethyl-phenoxy)pyridin-3-yl]-propionamide tan solid, mp. 183–185° C. Anal. For C$_{23}$H$_{32}$ClN$_3$O$_2$ calc, C, 66.09; H, 7.72; N, 10.05; found, C, 66.27; H, 7.87; N, 9.99.

2-Chloro-N-[4-(1-ethyl-propylamino-6-methyl-2-(2,4,6-trimethyl-phenoxy)-pyridin-3-yl]-propionamide mp. 170–172° C., Anal. For C$_{23}$H$_{32}$ClN$_3$O$_2$ calc. C, 66.09; H, 7.72; N, 10.05; found C, 66.20; H, 7.52; N, 10.09.

EXAMPLE 116

N3-Allyl-N-4-(1-ethyl-propyl)-6-methyl-2-(2,4,6-trimethyl-phenoxy)-pyridine-3,4-diamine To a solution of N4-(1-ethyl-propyl)-6-methyl-2-(2,4,6-trimethyl-phenoxy)pyridine-3,4-diamine (500 mg, 1.52 mmol) in dry THF was added 1 M in THF of lithium bis(trimethylsilyl)amide (1.6 ml, 1.6 mmol) at −78° C., After stirring at −78° C. for 10 min, allyl bromide (0.13 ml, 1.52 mmol) was added and the resulting mixture was stirred at that temperature for 20 min, then warmed to room temperature overnight. The mixture was quenched with water and extracted with ethyl acetate. The organic layer was dried over anhydrous sodium sulfate, filtered, and concentrated to dryness to give the title compound as a green-blue oil. The oil was purified through silica gel column chromatography using 5% ethyl acetate in hexane as eluent to give a yellow crystal, mp. 86–88° C.

1H NMR(CDCl$_3$) d 6.87(s,2H), 6.0(m,2H), 5.2–5.35(m, 2H), 4.8(d,1H). 3.54(d,2H), 3.3(m,1H), 3.05(s,1H), 2.30(s, 3H), 2.14(s,3H), 2.09(s,6H), 1.4–1.6(m,4H). 0.96(t,6H) ppm.

The following compounds were prepared by an analogous method:

N3-(3-Chloro-propyl)-N4-(1-ethyl-propyl)-6-methyl-2-(2,4,6-trimethyl-phenoxy)-pyridine-3,4-diamine 1H NMR(CDCl$_3$) d 6.85(s,2H), 6.05(s,1H), 4.9(d,1H), 3.8(m,2H), 3.3(m,1H), 3.1 (m,2H), 2.3(s,3H), 2.159-s, 3H), 2.04(s,6H), 1.79 m,2H), 1.5(m,2H), 1.0(m,6H) ppm.

N4-(1-Ethyl-propyl-6-methyl-N3-propa-1,2-dienyl-2-(2, 4,6-trimethyl-phenoxy)pyridine-3,4-diamine 1H NMR(CDCl$_3$) d 8.93(d,1H), 6.86(s,2H), 6.66(m,1H), 6.09(s,1H), 5.4–5.6(m,2H), "5.54(d,1H), 3.27(m,1H), 2.27(s,3H), 2.12(s,3H), 2.05(s,6H). 1.6(m,4H), 0.94(t, 6H) ppm.

EXAMPLE 117

2-[3-Amino-2-(4-chloro-2,6-dimethyl-phenoxy)-6-methyl-pyridin-4-(S)-ylamino]-butan-1-ol A mixture of 2-[2-(4-Chloro-2,6-dimethyl-phenoxy)-6-methyl-3-nitro-pyridin-4(S)-ylamino]-butan-1-ol (120 mg) and Fe (73 mg) in 12 ml of 1:1 of AcOH:H$_2$O was heated at reflux for 2 hr. The reaction mixture was concentrated to dryness. The residue was quenched with water, basified to pH 12 and filtered through celite. The filtrate was extracted with chloroform. The organic layer was washed with brine, dried and concentrated to give the title compound as a yellow solid. The solid was purified through silica gel column chromatography using 1:1 EtOAc:hexane as eluent to give the title compound as a white solid, mp. 161–162° C.

1H NMR(CDCl$_3$) d 7.03(s,2H), 6.15(s,1H), 3.75(m,2), 3.47(m,1H), 2.25(brs,3H), 2.08(s,6H), 1.5–1.8(m,2H), 0.98-t,3H) ppm

EXAMPLE 118

2-(4-Chloro-2,6-dimethyl-phenoxy)-4-(1 ethyl-propylamino)methyl-nicotinic acid methyl ester A mixture of 4-chloro-6-methyl-2-(4-Chloro-2,6-dimethyl-phenoxy)-nicotinic acid methyl ester (77 mg, 0.226 mmol) and 1-ethyl-propyl-amine in DMSO was heated at 120° C. for 4 hr. The mixture was quenched with sat. ammonium chloride, water, brine and extracted with ethyl acetate. The organic layer was dried and concentrated to give 140 mg of yellow solid.

1-HNMR(CDCl$_3$) d 8.10(d,1H), 7.03(s,2H), 6.09(s,1H), 3.88(s,3H), 3.35(m,1H), 2.10(s,3H), 2.08(s,6H), 1.5–1.7(m, 4H), 0.96(t,6H) ppm.

EXAMPLE 119

2-(4-Bromo-2,6-dimethyl-phenoxy)-4-(1-ethyl-propylaminoy-6-methylnicotinic acid methyl ester A mixture of 4-chloro-6-methyl-2-(4-bromo-2,6-dimethyl-phenoxy) nicotinic acid methyl ester and 1-ethyl-propyl-amine in DMSO was heated at 120° C. for 16 hr. The mixture was quenched with water, brine and extracted with ethyl acetate. The organic layer was dried and concentrated to dryness. The residue was purified through silica gel column chromatography using hexane to 3% ethyl acetate in hexane as eluent to give the title compound as a white solid.
1H NMR(CDCl$_3$) d 8.1(d,1H), 7.18(s,2H), 6.08(s,1H), 3.87 (s,3H), 3.35(m,1H), 2.10(s,3H), 2.08(s,6H), 1.4–1.7(m,4H), 0.96(t,6H) ppm.

EXAMPLE 120

4-(1(1-Ethyl-prop-2-ynylamino)-6-methyl-2-(2,4,6-trimethyl-phenoxy)nicotinic acid methyl ester A mixture of 4-chloro-6-methyl-2-(2,4,6-trimethyl-phenoxy)-nicotinic acid methyl ester and 1-ethyl-propyl-amine in DMSO was heated at 130° C. overnight. The mixture was quenched with water, brine and extracted with ethyl acetate. The organic layer was dried and concentrated to dryness. The residue was purified through silica gel column chromatography to give the title compound. 1H NMR(CDCl$_3$) d 8.26(d,1H), 6.87(s,2H), 6.26(s,1H), 4.11(m, 1H), 3.87(s,3H), 2.324(m,1H), 2.30(s,3H), 2.17-s,3H), 2.08 (s,6H), 1.92(q,2H), 1.16(t,3H) ppm.

EXAMPLE 121

4-(s)-(1-Hydroxymethyl-propylamino)-6-methyl-2-(2,4,6-trimethyl-phenoxy)-nicotinic acid methyl ester A mixture of 4-chloro-2-(2,4,6-trimethyl-phenoxy)-6-methyl-nicotinic acid methyl ester (500 mg, 1.56 mmol) and (S)$_2$-amino-1-butanol (696 mg, 7.82 mmol) in DMSO was heated in 130° C. oil bath for 24 hr. The mixture cooled to rt and quenched with water and extracted with ethyl acetate. The organic layer was separated, washed with water, dried over anhydrous sodium sulfate, filtered, and concentrated to dryness to give 610 mg of crude product as an oil. The oil was purified through silica gel column chromatography using 30% ethyl acetate in hexane as eluent to give the title compound. Anal. calc. for C$_{21}$H$_{28}$N$_2$O$_4$1/2H$_2$O: C, 66.11; H, 7.66; N. 7.34; found: C, 66.27; H. 7.60; N, 7.21.

EXAMPLE 122

4-(1-Ethyl-2-hydroxy-propylamino)-6-methyl-2-(2,4,6-trimethyl-phenoxy)-nicotinic acid methyl ester A mixture of 4-chloro-2-(2,4,6-trimethyl-phenoxy)-6-methyl-nicotinic acid methyl ester (250 mg, 0.78 mmol) and 3-amino-pentan-2-ol (320 mg, 3.13 mmol) in DMSO was heated in 130° C. oil bath for 24 hr. The mixture cooled to rt and quenched with water and extracted with ethyl acetate. The organic layer was separated, washed with water, dried over anhydrous sodium sulfate, filtered, and concentrated to dryness to give 280 mg of crude product as an oil. The oil was purified through silica gel column chromatography using 20% ethyl acetate in hexane as eluent to give the title compound as a yellow solid, mp 116–120° C.

1H NMR(CDCl3) d 8.17(m,1H), 6.87(s,2H), 6.21&6.14 (two s, 1H), 3.88(s,3H), 3.8–4.0(m,2H), 3.5(m,1H), 3.3(m, 1H), 2.30(s,3H), 2.12(s,3H), 2.09(s,6H), 1.8(d.1H), 1.5–1.8 (m,2H), 1.26(d,3H), 0.99(t,3H) ppm.

EXAMPLE 123

2-(4-Bromo-2,6-dimethyl-phenoxy)-4-(S)-(1-hydroxymethyl-propylamino)-6-methyl-nicotinic acid methyl ester A mixture of 4-chloro-2-(4-bromo-2,6-trimethyl-phenoxy)-6-methyl-nicotinic acid methyl ester (850 mg) and (S)-2-amino-1-butanol in DMSO was heated in 130° C. oil bath for 24 hr. The mixture cooled to rt and quenched with water and extracted with ethyl acetate. The organic layer was separated, washed with water, dried over anhydrous sodium sulfate, filtered, and concentrated to dryness to give 764 mg of crude product as an oil. The oil was purified through silica gel column chromatography to give the title compound. 1H NMR (CDCl$_3$) d 8.15(d,1H), 7.16(s,2H), 6.18(s,1H), 3.86 (s,3H), 3.72(m,1H), 3.70(m,1H), 3.54(m,1H), 2.10(s,3H), 2.06(s,6H), 1.5–1.8(m,2H), 1.00(t,3H) ppm.

EXAMPLE 124

2-(4-Bromo-2,6-dimethyl-phenoxy)-4-(S)(1-methoxymethyl-propylamino)methyl-nicotinic acid methyl ester A mixture of 4-chloro-2-(4-bromo-2,6-trimethyl-phenoxy)-6-methyl-nicotinic acid methyl ester and 1-methoxymethyl-propylamine in DMSO was heated in 130° C. oil bath for 24 hr. The mixture cooled to rt and quenched with water and extracted with ethyl acetate. The organic layer was separated, washed with water, dried over anhydrous sodium sulfate, filtered, and concentrated to dryness to give crude product. The cude compound was purified through silica gel column chromatography to give the title compound.

EXAMPLE 125

2-(4-Chloro-2,6-dimethyl-phenoxy)-4-(1-hydroxymethyl-propylamino)-6-methyl-nicotinic acid methyl ester A mixture of 4-chloro-2-(4-chloro-2,6-dimethyl-phenoxy)-6-methyl-nicotinic acid methyl ester (9.000-g, 26.45 mmol) and (S)-2-amino-1-butanol (12.7 ml) in 1-methyl-2-pyrrolidinone was heated at 130° C. for 2 hr, then at 100° C. overnight. The mixture cooled to rt and poured into ice-water and diluted with ethyl acetate. The organic layer was separated, washed with water, dried over anhydrous sodium sulfate, filtered, and concentrated to dryness to give 13.69 of crude product as a light yellow oil. The oil was purified through silica gel column chromatography using chloroform to 2% MeOH in chloroform as eluent to give 6.6839 g (64%) of the title compound as a white glass foam. The glass foam was triturated with hexane to give a white solid. The solid was recrystallized from di-iso-propyl ether to give a white crystals, mp 122.5–124° C. Anal. calc. for $C_{20}H_{25}ClN_2O_4$: C, 61.14; H. 6.41; N, 7.13; found: C, 60.98; H, 6.43; N, 6.95.

EXAMPLE 126

2-(4-Chloro-2-methoxy-phenoxy)-4—(S)-(1-hydroxymethyl-propylamino)-6-methyl-nicotinic acid methyl ester A mixture of 4-chloro-2-(4-Chloro-2-methoxy-phenoxy)-6-methyl-nicotinic acid methyl ester and (S)-2-amino-1-butanol in 1-methyl-2-pyrrolidinone was heated at 130° C. overnight. The mixture cooled to room temperature and poured into ice-water and diluted with ethyl acetate. The organic layer was separated, washed with water, dried over anhydrous sodium sulfate, filtered, and concentrated to dryness. The residue was purified through silica gel column chromatography to give the title compound as a solid mp. 92.893.8° C., Anal. For $C_{19}H_{23}N_2O_5Cl$ calc. C, 57.80; H, 5.87; 7.09; found, C, 57.70; H, 5.89; 7.02.

EXAMPLE 127

2-(4-Chloro-2,6-dimethyl-phenoxy)-4-(1-ethyl-2-hydroxy-propylamino)-6-methyl-nicotinic acid methyl ester A mixture of 4-chloro-2-(4-chloro-2,6-dimethyl-phenoxy)-6-methyl-nicotinic acid methyl ester (500 mg, 1.47 mmol) and 3-amino-pentan-2-ol (758 mg, 7.35 mmol) in 1-methyl-2-pyrrolidinone was heated in 130° C. oil bath for 24 hr. The mixture cooled to rt and quenched with water and extracted with ethyl acetate. The organic layer was separated, washed with water, dried over anhydrous sodium sulfate, filtered, and concentrated to dryness to give an oil. The oil was purified through silica gel column chromatography using 20% ethyl acetate in hexane as eluent to give the title compound as a white crystal, mp 133–135° C.

1H NMR(CDCl$_3$) d 8.19(m,1H), 7.00(s,2H), 6.20&6.14 (two sets of s,1H), 3.83.9(m,1H), 3.86(s,3H), 3.3&3.5(two sets of m,1H), 2.07(s,3H), 2.06(s,6H), 1.75(m,1H), 1.55(m, 1H), 1.24(d,3H), 0.96(t,3H) ppm.

EXAMPLE 128

2-(4-Chloro-2,6-dimethyl-phenoxy)-4-(1-ethyl-2-methoxy-propylamino-6-methyl-nicotinic acid methyl ester To a solution of 2-(4-chloro-2,6-dimethyl-phenoxy)-4-(1-ethyl-2-hydroxy-propylamino)-6-methyl-nicotinic acid methyl ester (50 mg, 0.123 mmol) in dry THF was added NaH and stirred for 20 min. An excess of MeI was added and the resulting mixture was stirred at rt overnight. The mixture cooled to rt and quenched with water and extracted with ethyl acetate. The organic layer was separated, washed with water, dried over anhydrous sodium sulfate, filtered, and concentrated to dryness to give an oil. The oil was purified through silica gel column chromatography using 20% ethyl acetate in hexane asan eluent to give the Uiole compound as a clear oil. 1H NMR(CDCl3) d 8.20(d,1H), 7.00(s,2H), 6.14&6.10(two sets of s,1H), 3.859-s,3H), 3.47(m,1H), 3.39&3.37(two sets of s,3H), 2.08(s,3H), 2.06(s,6H), 1.75 (m,1H), 1.58(m,1H), 1.1 4(t,3H), 0.95(t,3H) ppm.

EXAMPLE 129

2-(4-Chloro-2,6-dimethyl-phenoxy)-4-(1-ethyl-2-oxo-propylamino)-6-methyl-nicotinic acid methyl ester The title compound was prepared by Dess-Martin oxidation of 2-(4-chloro-2,6-dimethyl-phenoxy)-4-(1-ethyl-2-hydroxy-propylamino)-6-methyl-nicotinic acid methyl ester. A white solid was obtained after silica gel column chromatography. 1H NMR(CDCl$_3$) d 8.6(d,1H), 7.01 (s,2H), 5.899-s,1H), 3.9–4.0(m,1H), 3.90(s,3H), 2.17(s,3H), 2.07(s, 3H), 2.05(s,3H), 1.859-m,1H), 1.93(m,1H), 1.00(t,3H) ppm.

Example 130

2-(4-Chloro-2,6-dimethyl-phenoxy)-4-(1-formyl-propylamino)-6-methyl-nicotinic acid methyl ester The title compound was prepared by Dess-Martin oxidation of 2-(4-chloro-2,6-dimethyl-phenoxy)-4-(1-hydroxymethyl-propylamino)&methyl-nicotinic acid methyl ester. The title compound was obtained after column chromatography. 1H NMR (CDCl$_3$) 9.54(d,1H), 8.56(d,1H), 7.01(s,2H), 5.93(s,1H), 3.92(m,1H), 3.89(s,3H), 2.08(s,3H), 2.05(s,6H), 1.05(t,3H) ppm.

EXAMPLE 131

2-(4-Chloro-2,6-dimethyl-phenoxy)-4-(S)-(4-ethyl-2-oxo-oxazolidin-3-yl)-6-methyl-nicotinic acid methyl ester A mixture of 2-(4-chloro-2,6-dimethyl-phenoxy)$_4$-(1-hydroxymethyl-propylamino)& methyl-nicotinic acid methyl ester (106 mg, 0.27 mmol), triphosgene)$_{27}$ mg, 0.090 mmol), triethylamine (27 mg, 0.27 mmol) in dry THF was stirred at room temperature for 2 hr. The mixture was quenched with water and extracted with ethyl acetate. The organic layer was separated, washed with water, dried over anhydrous sodium sulfate, filtered, and concentrated to dryness to give 13.6-g of crude product as a white glass foam. The foam was triturated with hexane/diethyl ether to give a white solid, mp. 144–145.5° C., Anal. For $C_{21}H_{23}ClN_2O_5$ calc. C, 60.22; H, 5.53; N. 6.69; found: C, 60.10, H. 5.79; N, 6.66.

EXAMPLE 132

2-(4-Chloro-2,6-dimethyl-phenoxy)-4-(S)-(1-[(2-hydroxy-ethylamino)-methyl]-propylamino)-6-methyl-nicotinic acid methyl ester To a solution of 2-(4-chloro-2,6-dimethyl-phenoxy)-4-(1-formyl-propylamino)-6-ethyl-nicotinic acid methyl ester in dichloroethane was added 2-amino-ethanol, sodium cyanoborohydride, acetic acid, anhydrous sodium sulfate. The resulting mixture was heated at reflux and cooled to rt. The mixture was quenched with water and extracted with chloroform. The organic layer was separated, washed with water, dried over anhydrous sodium sulfate, filtered, and concentrated to dryness. After chromatography, the title compound was obtained as a white glass foam. 1H NMR (CDCl₃) d 8.3(d,1H), 7.0(s,2H), 6.1(s,1H), 3.9(s,3H), 3.84 (m,2H), 3.57(m,1H), 2.90(m,2H), 2.83(m,2H). 2.5(brs,2H), 2.09(s,3H), 2.06(s,6H), 1.65(m,2H), 0.97(t,3H) ppm.

EXAMPLE 133

4-[Ethyl-(2-hydroxy-ethyl)-amino"-methyl-2-(2,4,6-trimethyl-phenoxy)-nicotinic acid methyl ester A mixture of 4-chloro-6-methyl-2-(2,4,6-trimethyl-phenoxy) nicotinic acid methyl ester and 1-ethyl-propyl-amine in 1-methyl-2-pyrrolidinone was heated at 130° C. until starting material was consumed. The mixture was quenched with water, brine and extracted with ethyl acetate. The organic layer was dried and concentrated to dryness. The residue was purified through silica gel column chromatography to give the title compound. 1H NMR(CDCl₃) d 6.85(s,2H), 6.40(s,1H), 3.88(s,3H), 3.73(t,2H), 3.43(t,2H), 3.31(q,2H), 2.27(s,3H), 2.22(s,3H), 2.06(s,6H), 1.15(t,3H) ppm.

EXAMPLE 134

4-[Ethyl-(2-methanesulfonyloxy-ethyl)amino]-6-methyl-2-(2,4,64-trimethyl-phenoxy)-nicotinic acid methyl ester A mixture of 4-[ethyl-(2-hydroxy-ethyl)amino]+methyl-22,4,6-trimethyl-phenoxy)-nicotinic acid methyl ester, methanesulfonyl chloride and triethylamine in methylene chloride was stirred at rt until all starting material were consumed. The mixture was quenched with water, brine and extracted with methylene chloride. The organic layer was dried and concentrated to dryness. The residue was purified through silica gel column chromatography to give the title compound. 1H NMR(CDCl₃) d 6.83(s,2H), 6.25(s,1H), 4.34 (t,2H), 3.86(s,3H), 3.6(t,2H), 3.38(t,2H), 3.09-s,3H), 2.25(s, 3H), 2.20(s,3H), 2.04(s,6H), 1.18(t,3H) ppm.

EXAMPLE 135

4-[(2-Hydroxy-ethyl)-thiophen-2-ylmethyl-amino-methyl-2-(2,4,6-trimethyl-phenoxy)-nicotinic acid methyl ester A mixture of 4-chloro-6-methyl-2-(2,4,6-trimethyl-phenoxy) nicotinic acid methyl ester and 2-[(thiophen-2-ylmethyl)amino]-ethanol in 1-methyl-2-pyrrolidinone was heated at 130° C. overnight. The mixture was quenched with water, brine and extracted with ethyl acetate. The organic layer was dried and concentrated to dryness. The residue was purified through silica gel column chromatography to give the title compound. 1H NMR (CDCl₃) d 7.22(m,1H), 6.94-m,2H), 6.84(s,2H), 6.44(s,1H), 4.52(s,2H), 3.91(s,3H), 3.679-t,2H), 3.369-t,2H), 2.279-s,3H), 2.20(s,3H), 2.07(s, 6H) ppm.

EXAMPLE 136

The following compounds were prepared by the method analogous to that in Example 118, starting with an appropriate 4-chloro-6-methyl-2-(substituted-phenoxy) nicotinic acid alkyl ester with an appropriate alkyl- or dialkyl-amine.

4-(2,2-Dimethyl-4-phenyl-[1,3]dioxan-5-ylamino-6-methyl-2-(2,4,6-trimethyl-phenoxy)-nicotinic acid methyl ester 1H NMR (CDCl₃) d 8.71(d,2H), 7,1-7.4(m,5H), 6.82(s, 2H), 5.55(s,1H), 5.229-s,1H), 4.29(d,1H), 3.97(d,1H), 3.869-s,3H), 3.61(d,1H), 2.25(s,3H), 2.01(s,6H), 1.91(s, 3H), 1.65(s.3H), 1.61(s,3H) ppm.

2-(4-Chloro-2,6-dimethyl-phenoxy)-4—(S)(1-hydroxymethylpropylamino)-6-methyl-nicotinic acid ethyl ester 1H NMR(CDCl₃) d 8.71(d,1H), 7.02(s,2H), 6.17(s,1H), 4.33(q,2H), 3.71(m,1H), 3.66(m,1H), 3.54-m,1H). 2.10(s, 3H), 2.07(s,6H), 1.5–1.8(m,2H), 1.33(t,3H), 1.00(t,3H) ppm.

4-[Ethyl-(2-methoxy-ethyl)amino-4-methyl-2-(2,4,6-trimethyl-phenoxy) nicotinic acid methyl ester 1H NMR(CDCl₃) d 6.83(s,2H), 6.19(s,1H), 3.869-s,3H), 3.35–3.6(m,4H), 3.35(s,3H), 2.26(s,3H), 2.15(s,3H), 2.06(s, 6H), 1.1 79-t,3H) ppm.

2-(4-Chloro-2,6-dimethyl-phenoxy)₄—(S,R)-&(S,S)(1-ethyl-2-hydroxy-propylamino)-6-methyl-nicotinic acid methyl ester 1H NMR(CDCl₃) d 8.2(d,1H), 7.01(s2H), 6.20(s, 0.2H), 6.15(s,0.8H), 3.92(m,1H), 3.87(s,3H), 3.48(m,0.2H), 3.31 (m,0.8H), 2.08(s,3H), 2.06(s,6H), 1.5–1.8(m,2H), 1.25(d, 3H), 0.96(t,3H) ppm.

2-(4-Chloro-2,6-dimethyl-phenoxy)-4—(R)(1-hydroxymethylpropylamino)-6-methyl-nicotinic acid methyl ester 1H NMR(CDCl₃) 8.12(d,1H), 7.00(s,2H), 6.16(s,1H), 3.85(s,3H), 3.6–3.8(m,2H), 3.53(m,1H), 2.08(s,3H), 2.05(s, 6H), 1.5–1.8(m,2H), 0.98(t,3H) ppm.

4-(2-Hydroxy-1-hydroxymethyl-ethylamino)-6-methyl-2-(2,4,6-trimethyl-phenoxy)-nicotinic acid methyl ester 1H NMR(CDCl₃) d 8.44(d,1H), 6.84(s,2H), 6.17(s,1H), 3.8–4.0(m,4H), 3.85(s,3H), 3.70(m,1H), 2.60(s,3H), 2.27(s, 3H), 2.11(s,2H), 2.05(s,6H) ppm.

4-(2-Methoxy-1-methoxymethyl-ethylamino)-6-methyl-2-(2,4,6-trimethyl-phenoxy)-nicotinic acid methyl ester 1H NMR(CDCl₃) d 8.38(d,1H), 6.88(s,2H), 6.18(s,1H), 3.88(s,3H), 3.78(m,1H), 3.56(m,2H), 3.44(s,6H), 2.31(s, 3H), 2.15(s,3H), 2.09(s,6H) ppm.

4-(1-Hydroxymethyl-2-methoxy-ethylamino)-6-methyl-2-(2,4,6-trimethyl-phenoxy)-nicotinic acid methyl ester 1H NMR(CDCl₃) d 8.44(d,1H), 6.88(s,2H), 6.21(s,1H), 3.89(s,3H), 3.80(m,1H), 3.5–3.7(m,2H), 3.45(s,3H), 2.31(s, 3H), 2.16(s,3H), 2.09(s,6H) ppm.

2-(4-Chloro-2,6-dimethyl-phenoxy)-4-(1-ethyl-2-hydroxy-butylamino)-methyl-nicotinic acid methyl ester 1H NMR (CDCl₃) d 8.34(d,1H), 7.069-s,2H). 6.16(s,1H), 3.91(s,3H), 3.70(m,1H), 3.5(m,1H), 2.13(s,3H), 2.11 (s,6H), 1.5–1.9(m,4H), 1.01(m,6H) ppm.

EXAMPLE 137

[2-(4-Chloro-2,6-dimethyl-phenoxy)-4-(1-ethyl-propylamino)-6-methyl-pyridin-3-yl]-methanol A mixture of 4-(1-ethyl-propylamino)-6-methyl-2-(2,4,6-trimethyl-phenoxy)-nicotinic acid methyl ester (130 mg, 0.332 mmol) and an excess of 1M diisobutyl aluminum hydride in THF in dry THF was stirred at −78° C. for 10 min, then warmed to rt. The mixture was quenched with methanol and stirred at room temperature for 20 min, filtered through celite and washed with methanol and chloroform. The filtrate was concentrated to dryness. The residue was purified through silica gel column chromatography to give the title compound. 1-HNMR(CDCl₃) d 7.03(s,2H), 6.11(s,1H), 5.03(d,1H), 4.96(s,2H), 3.32(m,1H), 2.14(s,3H), 2.07(s,6H), 1.4–1.7(m,4H), 0.96(t,6H) ppm.,

[2(4-Bromo-2,6-dimethyl-phenoxy)-4-(1-ethyl-propylamino)-6-methyl-pyridin-3-yl]-methanol The title compound was prepared by the method analogous to that in the preceding paragraph. 1H NMR(CDCl₃) d 7.18(s,2H), 6.11(s,1H), 5.05(d,1H), 4.91(d,2H), 3.31(m, 1H), 2.14(s,3H), 2.07(s,6H), 1.4–1.7(m,4H), 0.96(t,6H) ppm.

EXAMPLE 138

2-[3-Hydroxymethyl-6-methyl-2-(2,4,6-trimethyl-phenoxy)-pyridin-4-(S)-ylamino]-butan-1-ol A mixture of 4-(s)(1-hydroxymethyl-propylamino-6-methyl-2-(2,4,6-trimethyl-phenoxy) nicotinic acid methyl ester and 1 M lithium aluminum hydride and aluminum chloride in THF in dry THF was heated at reflux. The mixture was cooled and quenched with water, 2N NaOH, then of water and stirred at room temperature for 10 min. White solid formed and was filtered through celite, washed with THF. The filtrate was concentrate to dryness to give the title compound as white solid after column chromatography, mp. 135–137° C.; Anal. For $C_{20}H_{28}N_2O_3$ calc. C, 69.74; H, 8.19; N. 8.13; found C, 69.42; H, 8.34; N. 7.95

The following compounds were prepared by the method analogous to that in the preceding paragraph, starting with the corresponding ester with lithium aluminum hydride and aluminum chloride.

3-[2-(4-Chloro-2,6-dimethyl-phenoxy)-3-hydroxymethyl-6-methyl-pyridin-4-ylamino]-pentan-2-ol mp. 180–182° C. 1H NMR($CDCl_3$) 7.0(s,2H), 6.18&6.15 (two sets of s,1H), 5.1 and 5.22(m,1H), 4.92(m,2H), 3.804.0 (m,1H), 3.20–3.5(m,1H), 2.11(s,3H), 2.04(s,6H), 1.4–1.8 (m,2H), 1.23(m,3H), 0.98(m,3H) ppm.

2-[2-(2,6-Dimethyl-phenoxy)-3-hydroxymethyl-6-methyl-pyridin-4-ylamino]-butan-1-ol 1H ($CDCl_3$) d 7.05(m,3H), 6.20(s,1H), 4.8–5.0(m,2H), 3.74(m,1H), 3.66(m,1H), 3.50(m,1H), 2.0-2.29-m,9H), 1.55–1.75(m,2H), 0.99(t,3H) ppm.

3-[3-Hydroxymethyl-6-methyl-2-(2,4,6-trimethyl-phenoxy pyridin-4-ylamino]-pentan-2-ol 1H NMR($CDCl_3$) d 6.86(s,2H), 6.17(s, 1H), 4.0(d,1H), 3.9(m,1H), 3.3(m,1H), 2.29(s,3H), 2.14(s,3H), 2.13(s,3H), 2.07(s,6H), 1.8(d,1H), 1.4–1.8(m,2H), 1.25(d,3H), 0.99(t, 3H) ppm.

2-[2-(4-Chloro-2-methoxy-phenoxy-3-hydroxymethyl-6-methyl-pyridin-4-ylamino]-butan-1-ol 1H NMR($CDCl_3$) 6.8–7.0(m,3H), 6.2(s,1H), 5.02(d,1H), 4.7(ABq,2H), 3.74(m,5H), 3.350–3.5(m,2H), 2.9(brs,2H), 2.18(s,3H), 1.4–1.7(m,2H), 1.23(m,3H), 0.95(t,3H) ppm.

EXAMPLE 139

2-[2-(4-Chloro-2,6-dimethyl-phenoxy)-3-hydroxymethylsmethyl-pyridin-4-ylamino]-butan-1-ol A mixture of 4-(s)-(1-hydroxymethylpropylamino)-6-methyl-2-(4-chloro-2,6-dimethyl-phenoxy)-nicotinic acid methyl ester and 1M lithium aluminum hydride in THF was stirred at rt for 2 hr. The mixture was cooled and quenched with water, 2N NaOH, then of water and stirred at room temperature for 10 min. White solid formed and was filtered through celite, washed with THF. The filtrate was concentrate to dryness to give the title compound as white solid after column chromatography, mp 133–135° C., 1H NMR ($CDCl_3$) 7.00(s,2H), 6.17(s,1H), 5.12(d,1H), 4.90(m,2H), 3.4–3.8(m,3H), 2.12(s,3H), 2.04(s,6H), 1.4–1.6(m,2H), 0.99 (t,3H) ppm.

The following compounds were prepared by the method analogous to that in the preceding paragraph, starting with the corresponding methyl ester with lithium aluminum hydride:

2-Ethyl-[3-hydroxymethyl-6-methyl-2-(2,4,6-trimethyl-phenoxy)pyridin-4-yl]-amino)-ethanol 1H NMR($CDCl_3$) d 1H NMR(CDCl3) 6.86(s,2H), 6.53 (s,1H), 4.94(s,2H), 3.67(m,2H), 3.1–3.3 (m,4H), 2.28(s,3H), 2.20(s,3H), 2.04(s,6H), 1.09(t,3H) ppm.

4-[2-(4-Chloro-2,6-dimethyl-phenoxy)-3-hydroxymethyl-6-methyl-pyridin-4-ylamino]-hexan-3-ol mp. 145–148° C. 1H NMR(CDCl3) d 1H NMR(CDCl3) 7.05(s,2H), 6.16(s,1H), 5.3(d,1H), 4.94(s,2H), 3.67(m,1H), 3.40 (m,1H), 2.151(s,3H), 2.09(s,6H), 1.4–1.8(m,4H), 1.23 (m,3H), 1.02(m,6H) ppm.

2-[24-Chloro-2-methoxy-phenoxy)-3-hydroxymethl-methyl-pyridin-4-(S)-ylamino]-butan-1-ol 1H NMR ($CDCl_3$) d 7.8-7.95(m,2H), 5.02(d,1H), 4.74 (ABq,2H), 3.74(s,3H), 3.72(m,2H). 3.45-m,1H), 2.98(brs, 1H), 2.18(s,3H), 1.4–1.7(m,2H), 0.95(t,3H) ppm.

4-[24-Chloro-2,6-dimethyl-phenoxy)-3-hydroxymethyl-6-methyl-pyridin-4-ylamino]-9 hexan-3-ol 1H NMR ($CDCl_3$) d 7.05(s,2H), 6.16(s,1H), 5.30(d,1H), 4.94(s,2H), 3.67(m,1H), 3.4(m,1H), 2.15(s,3H), 2.09(s,6H), 1.5–1.9(m,4H), 1.01(m,6H) ppm.

[2-(2,4-Dimethoxy-phenylamino)$_4$-(1-methoxymethyl-propoxy)$_6$-methyl-pyridin-3-yl]-methanol 1H NMR($CDCl_3$) d 6.90(d,1H), 6.42(s,1H), 6.40(d,1H), 5.91(s,1H), 4.42(m,1H), 4.28(s,2H), 3.79(s,3H), 3.76(s,3H), 3.56(m,2H), 3.40(s,3H), 2.33(s,3H), 1.5–1.85(m,2H), 1.02 (t,3H) ppm.

EXAMPLE 140

2-(4-Chloro-2,6-dimethyl-phenoxy)-4—(S)(1-hydroxymethyl-propylamino-6-ethyl-nicotinic acid A mixture of 244-chloro-2,6-dimethyl-phenoxy)$_4$—(S) 41-hydroxymethyl-propylamino)-6-methyl-nicotinic acid methyl ester (113 mg) and lithium hydroxide in dioxane/THF/water was stirred at room temperature over night. The mixture was quenched with ammonium chloride and extracted with chloroform. The organic layer was dried and concentrated to give 78 mg of the title compound as a white solid. 1H NMR(CDCl3) d 10.55(brs,1H), 9.2(d,1H), 7.06(s, 2H), 6.3(s,1H), 3.5–3.8(m,3H), 2.11(s,3H), 2.09(s,3H), 2.08 (s,3H). 1.78(m,1H), 1.62(m,1.H), 1.0-O(t,3H) ppm.

4-(1-Ethyl-prop-2-ynylamino)-6-methyl-2-(2,4,6-trimethyl-phenoxy)-nicotinic acid mp. 131–133° C., 1H NMR(CDC14) d 11.29(brs,1H), 9.35(d,1H), 6.91(s,2H), 6.38(s,1H), 4.12(m,1H), 2.88(m, 1H), 2.32(s,3H), 2.19(s,3H), 2.09(s,6H), 1.96(m,2H), 1.17 (t,6H) ppm.

2-(4-Bromo-2,6-dimethyl-phenoxy)-4-(S)-(1-methoxymethyl-propylamino)-6-methyl-nicotinic acid 1H NMR ($CDCl_3$) d 10.5(brs, 1H), 8.6(d,1H). 7.15(d,2H), 6.25(s,1H), 3.3–3.6(m,3H), 3.38(s,3H), 2.11 (s,3H), 2.09(s, 3H), 2.08(s,3H), 1.5–1.85(m,2H), 0.91 (t,3H) ppm.

4-(2-Methoxy-1-methoxymethyl-ethylamino)-6-methyl-2-(2,4,6-trimethyl-phenox)-nicotinic acid 1H NMR($CDCl_3$) d 9.44(d,1H), 6.92(s,2H), 6.30(s,1H), 3.80(m,1H), 3.58(m,2H), 3.44(s,6H), 2.33(s,3H), 2.16(s, 3H), 2.10(s,6H) ppm.

EXAMPLE 141

The following compounds were prepared by reacting the corresponding [2-(substituted-phenoxy)-3-chloromethyl-6-methyl-pyridin-4-yl]-(alkyl)-amine with an appropriate amine.

[24-Chloro-2,6-dimethyl-phenoxy)-3-isobutoxymethyl-6-methyl-pyridin-4-yl]-(1-ethyl-propyl)-amine 1H NMR($CDCl_3$) d 6.94(s,2H), 6.0(s,1H), 5.13(d,1H), 4.7(s,2H), 3.2(m,1H), 3.16(d,2H), 2.02(s,3H), 1.96(s,6H), 1.8(m,1H), 1.3–1.6(m,4H), 0.82(t,6H), 0.B(d,6H) ppm.

[3-Ethoxymethyl-6-methyl-2-(2,4,6-trimethyl-phenoxy) pyridin-4-yl]-(1-ethyl-propyl)-amine 1H NMR (CDCl$_3$) d 6.86(s,2H), 6.03(s,1H), 5.30(d,1H), 4.83(s,2H), 3.58(q,2H), 3.35(m,1H),2.29(s,3H), 2.15(s,3H), 2.06(s,6H), 1.5–1.78(m,4H), 1.23(t,3H), 0.967(t,6H) ppm.

2 ]-3-Butoxymethyl-6-methyl-2-(2,4,6-trimethyl-phenoxy)-pyridin-4-ylamino]-butan-1-ol 1H NMR(CDCl$_3$) d 6.85(s,2H), 6.179-s,1H), 5.3(d,1H), 4.82(Abq,2H), 3.5–3.8(m,2H), 3.5(t,2H), 2.3(s,3H), 2.15(s, 3H, 2.02(s,6H),1.75(brs,1H), 1.5–1.8(m,4H), 1.3–1.5(m, 2H), 1.02(t,3H), 0.9(t,3H) ppm.

EXAMPLE 142

1-[4(1-Ethyl-propylamino)-6-methyl-2-(2,4,6-trimethyl-phenoxy)-pyridin-3-yl]-ethanol The title compound was prepared by reacting 4-(1-ethyl-propylamino)-6-methyl-2-(2,4,6-trimethyl-phenoxy)-pyridine-3-carbaldehyde with methyllithium lithium in THF at −78° C. The desired product was isolated after silica gel column chromatography to give 60.1% of colorless oil. 1H NMR(CDCl$_3$) d 6.87(s,2H), 6.06(s,1H), 5.7(q,1H), 3.3(m, 1H), 2.29(s,3H), 2.12(s,6H), 2.069-s,3H), 1.4–1.7(m,4H), 1.59(d,3H), 0.8–1.0(m,BH) ppm.

EXAMPLE 143

Acetic acid 4-(1-ethyl-propylamino)-6-methyl-2-(2,4,6-trimethyl-phenoxy)-pyridin-3-ylmethyl ester The title compound was obtained by acetylation of [2-(2, 4,6-trimethyl-phenoxy-3-hydroxymethyl ethyl-pyridin-4-yq-(1-ethyl-propyl)-amine.

1H NMR(CCl$_3$) d 6.84(s,2H), 6.04(s,1H), 5.35(s,2H), 5.23(d,1H), 3.32(m,1H), 2.28(s,3H), 2.12(s,3H), 2.08(s,3H), 2.07(s,6H), 1.4–1.7(m,4H), 0.93(t,6H) ppm.

EXAMPLE 144

2-[2-(4-Chloro-2,6-dimethyl-phenoxy)-3-(1-hydroxy-1-methylethyl)$_6$-methyl-pyridin-4-(S) ylamino]butan-1-ol The title compound was prepared by reacting 2-(4-chloro-2,6-dimethyl-phenoxy)(1-hydroxymethyl-propylamino-6-methyl-nicotinic acid methyl ester with an excess of 1 M methyl magnesium bromide in THF at room temperature overnight. Standard work-up procedure to give the title compound after silica gel chromatography.

1H NMR(CDCl$_3$) d 7.4(brs,1H), 7.01(s,2H), 6.13(s,1H), 3.7(m,1H), 3.6(m,1H), 3.45(m,1H), 2.04(s,3H), 2.03(s,3H), 2.02(s,3H), 1.5–1.7(m,2H), 0.98(t,3H) ppm.

EXAMPLE 145

[2-(4-Chloro-2,6-dimethyl-phenoxy)-3,6-dimethyl-pyridin-4-yl]-(1-ethyl-propyl)-amine To a solution of (2-(4-Chloro-2,6-dimethyl-phenoxy)-3-chloromethyl-6-methyl-pyridin-4-yl]-(1-ethyl-propyl)-amine (75 mg, 0.196 mmol) in dry THF was added 1.0M BH$_3$ in THF (0.59 ml, 0.59 mmol) and stirred for 2 hr. The mixture was quenched with dilute HCl and stirred for 5 min. The reaction mixture was neutralized with 2N NaOH, water and extracted with ethyl acetate. The organic layer was separated, dried and concentrated to dryness. The residue was purified through silica gel column chromatography to give the title compound as a colorless oil.

1H NMR(CDCl$_3$) d 7.03(s,2H), 6.08(s,1H), 3.73(d,1H), 3.3(m,1H), 2.15(s,3H), 2.12(s,3H), 2.08(s,6H), 1.4–1.6 (m.4H). 0.96(t,6H) ppm.

EXAMPLE 146

[22,6-Dimethyl-phenoxy)-3,6-dimethyl-pyridin-4-yl]-(1-ethyl-propyl)-amine

To a solution of (2-(4-bromo-2,6-dimethyl-phenoxy)$_4$-(1-ethyl-propylamino)$_6$-methyl-pyridin-3-yl]-methanol (43 mg, 0.106 mmol) in dry THF was added 1.0M lithium aluminium hydride in diethyl ether (0.25 ml) and aluminum chloride (28 mg). The resulting mixture was stirred at room temperature overnight. The mixture was quenched with water, 2-NaOH, then water. Solid formed and filtered through celite, washed with THF, then chloroform. The filtrate was concentrated to dryness. The residue was diluted with water and ethyl acetate. The organic layer was separated, dried and concentrated to give the crude material. The title compound was isolated after silica gel chromatography. 1H NMR(CDCl$_3$) d 6.9-7.1(m,3H), 6.07(s,1H), 3.35 (d,1H), 3.33(m,1H), 2.14(s,3H), 2.13(s,3H), 2.12(s,6H), 1.51.8(m,4H), 0.97(t,6H) ppm.

EXAMPLE 147

[2-(4-Bromo-2,6-dimethyl-phenoxy)3,6-dimethyl-pyridin-4-yl]-(1-ethyl-propyl)-amine The title compound was prepared by the method analogous to that in Example 145 as a white solid. 1H NMR (CDCl$_3$) d 7.19(s,2H), 6.09(s,1H), 3.36(d,1H), 3.33(m,1H), 2.15(s,3H), 2.12(s,3H), 2.09(s,6H), 1.4–1.8(m,4H), 0.97(t, 6H) ppm.

EXAMPLE 148

4-[4-(1-Ethyl-propylamino)3,6-dimethyl-pyridin-2-yloxy]-3,5-dimethyl-benzaldehyde To a solution of [2-(4-bromo-2,6-dimethyl-phenoxy)-3,6-dimethyl-pyridin-4-yl]-(1-ethyl-propyl)-amine in dry THF was added n-butyllithium at −78° C. After stirring at −78° C. for 10 min, n,N-dimethylformamide was added and the resulting mixture was stirred at −78° C. for 20 min, the dry-ice bath was removed. After stirring for 5 min, the mixture was quenched with diluted HCl, water and adjusted to pH7.5 and extracted with ethyl acetate. The organic layer was separated, dried, and concentrated to dryness. The residue was purified through silica gel chromatography to give the tiUe compound. 1H NMR(CDCl$_3$) d 9.93(s,1H), 7.60(s,2H), 6.10(s,1H), 3.75(d,1H), 3.35(m1H), 2.17(s,6H), 2.13(s,3H), 2.12(s,3H), 1.4–1.8(m,4H), 0.97(t,6H) ppm.

EXAMPLE 149

{4-[4-(1-Ethyl-proplamino)-3,6-dimethyl-pyridin-2-yloxy]-3,5-dimethyl-phenyl)-methanol A mixture of 4-[4-(1-Ethyl-propylamino)-3,6-dimethyl-pyridin-2-yloxy]-3,5-dimethyl-benzaldehyde and sodium borohydride in methanol was stirred at room temperature. After standard work-up procedure and purification, the title compound was obtained as a solid. 1H NMR(CDCl$_3$) d 7.06(s,2H), 6.08(s,1H), 4.64(s,2H), 3.74(d,1H), 3.33(m,1H), 2.14(s,3H), ig jut-2.13(s,3H), 2.1 1(s,6H) ppm.,

EXAMPLE 150

(1-Ethyl-propyl)-[2-(4-methoxymethyl-2,6-dimethyl-phenoxyy-3,6-dimethyl-pyridin-4-yl]-amine To a solution of (4-[4-(1-Ethyl-propylamino)-3,6-dimethyl-pyridin-2-yloxy]-3,5-dimethyl-phenyl)methanol in dry THF was added 60% NaOH in oil and stirred for 5 min. Excess of MeI AL was added and stirred at room temperature for 2 hr. After standard worked up procedure and purification, the title compound was obtained as a clear golden oil. 1H NMR(CDCl$_3$) d 7.02(s,2H), 6.06(s,1H), 4.40(s,3H), 3.72(d,1H), 3.39(s,3H), 3.36(m,1H), 2.12(s,3H), 2.11(s,3H), 2.10(s,6H), 1.4–1.7(m,4H), 0.95(t,6H) ppm.

EXAMPLE 151

[2-(4-Ethyl-2,6-dimethyl-phenoxy)-3,6-dimethyl-pyridin-4-yl]-(1-ethyl-propyl)-amine To a solution of [2-(4-bromo-2,6-dimethyl-phenoxy)-3,6-dimethyl-pyridin-4-yl]-(1-ethyl-propyl)amine in dry THF was added n-butyllithium at −78° C. After stirring at −782 C. for 10 min, ethyl iodide was added and the resulting mixture was stirred at −78° C. for 30 min, the dry-ice bath was removed. After stirring for 5 min, the mixture was quenched with brine and extracted with ethyl acetate. The organic layer was separated, dried, and concentrated to dryness. The residue was purified through silica gel chromatography to give the title compound. 1H NMR(CDCl$_3$) d 6.89(s,2H). 6.07(s,1H), 3.72(d,1H), 3.34(m,1H), 2.58(q, 2H), 2.16(s,3H), 2.12(s,3H), 2.09(s,6H), 1.4–1.7(m,4H), 1.25(t,3H). 0.96(t,6H) ppm.

EXAMPLE 152

2-[4-[4-(1-Ethyl-propylamino)-3,6-dimethyl-pyridin-2-yloxy]-3,5-dimethyl-phenyl}-propan-2-ol To a solution of [2-(4-bromo-2,6-dimethyl-phenoxy)-3,6-dimethyl-pyridin-4-yl]-(1-ethyl-propyl)-amine in dry THF was added n-butyllithium at −78° C. After stirring at −78° C. for 10 min, acetone was added and the resulting mixture was stirred at −78° C. for 30 min, the dry-ice bath was removed. After stirring for 5 min, the mixture was quenched with brine and extracted with ethyl acetate. The organic layer was separated, dried, and concentrated to dryness. The residue was purified through silica gel chromatography to give the title compound. 1H NMR(CDCl$_3$) d 7.17(s,2H), 6.08(s,1H), 3.73(d,1H), 3.33(m,1H), 2.19(s,3H), 2.15(s,3H), 2.12(s,6H), 1.4–1.7(m,4H), 1.26(s,6H), 0.96(t,6H) ppm.

EXAMPLE 153

1-{4-[4-(1-Ethyl-propylamino)-3,6-dimethyl-pyridin-2-yloxy]-3,5-dimethyl-phenyl}-ethanol To a solution of 124-bromo-2,6-dimethyl-phenoxy)3.6-dimethyl-pyridin-4-yl]-(1-ethyl-propyl)amine in dry THF was added n-butyllithium at −78° C. After stirring at −78° C. for 10 min, acetaldehyde was added and the resulting mixture was stirred at −78° C. for 30 min, the dry-ice bath was removed. After stirring for 5 min, the mixture was quenched with brine and extracted with ethyl acetate. The organic layer was separated, dried, and concentrated to dryness. The residue was purified through silica gel chromatography to give the title compound. 1H NMR(CDCl$_3$) d 7.06(s,2H), 4.84(m,1H), 6.08(s,1H), 3.73(d,1H), 3.35(m, 1H), 2.14(s,3H), 2.12(s,3H), 2.11 (s,6H),1.4-1.7(m,4H), 1.51 (d,3H), 0.96(t,6H) ppm.

EXAMPLE 154

(1-Ethyl-propyly[24-isopropenyl-2,6-dimethyl-phenoxy) 3,6-dimethyl-pyridin-4-yl]-amine The title compound was prepared by reacting of 2-{4-[4-(1-Ethyl-propylamino)-3,6-dimethyl-pyridin-2-yloxy]-3,5-dimethyl-phenyl}-propan-2-ol with Burgess inner salt (Et$_3$NS(O)$_2$NCOOMe in benzene at reflux for 30 min. 1H NMR(CDCl$_3$) d 7.17(s,2H), 6.08(s,1H), 5.34(s,1H), 5.02(s, 1H), 3.72(d,1H), 3.32(m,1H), 2.12 and 2.15 (two sets of s, 12H), 1.4–1.6(m,4H), 0.97(t,6H) ppm.

EXAMPLE 155

(1-Ethyl-propyl)[24-isopropyl-2,6-dimethyl-phenoxy)-3,6-dimethyl-pyridin-4-yl]-amine The title compound was prepared by hydrogenation of (1-ethyl-propyl)[2-(4-isopropenyl-2,6-dimethyl-phenoxy)3,6-dimethyl-pyridin-yl]-amine using 10% Pd/C as catalyst in ethyl acetate at 55 psi until all starting material were consumed. The title compound was obtained as an oil after purification. 1H NMR(CDCl$_3$) d 6.93(s,2H), 6.10(s,1H), 3.73(brs,1H), 3.36(m,1H), 2.18(s,3H), 2.14(s,3H), 2.12(s, 6H), 1.4–1.8(m,4H), 1.27(d,6H), 0.98(t,6H) ppm.

EXAMPLE 156

[3,6-Dimethyl-2-(2,4,6-trimethyl-phenoxy)-pyridin-4-yl]-(1-ethyl-allyl)-amine

The title compound was prepared as a clear oil by reduction of 4-(1-Ethyl-prop-2-ynylamino)6-methyl-2-(2,4, 6-trimethyl-phenoxy)-nicotinic acid with lithium aluminum hydride and aluminum chloride. 1H NMR(CDCl$_3$) d 6.87 (s,2H), 6.08(s,1H). 5.7–5.9(m,1H), 5.1–5.3(m,2H), 3.75–4.0 (m,2H), 2.30(s,3H), 2.16(s,3H), 2.15(s,3H), 2.08(s,6H), 1.70(m,2H), 1.03(t,3H) ppm.

EXAMPLE 157

(1-Ethyl-propyly[2-(4-fluoro-2,6-dimethyl-phenoxy)-3, 6-dimethyl-pyridin-4-yl]-amine To a solution of [2-(4-bromo-2,6-dimethyl-phenoxy)-3,6-dimethyl-pyridin-4-yl]-(1-ethyl-propyl)-amine in dry THF was added n-butyllithium at −78° C. After stirring at −78° C. for 10 min. (PhSO2)2-NF was added and the resulting mixture was stirred at −78° C. for 30 min, the dry-ice bath was removed. After stirring for 5 min, the mixture was quenched with brine and extracted with ethyl acetate. The organic layer was separated, dried, and concentrated to dryness. The residue was purified through silica gel chromatography to give the title compound. 1H NMR(CDCl$_3$) d 6.77(s,1H), 6.73(s,1H). 6.08(s,1H), 3.3(m,1H), 2.12(s,3H), 2.09(s,6H), 2.08(s,3H), 1.4–1.8(m,4H), 0.97(t,6H) ppm.

EXAMPLE 158

2-[2-(2,6-Dimethyl-phenoxy)3,6-dimethyl-pyridin-4-ylamino]-butan-1-ol

The title compound was prepared by the method analogous to that in Example 146., 1H NMR(CDCl$_3$) d 7.05(m,3H), 6.24(s,1H), 3.4–3.8(m, 3H), 2.24(s,3H), 2.16(s,3H). 2.10(s,6H), 1.5–1.8(m,2H), 0.99(t3H) ppm.

EXAMPLE 159

2-[3,6-Dimethyl-2-(2,4,6-trimethyl-phenoxy)pyridin-4-(S)-ylamino]-butan-1-ol

To a solution of 2-(2,4,6-trimethyl-phenoxy)-4-(1-hydroxymethyl-propylamino)-methyl-nicotinic acid methyl ester in dry THF was added 1.0M lithium aluminium hydride in diethyl ether (0.25 ml) and aluminum chloride. The resulting mixture was heated at reflux for 2 hr. The mixture was quenched with of water, 2-NaOH, then water and stirred. Solid formed and was filtered through celite, washed with water and ethyl acetate. The organic layer was separated, dried, concentrated, and purification to give the tide compound as a white solid. Anal. For C$_{20}$H$_{28}$N$_2$O$_2$.1/2H$_{20}$ calc. C, 70.90; H, 8.52; N, 8.01; found C, 71.18; H, 8.66; N, 8.30

The following compounds were prepared by the method analogous to that in the preceding paragraph, using the corresponding 2-substituted phenoxy)₄alkyl-amino)methyl-nicotinic acid methyl ester with lithium aluminum hydride and aluminum chloride.

3-[3,6-Dimethyl-2-(2,4,6-trimethyl-phenoxy)pyridin-ylamino]-pentan-2-ol

1H NMR(CDCl₃) d 6.86(s,2H), 6.17&6.13(two sets of s, 1H), 5.0–5.2(m,1H), 4.9(s,2H), 3.9–4.1(m,1H), 3.5(m,1H), 3.3(m,1H), 2.29(s,3H), 2.14(s,3H), 2.08(s,6H), 1.4–1.8(m, 2H), 1.27(m,3H), 0.98(m,3H) ppm.

3-[2-(4-Chloro-2,6-dimethyl-phenoxy)3,6-dimethyl-pyridin-4-ylamino]-pentan-2-ol

1H NMR(CDCl₃) d 7.01(s,2H), 6.14&6.11(two sets of s,1H), 4.04&3.82(two sets of d,1H), 3.92(m,1H), 3.4&3.2 (m,1H), 2.13(s,3H), 2.11(s,3H), 2.05(s,6H), 1.4–1.8(m,2H), 1.25(two sets of d, 3H), 0.98&0.96(two sets of t,3H) ppm.

EXAMPLE 160

Benzyl-[3,6-dimethyl-2-(2,4,6-trimethyl-phenoxy)-pyridin-4-l]-ethyl-amine

A mixture of 4-bromo-3,6-dimethyl-2-(2,4,6-trimethyl-phenoxy)pyridine (250 mg, 0.78 mmol), benzylethylamine (127 mg, 0.937 mmol), Pd(OAc)2(3.6 mg, 0.0156 mmol), (S)-2,2'-bis(diphenylphosphino)-1,1'-binaphthyl (BINAP) (9.7 mg, 0.0156 mmol), potassium t-butoxide (105 mg, 0.781 mmol) in 25 ml of toluene was heated at reflux for 2 hr. The mixture was cooled to rt, quenched with water and extracted with ethyl acetate. The organic layer was separated, dried (Na₂SO₄), filtered, and concentrated to give a brown oil. The crude material was purified through silica gel column chromatography to give the title compound. 1H NMR(CDCl₃) d 7.2-7.4(m,5H), 6.86(s,2H), 6.41(s,1H), 4.23 (s,2H), 3.07(q,2H), 2.31(s,3H), 2.29(s,3H), 2.16(s,3H). 2.06 (s,6H), 1.05(t,3H) ppm.

The following compounds were prepared by the method analogous to that in the preceding paragraph, using an appropriate 4-bromo-2-(substituted phenoxy)-3-methyl-6-alkyl or 3 alkoxy-pyridine with an appropriate amine.

[2-(4-Chloro-2,6-dimethyl-phenoxy)-3,6-dimethyl-pyridin-4-yl]-(1-methoxymethyl-propyl)amine 1H NMR(CDCl₃) d 7.06(s,2H), 6.13(s,1H), 4.14(d,1H), 3.3–3.6(m,3H), 3.42(s,3H), 2.16(s,3H), 2.14(s,3H), 2.09(s, 6H), 1.5–1.8(m,2H0, 1.03(t,3H) ppm. 2-[3,6-Dimethyl-2-(2, 4,6-trimethyl-phenoxy) pyridin-4-ylamino]-3-phenyl-propan-1-ol 1H NMR(CDCl₃) d 8.6(d,1H), 7.2–7.4(m5H), 6.84(s,2H), 6.169s,1H), 4.099d,1H), 3.82(m,1H), 3.5–3.7(m,2H), 2.95 (d,2H), 2.96(s,3H), 2.27(s,3H), 2.14(s,3H), 2.05(s,6H) ppm.

[2-(4Chloro-2,6-dimethyl-phenoxy)-3,6-dimethyl-pyridin-4yl]-(1-methoxymethyl-propyl)amine 1H NMR(CDCl₃) d 7.06(s,2H). 6.13(s,1H), 4.2(m,1H), 3.53(m,2H), 3.42(s,3H), 2.19(s,3H), 2.14(s,3H), 2.10(s,6H), 1.5–1.8(m,2H), 1.03(t,3H) ppm.

[2-[4-Chloro-2,6-dimethyl-phenoxy)3,6-dimethyl-pyridin-4-yl]-(1-ethoxymethyl-propyl)-amine 1H NMR(CDCl₃) d 7.06(s,2H), 6.14(s,1H), 4.24(d,1H), 4.44.65(m,5H), 2.19(s,3H), 2.14(s,3H), 2.10(s,6H), 1.8(m, 1H), 1.65(m,1H), 1.25(t,3H), 1.03(t,3H) ppm.

[3,6-Dimethyl-2-(2,4,6-trimethoxy-phenoxy)pyridin-4-yl]-(1-methoxymethyl-propyl)-amine 1H NMR(CDCl₃) d 6.20(s 2H), 6.08(s,1H), 3.80(s,3H), 3.73(s,6H), 3.8(m,2H), 3.39(m,1H), 3.36(s,3H), 2.23(brs, 3H), 2.10(s,3H), 1.74(m,1H), 1.59(m,1H), 0.969t,3H) ppm.

[2-(4-Bromo-2,6-dimethyl-phenoxy)-3-methoxy-6-methyl-pyridin ll-(1-ethy-propyl)-amine 1H NMR(CDCl₃) d 7.18(s,2H), 6.09(s,1H), 4.43(d,1H), 3.89(s,3H), 3,25(m,1H), 2.10(s,9H), 1.4–1.8(m,4H), 0.95(t, 6H) ppm.

(1-Ethyl-propyl)-[3-methoxy-6-methyl-2-(2,4,6-trimethyl-phenoxy)-pyridin-4-yl]-amine 1H NMR(CDCl₃) d 6.85(s,2H), 6.07(s,1H), 4.44(m,1H). 3.89(s,3H), 3.23(m,1H), 2.27(s,3H), 2.09(s,6H), 2.08(s,3H), 1.65(m,2H), 1.45(m,2H), 0.93(m,6H) ppm.

[2-(4-Chloro-2,6-dimethyl-phenoxy)-6-methyl-3-propyl-pyridin-4-yl]-(1-ethyl-propyl)-amine

[2-(4-Bromo-2,6-dimethyl-phenoxy)-6-methyl-3-propyl-pyridin-4-yl]-(1-ethyl-propyl)-amine 1H NMR(CDCl₃) d 7.03(s,2H), 6.13(s,1H), 3.8(m.1H), 3.74(s,2H), 3.38(m,1H), 2.15(s,3H), 2.05(s,6H), 1.50–1.7 (m,4H), 0.97(t,6H) ppm.

(1-Ethyl-propyl)-[6-methyl-3-propyl-2-(2,4,6-trimethyl-phenoxy)pyridin-4-yl]-amine

[2(2,4-Dichloro-6-methyl-phenoxy)-3-methoxy-6-methyl-pyridin-4-yl]-ethyl-propyl)-amine 1 1H NMR(CDCl₃) 7.24(d,1H), 7.1(d,1H), 6.1(s,1H), 4.47(d,1H), 3.9(s,3H), 3.22(m,1H), 2.12(s,3H), 2.08(s,3H), 1.4–1.7(m,4H), 0.9(t,6H) ppm.

[2-(4-Chloro-2,6-dimethyl-phenoxy)-3-methoxy-6-methyl-pyridin-4-yl]-(1-ethyl-propyl)-amine 1H NMR(CDCl₃) 7.02(s,2H), 6.07(s,1H), 4.44(brs,1H), 3.8–3.95(m,3H), 3.23(m,1H), 2.09(s,6H), 2.08(s,3H), 1.4–1.7(m,4H), 0.93(t,6H) ppm.

[2(4-Chloro-2,6-dimethyl-phenoxy)-3-methoxy-6-methyl-pyridin-4-yl](1-methoxymethyl-propyl)-amine 1H NMR(CDCl₃) d 7.02(s,2H), 6.11(s,1H), 4.71(d,1H), 3.88(s,3H), 3.45(m,2H), 3.37(s,3H), 2.10(s,3H), 2.09(s,6H), 1.73(m,1H), 1.59(m,1H), 0.98(m,3H) ppm.

[2-(2,4-Dichloro-6-methyl-phenoxy)-3-methoxy-6-methyl-pyridin-4-yl]-(1-methoxymethyl-propyl)-amine 1H NMR (CDCl₃) d 7.1-7.25(m,2H), 6.13(s,1H), 4.74(d, 1H), 3.91(s,3H), 3.47(m,1H), 3.39(m,2H), 3.37(s,3H), 2.14 (s,3H), 2.10(s,3H), 1.78(m,1H), 1.59(m,1H), 0.98(t,3H) ppm.

[2-(4-Chloro-2-methoxy-phenoxy)-3-methoxy-6-methyl-pyridin yl]-(1-methoxymethyl-propyl)-amine 1H NMR (CDCl₃) d 6.8-7.0(m,3H), 6.17(s,1H), 4.76(d, 1H), 3.82(s,3H), 3.75(s,3H). 3.3-3.5(m,3H), 3.35(s,3H), 2.19(s,3H), 1.73(m,1H), 1.56(m,1H), 0.96(t,3H) ppm.

[2-(3-Chloro-2,6-dimethoxy-phenoxy)-3-methoxy-6-methyl-pyridin-4-yl]-(1-methoxymethyl-propyl)-amine 1H NMR(CDCl₃) d 7.12(d,1H), 6.64(d,1H), 6.12(s,1H)< 4.73(d,1H), 3.88(s,3H), 3.78(s,3H), 3.70(s,3H), 3.3–3.5(m, 3H), 3.35(s,3H), 2.11(s,3H), 1.5–1.8(m,2H), 0.96(t,3H) ppm.

(1-Methoxymethyl-propyl)-[3-methoxy-6-methyl-2-(2,4, 6-trimethoxy-phenoxy)-pyridin-4-yl]-amine 1H NMR(CDCl₃) d 6.19(s,2H), 6.10s,1H), 4.75(m,1H), 3.87(s,3H), 3.80(s,3H), 3.73(s,6H), 3.3–3.5(m,2H), 3.35(s, 3H), 2.17(s,3H), 1.78(m,1H), 1.5(m,1H), 0.96(t,3H) ppm.

[3-Methoxy-2-(4-methoxy-2,6-dimethyl-phenoxy)-6-methyl-pyridin-4-yl]-(1-ethoxymethyl-propyl)amine 1H NMR(CDCl₃) d 6.59(s,2H), 6.10(s,1H), 4.70(d,1H), 3.89s,3H), 3.77(s,3H), 3.48(m,1H), 3.39(m,2H), 3.37(s,3H), 2.11(s,3H), 2.10(s,6H), 1.74(m,1H), 1.57(m,1H), 0.98(t,3H) ppm.

[2-(4-Chloro-2,6-dimethyl-phenoxy)-3-ethoxy-6-methyl-pyridin-4-yl]-(1-methoxymethyl-,propyl)amine 1H NMR(CDCl₃) d 7.07(s,2H), 6.16(s,1H), 4.82(d,1H), 4.20(q,2H), 3.54(m,1H), 3.43(m,2H), 3.42(s,3H), 2.15(s, 3H), 2.13(s,6H), 1.51.9(m,2H), 1.439t,3H), 1.02(t,3H) ppm.

EXAMPLE 161

2-[2-(4-Chloro-2,6-dimethyl-phenoxy)-3,6-dimethyl-pyridin-4-(S)ylamino]-butan-1-ol To a solution of [1-(tert-butyl-dimethyl-silanyloxymethyl)-propyl]-[2-(4-chloro-2,6-dimethyl-phenoxy)-3,6-dimethyl-pyridin-4-yl]-amine in dry THF was added 1M tetrabutylammonium fluoride in THF at room temperature. The mixture was stirred at room temperature for 2 hr, quenched with water, extracted with ethyl acetate. The organic layer was separated, dried and concentrated to dryness. The residue was purified by Biotage using 15% ethyl acetate in hexane as eluent to give the title compound as a white solid. 1H NMR($CDCl_3$) d 7.06(s,2H), 6.18(s,1H), 4.04(d,1H), 3.74(m,1H), 3.69(m,1H), 3.53(m,1H), 2.18(s, 3H), 2.16(s,3H), 2.10(s,6H), 1.6–1.8(m,2H), 1.04(t,3H) ppm.

The following compounds were prepared by the method analogous to that in the preceding paragraph, starting with the corresponding tert-butyl-dimethyl-silanyloxymethyl derivative with tetrabutylammonium fluoride.

2-[3-Methoxy-6-methyl-2-(2,4,6-trimethyl-phenoxy)-pyridin-4-(S)-ylamino]-butan-1-ol 1H NMR ($CDCl_3$) d 6.85(s,2H), 6.15(s,1H), 4.57(d,1H), 3.91(s,3H), 3.72(m,1H), 3.61(m,1H), 3.41(m,1H), 2.27(s, 3H), 2.10(s,3H), 2.07(s,6H), 1.5–1.8(m,3H), 0.98(t,3H) ppm.

2-[2-(4-Chloro-2,6-dimethyl-phenoxy)-3-methoxy-6-methyl-pyridin-4-ylamino]butan-1-ol 1H NMR($CDCl_3$) d 7.02(s,2H), 6.16(s,1H), 4.60(d,1H), 3.91(s,3H), 3.71(m,1H), 3.61(m,1H), 3.40(m,1H), 2.10(s, 3H), 2.08(s,6H), 1.8(brs,1H), 1.71(m,1H), 1.68(m,1H), 0.99 (t,3H) ppm.

4-[4-(1-Hydroxymethyl-propylamino)-3-methoxy-methyl-pyridin-2-yloxy]-3,5-dimethyl-benzonitrile 1H NMR($CDCl_3$) d 7.35(s,2H), 6.19(s,1H), 4.7(brs,1H), 3.88(s,3H), 3.731(m,1H), 3.64(m,1H), 3.43(m,1H), 2.14(m, 9H), 1.8(brs,1H),1.71(m,1H), 1.58(m,1H), 0.99(t,3H) ppm.

EXAMPLE 162

3-[2-(4-Chloro-2,6-dimethyl-phenoxy)3,6-dimethyl-pyridin-4-ylamino]-pentan-2-ol

The title compound was prepared by Dess Martin oxidation of 2-(2-(4-chloro-2,6-dimethyl-phenoxy)-3,6-dimethyl-pyridin-4-(S)-ylamino]-butan-1-ol methylene chloride at room temperature, followed by Gringard reaction using methyl magnesium bromide in THF. 1H NMR($CDCl_3$) d 7.07(s,2H), 6.18(s,1H), 4.3(brs,1H), 4.0(m,1H), 3.32(m, 1H), 2.22(s,3H), 2.17(s,3H), 2.11 (s,6H), 1.6–1.8(m,2H), 1.30(d,3H), 1.01 (t,3H)ppm.

EXAMPLE 163

2-[2-Methyl-6-(2,4,6-trimethyl-phenoxy)pyridin-4-ylamino]-butan-1 ol

The title compound was prepared as an oil by heating 2-(2,4,6-trimethyl-phenoxy)-4-(S)-(1-hydroxymethyl-propylamino)-6-methyl-nicotinic acid in 160° C. until all starting material were consumed. Anal. For $C_{19}CH_{25}N_2O_2H_2O$ calc. C, 68.65; H, 8.49; N. 8.42; found C, 69.04; H, 8.14; N, 8.91

Example 164

(1-Ethyl-prop-2-ynyl)[2-methyl-6-(2,4,6-trimethyl-phenoxy)pyridin-4-yl]-amine]

The title compound was prepared by the method analogous to that in Example 163.

1H NMR($CDCl_3$) d 6.89(s,2H), 6.12(d,1H), 5.41(d,1H), 3.9–4.2(m,2H), 2.37s,3H), 2.30(s,3H), 227(m,1H), 1.76(m, 2H), 1.05(t,3H) ppm.

EXAMPLE 165

2-(4-Bromo-2,6-dimethyl-phenoxy)-4-(1-ethyl-propylamino)-6-methyl-pyridin-3-ol

To a solution of [2-(4-bromo-2,6-dimethyl-phenoxy)-3-methoxy-6-methyl-pyridin-4-yl]-(1-ethyl-propyl)amine in methylene chloride was added $BBr_3$ at 0° C. and stirred for hr. The mixture was quenched with water and extracted with chloroform. The organic layer was separated, dried, and concentrated to give the title compound. 1H NMR($CDCl_3$) d 7.20(s,2H), 6.12(s,1H), 4.77(d,1H), 3.27(m,1H), 2.13(s, 3H), 2.10(s,6H), 1.4–1.8(m, 4H), 0.97(t,6H) ppm.

The following compounds were prepared by the method analogous to that in the preceding paragraph, starting with an appropriate [2-(substituted phenoxy)-3-methoxy-6-methyl-pyridin-4-yl]-(alkyl)amine with $BBr_3$ or $BCl_3$.

4-(1-Ethyl-propylamino)-6-methyl-2-(2,4,6-trimethyl-phenoxy)pyridin-3-ol

1H NMR($CDCl_3$) d 6.85(s,2H). 6.10(s,1H), 5.12(brs,1H). 4.21(m,1H), 3.27(m,1H), 2.28(s,3H), 2.09(s,gH), 1.5–1.8 (m,4H), 0.96(m,6H) ppm.

4-(S)-(1-Hydroxymethyl-propylamino)-6-methyl-2-(2,4, 6-trimethyl-phenoxy)-pyridin-3-ol 1H NMR ($CDCl_3$) d 6.85(s,2H), 6.17(s,1H), 5.13(brs,1H), 4.28(d,1H), 3.73(m,1H), 3.60(m,1H), 3.50(m,1H), 2.27(s, 3H), 2.12(s,3H), 2.07(s,6H), 1.75(brs,1H), 1.5–1.7(m,2H), 0.99(t,3H) ppm.

2-(4-Chloro-2,6-dimethyl-phenoxy)-4-(1-hydroxymethyl-propylamino)$_6$-methyl-pyridin-3-ol 1H NMR($CDCl_3$) d 7.032(s,2H), 6.10(s,1H), 5.2(brs,1H), 4.35(brs,1H), 3.71(m,1H), 3.61(m,1H), 3.40(m,1H), 2.07(s, 9H), 1.8(brs,1H), 1.71(m,1H), 1.60(m,1H), 0.99(m,3H) ppm.

2-(4-Chloro-2,6-dimethyl-phenoxy)-4-(1-ethyl-propylamino)-6-methyl-pyridin-3-ol

1H NMR($CDCl_3$) d 7.02(s,2H), 6.10(s,1H), 5.02(brs,1H), 4.22(brs,1H), 3.25(brs,1H), 2.08(brs,9H), 1.62(m,2H), 1.52 (m,2H), 0.95(brs,6H) ppm.

EXAMPLE 166

Chloro-acetic acid 4-(1-ethyl-propylamino)-6-methyl-2-(2,4,6-trimethyl-phenoxy)-pyridin-3-yl ester The title compound was prepared by reacting 4-(1-ethyl-propylamino)-6-methyl-2-(2,4,6-trimethyl-phenoxy) pyridin-3-ol with chloroacetyl chloride/triethylamine in THF at 0° C. to rt. 1H NMR($CDCl_3$) d 6.84(s,2H), 6.15(s, 1H), 4.3(s,2H), 4.0(d,1H), 3.3(m,1H), 2.28(s,3H), 2.17(s, 3H), 2.08(s,6H), 1161.7(m,4H), 0.9(t,6H) ppm.

EXAMPLE 167

2-(4-Chloro-2,6-dimethyl-phenoxy)-4-[(1-ethyl-propylmethyl-amino]methyl-pyridin-3-ol 1H NMR($CDCl_3$) d 7.03(s,2H), 6.25(s,1H), 5.4(brs,1H), 3.93(m,1H), 2.70(s,3H), 2.12(s,3H), 2.08(s,6H),1.55(m, 4H), 0.89(t,6H) ppm.

EXAMPLE 168

[4-(1-Ethyl-propylamino)-6-methyl-2-(2,4,6-trimethyl-phenoxy)pyridin-3-yl]-acetonitrile 1H NMR(CDCl$_3$) d 6.87(s,2H), 6.13(s,1H), 3.83(d,1H), 3.79(S,2H), 3.38(m,1H), 2.30(s,3H), 2.27(s,3H), 2.21(s,6H), 1.4–1.8(m,4H), 1.00(t,6H) ppm.

EXAMPLE 169

4-(1-Ethyl-propylamino)-6-methyl-2-(2,4,6-trimethyl-phenoxy)-pyridine-3-carbaldehyde 1H NMR(CDCl$_3$) d 10.52(s,1H), 9.26(d,1H), 6.89(s,2H), 6.11(s,1H), 3.42(m,1H), 2.31 (s,3H0, 2.15(s,3H), 2.11(s,6H), 1.45–1.75(m,4H), 0.97(t,6H) ppm.

EXAMPLE 170

(1-Ethyl-propyl)-[3-[(1-ethyl-propylimino)-methyl]-6-methyl-2-(2,4,6-trimethyl-phenoxy)-pyridin-4-yl]-amine 1H NMR(CDCl$_3$) d 10.33(d,1H), 8.94(s,1H), 6.89(s,2H), 6.10(s,1H), 3.41(m,1H), 2.86(m,1H), 2.99(s,3H), 2.14(s,3H), 2.10(s,6H), 1.4-1.89m,8H), 0.94(t,6H), 0.87(t,6H) ppm.

EXAMPLE 171

2-[4-(1-Ethyl-propylamino)-6-methyl-2-(2,4,6-trimethyl-phenoxy)-pyridin-3-ylmethyl]-malonic acid dimethyl ester To a solution of dimethylmalonate (60 mg, 0.44 mmol) and 60% NaH in oil (20 mg, 0.44 mmol) in dry THF was added the title compound of Example 85 (50 mg, 0.146 mmol) at room temperature for 1 hr. The mixture was quenched with water and extracted with ethyl acetate. The organic layer was separated, dried and concentrated to dryness. The residue was purified through silica gel column chromatography to give the title compound as a clear oil. 1H NMR (CDCl$_3$) d 6.88(s,2H), 6.03(s,1H), 4.85(m,1H), 4.03 (t,1H), 3.73(s,6H), 3.26(m,1H), 3.18(d,2H), 2.30(s,3H), 2.13s,3H), 2.07(s,6H), 1.5–1.8(m,4H), 0.97(t,6H)ppm.

EXAMPLE 172

2-[4-(1-Ethl-propylamino)-6-methyl-2-(2,4,6-trimethyl-phenoxy)-pyridin-3-ylmethl]-malonic acid diisopropyl ester The title was prepared by the method analogous to that in Example 171. 1H NMR (CDCl$_3$) d 6.87(s,2H). 6.03(s,1H), 5.10(m,2H), 4.90(d,1H), 3.94(t,1H), 3.31(m,1H), 3.16(d,2H), 2.30(s,3H), 2.13s,3H0, 2.08(s,6H), 1.5–1.8(m,4H), 1.1–1.3(two sets of d, 6H), 0.97(t,6H)ppm.

EXAMPLE 173

4-(1-Ethyl-propoxy)-6-methyl-3-nitro-2-(2,4,6-trimethyl-phenoxy)pyridine

To a mixture of 2-chloro-4-(1-ethyl-propoxy)methyl-3-nitro-pyridine (500 mg, 1.93 mmol) and 2,4,6-trimethylphenol (289 mg, 2.13 mmol) in dry THF was added potassium t-butoxide. The resulting mixture was stirred at rt. overnight. The mixture was quenched with water, brine and extracted 3 times with ethyl acetate. The organic layer was separated, dried (MgSO$_4$) and concentrated to dryness. After silica gel column chromatography purification, the title compound was obtained as a light yellow crystal, mp 106–109° C. Anal. For C$_{20}$H$_{26}$N$_2$O$_4$ calc. C, 67.02; H, 7.31; N, 7.82; found, C, 67.34; H, 7.40; N, 7.42.

EXAMPLE 174

4-(1-Ethyl-propoxy)-6-methyl-2-(2,4,6-trimethyl-phenoxy)-pyridin-3-ylamine

A mixture of 4-(1-ethyl-propoxy)-6-methyl-3-nitro-2-(2,4,6-trimethyl-phenoxy)-pyridine (150 mg, 0.418 mmol) and 10% Pd/C (23 mg) in ethanol was hydrogenated at 50 psi for 15 hours. An additional 10Pd/C was added and the resulting mixture was hydrogenated for an additional 24 hr. The mixture was filtered through celite and the filtrate was concentrated to dryness to give 200 mg of the crude material. After column chromatography, the title compound was prepared as a the corresponding HCl salt as a white solid, mp 96–98° C.

EXAMPLE 175

[4-(1-Ethyl-propoxy)-6-methyl-2-(2,4,6-trimethyl-phenoxy)-pyridin-3-yl]-dimethyl-amine To a solution of 4-(1-ethyl-propoxy ethyl-2-(24,6-trimethyl-phenoxy)-pyridin-3-ylamine in dry THF was added lithium bis(trimethylsilyl)amide at −78° C. After stirring at −78° C. for 10 minutes, an excess of methyl iodide was added. The title compound was isolated after quenching with water and extracting with ethyl acetate. The crude material was purified by silica gel column chromatography to give the tide compound as a tan foam.

EXAMPLE 176

N-[4-(1-Ethyl-propoxy) 6-methyl-2-(2,4,6-trimethyl-phenoxy)pyridin-3-yl]-succinamic acid A mixture of 4-(1-ethyl-propoxy)-methyl-2-(2,4,6-trimethyl-phenoxy)-pyridin-3-ylamine (100 mg, 0.304 mmol), succinic anhydride 31 mg, 0.304 mmol) and triethylamine in methylene chloride was stirred at rt. overnight. The mixture was quenched with water, and extracted with methylene chloride. The organic layer was separated, dried and concentrated to give a solid. The title compound was isolated as a white crystal after silica gel column chromatography.

1H NMR(CDCl$_3$) d 6.90(brs,1H), 6.84(s,2H), 6.37(s,1H), 4.2(m,1H), 2.6–2.8(m,4H), 2.28(s,3H), 2.22(s,3H), 2.03(s,6H), 1.69(m,4H), 0.94(t,6H) ppm.

EXAMPLE 177

4-(1-Ethyl-propoxy-3,6-dimethyl-2-[3-(2,4,6-trimethyl-pyridinoxy)]-pyridine

To a solution of 3-pentanol (0.11 ml) in dry THF was added sodium hydride (60% in oil, 20 mg). After stirring for 5 min, a solution of 4-chloro-2,5-dimethyl-6-[3-(2,4,6-trimethyl-pyridinoxy)]-pyridine (92 mg, 0.332 mmol) in THF was added. DMSO was added and the resulting mixture was heated at 130° C. oil bath overnight. The mixture was quenched with water, brine and extracted 3 times with ethyl acetate. The organic layer was separated, dried (MgSO$_4$) and concentrated to dryness. After silica gel column chromatography purification, the title compound was obtained as a clear oil. 1H NMR (CDCl$_3$) d 6.88 (s,1H), 6.37(s,1H), 4.21(m,1H), 2.5(s,3H), 2.29(s,3H), 2.19(s,3H), 2.18(s,3H), 2.07(s,3H), 1.70(m,4H), 0.98(t,6H) ppm. The oil was prepared as the corresponding HCl salt to give a white solid (63 mg).

The title compounds of the following Examples 178 and 179 were prepared by the methods analogous to that in Example 177, starting with an appropriate 6-alkyl-4-cloro-or bromo-3-methyl-2-(2,4,6-trimethyl-phenoxy)-pyridine with 3-pentanol/NaH:

Example 178

6-Ethyl-4-(1-ethyl-propoxy)-3-methyl-2-(2,4,6-trimethyl-phenoxy)-pyridine

1H NMR(CDCl$_3$) d 6.87(s,2H), 6.28(s,1H), 4.20(m,1H), 2.46(q, 2H), 2.30(s,3H), 2.20(s,3H), 2.07(s,6H), 1.72(m, 4H), 1.05(t,3H), 0.99(t,6H) ppm.

EXAMPLE 179

4-(1-Ethyl-propoxy)-2-(4-fluoro-2,6-dimethyl-phenoxy)-3,6-dimethyl-pyridine colorless oil. Anal. For C$_{20}$H$_{26}$FNO$_2$ calc. C, 72.48; H, 7.91; N. 4.23; found C, 72.39; H, 7.77; N, 4.10.

EXAMPLE 180

[4-(1-Ethyl-propoxy)-3,6-dimethyl-pyridin-2-yl]-(2,4,6-trimethyl-phenyl)amine

To a solution of 4-(1-ethyl-propoxy)-6-methyl-2-(2,4,6-trimethyl-phenylamino)-nicotinic acid (240 mg, 0.673 mmol) in dry THF was added lithium aluminum hydride and aluminum chloride. The resulting mixture was heated at reflux for 3 hours. The mixture was quenched with 0.1 ml water and 0.1 ml 2N NaOH, then quenched with water and ethyl acetate. The organic layer was separated, dried and concentrated to give 250 mg of brown oil. After silica gel column chromatography, 170 mg(78%) of the title compound was obtained which was prepared as a HCl salt as a white solid, mp. 132–133° C. 1H NMR(CDCl$_3$) d 6.87(s, 2H), 6.09(s,1H), 5.399brs,1H), 4.13(m,1H), 2.27(s,3H), 2.22(s,3H), 2.15(s,6H), 1.98(s,3H), 1.67(m,4H), 0.94(t,6H) ppm.

EXAMPLE 181

[4-(1-Ethyl-propoxy)-6-methyl-2-(2,4,6-trimethyl-phenylamino)-pyridin-3-yl-methanol To a solution of 4-(1-ethyl-propoxy)$_6$-methyl-22,4,6-trimethyl-phenylamino)-nicotinic acid (100 mg, 0.281 mmol) in dry THF was added BH$_3$.DMS. The resulting mixture was heated at reflux overnight. The mixture was quenched with dilute HCl and stirred for 30 minutes, adjusted pH to 7.5–8.5, then extracted with ethyl acetate. The organic layer was separated, dried and concentrated to give 100 mg of brown oil. After silica gel column chromatography, 91 mg(95%) of the title compound was obtained as a white foam. Anal. For C$_{21}$H$_{30}$N$_2$O$_2$.1/2H$_2$O cal. C, 71.76; H, 8.89; N, 7.97; found: C, 71.97; H, 8.90; N, 7.69.

EXAMPLE 182

[4-(1-Ethyl-propoxy-6-ethyl-2-(2,4,6-trimethyl-phenylamino)-pyridin-3-yl]-oxo-acetonitrile The title compound was prepared by reacting [4-(1-ethyl-propoxy)-6-methyl-2-(2,4,6-trimethyl-phenylamino)-pyridin-3-yl]-methanol with thionyl chloride in benzene, concentrated to dryness, followed by reacting with diethylaluminum cyanide. After standard workup procedure and silica gel column chromatography, the title compound was obtained as a yellow crystal, mp. 108–110° C.

1H NMR(CDCl$_3$) d 8.57(s,1H), 6.97(s,2H), 6.37(s,1H), 4.46(m,1H), 2.35(s,3H), 2.34(s,3H), 2.09(s,6H), 1.6–1.8(m, 4H), 0.99(t,6H) ppm.

EXAMPLE 183

[4-(1-Ethyl-1-propoxy)-6-methyl-2-(2,4,6-trimethyl-phenylamino)pyridin-3-yl]-imidazol-1-yl-methanone To a solution of 4-(1-ethyl-propoxy-6-methyl-2-(2,4,6-trimethyl-phenylamino)-nicotinic acid (250 mg, 0.701 mmol) in 2 ml of DMF was added carbonyldiimidazole (190 mg, 1.19 mmol) and the resulting mixture was stirred at room temperature overnight. After standard workup procedure and silica gel column chromatography, 260 mg(91.2%) of the title compound was obtained as a golden crystal, mp. 120–122° C., Anal. For C$_{24}$H$_{30}$N$_4$O$_2$.114H$_2$O calc: C, 70.13; H. 7.48; N, 13.63; Found: C, 70.06; H. 7.69; N. 13.37.

EXAMPLE 184

2-[4(1-Ethyl-propoxy)-methyl-2-(2,4,6-trimethyl-phenylamino)-pyridin-3-yl]-propan-2-ol The title compound was prepared by reacting (4-(1-ethyl-propoxy)-6-methyl-2-(2,4,6-trimethyl-phenylamino)-pyridin-3-yl]-imidazol-1-yl-methanone with an excess MeMgBr in THF at rt. After standard workup procedure and silica gel column chromatography, the title compound was obtained as a tan solid, mp. 81–83° C.; Anal. For C$_{22}$H$_{30}$N$_2$O$_2$. 1.5H$_2$O calc.: C, 69.49; H, 9.38; N, 7.04; found: C, 69.49; H. 9.27; N, 6.86

EXAMPLE 185

2-[4-(1-Ethyl-propoxy)-6-ethyl-2-(2,4,6-trimethyl-phenylamino)-pyridin-3-ylmethyl]-malonic acid dimethyl ester The title compound was prepared by reacting [4-(1-ethyl-propoxy)-6-methyl-2-(2,4,6-trimethyl-phenylamino)-pyridin-3-yl]-methanol with thionyl chloride in benzene, concentrated to dryness, followed by reacting with methyl malonate/NaH in DMSO. After standard workup procedure and silica gel column chromatography, the title compound was obtained as a solid, mp. 9S98,C; Anal. For C$_{26}$H$_{36}$N$_2$O$_5$. 1/3H$_2$O calc.: C,67.51; H, 7.99; N. 6.04; found: C, 67.48; H, 7.99; N. 6.02.

EXAMPLE 186

3-[4-(1-Ethyl-propoxy)-6-methyl-2-(2,4,6-trimethyl-phenylamino)-pyridin-3-yl]-propionic acid Hydrolysis of 2-[4-(1-ethyl-propoxy)-6-methyl-2-(2,4,6-trimethyl-phenylamino)-pyridin-3-ylmethyl]-malonic acid dimethyl ester with phosphoic/water at reflux to give the title compound as a white foam. Anal. For C$_{23}$H$_{32}$N$_2$O$_3$. 3/4H$_2$O calc.: C,69.40; H. 8.48; N, 7.04; found: C, 69.17; H, 8.62; N. 6.90.

EXAMPLE 187

[3-Aminomethyl-4-(1-ethyl-propoxy)-6-methyl-pyridin-2-yl]-(2,4,6-trimethyl-phenyl)-amine The title compound was prepared by reacting [4-(1-ethyl-propoxy)methyl-2-(2,4,6-trimethyl-phenylamino)pyridin-3-yl-methanol with thionyl chloride in benzene, concentrated to dryness, followed by reacting with NH$_3$(g) at room temperature. After standard workup procedure and silica gel column chromatography, the title compound was obtained as a golden oil (80%), Anal. For C$_{21}$H$_{31}$N$_3$O. calc.: C,73.86; H, 9.15; N, 12.3; found: C, 73.50; H, 9.25; N, 11.39.

EXAMPLE 188

2-Chloro-N-[4-(1-ethyl-propoxy)-6-methyl-2-(2,4,6-trimethyl-phenylamino)-pyridin-3-ylmethyl]-acetamide The title compound was prepared by acylation of 3-aminomethyl-4(1-ethyl-propoxy)-6-methyl-pyridin-2-yl]-(2,4,6-trimethyl-phenyl)-amine with chloroacetyl chloride. After standard workup procedure and silica gel column chromatography, the title compound was obtained as an off-white crystal, mp. 142–144° C.; Anal. For $C_{23}H_{32}ClN_3O_2$. calc.: C, 66.09; H, 7.72; N, 10.05; found: C, 65.81; H, 7.64; N. 9.86.

EXAMPLE 189

[3-Dimethylaminomethyl-4-(1-ethyl-propoxy)-6-methyl-pyridin-2-yl]-(2,4,6-trimethyl-phenyl)-amine hydrochloride salt The title compound was prepared by reacting [4-ethyl-propoxy)-6-methyl-2-(2,4,6-trimethyl-phenylamino)-pyridin-3-yl]-methanol with thionyl chloride in benzene, concentrated to dryness, followed by reacting with dimethylamine at room temperature. After standard work-up procedure and silica gel column chromatography, the title compound was obtained as an oil. The corresponding HCl salt was prepared as a white solid, mp. 85–88° C.; Anal. For $C_{23}H_{35}N_3O2HCl$. $1.5H_2O$ calc.: C, 58.83; H, 8.588; N, 8.94; found: C, 58.32; H, 8.5327; N, 8.64.

EXAMPLE 190

Dithiocarbonic acid O-ethyl ester S-[4-(1-ethyl-propoxy)-6-methyl-2-(2,4,6-trimethyl-phenylamino)pyridin-3-ylmethyl]ester The title compound was prepared by reacting [4(1-ethyl-propoxy)-6-methyl-2-(2,4,6 trimethyl-phenylamino)-pyridin-3-yl]-methanol with thionyl chloride in benzene, concentrated to dryness, followed by reacting with NaSC-SOEt at room temperature. After standard work-up procedure and silica gel column chromatography, the title compound was obtained as a white solid, mp. 55–57° C.; Anal. For $C_{24}H_{34}N_2O_2S_2$. calc.: C,64.54; H, 7.67; N, 6.27; found: C, 64.67; H, 7.78; N, 6.26.

EXAMPLE 191

4-(1-Ethyl-propoxy)-6-methyl-22,4,6-trimethyl-phenylamino)-nicotinamide

The title compound was prepared by reacting 4-(1-ethyl-propoxy)-6-methyl-2-(2,4,6-trimethyl-phenylamino)-nicotinic acid with thionyl chloride in benzene, concentrated to dryness, followed by reacting with $NH_3(g)$ at room temperature. After standard work-up procedure and silica gel column chromatography, the title compound was obtained an oil. The corresponding HCl salt was prepared as an off-white solid, mp 185–187° C.; Anal. For $C_{21}H_{29}N_3O_2$. calc.: C,70.96; H. 8.22; N, 11.82; found: C, 71.30; H, 8.33; N, 11.78.

EXAMPLE 192

4-(1-Ethyl-propoxy)-6-methyl-2-(2,4,6-trimethyl-phenylamino)-nicotinonitrile

The title compound was prepared by reacting 4-(1-ethyl-propoxy)$_6$-methyl-2-(2,4,6-trimethyl-phenylamino)-nicotinamide with triphosgen/triethylamine in THF. mp 105–107° C., 1H NMR(CDCl$_3$) d 6.90(s,2H), 6.26(brs,1H), 6.05(s,1H), 4.24(m,1H), 2.28(s,3H), 2.25(s,3H), 2.17(s,6H), 1.72(m,4H), 0.97(t,6H) ppm.

EXAMPLE 193

4-(1-Ethyl-propoxy)-6,N,N-trimethyl-2-(2,4,6-trimethyl-phenylamino)-nicotinamide The title compound was prepared by reacting 4-(1-ethyl-propoxy)-6-methyl-2-(2,4,6-trimethyl-phenylamino)-nicotinic acid with thionyl chloride in benzene, concentrated to dryness, followed by reacting with dimethylamine at room temperature. After standard work-up procedure and silica gel column chromatography, the title compound was obtained an oil. The corresponding HCl salt was prepared as a white solid, mp. 197-200° C.; Anal. For $C_{23}H_{33}N_3O_2.H_2O$. calc.: C,63.07; H, 8.28; N, 9.59; found: C, 63.24; H. 8.07; N, 9.61.

EXAMPLE 194

[4(1-Ethyl-propoxy)-6-methyl-2-(2,4,6-trimethyl-phenylamino)-pyridin-3-yl]-acetonitrile The title compound was prepared by reacting [4-(1-ethyl-propoxy-6-methyl-2-(2,4,6-trimethyl-phenylamino)-pyridin-3-yl]-methanol with thionyl chloride in benzene, concentrated to dryness, followed by reacting with potassium cyanide in DMSO at room temperature. After standard work-up procedure and silica gel column chromatography, the title compound was obtained as a pale orange solid, mp. 112–115° C., 1H NMR(CDCl$_3$) d 6.9(s,2H), 6.14(s1H), 5.6(brs,1H), 4.22(m,1H), 3.49(s,2H), 2.28(s,3H), 2.22(s, 3H), 2.16(s,6H), 1.71(m,4H), 0.95(t,6H)

EXAMPLE 195

[2-(4-Bromo-2,6-dimethyl-phenylamino)4-(1-ethyl-propoxa)-6-methyl-pyridin-3-yl]-methanol To a solution of 41(1-ethyl-propoxy-6-methyl-2-(4-bromo-2.6-dimethyl-phenylamino) nicotinic acid (130 mg, 0.309 mmol) in dry THF was added BH$_3$.DMS. The resulting mixture was heated at reflux overnight. The mixture was quenched with dilute HCl and stirred for 30 min, adjusted pH to 7.5–8.5, then extracted with ethyl acetate. The organic layer was separated, dried and concentrated to give 100 mg of brown oil. After silica gel column chromatography, 110 mg(87.3%) of the title compound was obtained as a white semi-solid. 1H NMR(CDCl$_3$) d 7.25(s,2H), 6.85(brs,1H), 4.8(brs,2H), 4.18(m,1H), 2.2(s,3H), 2.07(s,6H), 1.7(m,4H), 0.95(t,6H) ppm.

EXAMPLE 196

[2-(4-chloro-2,6-dimethyl-phenylamino)-4-ethyl-propoxy)-6-methyl-pyridin-3-yl]-methanol To a solution of 4-(1-ethyl-propoxy)-6-methyl-2-(4-chloro-2,6-dimethyl-phenylamino) nicotinic acid in dry THF was added BH$_3$.DMS. The resulting mixture was heated at reflux overnight. The mixture was quenched with dilute HCl and stirred for 30 minutes, adjusted pH to 7.5–8.5, then extracted with ethyl acetate. The organic layer was separated, dried and concentrated to give a brown oil. After silica gel column chromatography, the title compound was obtained as a green oil. 1H NMR(CDCl$_3$) d 7.02(s,2H), 6.83(brs,1H), 4.78(s,2H), 4.14(m,1H), 2.2(s,3H), 2.13(s, 6H), 1.66(m,4H), 0.93(9t,6H) ppm.

EXAMPLE 197

[2-(2,4-Dichloro-phenylamino)-4-(1-ethyl-propoxy)-6-methyl-pyridin-3-yl]-methanol To a solution of 4-(1-ethyl-propoxy)-6-methyl-2-(2,4-dichloro-phenylamino)-nicotinic acid in dry THF was added BH$_3$.DMS. The resulting mixture was heated at reflux overnight. The mixture was quenched with dilute HCl and stirred for 30 min, adjusted pH to 7.5–8.5, then extracted with ethyl acetate. The organic layer was separated, dried and concentrated to give a golden oil. After silica gel column chromatography, the Ute compound was obtained as a golden oil. 1H NMR(CDCl$_3$) d 8.44(d,1H), 8.18(s,1H), 7.32(d,1H), 7.179d,1H), 6.28(s,1H), 4.82(s,2H), 4.21(m, 1H), 2.42(s,3H), 1.6–1.8(m,4H), 0.94(t,6H) ppm.

EXAMPLE 198

[2-(2,4-Dimethoxy-phenylamino)-4-(1-methoxymethyl-propoxy)-6-methyl-pyridin-3-yl]-methanol The title compound was prepared by a method analogous to that described for Example 197, starting with the corresponding nicotinic acid with BH$_3$.DMS. 1H NMR(CDCl$_3$) d 6.91(d,1H), 6.50(m,2H),5.91(s,1H), 4.42(m,1H), 4.281(s, 2H), 3.79(s,3H), 3.76(s,3H), 3.56(m,2H), 3.40(s,3H), 2.33 (s,3H), 1.6–1.8(m,2H), 1.02(t,3H) ppm.

EXAMPLE 199

[4-(1-Ethyl-propylamino)-6-methyl-2-(2,4,6-trimethyl-phenoxy)pyridin-3-yl]-imidazol-1-yl-methanone The title compound was prepared by a method analogous to that described for Example 183, starting with the corresponding nicotinic acid with carbonyldiimidazole.

1HNMR(CDCl$_3$) d 8.1(s,1H), 7.52(s,1H), 7.05(s,1H), 6.78(s,2H), 6.17(s,1H), 5.97(d,1H), 3.3(m,1H), 2.23(s,3H), 2.18(s,3H), 2.00(s,6H), 1.4–1.7(m,4H), 0.93(t,6H) ppm.

EXAMPLE 200

1-[4-(1-Ethyl-propylamino)-6-methyl-2-(2,4,6-trimethyl-phenoxy)-pyridin-3-yl]-ethanone The title compound was prepared by reacting [4-(1-Ethyl-propylamino-6-methyl-2-(2,4,6-trimethyl-phenoxy)-pyridin-3-yl]-imidazol-1-yl-methanone with methylmagnesium bromide/ethyl ether in methylene chloride. 1H NMR (CDCl$_3$) d 9.7(d,1H), 6.88(s,2H), 6.10(s,1H), 3.32(m,1H), 2.73(s,3H), 2.31(s,3H), 2.10(s,3H), 2.09(s,6H), 1.5–1.7(m, 4H), 0.95(t,6H)ppm.

EXAMPLE 201

(1-Ethyl-propyl)[6-methyl-3-propyl-2(2,4,6-trimethyl-phenoxy)pyridin-4-yl]-amine 1H NMR(CDCl$_3$) d 6.84(s,2H), 6.04(s,1H), 3.81(d,1H), 3.31(m,1H), 2.56(t,2H), 2.27(s,3H), 2.12(s,3H), 2.04(s,6H), 1.4–1.7(6H), 1.02(t,3H), 0.93(t,6H) ppm.

EXAMPLE 202

2-[4-(1-Ethyl-propylamino-6-methyl-2-(2,4,6-trimethyl-phenoxy)pyridin-3-ylmethyl]-2-methyl-malonic acid dimethyl ester The title compound was prepared by a method analogous to that described for Example 185. 1H NMR(CDCl$_3$) 6.87 (s,2H), 6.01(s,1H), 5.05(m,1H), 3.70(s,6H), 3.4(s,2H), 3.3 (m,1H), 2.27(s,3H), 2.12(s,3H), 2.07(s,6H), 1.4–1.7(m,4H), 1.48(s,3H), 0.949t,6H) ppm.

EXAMPLE 203

[4-(1-Ethyl-propoxy)-6-methyl-pyridin-2-yl]2,4,6-trimethyl-phenyl amine

The title compound was prepared by decarboxylation of the corresponding nicotinic acid at 160° C. oil bath. mp. 98–100° C.; Anal. For C$_{20}$H$_{28}$N$_2$O calc. C, 76.88; H, 9.03; N. 8.97; found: C, 76.97; H, 9.21; N. 8.99.

The following title compounds of Examples 204 and 205 were prepared by reacting of 3-methoxy-6-methyl-2-(2,4,6-trimethyl-phenoxy)pyridine-4-carbaldehyde with alkyl-magnesium bromide in THF:

Example 204

2-Ethyl-1-[3-methoxy-6-methyl-2-(2,4,6-trimethyl-phenoxy)pyridin-04-yl]butan-1-ol 1H NMR(CDCl$_3$) 6.87(s,2H), 6.72(s,1H), 4.90(t,1H), 4.00(s,3H), 2.29(s,3H), 2.19(s,3H), 2.06(s,6H), 1.2–1.6(m, 5H), 6.92(t,3H), 0.88(t,3H) ppm.

EXAMPLE 205

1-[3-Methoxy-6-methyl-2-(2,4,6-trimethyl-phenoxy) pyridin-4-yL]-2-methyl-butan-1-ol 1H NMR(CDCl$_3$) 6.88(s,2H), 6.74(s,1H), 5.00(m,1H), 4.00(s,3H), 2.29(s,3H), 2.19(s,3H), 2.06(s,6H), 1.4–1.9(m, 3H), 0.992(t,3H), 0.989(d,3H) ppm.

EXAMPLE 206

1-[3,6-Dimethyl-2-(2,4,6-trimethyl-phenoxy)pyridin-4-yl]-propan-1-ol

To a −78° C. solution of 4-bromo-3,6-dimethyl-2-(2,4,6-trimethyl-phenoxy)pyridine in dry THF was added nBuli and stirred at that temperature for 20 minutes. Excess propionaldehyde was added and stirred for 2 hours at −78° C. The mixture was quenched with water, extracted with ethyl acetate. The organic layer was washed with brine, dried and concentrated. After column chromatography, an off-white solid was obtained, mp. 119–120° C. 1H NMR (CDCl$_3$) d 6.86(s,3H), 4.90(m,1H), 2.281(s,3H), 2.28(s,3H), 2.21(s,3H), 2.02(s,6H), 1.65–1.8(m,2H), 1.00(t,3H) ppm.

EXAMPLE 207

4(1-Methoxy-propyl)3,6-dimethyl-2-(2,4,6-trimethyl-phenoxy)-pyridine

The title compound was prepared by reaction of 1-[3,6-Dimethyl-2-(2,4,6-trimethyl-phenoxy)-pyridin-4-yl]-propan-1-ol with sodium hydride, followed by quenching with methyl iodide. 1H NMR(CDCl$_3$) d 6.87(s,2H), 6.74(s, 1H), 4.33(m,1H), 3.25(s,3H), 2.28(s,3H), 2.27(s,3H), 2.21 (s,3H), 2.03(s,6H), 1.61.8(m,2H), 0.94(t,3H) ppm.

EXAMPLE 208

4-(1-Ethoxy-propyl)-3,6-dimethyl-2-(2,4,6-trimethyl-phenoxy)-pyridine

The title compound was prepared by reaction of 1[3,6-Dimethyl-2-(24,6-trimethyl-phenoxy)-pyridin-4-yl]-propan-1-ol with sodium hydride, followed by quenching with ethyl iodide.

1H NMR(CDCl$_3$) d 6.86(s,2H), 6.77(s,1H), 4.41(m,1H), 3.22–3.45(m,2H), 2.28(s,3H), 2.27(s,3H), 2.21 (s,3H), 2.03 (s,6H), 1.61.8(m,2H), 1.20(t,3H), 0.95(t,3H) ppm.

EXAMPLE 209

4-(1-Allyloxy-propyl)-3,6-dimethyl-2,4,6-trimethyl-phenoxy)-pyridine

The title compound was prepared by reaction of 1-[3,6-Dimethyl-2-(2,4,6-trimethyl-phenoxy)pyridin-4-yl]-propan-1-ol with sodium hydride, followed by quenching with allyl bromide.

1H NMR(CDCl$_3$) d 6.87(s,2H), 6.78(s,1H), 5.93(m,1H), 5.1–5.3(m,2H), 4.48(m,1H), 3.95(m,1H), 3.76(m,1H), 2.29

(s,3H), 2.26(s,3H), 2.21(s,3H), 2.03(s,6H), 1.6–1.8(m,2H), 0.96(t,3H) ppm.

EXAMPLE 210

4-(1-Butoxy-propyl)-3,6-dimethyl-2-(2,4,6-trimethyl-phenoxy)pyridine

The title compound was prepared by reacting of 1-[3,6-Dimethyl-2-(2,4,6-trimethyl-phenoxy)-pyridin-4-yl]-propan-1-ol with sodium hydride, followed by quenching with butyl iodide.

1H NMR(CDCl$_3$) d 6.86(s,2H), 6.76(s,1H), 4.37(m,1H), 3.35(m,1H), 3.25(m,1H), 2.28(s,3H), 2.26(s,3H), 2.20(s,3H), 2.03(s,6H), 1.6–1.8(m,2H), 1.5–1.65(m,2H), 1.3–1.5(m,2H), 0.96(t,3H), 0.89(t,3H) ppm.

The title compounds of the following Examples 211 through 215 were prepared by a method analogous to that described in Example 206 starting with an appropriate 4-bromo-2-(substituted-phenoxy)pyridine derivative with nBuLi, followed by quenching with an appropriate aldehyde.

EXAMPLE 211

1-[2-(2,4-Dichloro-6-methyl-phenoxy)-3-methoxy-6-methyl-pyridin-4-yl]-2-ethyl-butan-1-ol one racemate 1H NMR(CDCl$_3$) d 7.28(d,1H), 7.14(d,1H), 6.80(s,1H), 4.92(d,1H), 4.00(s,3H), 2.21(s,3H), 2.13(s,3H), 1.3–1.65(m,5H), 0.93(t,3H), 0.87(t,3H) ppm.

The other racemate 1H NMR (CDCl$_3$) d 7.18(s,1H), 7.08(d,1H), 6.74(d,1H), 5.17(m,1H), 3.93(s,3H), 2.75(m,1H), 2.1–2.25(m,1H), 2.16(s,3H), 2.13(s,3H), 1.6–1.8(m,2H), 1.0–1.3(m,2H), 0.93(t,3H), 0.72(t,3H) ppm.

EXAMPLE 212

1-[3,6-Dimethyl-2-(2,4,6-trimethyl-phenoxy)-pyridin-4-yl]-2,2,2-trifluoro-ethanol mp. 134–139° C., Anal. For $C_{18}H_{20}F_3NO_2$ calc.: C, 63.71; H, 5.94; N. 4.13; found: C, 63.59; H, 6.00; N, 4.02.

EXAMPLE 213

1-[2-(4-Chloro-2,6-dimethyl-phenoxy)3,6-dimethyl-pyridin-4-yl]-2,2,2-trifluoro-ethanol 1H NMR(CDCl$_3$) d 6.979s,2H), 6.19(s,1H), 2.14(s,6H), 2.06(s,6H) ppm.

EXAMPLE 214

[2-(4-Chloro-2,6-dimethyl-phenoxy)-3,6-dimethyl-pyridin-4-yl]-pyridin-2-yl-methanol 1H NMR(CDCl$_3$) d 8.61(d,1H), 7.71(m,1H), 7.30(m,1H), 7.10(m,1H), 7.03(s,2H),6.70(s,1H), 6.03(s,1H), 2.37(s,3H), 2.16(s,3H), 2.03(s,6H), ppm.

EXAMPLE 215

1-[2-(4-Chloro-2,6-dimethyl-phenoxy)-3-methoxy-6-methyl-pyridin-4-yl]-2-ethyl-butan-1-ol 1H NMR(CDCl$_3$) d 7.05(s,2H), 6.759s,1H), 4.90(t,1H), 3.98(s,3H), 2.19(s,3H), 2.06(s,6H), 2.13(d,1H), 1.25–1.65(m,5H), 0.92(t,3H), 0.87(t,3H) ppm.

The title compounds of the following Examples 216 through 219 were prepared by oxidation of the corresponding alcohol with Dess Martin reagent in DMSO/methylene chloride or pyridinium chlorochromate in methylene chloride.

EXAMPLE 216

1-[3.6-Dimethyl-2-(2,4,6-trimethyl-phenoxy)pyridin-4-yl]-propan-1-one mp. 82–85.5° C., Anal. For $C_{19}H_{25}NO_2$ calc.: C, 76.74; H, 7.80; N, 4.71; Found: C, 76.61; H, 7.94; N, 4.66.

EXAMPLE 217

1-[2-(4-Chloro-2,6-dimethyl-phenoxy)-3,6-dimethyl-pyridin-4-yl]-2,2,2-trifluoro-ethanone 1H NMR(CDCl3) d 7.06(s,2H), 6.99(s,1H), 2.42(s,3H), 2.30(s,3H), 2.03(s,6H) ppm.

EXAMPLE 218

[2(4-Chloro-2,6-dimethyl-phenoxy)-3,6-dimethyl-pyridin-4-yl]-pyridin-2-yl-methanone 1H NMR($C_0$–$C_{13}$) d 8.72(d,1H), 8.17(d,1H), 7.95(m,1H), 7.52(m,1H), 7.05(s,2H),6.75(s,1H), 2.25(s,3H), 2.22(s,3H), 2.07(s,6H) ppm.

EXAMPLE 219

1-[2-(4-Chloro-2,6-dimethyl-phenoxy)-3-methoxy-6-methyl-pyridin-4-yl]-2-ethyl-butan-1-one 1H NMR(CDCl$_3$) d 7.05(s,2H), 6.67(s,1H), 3.98(s,3H), 3.09(m,1H), 2.61(s,3H), 2.06(s,6H), 1.76(m,2H), 1.51(m,2H), 0.92(t,6H) ppm.

EXAMPLE 220

4-(1-Ethoxy-2,2,2-trifluoro-ethyl)-3,6-dimethyl-2-(2,4,6-trimethyl-phenoxy)pyridine The title compound was prepared by reacting the corresponding alcohol with NaH, followed by quenching with ethyl iodide.

1H NMR(CDCl$_3$) d 6.92(s,1H), 6.87(s,2H), 4.92(m,1H), 3.60(m2H), 2.349s,3H), 2.29(s.3H), 2.26(s,3H), 2.03(s,6H), 1.26(t,3H) ppm.

The title compounds of the following Examples 221 through 222 were prepared by reacting of the corresponding ketone with alkyl lithium or alkyl magnesium.

Example 221

2-[3,6-Dimethyl-2-(2,4,6-trimethyl-phenoxy)-pyridin-4-yf-butan-2-ol

1H NMR(CDCl$_3$) d 6.86(m,3H), 2.48(s,3H), 2.28(s.3H), 2.21(s,3H), 2.02(s,6H), 1.8–2.1(m,2H), 1.61(s,3H), 0.84(t,3H) ppm.

EXAMPLE 222

3-[3,6-Dimethyl-2-(2,4,6-trimethyl-phenoxy)-pyridin-4-yl]-pentan-3-ol

1H NMR(CDCl$_3$) d 6.87(s,1H), 6.86(s,2H),. 2.43(s,3H), 2.28(s,3H0, 2.21(s,3H), 2.0–2.2(m,2H), 2.02(s,6H), 1.7–1.9(m,2H), 1.69(brs,1H), 0.8(t,6H) ppm.

EXAMPLE 223

1-[2-(4-Chloro-2,6-dimethyl-phenoxy)-3-hydroxy-6-methyl-pyridin-4-yl]-2-ethyl-butan-1-one The title compound was prepared by reacting i-[2-(4-Chloro-2,6-dimethyl-phenoxy)3-methoxy-6-methyl-pyridin-4-yl]-2-ethyl-butan-1-one with BBr$_3$ or BCl$_3$ in THF or methylene chloride.

1H NMR (CDCl$_3$) d 7.04(s,2H), 7.01(s,1H), 3.26(m,1H), 2.24(s,3H), 2.08(s,6H), 1.80(m.2H), 1.63(m,2H), 0.91(t,6H) ppm.

EXAMPLE 224

4-(1-Ethyl-propylamino)-6-methyl-2-(2,4,6-trimethyl-phenoxy)-nicotinamide

To a solution of 4-(1-ethyl-propylamino)-6-methyl-2-(2,4,6-trimethyl-phenoxy)-nicotinic acid in anhydrous methylene chloride was added thionyl chloride. After stirring for 1 hr. the reaction mixture was concentrated to dryness. The residue was dissolved in dry THF and $NH_3(g)$ was bubbled in. The reaction mixture was quenched with water and extracted with ethyl acetate. The organic layer was separated, dried and concentrated to give a light yellow solid. The solid was purified through silica gel column chromatography using 1% methanol in chloroform as eluent to give the title compound as a white solid, mp. 858° C. 1H NMR(CDCl$_3$) d 9.69(brs,1H), 8.01(brs,1H), 6.87(s,2H), 6.11(s,1H), 5.48(brs,1H). 3.31(m,1H), 2.29(s,3H), 2.10(s, 3H), 2.07(s,6H), 1.60(m.4H), 0.95(t,6H) ppm.

The tide compounds of the following Examples 225 through 231 were prepared by a method analogous to that described in the preceding paragraph, starting with the corresponding nicotinic acid or pyrimidine-5-carboxylic derivative and quenching with an appropriate nucleophile.

EXAMPLE 225

4-(1-Ethyl-propylamino)$_6$,N-dimethyl-2-(2,4,6-trimethyl-phenoxy)-nicotinamide

1H NMR(CDCl$_3$) d 9.8(brs,1H), 8.21(brs,1H), 6.88(s, 2H), 6.11(s,1H), 3.31(m,1H), 2.92(d,3H),2.30(s,3H), 2.10(s, 3H), 2.07(s,6H), 1.60(m,4H), 0.95(t,6H) ppm.

EXAMPLE 226

2-(4-Chloro-2,6-dimethyl-phenoxy)-(S)-1-hydroxymethyl-propylamino)-6-methyl nicotinamide 1H NMR(CDCl$_3$) d 9.7(d,1H), 7.9(brs,1H), 7.0(s,2H), 6.2(s,1H), 5.6(brs,1H), 3.7(m,1H), 3.66(m,1H), 3.54(m,1H), 2.07(s,3H), 2.068(s,3H). 2.06(s,3H), 1.7(m,1H), 1.6(m,1H), 0.99(t,3H) ppm.

EXAMPLE 227

2-(4-Chloro-2,6-dimethyl-phenoxy)-4-(S)-(1-hydroxymethyl-propylamino)-6-methyl-nicotinic acid hydrazide 1H NMR(CDCl$_3$) d 9.15(s,1H), 7.04(s,2H), 6.23(s,1H), 3.6–3.8(m,2H), 3.53(m,1H), 2.08(s,6H), 2.05(s,3H), 2.04(s, 3H), 1.5–1.8(m,2H), 1.01(t,3H) ppm.

EXAMPLE 228

2-(4-Chloro-2,6-dimethyl-phenoxy)-N-ethyl-4S)(1-hydroxymethyl-propylamino)-6-methyl-nicotinamide 1H NMR(CDCl$_3$) d 9.74(d,1H), 8.12(s,1H), 7.05(s,2H), 6.23(s,1H), 3.53.8(m,3H), 3.43(m,2H), 2.06(s,9H), 1.8(brs, 1H), 1.5–1.7(m,2H), 1.19(t,3H), 1.00(t,3H) ppm.

EXAMPLE 229

2-(4-Chloro-2,6-dimethyl-phenoxy)-4(S)-(1-hydroxymethyl-propylamino)-6,N-dimethyl-nicotinamide 1H NMR(CDCl$_3$) d 9.80(d,1H), 8.12(s,1H), 7.04(s,2H), 6.22(s,1H), 3.5–3.8(m,3H), 2.93(d,3H), 2.06(s,9H), 1.8(brs, 1H), 1.5–1.7(m,2H), 0.99(t,3H) ppm.

EXAMPLE 230

2-(4-Chloro 2,6-dimethyl-phenoxy)-N-cyclopentyl-4-(S)(1-hydroxymethyl-propylamino) 6-methyl-nicotinamide 1H NMR(CDCl$_3$) d 9.69(d,1H), 8.13(d,1H), 7.04(s,2H), 6.22(s,1H), 4.35(m,1H), 3.4–3.8(m,3H), 2.056(s,9H), 1.4–2.0(m, 10H), 0.99(t,3H) ppm.

EXAMPLE 231

2-(4-Chloro-2,6-dimethyl-phenoxy)-N-cyclopropyl-methyl4-(S)-(1-hydroxymethyl-propylamino)-6-methyl-nicotinamide 1H NMR(CDCl$_3$) d 9.71(d,1H), 8.24(s,1H), 7.05(s,2H), 6.23(s,1H), 3.53.8(m,3H), 3.27(t,2H), 2.08(s,6H), 2.07(s, 3H), 1.8(brs,1H), 1.51.75(m,2H), 0.99(t,3H), 0.46(m,2H), 0.21 (m,2H) ppm.

The title compounds of the following Examples 232 through 236 were prepared by a method analogous to that described for Example 224.

EXAMPLE 232

4-(1-Ethyl-propylamino)-6-methyl-22,4,6-trimethyl-phenylamino)-nicotinamide A brown solid, mp. 204–206° C.

EXAMPLE 233

4-(1-Ethyl-propoxy)-2-methyl-6-(2,4,6-trimethyl-phenylamino)pyrimidine-5-carboxylic acid amide Mp. 174–176° C.; Anal. For $C_{20}H_{28}N_4O_2$ calc.: C, 67.39; H, 7.92; N. 15.72; found: C, 67.90; H, 8.19; N, 14.66. 1H NMR(CDCl$_3$) d 7.95(s,1H), 6.89(s,2H), 5.58(s,1H), 5.4(m, 1H), 228(s,3H), 2.25(s,3H), 2.15(s,6H), 1.75(m,4H), 0.96(t, 6H) ppm.

EXAMPLE 234

4-(1-Ethyl-propylamino)-6-methyl-2-(2,4,6-trimethyl-phenoxy)-nicotinonitrile

1H NMR(CDCl$_3$) d 6.85(s,2H). 6.06(s,1H), 4.72(d,1H), 3.36(m,1H). 2.28(s,3H). 2.17(s,3H), 2.09(s,6H), 1.5–1.8(m, 4H), 0.96(t,6H) ppm.

EXAMPLE 235

[4-(1-Ethyl-propoxy)-methyl-3-nitro-pyridin-2-yl]-2,4,6-trimethyl-phenyl)-amine

The title compound was prepared by heating 2-bromo (or chloro)-4-(1-ethyl-propoxy)-6-methyl-3-nitro-pyridine with 2,4,6-trimethylaniline in DMSO at 130° C. The reaction mixture was quenched with water and extracted with ethyl acetate. The organic layer was separated, dried and concentrated to give crude material. The material was purified through silica gel column chromatography to give the title compound as a yellow solid. 1H NMR(CDCl$_3$) d 8.52(s,1H), 6.92(s,2H), 6.12(s,1H), 4.31(m,1H), 2.32(s,3H), 2.24(s,3H), 2.18(s,6H), 1.77(m,4H0, 1.01(t,6H) ppm.

EXAMPLE 236

4-(1-Ethyl-propoxy)-6-methyl-N-2-(2,4,6-trimethyl-phenyl)pyridine-2,3-diamine

The title compound was prepared by hydrogenation of the corresponding 3-nitro derivative with 10% Pd/C in ethanol at 50 psi. A pale gray solid was obtained in 97% yield, mp. 73–75° C. 1H NMR(CDCl$_3$) d 6.89(s,2H), 6.18(s,1H), 4.22 (m,1H), 3.2(brs,2H), 2.29(s,3H), 2.19(s,6H), 1.7(m,4H), 0.97(t,6H) ppm.

EXAMPLE 237

2-Chloro-N-[4-(1-ethyl-propoxy)-6-methyl-2-(2,4,6-trimethyl-phenylamino)-pyridin-3-yl]-acetamide The title compound was prepared by acylation of 4-(1-ethyl-propoxyy-6-methyl-N-2-(2,4,6-trimethyl-phenyl)-pyridine-2,3-diamine with chloroacetyl chloride, $NEt_3$ in THF at room temperature. A tan solid was isolated, mp. 7982° C. Anal. For $C_{22}H_{30}ClN_3O_2$ calc. C, 65.41; H, 7.49; N, 10.40; found: C, 65.56; H. 7.62; N, 10.98.

EXAMPLE 238

N-Butyl-N-ethyl-6-methyl-3-nitro-N-(42,4,6-trimethyl-phenyl)-pyridine-2,4-diamine A mixture of butyl-(2-chloromethyl-3-nitro-pyridin-4-yl) ethylamine (700 mg, 2.58 mmol) and 2,4,6-trimethylaniline in DMSO was heated in 140° C. oil bath for overnight. An additional 0.75 ml of 2,4,6-trimethylaniline was added and the resulting mixture was heated for an additional 48 hours. The mixture was quenched with water, brine and extracted 3 times with ethyl acetate. The organic layer was separated, dried ($MgSO_4$) and concentrated to dryness. After silica gel column chromatography purification, the title compound was obtained as an oil.

EXAMPLE 239

4-(1-Ethyl-propylamino)-6-methyl-2-(2,4,6-trimethyl-phenylamino)-nicotinic acid

The title compound was prepared by heating 2-chloro-4 (1-ethyl-propylamino)-6-methyl-nicotinic acid and trimethylaniline in the presence of potassium carbonate and copper in DMF. The desired product was isolated by silica gel column chromatography using 5% methanol in chloroform as solvent to give a tan solid, mp. 130–135° C.

EXAMPLE 240

4-(1-Ethyl-propylamino)-6-methyl-2-(2,4,6-trimethyl-phenylamino)-nicotinic acid methyl A mixture of 2-chloro-4(1-ethyl-propylamino)-6-methyl-nicotinic acid methyl ester, trimethylaniline, potassium carbonate, copper in DMF was heated at reflux. The mixture was quenched with ammonium chloride and stirred for 20 min, filtered through celite and washed with ethyl acetate. The filtrate was extracted with ethyl acetate. The organic layer was as separated, dried and concentrated to dryness. The residue was purified through silica gel column chromatography using 2% methanol in chloroform as eluent to give the title compound as a solid.

1H NMR($CDCl_3$) d 8.9(s,1H), 8.0(d,1H). 6.91(s,2H), 5.79-s,1H), 3.92(s,3H), 3.37(m,1H), 2.30(s,3H), 2.17(s,3H), 2.10(s,6H), 1.5–1.7(m,4H), 0.96(t,6H) ppm.

EXAMPLE 241

N4-(1-Ethyl-propyl)-3,6-dimethyl-N2(2,4,6-trimethyl-phenyl)pyridine-2,4-diamine

The title compound was prepared by reduction of 41(ethyl-propylamino)-6-methyl-2-(2,4,6-trimethyl-phenylamino)-nicotinic acid with 1 M of lithium aluminium hydride in diethyl ether and aluminium trichloride at reflux. 1H NMR($CDCl_3$)6.9(s,2H), 6.0(s,1H), 5.4(brs,1H), 3.6(d, 1H), 3.3(m, 1H), 2.32(s,3H), 2.2(s,3H), 2.15(s,6H), 1.4–1.7 (m,4H), 1.0(t,6H) ppm.

EXAMPLE 242

2-[41-Ethyl-propylamino)-6-methyl-2-(2,4,6-trimethyl-phenylamino)pyridin-3-ylmethyl]-malonic acid dimethyl ester Mp. 136–138° C.; Anal. For $C_{26}H_{37}N_3O_4$. $3/4H_2O$ calc.: C,66.57; H, 8.27; N, 8.96; found: C, 66.67; H, 7.95; N. 8.88.

EXAMPLE 243

[2-(4-Bromo-2,6-dimethyl-phenylamino)-4-(1-ethyl-propylamino)-6-methyl-pyridin-3-yl]-methanol The title compound was prepared by reduction of the corresponding nicotinic acid derivative with $BH_3$.DMS in THF at reflux. Standard work-up procedure to give the title compound as a white foam. 1H NMR($CDCl_3$) 7.15(s,2H), 6.2(brs,1H), 5.92(s,1H), 4:479m,1H), 4.43(s,2H), 3.25(m, 1H), 2.17(s,3H), 2.10(s,6H), 1.58(m,2H), 1.47(m,2H), 0.90 (t,6H) ppm.

EXAMPLE 244

N2-(2,4-Dichloro-phenyl)-N-4-(1-ethyl-propyl)-3,6-dimethyl-pyridine-2,4-diamine The title compound was prepared by a method analogous to that described for example 146. 1H NMR($CDCl_3$) d 7.79(dd,1H), 7.30(d,1H), 7.10(dd, 1H), 6.53(brs,1H), 6.13(s,1H), 3.79(d,1H), 3.2–3.4(m,1H), 2.36(s,3H), 1.92(s,3H), 1.4–1.6(m,4H), 0.93(t,6H) ppm.

EXAMPLE 245

[2-(2,4-Dichloro-phenylamino)-4-(1-ethyl-propylamino)-6-methyl-pyridin-3-yl]-methanol The title compound was prepared by reduction of the corresponding nicotinic acid derivative with $BH_3$.DMS in THF at reflux. 1H NMR($CDCl_3$) d 7.22(d,1H), 7.07(d,1H), 7.00(d,1H), 6.10(s,1H), 5.7(brs,1H), 4.4(s,2H), 3.3 (m,1H), 2.35(s,3H), 2.02(s,3H), 1.4–1.6(m,4H), 0.92&0.91 (two sets of t,6H) ppm.

EXAMPLE 246

2-[6-Methyl-3-nitro-2(2,4,6-trimethyl-phenylamino)-pyridin-4]amino]-butan-1-ol

The title compound was prepared by heating 2-[6-methyl-3-nitro-2-chloro-pyridin-4-ylamino]butan-1-ol with trimethylaniline in DMSO at 130° C. 1H NMR($CDCl_3$) d 9.38(brs,1H), 6.93(s,3H), 3.7–3.8(m,3H), 2.30(s,3H), 2.12 (s,6H), 1.8(m,1H), 1.65(m,1H), 1.02(t,3H) ppm

EXAMPLE 247

2-[4-(1-Ethyl-propylamino)-2-methyl-2,4,6-trimethyl-phenoxy)pyrimidin-5-yl]-propionic acid ethyl ester 1H NMR($CDCl_3$) d 6.85(s,2H), 5.16(d,1H), 4.49(q,1H), 4.04.2(m,3H), 2.289s,3H0, 2.20(s,3H), 2.06(s,6H), 1.41.7 (m,4H), 1.44(d,3H), 1.21(t,3H), 0.93(t,3H), 0.87(t,3H) ppm.

EXAMPLE 248

[3-Aminomethyl-6-methyl-2-(2,4,6-trimethyl-phenoxy)-pyridin-4-yl]-(1-ethyl-propyl)-amine The title compound was prepared by a method analogous to that described for Example 188. mp. 117–119° C.; Anal. For $C_{21}H_{31}N_3O$. $1/3H_2O$ calc.: C,72.58; H, 9.18; N, 12.09; found: C, 72.93; H, 9.28; N, 12.02.

The following title compounds of Examples 249–251 were prepared by reacting [4-(1-ethyl-propylamino)-6-methyl-2-(4-halo-2,6-dimethyl-phenoxy)-pyridin-3-yl]-methanol with thionyl chloride in benzene, concentrated to dryness, followed by reacting with potassium cyanide in DMSO at room temperature.

EXAMPLE 249

[2-(4-Bromo-2,6-dimethyl-phenoxy)-4-(1-ethyl-propylamino)-6-methyl-pyridin-3-yl]-acetonitrile 1H NMR(CDCl$_3$) d 7.2(s,2H), 6.1(S,1H), 3.82(d,1H), 3.7(s,2H), 3.34(m,1H), 2.1(s,3H), 2.03(s,6H), 1.45–1.7(m, 4H), 0.99(t,6H) ppm.

EXAMPLE 250

[2-(4-Chloro-2,6-dimethyl-phenoxy)-4-(1-ethyl-propylamino)-6-methyl-pyridin-3-yl]-acetonitrile hydrogen chloride 1H NMR(CDCl$_3$) d 7.08(s,2H), 6.2(s,1H), 4.92(d,1H), 3.45(m,1H), 2.71(s,3H), 2.549m,2H), 2.14(s,6H), 1.7(m, 2H), 1.40–1.6(m,4H), 0.95(t,6H) ppm.

EXAMPLE 251

[6(1-Ethyl-propoxy)-2-methyl-pyrimidin-4-yl]-(2,4,6-trimethyl-phenyl)amine

MP. 149–151° C., Anal. For C$_{20}$H$_2$eN$_4$O calc.: C, 72.81; H. 8.68; N, 13.41; found: C, 4 d 72.70; H, 8.86; N, 13.14

EXAMPLE 252

2-[2-(4-Chloro-2,6-dimethyl-phenoxy)-6-methyl-pyridin-4-(S)-ylamino]-buten-1-ol

The title compound was prepared by heating the corresponding nicotinic acid derivative at 160–170° C. oil bath. 1H NMR (CDCl3) d 7.05(s,2H), 6.09(s,1H), 5.35(s,1H). 4.43(s.1H), 3.68(m,1H), 3.64(m,1H), 3.29(m,1H), 2.30(s, 3H), 2.09(s,6H), 1.60(m,1H), 1.47(m,1H), 0.89(t,3H) ppm.

EXAMPLE 253

[3-Aminomethyl-24-chloro-2,6-dimethyl-phenoxy)-6-methyl-pyridin-4-(S)-yl]-(1-chloromethyl-propylamine The title compound was prepared by reaching [2-(2-(4-chloro-2,6-dimethyl-phenoxy)3-pyridin-4-(S)-ylamino] butan-1-ol with thionyl chloride in benzene, concentrated to dryness, followed by reacting with NH$_3$(g) at room temperature. After standard workup procedure and silica gel column chromatography, the title compound was obtained. 1H NMR(CDCl$_3$) d 7.00(s,2H), 6.3(brs,1H), 6.07(s,1H), 4.0–4.2(m,2H), 3.9(brs,2H), 3.5–3.8(m,3H), 2.12(s,3H), 2.03(s,6H), 1.6–1.9(m,2H), 1.00(t,3H) ppm The following title compounds of Examples 254 and 255 were prepared by reacting (2-[2-(4-chloro-2,6-dimethyl-phenoxy)-3-pyridin-4-(S)-ylamino]-butan-1-ol with thionyl chloride in benzene, concentrated to dryness, followed by reacting with an appropriate amine in THF at room temperature. After standard workup procedure and silica gel column chromatography, the title compound was obtained.

EXAMPLE 254

2-[2-(4-Chloro-2,6-dimethyl-phenoxy)-6-methyl-3-methylaminomethyl-pyridin-4-(S)-ylamino]-butan-1-ol 1H NMR(CDCl$_3$) d 7.01(s,2H), 6.14(s,1H), 4.55(brs,1H), 3.6–3.8(m,2H), 3.4(m,1H), 2.6(s,3H), 2.11(s,3H), 2.02(brs, 6H), 1.65(m,2H), 0.97(t,3H)ppm.

EXAMPLE 255

2-[3-Aminomethyl-2-(4-chloro-2,6-dimethyl-phenoxy)-6-methyl-pyridin-4-(S)-ylamino]-butan-1 ol 1H NMR(CDCl$_3$) d 6.999s,2H), 6.10(s,1H), 4.4.00(Abq, 2H), 3.5–3.75(m,2H), 3.4(m,1H), 2.73(brs,4H), 208(s,3H), 2.00(s,6H), 1.58(m,4H), 0.94(t,3H) ppm.

The title compounds of the following Examples 256 through 262 were prepared by bromination or chlorination of 2-(2-(substituted-phenoxy)$_6$-methyl-pyridin-4-alkylamine with NBS or NCS in methylene chloride or chloroform at room temperature.

EXAMPLE 256

[3-Bromo-6-methyl-2-(2,4,6-trimethyl-phenoxy)-pyridin-4-yl]-(1-ethyl-propyl)-amine 1H NMR(CDCl$_3$) d 6.85(s,2H), 6.04(s,1H), 4.62(d,1H), 3.33(m,1H), 2.27(s.3H), 2.13(s,3H), 2.08(s,6H), 1.51.7(m, 2H), 0.95(t,3H) ppm.

EXAMPLE 257

2-[3,5-Dibromo-2-(4-chloro-2,6-dimethyl-phenoxy)-6-methyl-pyridin-4-ylamino]-butan-1-l ol 1H NMR(CDCl$_3$) d 7.02(s,2H), 4.34(m,1H), 3.6–3.8(m, 2H), 2.30(s,3H), 2.05(s,6H), 1.5–1.8(m.2H), 0.98(t,3H) ppm.

EXAMPLE 258

2-[3-Bromo-6-(4-chloro-2,6-dimethyl-phenoxy)-2-methyl-pyridin-4-(S)-ylamino]butan-1-ol 1H NMR(CDCl$_3$) d 7.05(s,2H), 5.62(s,1H), 4.86(d,1H), 3.55–3.7(m,2H), 3.3(m,1H), 2.428(s,3H), 2.09(s,6H), 1.4–1.7(m,3H), 0.91(t,3H) ppm.

EXAMPLE 259

2-[3-Bromo-2-(4-chloro-2,6-dimethyl-phenoxy)-6-methyl-pyridin-4-(S)-ylamino]-butan-1-ol 1H NMR(CDCl$_3$) d 7.02(s,2H), 6.14(s,1H), 4.81(d,1H), 3.6–3.8(m,2H), 3.45(m,1H), 2.12(s,3H), 2.08(s,6H). 1.51.8 (m,2H), 1.00(t,3H) ppm.

EXAMPLE 260

2-[3-Chloro-2-(4-chloro-2,6-dimethyl-phenoxy)-6-methyl-pyridin-4(S)-ylamino]-butan-1-

1H NMR(CDCl$_3$) d 7.02(s,2H), 6.18(s,1H), 4.76(d,1H), 3.6–3.8(m,2H), 3.45(m,1H), 2.13(s,3H), 2.07(s,6H), 1.5–1.8 (m,2H), 0.99(t,3H) ppm.

EXAMPLE 261

2-[3,5-Dichloro-2-(4-chloro-2,6-dimethyl-phenoxy)-6-methyl-pyridin-4-ylamino]-butan-1-ol 1H NMR(CDCl$_3$) d 7.03(s,2H), 4.34(m,1H), 3.6–3.8(m, 2H), 2.40(s,3H), 2.05(s,6H), 1.5–1.8(m,2H), 0.99(t,3H) ppm.

EXAMPLE 262

2-[3-Chloro-6-(4-chloro-2,6-dimethyl-phenoxy)-2-methyl-pyridin-4-(S)-ylamino]-butan-1-ol 1H NMR(CDCl$_3$) d 7.05(s,2H), 5.66(s,1H), 4.86(brs,1H), 3.53.8(m,2H), 3.3(m,1H), 2.38(s,3H), 2.09(s,6H), 1.4–1.7 (m,3H), 0.91(t,3H) ppm.

EXAMPLE 263

2-(4-Chloro-2,6-dimethyl-phenoxy)-4—(S)-(4-ethyl-2-oxo-oxazolidin-3-yl)-6-methyl-nicotinonitrile The title compound was prepared by reacting with 2-(4-chloro-2,6-dimethyl-phenoxy)-4-(1-hydroxymethyl-propylamino)-6-methyl-nicotinic acid with triphosgene/ NEt$_3$ in THF. 1H NMR(CDCl$_3$) d 7.18(s,1H), 7.06(s,2H), 5.00(m,1H), 4.64(t,1H), 4.23(dd,1H), 2.339-s,3H), 2.08(s, 6H). 1.5-1.8(m,2H), 0.949t,3H) ppm.

EXAMPLE 264

2-(2,4-Dimethoxy-phenylamino)-4(1-methoxymethyl-propoxy)-6-methyl nicotinic acid 1H NMR(CDCl$_3$) d 8.3(brs,1H), 6.5(m,3H), 6.26(s,1H), 4.66(m,1H), 3.92(s,3H), 3.85(s,3H), 3.66(m,2H). 3.43(s, 3H), 2.52(s,3H), 1.91(m,2H), 1.07(t,3H) ppm.

EXAMPLE 265

4-(1-Ethyl-propoxy)-2-methyl-6-(2,4,6-trimethyl-phenylamino)-7-pyrimidine-5-carbonitrile 1H NMR(CDCl$_3$) d 6.92(s,2H), 6.45(s,1H), 5.22(m,1H), 2.29(s,6H), 2.16(s,6H), 1.70(m,4H), 0.93(t,6H) ppm.

EXAMPLE 266

N-(1-Ethyl-propyl)2,5-dimethyl-N'-(2,4,6-trimethyl-phenyl)-pyrimidine-4,6-diamine 1H NMR(CDCl$_3$) d 8.9(s,1H), 6.85(s,2H), 4.95(d,1H), 4.21(m,1H), 2.5(s,3H), 2.25(s,3H), 2.13(s,6H), 1.4–1.7(m, 4H), 1.3(s,3H), 0.85(t,6H) ppm

EXAMPLE 267

5-Chloro-N-4-(1-ethyl-propy)-2-methyl-N-6-(2,4,6-trimethyl-phenyl)pyrimidine-4,6-diamine 1H NMR(CDCl$_3$) d 6.85(s,2H), 6.0(s,1H), 4.D(m,1H), 4.2(m,1H), 2.3(s,3H), 2.22(,3H), 2.1 7(s,6H), 1.4–1.70(m, 4H), 0.97(t,6H) ppm.

EXAMPLE 268

5-Bromo-N-(1-ethyl-propyl)-2-methyl-N'-2,4,6-trimethyl-phenyl)-pyrimidine-4,6-diamine MP. 117–119° C. Anal. For $C_{19}H_{21}BrN_4$ caic.: C, 58.31; H, 6.95; N, 14.32; found: C, 58.43; H, 7.08; N. 14.23.

EXAMPLE 269

4-(1-Ethyl-propylamino)-2-methyl-62,4,6-trimethyl-phenylamino(pyrimidine-5-carboxylic acid 1H NMR(CDCl$_3$) d 12.2(brs,1H), ll.1(brs,1H), 6.84(s, 2H), 4.18(m,1H), 2.38(s.3H), 2.18(s,3H), 2.15(s,6H), 1.56 (m,4H), 0.90(t,6H) ppm.

EXAMPLE 270

[4-(Cyclopropylmethyl-propyl-amino)-2-methyl-6-(2,4,6-trichloro-phenylamino)-pyrimidin-5-yl]-methanol 1H NMR(CDCl$_3$) d 7.49s,2H), 4.95(s,2H), 4.92(s,1H), 3.28(brs,4H), 2.359s,3H). 1.54(m,2H), 0.95(m. 1H), 0.81(t, 3H), 0.44(m,2H), 0.19(m,2H) ppm.

EXAMPLE 271

6-(1-Ethyl-propoxy-2,N5,N5-trimethyl-N4-(2,4,6-trimethyl-phenyl)-pyrimidine-4,5-diamine The title compound was prepared by methylation of 6-(1-ethyl-propoxy)-2-methyl-N-4-(2,4,6-trimethyl-phenyl)-pyrimidine-4,5-diamine with lithium bis (trimethylsilyl)amide in THF, followed by quenching with methyl iodide. 1H NMR(CDCl$_3$) d 7.35(s,1H), 6.90(s,2H), 5.16(m,1H), 2.73(s,6H), 2.29(s,3H), 2.27(s,3H), 2.18(s,6H), 1.6–1.8(m,4H), 0.96(t,6H) ppm.

EXAMPLE 272

[5-Bromo-6-(1-ethyl-propoxy)-2-methyl-pyrimidin-4-yl]-(2,4,6-trimethyl-phenyl)-amine The title compound was prepared by reacting [5-bromo-6-(1-ethyl-propoxy)-2-methyl-pyrimidin-4-yl]-(2,4,6-trimethyl-phenyl)-amine with 3-pentanol/NaH in THF at reflux overnight. After standard work-up and purification, the title compound was obtained as a white solid, mp. 94–96° C. 1H NMR(CDCl$_3$) d 6.91(s,2H), 6.41(s,1H), 5.13 (m.1H), 2.29(s,3H), 2.26(,3H). 2.17(s,6H), 1.70(m,4H), 0.95(t,6H) ppm.

EXAMPLE 273

4-(1-Ethyl-propoxy) 2-methyl-6-(2,4,6-trimethyl-phenylamino)-pyrimidine-5-carboxylic acid To a solution of n-BuLi in THF was added a solution of [5-bromo-6-(1-ethyl-propoxy)-2-methyl-pyrimidin-4-yl]42, 4,6-trimethyl-phenyl)-amine in THF at −78° C. After stirring for 10 minutes, $CO_2$(g) was added at −78° C. and stirred at that temperature for 1 hour, then gradually warmed to room temperature. The resulting mixture was quenched with water and adjusted to pH 2 to 3 and extracted with chloroform. The organic layer was separated, dried and concentrated to dryness. The residue was purified through silica gel column chromatography to give the fide compound as a solid, mp. 118–120° C., Anal. For $C_{20}H_{21}N_3O_3$ calc.: C, 67.20; H. 7.61; N, 11.76; found: C, 67.25; H, 7.87; N, 11.48.

EXAMPLE 274

[4(1-Ethyl-propoxy)-2-methyl-6-(2,4,6-trimethyl-phenylamino)-pyrimidin-5-yl]-methenol To a solution of 4-(1-ethyl-propoxy)-2-methyl(2,4,6-trimethyl-phenylamino)-pyrimidine-5-carboxylic acid in dry THF was added $BH_3$.DMS. The resulting mixture was heated at reflux. The mixture was quenched with dilute HCl and stirred for 30 minutes, adjusted pH to 7.5–8.5, then extracted with ethyl acetate. The organic layer was separated, dried and concentrated to give a crude material. The crude material was purified through silica gel column chromatography to give the title compound as a solid, mp. 121–123*C, Anal. For $C_{20}H_{29}N_3O_2$ calc. C, 69.94; H, 8.51; N, 12.23; found: C, 69.73; H, 8.47; N, 1 1.99.

EXAMPLE 275

[6-(1-Ethyl-propoxy)-5-methoxymethyl-2-methyl-pyrimidin-4-yl]-(2,4,6-trimethyl-phenyl)-amine The title compound was prepared by reacting [4-(1-ethyl-propoxy)-2-methyl(2,4,6-trimethyl-phenylamino)-pyrimidin-5-yl]-methanol with NaH, followed by quenching with Mel. 1H NMR(CDCl$_3$) d 7.0(s,1H). 6.89(s,2H), 5.12 (m,1H), 4.62(s,2H), 3.33(s,3H), 2.28(s,3H0, 2.27(s,3H), 2.14(s,BH), 1.66(m,4H), 0.91(t,6H) ppm.

EXAMPLE 276

[5-Aminomethyl-6-(1-ethyl-propoxy)-2-methyl-pyrimidin-4-yl]-(2,4,6-trimethyl-phenyl)-amine To a solution of [4-(1-ethyl-propoxy)-2-methyl-6-(2,4,6-trimethyl-phenylamino) pyrimidin-5-yl]-methanol in anhydrous methylene chloride was added thionyl chloride. After stirring for 1 hour, the reaction mixture was concentrated to dryness. The residue was dissolved in dry THF and $NH_3$(g) was bubbled in. The reaction mixture was quenched with water and extracted with ethyl acetate. The reaction was worked-up and purified by standard procedure to give the title compound.

1H NMR(CDCl$_3$) d 8.50(s,1H). 6.88(s,2H), 5.08(m,1H), 3.97(s,2H), 2.279s,3H), 2.25(s,3H), 2.159s,6H), 1.74(brs, 2H), 1.65(m,4H), 0.91(t,6H) ppm.

EXAMPLE 277

7(1-Ethyl-propoxy)-5-methyl-3(2,4,6-trimethyl-phenyl)-3H-imidazo[4,5-b]pyridin-2-ylamine The title compound was prepared by reacting 41-ethyl-propoxy)-6 methyl-N-2-(2,4,6-trimethyl-phenyl)-pyridine-2,3-diamine with BrCN in acetonitrile at room temperature overnight. The mixture was quenched with water and adjusted to pH 8.0 with saturated sodium bicarbonate and extracted with ethyl acetate. The organic layer was separated, dried and concentrated to give crude material. The material was purified through silica gel column chromatography to give the title compound as a white solid, mp. 159–161° C. 1H NMR(CDCl$_3$) d 7.05(s,2H), 6.5(s,1H), 4.6(m,1H), 4.3(m,2H), 2.45(s,3H), 2.35(s,3H), 2.0(s,6H), 1.7(m,4H). 1.0(t,6H) ppm.

EXAMPLE 278

7-(1-Ethyl-propoxy)-5-methyl-32,4,6-trimethyl-phenyl)-3H-imidazo[4,5-b]pyridine

A mixture of 41-ethyl-propoxy)$_6$-methyl-N22,4,6-trimethyl-phenyl)-pyridine-2,3-diamine, trimethyl orthoformate, p-toluenesulfonic acid monohydrate in toluene was heated at reflux using Dean-Stark apparatus for 24 hours. The mixture was heated at reflux overnight. The mixture was quenched with water, sat. NaHCO$_3$, extracted with ethyl acetate. The organic layer was separated, dried (MgSO$_4$) and concentrated to dryness. After purification, the title compound was isolated. Anal. For C$_{21}$H$_{29}$N$_3$O 1/4H$_2$O calc. C, 73.76; H, 8.10; N, 12.29; found: C, 73.22; H, 7.96; N, 12.42.

EXAMPLE 279

7-(1-Ethyl-propoxy)-5-methyl-3-(2,4,6-trimethyl-phenyl)-1,3-dihydro-imidazo[4,5-b]pyridin-2-one The title compound was prepared by reacting 4-(1-ethyl-propoxy)$_6$-methyl-N-2-(2,4,6 trimethyl-phenyl)pyridine-2,3-diamine with triphosgene, NEt$_3$ in THF at room temperature. A white solid was isolated, mp. 184–186° C. Anal. For C$_{21}$H$_{27}$N$_3$O$_2$ calc. C, 71.36; H. 7.70; N, 11.89; found: C, 71.09; H, 7.75; N. 11.63.

EXAMPLE 280

7-(1-Ethyl-propoxy)-1,5-dimethyl-3-(2,4,6-trimethyl-phenyl)-1,3-dihydro-imidazo[4,5-b]pyridin-2-one The title compound was prepared by reacting 7-(1-ethyl-propoxy)-5-methyl-3-(2,4,6-trimethyl-phenyl)-1,3-dihydro-imidazo[4,5-b]pyridin-2-one with lithium bis(trimethylsilyl)amide, followed by quenching with methyl iodide. Mp. 151–153° C. Anal. For C$_{22}$H$_2$N$_3$O$_2$. 1/4H$_2$O calc. C, 71.03; H, 7.99; N, 11.30; found: C, 71.29; H, 8.01; N, 11.03.

EXAMPLE 281

(1-Ethyl-propyl)[5-methyl-3-(2,4,6-trimethyl-phenyl)-3H-imidazo[4,5-b]pyridin-7-yl]-amine A mixture of N-4-(1-ethyl-propyl)-6-methyl-N-2-(2,4,6-trimethyl-phenyl)-pyridine-2,3,4-triamine (250 mg, 0.77 mmol), trimethyl orthoformate (0.081 g, 0.766 mmol), p-toluenesulfonic acid monohydrate (0.01 g) in benzene was heated at reflux using Dean-Stark apparatus for 24 hours. Benzene was removed and toluene was added and an excess of trimethyl orthoformate (0.084 ml) was added to the reaction mixture. The mixture was heated at reflux overnight. The mixture was quenched with water, sat. NaHCO$_3$, extracted with ethyl acetate. The organic layer was separated, dried (MgSO$_4$) and concentrated to dryness. After purification, the title compound was isolated as a white crystal, mp 78–80° C.

EXAMPLE 282

[2,5-Dimethyl-3-(2,4,6-trimethyl-phenyl)-3H-imidazo[4,5-b]pyridin-7-yl]-(1-ethyl-propyl)-amine A mixture of N-4-(1-ethyl-propyl)-6-methyl-N-2-(2,4,6-trimethyl-phenyl)-pyridine-2,3,4-triamine (250 mg, 0.77 mmol), trimethyl orthoacetate (0.184 g, 1.532 mmol), p-toluenesulfonic acid monohydrate (0.01 g) in toluene was heated at reflux using Dean-Stark apparatus for 3 hours. The mixture was quenched with water, brine, extracted with ethyl acetate. The organic layer was separated, dried (MgSO$_4$) and concentrated to dryness. After purification, the title compound was obtained as a white crystal, mp 101–103° C. Anal. For C$_{22}$H$_{30}$N$_4$ calc. C, 75.39; H, 8.63; N, 15.98; found, C, 75.44; H, 8.95; N, 15.95.

EXAMPLE 283

N7(1-Ethyl-propyl)-5-methyl-3-(2,4,6-trimethyl-phenyl)-3H-imidazo[4,5-bipyridine-2,7-diamine The title compound was prepared by reacting N4-(1-ethyl-propyl)-6-methyl-N-2-(2,4,6-trimethyl-phenyl)-pyridine-2,3,4-triamine with BrCN in acetonitrile at room temperature overnight. The mixture was quenched with water and adjusted to pH 8.0 with saturated sodium bicarbonate and extracted with ethyl acetate. The organic layer was separated, dried and concentrated to give crude material. The material was purified through silica gel column chromatography to give the title compound as a brown solid, mp. 158–160° C.; Anal. For C$_{21}$H$_{21}$Ns 1/4H$_2$O calc. C, 70.85; H. 8.35; N, 19.67; found: C, 71.07; H. 8.30; N, 19.63.

EXAMPLE 284

6-(1-Ethyl-propylamino)-2,7-dimethyl-9-(2,4,6-trimethyl-phenyl)-7,9-dihydro-purin-8-one The title compound was prepared by methylation of 6-(1-ethyl-propylamino)-2-methyl-9-(2,4,6-trimethyl-phenyl)-7,9-dihydro-purin-8-one with lithium bis(trimethylsilyl)amide in THF, followed by quenching with methyl iodide. 1H NMR(CDCl$_3$) d 6.98(s,2H), 4.45(d,1H), 4.3(m,1H), 3.7(s,3H), 2.4(s,3H), 2.3(s,3H), 2.1 (s,6H), 1.5–1.8(m,4H), 1.0(t,6H) ppm.

EXAMPLE 285

6-(1-Ethyl-propoxy) 2,7-dimethyl-92,4,6-trimethylphenyl-7,9-dihydro-purin-8-one

The title compound was prepared by methylation of 6-(1-Ethyl-propoxy)$_2$-methyl-9-(2,4,6-trimethyl-phenyl)7,9 dihydropurin-8-one with lithium bis(trimethylsilyl)amide in THF, followed by quenching with methyl iodide. 1H NMR (CDCl$_3$) d7.00(s,2H), 5.31(m,1H), 3.66(s,3H), 2.479s,3H), 2.33(s,3H), 2.06(s,6H), 1.79(m,4H), 1.0i(t,6H) ppm.

EXAMPLE 286

[2-(4-Methoxy-2,6-dimethyl-phenoxy)-6-methyl-3-nitro-pyridin-4-yl]-(1-methoxymethyl-propyl)amine 1H NMR(CDCl$_3$) d 7.71(d,1H), 6.57(s,2H), 6.21(s,1H), 3.76(s,3H), 3.59(m,1H), 3.48(m,1H), 3.45(m,1H), 3.37(s, 3H), 2.13(s,3H), 2.08(s,6H), 1.6–1.8(m,4H), 0.86(t,3H) ppm.

EXAMPLE 287

(1-Ethyl-propyl)-[2-(4-methoxy-2,6-dimethyl-phenoxy)-3,6-dimethyl-pyridin-4-yl]-amine 1H NMR(CDCl$_3$) d 6.64(s.2H), 6.12(s.1H), 3.82(s,3H), 3.36(m,1H), 2.26(s.3H), 2.13(s,6H), 2.10(s,3H), 1.5-t.8m, 4H), 0.99(t,6H).

EXAMPLE 288

2[-2(4-Methoxy-2,6-dimethyl-phenoxy-3,6-dimethyl-pyridin-4-ylamino]-butan-1-ol

1H NMR(CDCl$_3$) d 6.64(s,2H), 6.13(s,1H), 4.10(m,1H), 3.76(s,3H), 3.7–3.8(m,21H), 3.57(m,1H), 2.21(s,3H), 2.19 (s,6H), 2.12(s,3H), 1.6–1.8(m,2H), 1.04(t,3H) ppm.

EXAMPLE 289 sec-Butyl-[3-methoxy-2-(4-methoxy-2,6-dimethyl-phenoxy)-6— methyl-pyridin-4-yl]-amine 1H NMR(CDCl$_3$) d 6.64(s,2H), 6.13(s,1H), 4.51(d,1H), 3.92(s.3H), 3.82(s,3H), 3.469m,1H), 2.18(s,3H). 2.15(s,6H), 1.60(m,2H), 1.26(d,3H), 1.00(t,3H) ppm.

EXAMPLE 290

2-(4-Chloro-2,6-dimethyl-phenoxy)-4-(4-ethyl-oxazolidin-3-yl)3,6dimethyl-pyridine 1H NMR(CDCl$_3$) d 7.07(s,2H), 6.36(s,1H), 4.98(m,1H), 4.78(m,1H), 4.23(m,1H), 9=, 3.83(m,1H), 3.71(m,1H), 2.28 (s,3H), 2.20(s,3H), 2.09(s,6H), 1.81(m,1H), 1.58(m,1H), 0.98(t,3H) ppm.

EXAMPLE 291

4-(4-Ethyl-oxazolidin-3-yl)-2-(4-methoxy-2,6-dimethyl-phenoxy)-3,6-dimethyl-pyridine 1H NMR(CDCl$_3$) d 6.65(s,2H), 6.36(s,1H), 4.98(m,1H), 4.77(m,1H), 4.23(m,1H), 3.83(s,3H). 3.71(m,1H)2.29(s, 3H), 2.22(s,3H), 2.119(s,6H), 1.82(m,1H), 1.56(m,1H), 0.99 (t,3H) ppm

EXAMPLE 293

2-(4-Methoxy-2,6-dimethyl-phenoxy)-N %4&-(1-methoxymethyl-propyl-6-methyl-pyridine-3,4-diamine 1H NMR(CDCl$_3$) d. 6.64(s,2H), 6.16(s,1H), 4.3(m,1H), 3.82(s,3H), 3.6–3.8(m,2H), 3.42(s,3H), 3.2(brs,2H), 2.18(s, 3H), 2.13(s,6H), 1.6–1.8(m,2H), 1.03(t,3H) ppm.

EXAMPLE 294

3-[2-(4-Chloro-2,6-dimethyl-phenoxy)-3-hydroxymethyl-6-methyl-pyridin-4-ylamino]-pentan-2-ol 1H NMR(CDCl$_3$) d 7.01(s,2H), 6.16(s,1H), 5.19(d,1H), 4.94(m,2H), 3.88(m,1H), 3.27(m,1H), 2.11(s,3H), 2.05(s, 6H), 1.73(m,1H), 1.57(m,1H), 1.24(d,3H), 0.97(t,3H)ppm.

EXAMPLE 295

2-(4-Chloro-2,6-dimethyl-phenoxy)-4-ethyl-2-oxo-propylamino)$_6$-methyl-nicotinic acid methyl ester 1H NMR(CDCl$_3$) d 8.63(d,1H), 7.01(s,2H), 5.90(s,1H), 3.95(m,1H), 3.90(s,3H), 2.08(s,3H), 2.05(s,3H), 2.03(s,6H), 1.8–2.0(m,2H), 1.00(t,3H) ppm.

EXAMPLE 296

3-[2(4-Chloro-2,6-dimethyl-phenoxy-3-methoxymethyl-6-methyl-pyridin-4-ylamino]-pentan-2-ol 1H NMR(CDCl$_3$) d 7.08(s,2H), 6.21(s,1H), 5.40(brs,1H), 4.83(q,2H), 3.91(m,1H), 3.40(s,3H), 3.33(m,1H), 2.20(s, 3H), 2.10(s,6H), 1.78(m,1H). 1.58(m,1H), 1.29(d,3H), 1.01 (t,3H) ppm.

EXAMPLE 297

3-[2-(4-Methoxy-2,6-dimethyl-phenoxy)-3,6-dimethyl-pyridin-4-ylamino]-pentan-2-ol 1H NMR(CDCl$_3$) d 6.66(s,2H), 6.27(s,1H), 4.05(m,1H), 3.82(s,3H), 3.38(m,1H), 2.35(s,3H). 2.21(s,3H), 2.14(s,6H), 1.6–1.9(m,2H), 1.30(m,3H), 1.01(t,3H)ppm.

EXAMPLE 298

4-sec-Butylamino-2-(4-methoxy-2,6-dimethyl-phenoxy)-6-methyl-nicotinic acid methyl ester 1H NMR(CDCl$_3$) d 8.01(d,1H), 6.58(s,2H), 6.06(s,1H), 3.85(s,3H), 3.77(s,3H), 2.10(s,3H), 2.07(s,6H), 1.21(d,3H0, 0.97(t,3H) ppm.

EXAMPLE 299

2-(4-Chloro-2,6-dimethyl-phenoxy)-4(1-ethyl-2-hydroxy-2-methyl-propylamino-6-methyl-nicotinic acid methyl ester 1H NMR(CDCl$_3$) d 8.28(d,1H), 7.06(s,2H), 6.32(s,1H), 3.92(s,3H), 3.41(m,1H), 2.14(s,3H), 2.12(s,6H), 1.91(m, 1H), 1.44(m,1H), 1.33(s,3H), 1.30(s,3H0, 0.99(s,3H) ppm.

EXAMPLE 300

4-(1-Hydroxymethyl-propylamino)-2-(4-methoxy-2,6-dimethyl-phenoxy)-6-methyl-nicotinic acid methyl ester 1H NMR(CDCl$_3$) d 8.13(d,1H), 6.63(s,2H), 6.21(s,1H), 3.91(s,3H0, 3.82(s,3H0, 3.81(m,2H), 3.59(m,1H), 2.16(s, 3H), 2.12(s,6H), 1.6-1.859m,2H), 1.05(t,3H) ppm.

EXAMPLE 301

2-(4-Chloro-2,6-dimethyl-phenoxy)-4-(1-hydroxymethyl-3-methylsulfanyl-propylamino)-6-methyl-nicotinic acid methyl ester 1H NMR(CDCl$_3$) d 8.25(d,1H), 7.02(s,2H), 6.30(s,1H), 3.85(s,3H), 3.6–3.9(m,3H), 2.5–2.7(m,2H), 2.14(s,3H), 2.10 (s,3H), 2.06(s,6H), 1.8–2.1(m,2H)ppm.

EXAMPLE 301

2-(4-Chloro-2,6-dimethyl-phenoxy)-methyl-4-(tetrahydro-furan-3-ylamino)-nicotinic acid methyl ester 1H NMR(CDCl$_3$) d 8.25(d,1H), 7.01(s,2H), 6.05(s,1H), 4.11(m,1H). 3.9–4.1(m,2H), 3.8–3.9(m,1H), 3.86(s,3H), 3.73(m,1H), 2.2–2.4(m,1H), 2.11(s,3H), 2.05(s,6H), 1.95 (m,1H) ppm.

EXAMPLE 302

{3-[2(4-Chloro-2,6-dimethyl-phenoxy)-3-methoxycarbonyl-6-methyl-pyridin-4-ylamino]-4-hydroxy-butyl}-dimethyl-sulfonium iodide 1H NMR(CD$_3$OD) d 7.11(s,2H), 6.61(s,1H), 4.00(m,1H), 3.86(s,3H), 3.6–3.9(m,3H), 2.95(d,6H), 2.5–2.7(m,2H), 2.22(s,3H), 2.07(s,6H), 1.8–2.1(m,2H) ppm.

EXAMPLE 303

4(1-Hydroxymethyl-3-methylsulfanyl-propylamino)-2-(4-methoxy-2,6-dimethyl-phenoxy)$_6$-methyl-nicotinic acid methyl ester 1H NMR(CDCl$_3$) d 8.15(d,1H), 6.58(s,2H), 6.28(s,1H), 3.85(s,3H), 3.76(s,3H), 3.6–3.9(m,3H), 2.5–2.7(m,2H), 2.12 (s,3H), 2.09(s,3H), 2.07(s,6H), 1.8–2.1(m,2H) ppm.

EXAMPLE 304

4-(1-Hydroxymethyl-propylamino)-2-(4-methoxy-2.6-dimethyl-phenoxy)-6,N-dimethyl-nicotinamide 1H NMR(CDCl$_3$) d 9.84(d,1H), 8.31(m,1H), 6.66(s,2H), 6.29(s,1H), 3.81(s,3H), 3.5–3.9(m,3H), 2.98(d,3H), 2.15(s, 3H), 2.12(s,6H), 1.6–1.8(m,2H), 1.05(t,3H) ppm.

EXAMPLE 305

4-sec-Butylamino-2-(4-methoxy-2,6-dimethyl-phenoxy)-6,N-dimethyl-nicotinamide

1H NMR(CDCl$_3$) d 9.77(brs,1H), 8.22(brs,1H), 6.61(s, 2H), 6.11(s,1H), 3.78(s,3H), 3.45(m,1H), 2.93(d,3H), 2.10 (s,3H), 2.07(s,6H), 1.5–1.7(m,2H), 1.23(m,3H), 0.98(t,3H) ppm.

EXAMPLE 306

2-(4-Methoxy-2,6-dimethyl-phenoxy)methyl-4-tetrahydro-furan-3-ylamino)-nicotinic acid methyl ester 1H NMR(CDCl$_3$) d 8.28(d,1H), 6.63(s,2H), 6.09(s,1H), 4.15(m,1H), 3.984.1(m,2H), 3.8–3.98(m,1H), 3.90(s,3H), 3.81(s,3H), 3.76(m,1H), 2.32–2.36(m,tH), 2.19(s,3H), 2.11 (s,6H), 1.95(m,1H) ppm.

EXAMPLE 307

4-sec-Butylamino-2-(4-methoxy-2,6-dlmethyl-phenoxy)$_6$-methyl-nicotinamide

1H NMR(CDCl$_3$) d 9.74(ds,1H), 8.05(brs,1H), 6.65(s, 2H), 6.16(s,1H), 5.55(brs,1H), 3.83(s,3H), 3.51(m,1H), 2.16 (s,3H), 2.12(s,6H), 1.5–1.7(m,2H), 1.26(d,3H), 1.02(t,3H) ppm.

Preparation A (6-Chloro-2,5-dimethylpyrimidin-4-yl)-(2,4,6-trimethylphenyl)-amine A mixture of 2,5-dimethyl-4,6-dichloropyrimidine (1.77 g, 10 mmol) and trimethylaniline (2.70 g, 20 mmol) in 5 ml of DMSO was heated in an oil bath of 160° C. for 4 hours. The mixture was quenched with water and extracted with ethyl acetate. The organic layer was separated, dried and concentrated to give the crude material. After silica gel column purification, and titration with hexane, white crystals (790 mg) were obtained; high MS calc, 275.1185, found 275.11667; IR(KBr) 3290, 3240, 2900, 1540 cm–1. 1H NMR (CDCl$_3$) δ 6.91 (s, 2H), 5.85 (s, 1H), 2.33 (s, 3H), 2.87 (s, 3H), 2.24 (s, 3H), 2.12 (s, 6H) ppm.

Preparation B (6-Chloro-2,5-dimethylpyrimidin-4-yl)-methyl-(2,4,6-trimethylphenyl)-amine A solution of (6-chloro-2,5-dimethylpyrimidin-4-yl)-(2,4, 6-trimethylphenyl)-amine (276 mg, 1 mmol) in dry THF (2 ml) was treated with sodium hydride (60% in oil, 60 mg, 1.5 mmol) at room temperature. After stirring for 2 minutes, an excess of methyl iodide (0.5 ml) was added and the resulting mixture was stirred at room temperature for 20 minutes. The mixture was quenched with saturated ammonium chloride and extracted with ethyl acetate. The organic layer was separated, dried and concentrated to give a pale yellow solid (255 mg). 1H NMR (CDCl$_3$) δ 6.85 (s, 2H), 3.26 (s, 3H), 2.50 (s, 3H), 2.27 (s, 3H), 2.03 (s, 6H), 1.39 (s, 3H) ppm.

Preparation C

4-Chloro-2,5-dimethyl-62,4,6-trimethylphenoxy)pyrimidine

A solution of 2,4,6-trimethylphenol (2.720 g, 20 mmol) in 60 ml of dry THF was treated with NaH (60% in oil, 1.200 9, 30 mmol) at room temperature. After stirring at room temperature for 15 minutes, 2,5-dimethyl-4,6-dichloropyrimidine (3.34 g, 20 mmol) was added and the resulting mixture was heated at reflux for 15 hours. The mixture was quenched with saturated ammonium chloride and extracted with ethyl acetate. The organic layer was dried and concentrated to give 5.4528 g of beige solid. The solid was recrystallized from isopropanol to give 5.1345 g of pale yellow solid, mp 86–87° C.; high MS (C$_{15}$H$_{17}$ClN$_{20}$) calc. 276.1025, found 276.10359. $^1$H NMR (CDCl$_3$) δ 6.87 (s, 2H), 2.37 (s, 6H), 2.28 (s, 3H), 2.01 (s, 6H) ppm.

Preparation D 2,4-Dichloro-3,6-dimethyl-pyridine

A mixture of 2,4-dihydroxy-3,6-dimethyl-pyridine (2.86 g, 20.58 mmol), POCl$_3$ (15 ml) and N,N-diethylaniline (3.6 ml, 22.64 mmol) was heated at reflux for 3 hours. The mixture was cooled, poured into ice water and extracted with diethyl ether. The organic layer was dried and concentrated to give 3.02 g of the crude material. After silica gel column chromatography using chloroform as eluent, 1.3102 g of the title compound was obtained as a yellow oil. 1H NMR (CDCl$_3$) δ 7.07 (s, 1H), 2.43 (s, 3H), 2.39 (s, 3H) ppm.

Preparation E

4-Chloro-3,6-dimethyl-2-(2,4,6-trimethyl-phenyoxy)-pyridine

A solution of 2,4,6-trimethylphenol (450 mg, 3.31 mmol) in 2 ml of DMSO was treated with NaH (60% in oil, 180 mg, 4.5 mmol). After 5 min, 2,4-Dichloro-3,6-dimethyl-pyridine (528 mg, 3 mmol) was added. The mixture was heated in the oil bath of 130° C. for 6 hours. The mixture was quenched with water and extracted with EtOAc. The organic layer was dried and concentrated to give 812.5 mg of crude material with two regioisomers. After silica gel column chromatography using 1:1 of CHCl$_3$:hexane as eluent, the title compound was isolated as white crystals (141 mg). mp 57–62° C.; high MS for C$_{15}$H$_{18}$ClNO: calc, 275.1072, found 275.70172; IR(KBr) 2951, 2920, 1592, 1564 cm$^{-1}$; 1H NMR (CDCl$_3$) δ 6.87 (s, 2H), 6.77 (s, 1H), 2.39 (s, 3H), 2.29 (s, 3H), 2.18 (s, 3H), 2.03 (s, 6H) ppm. The regiochemistry was determined by X-ray structural analysis of the undesired regioisomer, 2-chloro-3,6-dimethyl-442,4,6-trimethyl-phenyoxy)-pyridine.

To a solution of 4-chloro-2,5-dimethyl-642,4,6-trimethyl-phenoxy)-pyridine 1-oxide (34 mg) in 1 ml dry methylene chloride was added 2M PCl$_3$ in methylene chloride (0.022 ml). After addition, the mixture was heated at reflux for 0.5 hours, cooled and concentrated to dryness. The residue was poured into ice-water and extracted with methylene chloride. The organic layer was washed with brine, neutralized with sat, sodium carbonate, dried and concentrated to give 47 mg of the crude material. The crude material was crystallized out upon standing to give 31 mg (95%) of white crystals of the title compound.

Preparation F (6-Chloro-2,5-dimethylpyrimidin-4-yl(2,4,6-trimethylphenyl)-acetonitrile To a solution of mesitylacetonitrile (0.900 g, 5.65 mmol) in 8 ml dry THF was added sodium hydride (60% in oil, 0.250 g, 6.21 mmol) and the mixture was stirred at room temperature for 40 minutes. 2,5-Dimethyl-4,6-dichloropyrimidine (1.000 g, 5.65 mmol) was added and the resulting mixture was heated at reflux for 5 hours. The mixture was quenched with water and extracted with ethyl acetate. The organic layer was dried and concentrated to give 1.800 g of a yellow oil. The oil residue was purified through silica gel column chromatography using 10% ethyl acetate in hexane as eluent to give 0.986g(58.3%) of the title compound as a white solid, Mp 100–102° C. 1H NMR (CDCl$_3$) δ 6.86 (s, 2H), 5.60 (s, 1H), 2.69 (s, 3H), 2.25 (s, 3H), 2.18 (s, 6H), 1.92 (s. 3H) ppm.

Preparation G 2-(6-Chloro-2,5-dimethylpyrimidin-4-yl)22,4,6-trimethyl-phenyl)-propionitrile A solution of (6-chloro-2,5-dimethylpyrimidin-4-yl(2,4,6-trimethylphenyl)-acetonitrile (0.250 g, 0.834 mmol) in 4 ml of dry THF was cooled to −78° C. and treated with lithium bistrimethylsilylamide (1.0 M in THF, 0.92 ml) and stirred at that temperature for 45 minutes. Methyl iodide (0.426 g, 3.00 mmol) was added. The reaction mixture was gradually warmed to room temperature and stirred for 1 hour. The reaction mixture was quenched with water and extracted with ethyl acetate. The organic layer was dried and concentrated to give a yellow oil. The oil residue was purified through silica gel chromatotron using ethyl acetate/hexane (4:6) as eluent to give 161 mg (62%) of yellow solid, mp 181–183° C. 1H NMR (CDCl$_3$) δ 6.980 (s, 2H), 3.45 (s, 3H), 2.40 (s. 3H), 2.24 (s, 3H), 2.21 (s, 6H), 1.25 (s, 3H) ppm.

Preparation H

4-Hydroxy-2,5-dimethyl-6-(2,4,6-trimethyl-benzyl)-pyrimidine

A mixture of 6-chloro-2,5-dimethylpyrimidin-4-yl-(2,4,6-trimethylphenyl)-acetonitrile (1.5 g, 5.0 mmol) and 60 ml of 85% phosphoric acid was heated at reflux for 2 hours. The mixture was cooled at rt and diluted with water and extracted with chloroform. The organic layer was washed with brine, dried and concentrated to give 1.21 g (95%) of the title compound as a white solid, mp 260–262° C.

Preparation I

4-Chloro-2,5-dimethyl-6-(2,4,6-trimethyl-benzyl)-pyrimidine

A mixture of 4-hydroxy-2,5-dimethyl(2,4,6-trimethyl-benzyl)-pyrimidine (1.2 g. 4.68 mmol) and POCl$_3$ (25 ml) was heated at reflux for 1 hour. The mixture was cooled and evaporated to dryness. The residue was poured into ice-water and extracted with ethyl acetate. The organic layer was washed with brine, dried and concentrated to dryness to give 1.24 g (97%) of golden crystals, mp 824° C.

Preparation J

The following compounds were prepared by the methods analogous to that in Preparation C starting with 5-substituted-4,6-dichloro-2-methyl-pyrimidine and substituted phenol in tetrahydrofuran in the presence of a base (sodium hydride) at the temperature indicated below.

5-tert-Butyl-4-chloro-2-methyl-6-(2,4,6-trimethyl-phenoxy)pyrimidine

The reaction was carried out at reflux in THF to give white crystals, mp 70–72° C., 1H NMR. (CDCl$_3$) δ 6.82 (s, 2H), 2.28 (s, 3H), 2.24 (s, 3H), 1.96 (s, 6H), 1.60 (s, 9H) ppm.

4-Chloro-5-isopropyl-2-methyl-6(2,4,6-trimethyl-phenoxy)pyrimidine

The reaction was carried at reflux in THF to give white crystals, mp 68–70° C. 1H NMR (CDCl$_3$) δ 6.88 (s, 2H), 3.60 (m, 1H), 2.36 (s, 3H), 2.29 (s, 3H), 2.00 (s, 6H), 1.43 (s, 3H), 1.41 (s, 3H) ppm., 4,5-Dichloro-2-methyl-6-(2,4,6-trimethyl-phenoxy)-pyrimidine The reaction run at room temperature to give white crystals, mp 68–70° C. 1H NMR (CDCl$_3$) δ 6.88 (s, 2H), 2.41 (s, 3H), 2.29 (s, 3H), 2.04 (s, 6H) ppm. 4-Chloro-5-bromo-2-methyl-6-(2,4,6-trimethyl-phenoxy)-pyrimidine The reaction was run at 0° C. to room temperature. 1H NMR (CDCl$_3$) δ 6.88 (s, 2H), 2.41 (s, 3H), 2.29 (s, 3H), 2.03 (s, 6H) ppm.

4-Chloro-2-methyl-6-(2,4,6-trimethyl-phenoxy)-pyrimidine-5-carbonitrile

The reaction was run at −40° C. to give yellow crystals, mp 89–91° C. 1H NMR (CDCl$_3$) δ 6.89 (s, 2H), 2.51 (s, 3H), 2.29 (s, 3H), 2.04 (s, 6H) ppm.

Preparation K 2,4-Dichloro-3,diemthyl-pyridine 1-oxide

A mixture of 2,4-dichloro-3,6-dimethyl-pyridine (790 mg, 4.49 mmol) and 50% m-chloro-perbenzoic acid (1.544 g, 4.49 mmol) in 10 ml of chloroform was stirred at room temperature for 20 hours. The mixture was quenched with water, washed with saturated sodium thiosulfate and saturated sodium carbonate, brine and extracted with chloroform. The organic layer was dried and concentrated to give 954 mg of crude material. The material was purified through silica gel to give 662 mg of the title compound as a white crystals, mp 131–132° C. 1H NMR (CDCl$_3$) δ 7.22 (s, 1H), 2.51 (s, 3H), 2.47 (s, 3H) ppm.

Preparation L

The following compounds were prepared by the method analogous to that described in Preparation K starting with an appropriate 2,4-dichloro-pyridine and an oxidizing agent.

2,4-Dichloro-6-methyl-1-oxy-nicotinic acid methyl ester

M.p. 90–91.5° C. 1H NMR (CDCl$_3$) δ 7.26 (s, 1H), 3.98 (s,3H), 2.54 (s, 3H) ppm.

(2,4-Dichloro-6-methyl]-oxy-pyridin-3-yl)methanol

M.p. 188–191° C. 1H NMR (CDCl$_3$) δ 7.13 (s, 1H), 4.87 (d, 2H), 2.47 (s, 3H), 2.38 (t, 1H, OH) ppm.

2,4-Dichloro-3,5,6-trimethylpyridine 1-oxide

M.p. 146148° C. 1H NMR (CDCl$_3$) δ 2.57 (s, 3H), 2.49 (s, 3H), 2.38 (s, 3H)) ppm.

2,4-Dichloro-6-methyl-pyridine 1 oxide

M.p. 100–102° C. 1H NMR (CDCl$_3$) δ 7.42 (d, 1H), 7.22 (d, 1H), 2.55 (s, 3H) ppm.

Preparation M

4-Chloro-2,5-dimethyl 2,4,6-trimethyl-phenoxy)-pyridine-1-oxide

To a solution of 2,4,6-trimethylphenol (415 mg, 3.05 mmol) in dry THF (20 ml) was treated with 60% sodium hydride in oil (122 mg, 3.05 mmol) at room temperature. After all H$_2$ was evolved, 2,4-dichloro-3,6-dimethyl-pyridine 1-oxide (585.4 mg, 3.05 mmol) was added and the resulting mixture was heated at reflux for 2 hours. The mixture was quenched with saturated ammonium chloride and extracted with ethyl acetate. The organic layer was dried and concentrated to dryness to give solid. The solid was recrystallized from pet ether to give 802 mg (90%) of the title compound as white crystals. mp 106107° C. 1H NMR (CDCl$_3$) δ 7.04 (s, 1H), 6.78 (s, 2H), 2.41 (s. 3H). 2.36 (s, 3H), 2.22 (s. 3H), 2.06 (s, 6H) ppm.

Preparation N

The following compounds were prepared by the method analogous to that described in Preparation M starting with an appropriate 2,4-dichloro-pyridine-1-oxide with an appropriate phenol or thiophenol in the presence of a base (potassium tert-buoxide, sodium hydride, or potassium hydride) at temperature between room temperature to reflux in dry THF.

2-(4-Bromo-2,6-dimethyl-phenoxy)-4-chloro-3,6-dimethyl-pyridine 1-oxide

White crystals, mp 137–139° C. 1H NMR (CDCl$_3$) δ 7.12 (s, 2H), 7.08 (s, 1H), 2.42 (s, 6H), 2.09 (s, 6H) ppm.

4-Chloro-2-(4-chloro-2,6-dimethyl-phenoxy)-3,6-dimethyl-pyridine 1-oxide

1H NMR (CDCl$_3$) δ 7.08 (s,1H), 6.97 (s, 2H), 2.42 (s, 6H), 2.09 (s, 6H) ppm,

4-Chloro-4-methyl-2-(2,4,6-trimethyl-phenoxy)-1-oxy-nicotinic acid methyl ester

1H NMR (CDCl$_3$) δ 7.04 (s, 1H), 6.78 (s, 2H), 3.48 (s, 3H), 2.52 (s, 3H), 2.22 (s, 3H), 2.08 (s, 6H) ppm. 4-Chloro-2,3,5-trimethyl-6-(2,4,6-trimethyl-phenoxy)-pyridine 1-oxide White crystals, mp 132–134° C. 1H NMR (CDCl$_3$) δ 6.75 (s, 2H), 2.47, (s, 3H), 2.38 (s, 3H), 2.35 (s, 3H), 2.20 (s, 3H), 2.04 (s, 6H) ppm.

4-Chloro-2-methyl-6-(2,4,6-trimethyl-phenoxy)-pyridine 1-oxide

White crystals. mp 191–193° C. 1H NMR (CDCl$_3$) δ 6.96 (s, 1H), 6.95 (s, 2H), 2.62 (s, 3H), 2.32 (s, 3H), 2.13 (s, 6H) ppm. 4-Chloro-2-(2,4-dimethyl-phenylsulfanyl)-3,6-dimethyl-pyridine 1-oxide white crystals, mp 148–151° C. 1H NMR (CDCl$_3$) δ 7.23 (s, 1H), 7.02 (s, 1H), 6.88 (s, 2H), 2.46 (s, 3H), 2.41 (s, 3H), 2.39 (s, 3H), 2.27 (s, 3H) ppm.

4-Chloro-2-(2,4,6-trimethyl-phenylsulfanyl)3,6-dimethyl-pyridine 1-oxide

White crystals, mp 132–134° C. 1H NMR (CDCl$_3$) δ 7.13 (s, 1H), 6.91 (s, 2H), 2.46 (s, 3H), 2.31 (s, 6H), 2.27 (s, 3H), 2.10 (s, 3H) ppm.

Preparation O

The following compounds were prepared by the method analogous to that described in Preparation E, second paragraph, starting with an appropriate 4-chloro-6-substituted phenoxy-pyridine 1-oxide and phosphorous trichloride.

2-(4-Bromo-2,6-dimethyl-phenoxy-4-chloro-3,6-dimethyl-pyridine

White crystals. $^1$H NMR (CDCl$_3$) δ 7.22 (s, 2H), 6.81 (s, 1H), 2.40 (s, 3H), 2.20 (s, 3H), 2.05 (s, 6H) ppm.

4-Chloro-2-(4-chloro-2,6-dimethyl-phenoxy)-3,6-dimethyl-pyridine

White crystals. $^1$H NMR (CDCl$_3$) δ 7.07 (s, 2H), 6.81 (s, 1H), 2.41 (s, 3H), 2.20 (s, 3H), 2.06 (s, 6H) ppm.

4-Chloro-6-methyl-2-(2,4,6-trimethyl-phenoxy)-nicotinic acid methyl ester

Yellow crystals, mp 122–125° C. 1H NMR (CDCl$_3$) δ 6.84 (s, 2H), 6.82 (s, 1H), 3.94 (s, 3H), 2.27 (s, 3H), 2.25 (s, 3H). 2.04 (s, 6H) ppm.

4-Chloro-2,3,5-trimethyl-62,4,6-trimethyl-phenoxy)-pyridine

White crystals, mp 101–103° C. 1H NMR (CDCl$_3$) δ 6.85 (s, 2H), 2.39 (s, 3H), 2.28 (s, 3H), 2.22 (s, 3H), 2.20 (s, 3H). 2.01 (s, 6H) ppm.

4-Chloro-2-methyl-6-(2,4,6-trimethyl-phenoxy)pyridine

White crystals, mp 46–48° C. 1H NMR (CDCl$_3$) δ 6.92 (s, 2H), 6.84 (s, 1H), 2.62 (s, 3H), 2.32 (s, 3H), 2.13 (s, 6H) ppm.

4-Chloro-2-(2,4-dimethyl-phenylsulfanyl)3,6-dimethyl-pyridine

White crystals. mp 148–151° C. 1H NMR (CDCl$_3$) δ 7.23 (s, 1H), 7.02 (s, 1H), 6.88 (s, 2H), 2.46 (s, 3H), 2.41 (s, 3H). 2.39 (s, 3H), 2.27 (s, 3H) ppm.

4-Chloro-2-(2,4,6-trimethyl-phenylsulfanyl)-3,6-dimethyl-pyridine

White crystals, mp 132–134° C. 1H NMR (CDCl$_3$) δ 7.13 (s, 1H), 6.91 (s, 2H), 2.46 (s, 3H), 2.31 (s, 6H), 2.27 (s, 3H), 2.10 (s, 3H) ppm.

Preparation P

2-Chloro-4-(1-ethyl-propylamino)-6-methyl-nicotinic acid methyl ester

A mixture of 2,4-dichloro-6-methyl-nicotinic acid methyl ester (2.228 g, 10.13 mmol) and 1-ethyl-propyl amine (1.762 g, 20.26 mmol) in DMSO (4 ml) was heated at 110° C. for 5 hours, then at room temperature overnight. The mixture was quenched with water and extracted with ethyl acetate. The organic layer was dried and concentrated to give 1.796 g of crude material. The crude material was purified through silica gel column chromatography using chloroform to 5% methanol in chloroform as eluent to give 1.167 g (43%) of the title compound as a colorless oil. $^1$H NMR (CDCl$_3$) δ 7.14 (brs, 1H), 6.27 (s, 1H), 3.86 (s, 3H), 3.27 (m, 1H), 2.33 (s, 3H), 1.3–1.6 (m, 4H), 0.88 (t, 6H) ppm.

Preparation Q (2-Chloro-6-methyl-3-nitro-pyridin-4-yl(1-ethyl-propyl)-amine

A mixture of 2,4-dichloro-6-methyl-3-nitro-pyridine (250 mg, 1.21 mmol) and 1-ethyl-propyl amine (105 mg, 1.21 mmol) in DMSO (4 ml) was stirred at room temperature for 15 hours. The mixture was quenched with water and extracted with ethyl acetate. The organic layer was dried and concentrated to give 280 mg of yellow oil. The oil was purified through silical gel column chromatography using 65% chloroform in hexane as eluent to give 110 mg (35%) of the title compound as a yellow crystal, mp 82–84° C. 1H NMR (CDCl$_3$) δ 6.57 (d, 1H), 6.46 (s, 1H), 3.39 (m,1H). 2.42 (s, 3H), 1.4–1.8 (m, 4H), 0.94 (t, 6H) ppm Preparation R (6-Chloro-2-methyl-5-nitro-pyrimidin-4-yl(1-ethyl-propyl)amine A mixture of 2-methyl-5-nitro-4,6-dichloro-pyrimidine (208 mg, 1.00 mmol) and 1-ethyl-propyl-amine (87 mg, 1.03 mmol) in 2 ml of dry THF was stirred at −78° C. for 4 hours. The mixture was quenched with water and extracted with ethyl acetate. The organic layer was washed with brine, dried and concentrated to give a green oil. The oil was purified through silica gel column chromatography using chloroform to 1:1 hexane/chloroform as eluent to give the title compound (93 mg, 35%). $^1$H NMR (CDCl$_3$) δ 7.50 (brs, 1H), 4.29 (m, 1H), 2.51 (s, 3H), 1.4–1.8 (m, 4H), 0.92 (t, 6H) ppm.

Preparation S (6-Chloro-2-methyl-5-nitro-pyrimidin-4-yl)(2,4,6-trimethyl-pyridin-3-yl)amine A solution of 2-methyl-5-nitro-4,6-dichloro-pyrimidine (208 mg, 1.00 mmol) in 2.5 ml of acetonitrile was treated with 2,4,6-trimethyl-3-amino-pyridine (273 mg, 2 mmol) stirred at room temperature 2 hours. The mixture was quenched with water and extracted with ethyl acetate. The organic layer was washed with brine, dried and concentrated to give red residue. The residue was purified through silica gel column chromatography using chloroform to 6% methanol in chloroform as eluent to give the title compound (110 mg, 36%) as an orange oil. 1H NMR (CDCl$_3$) δ 8.78 (brs, 1H), 6.97 (s, 1H), 2.54 (s, 3H), 2.43 (s, 3H), 2.40 (s, 3H), 2.17 (s, 3H) ppm.

Preparation T

2-Chloro-4-(1-ethyl-propylamino)-6-methyl-nicotinic acid

The title compound was prepared by reaction of 2-chloro-4-(1-ethyl-propylamino)-6-methyl-nicotinic acid methyl ester with LiOH.H$_2$O in a mixture of water and dioxane at room temperature. The desired product was acidified to pH 3 and extracted with ethyl acetate. The organic layer was dried and concentrated to dryness. The title compound was obtained as white crystals after titration with ethyl acetate. mp. 164–165° C.; anal. For C$_{12}$H$_{17}$C$_2$ cacl. C, 56.14; H, 6.67; N, 10.91; found: C, 56.40; H, 6.53; H, 10.93.

Preparation U

4-Chloro-6-ethyl-3-methyl-2-(2,4,5-trimethyl-phenoxy)-pyridine 1-oxide

To a solution of 2,4,6-trimethylphenol in dry THF was added NaH and stirred at room temperature for 20 minutes. A solution of 2,4-dichloro-6-ethyl-3-methyl-pyridine 1-oxide was added and the resulting mixture was heated at reflux for 1.5 hour. The mixture was cooled to room temperature, quenched with water, extracted with ethyl acetate. The organic layer was separated, dried and concentrated to give the title compound which was used directly for the next step reaction.

Preparation V

4-Chloro-6-ethyl-3-methyl-2-(2,4,6-trimethyl-phenoxy)-pyridine

To a solution of 4-Chloro-6-ethyl-3-methyl-2-(2,4,6-trimethyl-phenoxy)pyridine 1-oxide in methylene chloride was added PCl$_3$ and the resulting mixture was heated at reflux for 20 min, cooled to rt. The mixture was concentrated to dryness. The residue was worked-up using standard procedure to give the title compound. After silica gel purification, the title compound was prepared as a white solid, mp. 42–44° C. Anal. For C$_{17}$H$_{20}$ClNO calc. C, 70.46; H, 6.96; N. 4.83; found, C, 70.35; H, 7.13; N, 4.58.

Preparation W

2-[4-Chloro-6-methyl-2-(2,4,6-trimethyl-phenoxy) pyridin-3-ylmethy]-malonic acid dimethyl ester The title compound was prepared by reacting 4-chloro-3-chloromethyl-6-methyl-2-(2,4,6-trimethyl-phenoxy)-pyridine with dimethyl malonate/NaH in methanol. The title compound was isolated as a colorless oil.

Preparation X

4-Chloro-3,6-dimethyl-2-(2,4,6-trimethyl-3-pyridyl)-pyridine

Preparation Y

2-Chloro-4-(1-methoxymethyl-propoxy)-6-methyl-nicotinic acid ethyl ester

1H NMR(CDCl$_3$) d 6.72(s,1H), 4.5(m,1H), 4.4(q, 2H), 3.49(d,2H), 3.31(s,3H), 2.46(s,3H), 1.68(m,2H), 1.34(t,3H), 0.93(t,3H) ppm.

Preparation Z

2-Chloro-4-(1-methoxymethyl-propoxy)-6-methyl-nicotinic acid

1H NMR(CDCl$_3$) d 6.81(s,2H), 4.51(m,1H), 3.60(m,2H), 3.40(s,3H), 2.55(s,3H), 1.77(m,2H), 1.02(t,3H)ppm.

Preparation AA (2-Chloro-methyl-6-nitro-pyridin-4-ly)-(1-methoxymethyl-propyl)-amine mp. 63–45° C., Anal. For C$_{11}$H$_{16}$N$_3$O$_3$C$_1$ calc. C, 48.27; H, 5.89, N. 15.35; found C, 48.65; H, 6.03, N, 15.11.

Preparation BB (5-Bromo-6-chloro-2-methyl-pyrimidin-4-yl)-(2,4-dichloro-phenyl)amine Mp. 165–167° C.; Anal. For C$_{11}$H$_7$BrCl3 calc.: C, 35.95; H. 1.92; N, 11.43; found: C, 36.41; H, 1.91; N. 11.05.

Preparation CC (6-Chloro-2-methyl-pyrimidin-4-yl)(2,4-dichloro-phenyl)-amine

Mp. 134–136° C.; Anal. For C$_{11}$H$_5$Cl$_3$N$_3$ calc.: C, 45.79; H. 2.79; N, 14.56; found: C, 45.91; H, 2.69; N. 14.50.

Preparation DD

[4-Chloro-6(1-ethyl-propylamino)$_2$-methyl-pyrimidin-5-yl]-acetic acid ethyl ester Mp. 78–80° C., anal. For C$_{14}$H$_{22}$ClN$_3$O$_2$ calc.: C, 56.09; H, 7.40; N, 14.02; found: C, 56.31; H, 7.60; N, 13.94.

Preparation EE

2-[4-Bromo-2-methyl(2,4,6-trimethyl-phenoxy) pyrimidin-5-yl]-propionic acid ethyl ester 1H NMR(CDCl$_3$) d 6.86(s,2H), 4.2–4.359m,2H), 4.0–4.15(m,1H), 2.4(s,3H), 2.28(s,3H), 1.99(s,3H), 1.97(s, 3H), 1.58(d,3H), 1.22(t,3H) ppm.

Preparation FF 2-(4,6-Dibromo-2-methyl-pyrimidin-5yl)-propionic acid ethyl ester 1H NMR(CDCl3) 4.36(m,1H), 4.19(m,2H), 2.68(s,3H), 1.549d,3H), 1.22(t,3H) ppm.

Preparation GG

4-Bromo-3-methoxy-methyl-2-(2,4,6-trimethyl-phenoxy)-pyridine

1H NMR(CDCl$_3$) d 6.92(s,1H), 6.87(s,2H), 4.00(s,3H), 2.299s,3H), 2.18(s,3H), 2.059s,6H) ppm.

Preparation HH

4-Bromo-2-(4-chloro-2,6-dimethyl-phenoxy)-3,6-dimethyl-pyridine

1H NMR(CDCl$_3$) d 7.04(s,2H), 6.97(s,1H), 2.42(s,3H), 2.17(s,3H), 2.03(s,6H) ppm.

Preparation II

4-Bromo-2-(2,4-dichloro-6-methyl-phenoxy-3-methoxy-6-methyl-pyridine

1H NMR(CDCl$_3$)d 7.3(d,1H), 7.18(d,1H), 4.0(s,3H), 2.2 (s,3H), 2.15(s,3H) ppm.

Preparation JJ

4-Bromo-2-(4-chloro-2,6-dimethyl-phenoxy)-3-methoxy-6-methyl-pyridine

Anal. For C$_{15}$H$_{15}$BrClNO$_2$ calc.: C, 50.52; H, 4.24; N, 3.93; found: C, 50.52; H, 4.37; N, 3.91.

Preparation KK

4-Bromo-2-(4-chloro-2-methoxy-phenoxy)-3-methoxy-6-methyl-pyridine

1H NMR(CDCl$_3$) d 6.9–7.1(m,4H), 3.94(s,3H), 3.71(s, 3H), 2.21s,3H) ppm.

Preparation LL

4-Bromo-2-(3-chloro-2,6-dimethoxy-phenoxy)-3-methoxy-6-methyl-pyridine

1H NMR(CDCl$_3$) d 7.17(d,1H), 6.96(s,1H), 6.66(d,1H), 3.97(s,3H), 3.79(s,3H), 3.70(s,3H), 2.18(s,3H) ppm.

Preparation MM

4-Bromo-3-methoxy-6-methyl-2-(2,4,6-trimethoxy-phenoxy)pyridine

1H NMR(CDCl$_3$) d 6.90(s,1H), 6.19(s,2H), 3.968(s,3H), 3.80(s,3H), 3.71(s,6H), 2.18(s,3H) ppm.

Preparation NN

4-Bromo-3-methoxy-2-(4-methoxy-2,6-dimethyl-phenoxy)-6-methyl-pyridine

1H NMR(CDCl₃) d 6.92(s,1H), 6.60(s,2H), 3.98(s,3H), 3.78(s,3H), 2.18(s,3H), 2.07(s,6H) ppm.

Preparation OO

4-Bromo-2-(4-chloro-2,6-dimethyl-phenoxy)-3-ethoxy-6-methyl-pyridine

1H NMR(CDCl₃) d 7.099s,2H), 7.00(s,1H), 4.28(q, 2H), 2.22(s,3H), 2.10(s,6H), 1.51 (t,3H) ppm.

Preparation PP

4-Bromo-3,6-dimethyl-2-(2,4,6-trimethoxy-phenoxy) pyridine

1H NMR(CDCl₃) d 6.99(s,1H), 6.25(s,2H), 3.86(s,3H), 3.77(s,6H), 2.47(s,3H), 2.25(s,3H) ppm.

Preparation QQ

4-Chloro-2-(4-chloro-2,6-dimethyl-phenoxy)-6-methyl-1-oxy-nicotinic acid methyl ester Preparation RR 4-Chloro-2-(4-chloro-2,6-dimethyl-phenoxy-6-ethyl-nicotinic acid methyl ester 1H NMR(CDCl₃) d 7.03(s,2H), 6.869s, 1H), 3.969s, 3H), 2.259s,3H), 2.05(s,6H) ppm.

Preparation SS

4-Chloro-6-methyl-2-(2,4,6-trimethyl-phenoxy)-pyridine-3-carbaldehyde

The title compound was prepared by oxidation of 4-chloro-6-methyl-2-(2,4,6-trimethyl-phenoxy)-pyridin-3-yl-methanol with pyridinium chlorochromate in methylene chloride at room temperature. The desired product was isolated after column chromatography to give a green solid (80% yield). 1H NMR(CDCl₃) d 10.66(s, 1H), 6.91(s,3H), 2.31(s,3H), 2.07(s,3H) ppm.

Preparation TT 2-(4-Bromo-2,6-dimethyl-phenoxy)-4-chloro-6-methyl-nicotinic acid methyl ester mp. 108–110° C.; Anal. For C₁₆H₁₅BrClNO₃ calc., 49.96; H, 3.93; N, 3.64; found: C, 50.07; H, 4.10; N, 3.57.

Preparation UU

4-Chloro-2-(4-chloro-2-methoxy-phenoxy)-6-methyl-1-oxy-nicotinic acid methyl ester mp. 117–120° C., Anal. For C₁₅H₁₃NO₄Cl₂ calc.: C, 50.30; H, 3.66; N, 3.91; Found: C, 50.41; H, 3.55; N, 4.00.

Preparation VV

4-Chloro-2-(4-chloro-2-methoxy-phenoxy)-6-methyl-nicotinic acid methyl ester mp. 92–93° C., Anal. For C₁₅H₁₃NO₄Cl₂ calc.: C, 52.65; H, 3.83; N, 4.09; found: C, 52.34; H, 3.85; N, 4.13.

Preparation WW

[1-(tert-Butyl-dimethyl-silanyloxymethyl)propyl]-[2(4-chloro-2,6-dimethyl-phenoxy)-3,6-dimethyl-pyridin-4-yl]-amine 1H NMR(CDCl₃) d 7.06(s,2H), 6.12(s,1H), 4.3(d,1H), 3.6–3.8(m,2H), 3.4(m,1H), 2.16(s,3H), 2.14(s,3H), 2.10(s,6H), 1.5–1.8(m,2H), 1.03(t,3H), 0.95(s,9H), 0.09(m,6H) ppm.

The following compounds were prepared by a method analogous to that described in Example 160, using an appropriate 4-bromo-2-(substituted phenoxy)-6-alkyl or alkoxy-pyridine with 1-(tert-Butyl-dimethyl-silanyloxymethyl)-propylamine.

Preparation XX

[1-(tert-Butyl-methyl-silanyloxymethyl)propyl]-[3-methoxy-6-methyl-2-(2,4,6-trimethyl-phenoxy)-pyridin-4-(S)-yl]-amine 1H NMR (CDCl₃) d 6.84(s,2H), 6.08(s,1H), 4. 8(d,1H), 3.88(s,3H), 3.5–3.7(m,2H), 3.3(m,1H), 2.27(s,3H), 2.099s, 3H), 2.07(s,6H), 1.75(m,1H), 1.55(m,1H), 0.97(t,3h), 0.89 (s,9H), 0.04(s,6H) ppm.

Preparation YY

[1-(tert-Butyl-dimethyl-silanyloxymethyl)propyl-]-[2-(4-chloro-2,6-dimethyl-phenoxy)-3-methoxy-6-methyl-pyridin-4-yl]-amine 1H NMR(CDCl₃) d 7.02(s,2H), 6.10(s,1H), 4.80(d,1H), 3.87(s,3H), 3.6–3.7(m,2H). 3.30(m,1H), 2.09(s,3H), 2.08(s, 6H), 1.75(m,1H), 1.55(m,1H), 0.97(t,3H), 0.89(s,9H), 0.03 (s,6H) ppm.

Preparation ZZ

4-[1-(tert-Butyl-dimethyl-silanyloxymethyl)-propylamino]-2-(4-chloro-2,6-dimethyl-phenoxy)-6-methyl-pyridin-3-ol 1H NMR(CDCl₃) d 7.01 (s,2H), 6.15(s,1H), 4.46(d,1H), 3.7(m,1H), 3.6(m,1H), 3.4(m,1H), 2.09(s,3H), 2.08(s,6H), 1.51.8(m,2H), 1.06(s,9H), 0.98(t,3H), 0.24(s,6H) ppm.

Preparation AAA

[1 tert-Butyl-dimethyl-silanyloxymethyl)-propyl]-[3-methoxy-6-methyl-2-(2,4,6-trimethoxy-phenoxy)pyridin-4-yl]-amine 1H NMR(CDCl₃) d 6.19(s,2H), 6.09(s,1H), 3.86(s,3H), 3.80(s,3H), 3.73(s,6H), 3.3(m,1H), 2.16(s,3H), i.75(m,1H), 1.5(m,1H), 0.95(t,3H), 0.89(s,9H), 0.04(s,6H) ppm.

Preparation BBB

4-[4-(1-tert-Butyl-dimethyl-silanyloxymethyl) propylamino]-3-methoxy-6-methyl-pyridin-2-yloxy)-3,5-dimethyl-benzonitrile 1H NMR(CDCl₃) d 7.40(s,2H), 6.19(s,1H), 4.90(brs,1H), 3.87(s,3H), 3.70(m,2H), 3.3(m,1H), 2.19(m,9H), 1.51.8(m, 2H), 1.02(t,3H), 093(s,9H), 0.09(s,6H) ppm.

What is claimed is:

1. A compound of the formula

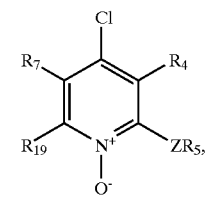

X

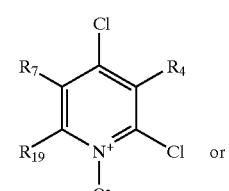

XI

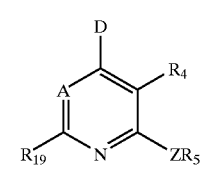

IV wherein R₇ is hydrogen, methyl, fluoro, chloro, bromo, iodo, cyano, hydroxy, —O(C₁–C₄ alkyl), —C(O) (C₁–C₄alkyl), —C(O)O(C₁–C₄ alkyl), —OCF₃, CF₃, —CH₂OH, —CH₂OCH₃ or —CH₂OCH₂CH;

D is chloro, hydroxy or cyano;

R₁₉ is methyl or ethyl;

R₅ is phenyl or pyridyl and R₅ is substituted by two or three substituents independently selected from C₁–C₄ alkyl, chloro and bromo, except that no more than one such substituent can be bromo;

R₄ is hydrogen, C₁–C₄ hydrocarbyl, fluoro, chloro, bromo, iodo, C₁–C₄ alkoxy, trifluoromethoxy, —CH$_2$OCH$_3$, C—CH$_2$CH$_2$OCH$_3$, CH$_2$OCF$_3$, CF$_3$, amino, nitro, —NH(C$_1$–C$_4$ alkyl), —N(CH$_3$)$_2$, —NHCOCH$_3$, —NHCONHCH$_3$, —SO$_n$(C$_1$–C$_4$ alkyl) where n is 0, 1 or 2, cyano, hydroxy, —CO(C$_1$–C$_4$ alkyl), —CHO, or —COO(C$_1$–C$_4$ alkyl) wherein said C$_1$–C$_4$ hydrocarbyl may optionally contain one double or triple bond and may optionally be substituted with one substituent selected from hydroxy, amino, —NHCOCH$_3$, —NH(C$_1$–C$_2$ alkyl), —N(C$_1$–C$_2$ alkyl)$_2$, —COO(C$_1$–C$_4$ alkyl), —CO(C$_1$–C$_4$ alkyl), C$_1$–C$_3$ alkoxy, C$_1$–C$_3$ thioalkyl, fluoro, chloro, cyano and nitro;

A is N, CH or CCH$_3$;

and Z is O, NH, N(CH$_3$), S or CH$_2$, with the proviso that when A is CH or CCH$_3$, then Z must be O or S.

2. A compound according to claim 1 having the formula XI wherein R$_7$ is hydrogen or methyl and R$_4$ is hydrogen, C$_1$–C$_4$ hydrocarbyl, —O(C$_1$–C$_4$ alkyl), chloro or cyano.

3. A compound of the formula

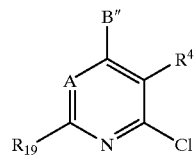

XII wherein R$_{19}$ is methyl or ethyl;

R$_4$ is hydrogen, C$_1$–C$_4$ hydrocarbyl, fluoro, chloro, bromo, iodo, C$_1$–C$_4$ alkoxy, trifluoromethoxy, —CH$_2$OCH$_3$, —CH$_2$OCH$_2$CH$_3$, —CH$_2$CH$_2$OCH$_3$, —CH$_2$OCF$_3$, CF$_3$, amino, nitro, —NH(C$_1$–C$_4$ alkyl), —N(CH$_3$)$_2$, —NHCOCH$_3$, —NHCONHCH$_3$, —SO$_n$ (C$_1$–C$_4$ alkyl) where n is 0, 1 or 2, cyano, hydroxy, —CO(C$_1$–C$_4$ alkyl), —CHO, —COOH or —COO (C$_1$–C$_4$ alkyl) wherein said C$_1$–C$_4$ hydrocarbyl may optionally contain one double or triple bond and may optionally be substituted with one substituent selected from hydroxy, amino, —NHCOCH$_3$, —NH(C$_1$–C$_2$ alkyl), —N(C$_1$–C$_2$ alkyl)$_2$, —COO(C$_1$–C$_4$ alkyl), —CO(C$_1$–C$_4$ alkyl), C$_1$–C$_3$ alkoxy, C$_1$–C$_3$ thioalkyl, fluoro, chloro, cyano and nitro;

A is N, CH or CCH$_3$

B" is —NR$_3$R$_2$, —CR$_1$R$_2$R$_{11}$, —C(=CR$_2$R$_{12}$)R$_1$, —NHCHR$_1$R$_2$, —OCHR$_1$R$_2$, —SCHR$_1$R$_2$, —CHR$_2$OR$_{12}$, —CHR$_2$SR$_{12}$, —C(S)R$_2$ or C(O)R$_2$ or cyano;

wherein R$_1$ is C(O)H, C(O)(C$_1$–C$_6$ hydrocarbyl, C(O) (C$_1$–C$_6$ alkylene) (C$_3$–C$_8$ cyclohydrocarbyl), C(O)(C$_1$–C$_6$ hydrocarbyl), C(O)(C$_1$–C$_6$ alkylene) (C$_4$–C$_8$ heterocyclohydrocarbyl), —C(O)(C$_3$–C$_8$ cycloalkylene) (C$_4$–C$_8$ heterocyclohydrocarbyl). C$_1$–C$_6$ hydrocarbyl, C$_3$–C$_8$ cyclohydrocarbyl, C$_4$–C$_8$ heterocyclohydrocarbyl, —(C$_1$–C$_6$ alkylene) (C$_3$–C$_8$ cyclohydrocarbyl), —(C$_3$–C$_8$ cycloalkylene) (C$_3$–C$_8$ cyclohydrocarbyl), —(C$_1$–C$_6$ alkylene) (C$_4$–C$_8$ heterocyclohydrocarbyl), —(C$_3$–C$_8$ cycloalkylene) (C$_4$–C$_8$ heterocyclohydrocarbyl), or —O— aryl, or —O—(C$_1$–C$_6$ alkylene)-aryl;

wherein said aryl, C$_4$–C$_8$ heterocyclohydrocarbyl, C$_1$–C$_6$ hydrocarbyl, C$_3$–C$_8$ cyclohydrocarbyl, C$_3$–C$_8$ cycloalkylene, and C$_1$–C$_6$ alkylene groups may each independently be optionally substituted with from one to six fluoro and may each independently be optionally substituted with one or two substituents R$_3$ independently selected from the group consisting of C$_1$–C$_4$ hydrocarbyl, C$_3$–C$_8$ cycloalkyl, hydroxy, fluoro, chloro, bromo, iodo, CF$_3$, —O—(C$_1$–C$_6$ hydrocarbyl), —O—(C$_3$–C$_5$ cycloalkyl), —O—CO—(C$_1$–C$_4$ hydrocarbyl), —O—CO—NH(C$_1$–C$_4$ hydrocarbyl), —O—CO—N(R$_{24}$)(R$_{25}$), —N(R$_{24}$)(R$_{25}$)—S(C$_1$–C$_4$ hydrocarbyl), —S(C$_3$–C$_5$ cycloaklyl), —N(C$_1$–C$_4$ hydrocarbyl)CO(C$_1$–C$_4$ hydrocarbyl), —NHCO (C$_1$–C$_4$ hydrocarbyl), —COO(C$_1$–C$_4$ hydrocarbyl), —CONH(C$_1$–C$_4$ hydrocarbyl), —CON(C$_1$–C$_4$ hydrocarbyl) (C$_1$–C$_2$ hydrocarbyl), CN, NO$_2$, —OSO$_2$ (C$_1$–C$_4$ hydrocarbyl), —S(C$_1$–C$_4$ hydrocarbyl) (C$_1$–C$_2$alkyl) 1, —SO(C$_1$–C$_4$ hydrocarbyl) and —SO$_2$ (C$_1$–C$_4$ hydrocarbyl); and wherein the C$_4$–C$_6$ hydrocarbyl, C$_1$–C$_6$ alkylene C$_3$–C$_8$ cyclohydrocarbyl, C$_3$–C$_8$ cycloalkylene, and C$_4$–C$_8$ heterocyclohydrocarbyl moieties of R$_1$ may optionally independently contain from one to three double or triple bonds; and wherein the C$_1$–C$_4$ hydrocarbyl moieties and the C$_1$–C$_6$ hydrocarbyl moieties of R$_8$ can optionally independently be substituted with hydroxy, C$_1$–C$_4$ alkyl, amino, aryl, —CH$_2$-aryl, —C$_3$–C$_5$ cycloalkyl, or —O—(C$_1$–C$_4$ alkyl), and can optionally independently be substituted with from one to five fluoro, and can optionally contain one or two double or triple bonds; and wherein each heterocyclohydrocarbyl group of R$_1$ contains from one to three heteromoieties selected from oxygen, S(O)$_m$, nitrogen and NR$_{12}$;

wherein R$_2$ is hydrogen, C$_1$–C$_{12}$ hydrocarbyl, C$_3$–C$_8$ cyclohydrocarbyl, C$_4$–C$_8$ heterocyclohydrocarbyl, —(C$_1$–C$_6$ alkylene) C$_3$–C$_8$ cyclohydrocarbyl), —(C$_3$–C$_8$ cycloalkylene) (C$_3$–c$_8$ cyclohydrocarbyl), —(c$_1$–C$_6$ alkylene) (C$_4$–C$_8$ heterocyclohydrocarbyl), —(C$_3$–C$_8$ cycloalkylene) (C$_4$–C$_8$ heterocyclohydrocarbyl), aryl, —(C$_1$–C$_6$ alkylene) aryl, or —(C$_3$–C$_8$ cycloalkylene) (aryl); wherein each of the foregoing R$_2$ groups may optionally be substituted with from one three substituents independently selected from chloro, fluoro, and C$_1$–C$_6$ alkyl, wherein one of said one to three substituents can further be selected from bromo, iodo, C$_1$–C$_6$ alkoxy, —OH, —O—CO—(C$_1$–C$_6$ alkyl), —O—CO—N(C$_1$–C$_4$ alkyl) (C$_1$–C$_2$ alkyl), —S(C$_1$–C$_6$ alkyl), —S(O)(C$_1$–C$_6$ alkyl), —S(O)$_2$(C$_1$–C$_6$ alkyl), S$^+$(C$_1$–C$_6$ alkyl)(C$_1$–C$_2$ alkyl)1$^-$, CN, and NO$_2$; and wherein the C$_1$–C$_{12}$ hydrocarbyl, —(C$_1$–C$_6$ alkylene), (—C$_3$–C$_8$ cyclohydrocarbyl), (C$_3$–C$_8$ cycloalkylene), and (—C$_4$–C$_8$ heterocyclohydrocarbyl) moieties of R$_2$ may optionally independently contain from one to three double or triple bonds; and wherein each heterocyclohydrocarbyl group of R$_2$ contains from one to three heteromoieties selected from oxygen, S(O)$_m$, nitrogen, and NR$_{12}$;

or where R$_1$ and R$_2$ are as in —NHCHR$_1$R$_2$, —OCHR$_1$R$_2$, —SCHR$_1$R$_2$, —CHR$_1$R$_2$, or —NR$_1$R$_2$, R$_1$ and R$_2$ of B may form a saturated 5- to 8-membered ring which may optionally contain one or two double bonds and in which one or two of the ring carbons may optionally be replaced by an oxygen, S(O)$_m$, nitrogen or NR$_{12}$, and which carbocyclic sing can optionally be substituted with from 1 to 3 substituents selected from the group consisting of hydroxy, C$_1$–C$_4$ alkyl, fluoro, chloro, bromo, iodo, CF$_3$, —O—(C$_1$–C$_4$ alkyl), —O—CO—(C$_1$–C$_4$ alkyl), —O—CO—NH(C$_1$–C$_4$ alkyl), —O—CO—N(C$_1$–C$_4$ alkyl) (C$_1$–C$_2$ alkyl), —NH(C$_1$–C$_4$ alkyl), —N(C$_1$–$_2$ alkyl)(C$_1$–C$_4$ alkyl), —S(C$_1$–C$_4$ alkyl), —N(C$_1$–C$_4$ alkyl) CO(C$_1$–C$_4$ alkyl), —NHCO(C$_1$–C$_4$ alkyl), —COO(C$_1$–C$_4$ alkyl), —CONH(C$_1$–C$_4$ alkyl), —CON(C$_1$–C$_4$ alkyl)(C$_1$–C$_2$ alkyl), CN, NO$_2$, —OSO$_2$(C$_1$–C$_4$ alkyl), —SO(C$_1$–C$_4$ alkyl), —SO$_2$(C$_1$–C$_4$ alkyl), wherein one of said one to three substituents can further be selected from phenyl;

wherein each m is independently zero, one or two;

wherein R$_{11}$ is hydrogen, hydroxy, fluoro, ethoxy, or methoxy;

wherein R$_{12}$ is hydrogen or C$_1$–C$_4$ alkyl;

with the proviso that when A is N then B" and R$_4$ are defined, respectively, as B" R$_4$ are defined above and when A is CH or CCH$_3$, then B" is —NR$_1$R$_2$—NHCHR$_1$R$_2$, —OCHR$_1$R$_2$ or cyano and R$_4$ is an electron deficient group.

4. A compound according to claim 3, wherein B" is NR$_1$R$_2$, —NHCHR$_1$R$_2$, and A is CH or CCH$_3$.

5. A compound according to claim 3 wherein the electron deficient group is selected from the group consisting of NO$_2$, —COO(C$_1$–C$_4$ alkyl), —C(=O)CH$_3$, —COOH and cyano.

6. 4-Chloro-2-(4-chloro-2,6-dimethyl-phenoxy)-3,6-dimethyl-pyridine.

7. The compound according to claim 1, wherein the compound has the formula X and Z is O, NH, S or CH$_2$.

8. The compound according to claim 1, wherein the compound has the formula XI.

9. A process for preparing a compound of formula X shown below comprising:

providing the compound of claim 8; and (b) reacting the compound of claim 8 with a compound of the formula R$_5$OH or R$_5$SH in the presence of a base to form the compound of formula X:

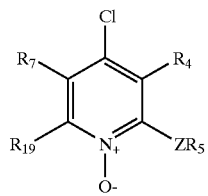

X wherein Z is O, S or CH$_2$, and R$_4$, R$_5$, R$_7$ and R$_{19}$ are as described above or in claim 8.

10. The compound according to claim 1, wherein the compound has the formula IV.

11. A process for preparing a compound of formula IV shown below comprising:

(a) providing the compound of claim 1, wherein the compound has the formula X and D is chloro; and (b) reacting the compound of claim 1 with phosphorus trichloride to form the compound of formula IV:

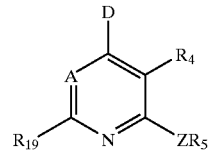

IV wherein R$_4$, R$_5$, R$_{19}$, Z, A and D are as described above or in claim 1.

12. A process for preparing a compound of formula I shown below or a pharmaceutically acceptable salt thereof comprising:

(a) providing the compound of claim 3;

(b) providing a compound of formula R$_5$ZH, wherein

R$_5$ is phenyl or pyridyl, and R$_5$ is substituted with from one to three substituents independently selected from fluoro, chloro, C$_1$–C$_6$ alkyl, and C$_1$–C$_6$ alkoxy, or with one substituent selected from hydroxy, iodo, bromo, formyl, cyano, nitro, trifluoromethyl, amino, C$_1$–C$_6$ alkyl)O(C$_1$–C$_6$)alkyl, —NHCH$_3$, —N(CH$_3$)$_2$, —COOH, —COO(C$_1$–C$_4$ alkyl), —CO(C$_1$–C$_4$ alkyl), —SO$_2$NH(C$_1$–C$_4$ alkyl), —SO$_2$N(C$_1$–C$_4$ alkyl)(C$_1$–C$_2$ alkyl), —SO$_2$NH$_2$, —NHSO$_2$(C$_1$—C, alkyl), —S(C$_1$–C$_6$ alkyl) and —SO$_2$(C$_1$–C$_6$ alkyl), and wherein the C$_1$–C$_4$ alkyl and C$_1$–C$_6$ alkyl moieties of the foregoing R$_5$ groups may optionally be substituted with one or two fluoro groups or with one substituent selected form hydroxy, amino, methylamino, dimethyl amino and acetyl;

and;

Z is NH, O, S, —N(C$_1$–C$_2$ alkyl) or —C(R$_{13}$ and R$_{14}$), wherein R$_{13}$ and R$_{14}$ are each, independently, hydrogen, trifluoromethyl or methyl, or one of R$_{13}$ and R$_{14}$ is cyano and the other is hydrogen or methyl;

(b) reacting the compound of claim 3 with the compound of the formula R$_5$ZH to form the compound of formula I:

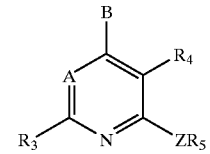

I wherein B is the same as B", and R$_3$ is methyl, ethyl, fluoro, chloro, bromo, iodo, cyano, methoxy, OCF$_3$, methylthio, methylsulfonyl, CH$_2$OH, or CH$_2$OCH$_3$ and R$_4$,R$_5$, Z and A are as described above or in claim 3; and (c) optionally converting the compound of formula I into a pharmaceutically acceptable salt.

13. The process of claim 12, wherein R$_4$ is nitro.

* * * * *